United States Patent
Claussen et al.

(10) Patent No.: US 10,319,537 B2
(45) Date of Patent: Jun. 11, 2019

(54) MODIFIED GRAPHITIC ELECTRODES FOR ELECTROCHEMICAL ENERGY STORAGE ENHANCEMENT

(71) Applicant: PURDUE RESEARCH FOUNDATION, West Lafayette, IN (US)

(72) Inventors: Jonathan Clay Claussen, San Diego, CA (US); Anurag Kumar, West Lafayette, IN (US); Timothy S. Fisher, West Lafayette, IN (US); Ronald G. Reifenberger, Lafayette, IN (US); Guoping Xiong, West Lafayette, IN (US); David Benjamin Jaroch, Tonawanda, NY (US); David Marshall Porterfield, West Lafayette, IN (US); Rajib Paul, Kaliyaganj (IN)

(73) Assignee: Purdue Research Foundation, West Lafayette, IN (US)

( * ) Notice: Subject to any disclaimer, the term of this patent is extended or adjusted under 35 U.S.C. 154(b) by 735 days.

(21) Appl. No.: 14/181,106

(22) Filed: Feb. 14, 2014

(65) Prior Publication Data
US 2014/0322608 A1    Oct. 30, 2014

Related U.S. Application Data

(63) Continuation of application No. PCT/US2012/051008, filed on Aug. 15, 2012, which
(Continued)

(51) Int. Cl.
*H01G 11/36*    (2013.01)
*G01N 27/327*    (2006.01)
(Continued)

(52) U.S. Cl.
CPC ............ *H01G 11/36* (2013.01); *C01B 32/15* (2017.08); *C01B 32/18* (2017.08);
(Continued)

(58) Field of Classification Search
CPC . H01G 11/36; C01B 31/0206; C01B 31/0293; G01N 27/3272
See application file for complete search history.

(56) References Cited

U.S. PATENT DOCUMENTS

| | | | |
|---|---|---|---|
| 2002/0006547 A1 | 1/2002 | Miyamoto | |
| 2010/0075835 A1* | 3/2010 | Yuge | B01J 21/185 502/150 |

(Continued)

OTHER PUBLICATIONS

Ming-Chieh Tsai, Yu-Chen Tsai, "Adsorption of glucose oxidase at platinum-multiwalled carbon nanotube-alumina-coated silica nanocomposite for amperometric glucose biosensor", Sensors and Actuators B 141 (2009), 592-598.*

(Continued)

*Primary Examiner* — Jonathan G Jelsma
(74) *Attorney, Agent, or Firm* — Maginot, Moore & Beck LLP

(57) ABSTRACT

A method of graphitic petal synthesis includes a step of providing a flexible carbon substrate, such as that including carbon microfibers. The method further includes the step of subjecting flexible carbon substrate to microwave plasma enhanced chemical vapor deposition. The resulting synthesized graphitic petal structure may optionally be coated with PANI.

8 Claims, 83 Drawing Sheets

Related U.S. Application Data is a continuation of application No. PCT/US2013/032446, filed on Mar. 15, 2013.

(60) Provisional application No. 61/523,646, filed on Aug. 15, 2011, provisional application No. 61/644,717, filed on May 9, 2012, provisional application No. 61/723,757, filed on Nov. 7, 2012.

(51) Int. Cl.
| | |
|---|---|
| *H01M 4/587* | (2010.01) |
| *H01G 11/30* | (2013.01) |
| *C01B 32/15* | (2017.01) |
| *C01B 32/18* | (2017.01) |
| *B82Y 30/00* | (2011.01) |
| *B82Y 40/00* | (2011.01) |
| *H01M 10/0525* | (2010.01) |

(52) U.S. Cl.
CPC ......... *G01N 27/3272* (2013.01); *H01G 11/30* (2013.01); *H01M 4/587* (2013.01); *B82Y 30/00* (2013.01); *B82Y 40/00* (2013.01); *H01M 10/0525* (2013.01); *Y02E 60/13* (2013.01); *Y10S 977/742* (2013.01)

(56) References Cited

U.S. PATENT DOCUMENTS

| | | |
|---|---|---|
| 2011/0163298 A1 | 7/2011 | Sung |
| 2011/0203936 A1* | 8/2011 | Kulinsky ............... C25D 5/02 205/95 |

OTHER PUBLICATIONS

Hong Wu, Jun Wang, Xinhuang Kang, Chongmin Wang, Donghai Wang, Jun Liu, Ilhan Aksay, and Yuehe Lin, "Glucose biosensor based on immobilization of glucose oxidase in platinum nanoparticles/graphene/chitosan nanocomposite film", Talanta, vol. 80, Issue 1, Nov. 15, 2009, pp. 403-406.*
Jeong, Hyung Mo et al., Nitrogen-Doped Graphene for High-Performance Ultracapacitors and the Importance of Nitrogen-Doped Sites at Basal Planes, Nano Letters, 2011, pp. 2472-2477, vol. 11, Issue 6.
Lin, Tsung-Wu et al., Converting Graphene Oxide Monolayers into Boron Carbonitride Nanosheets by Substitutional Doping, Small Journal, 2012, pp. 1384-1391, vol. 8, No. 9.
Vinu, Ajayan et al., Synthesis of Mesoporous BN and BCN Exhibiting Large Surface Areas via Templating Methods, Chemistry of Materials, 2005, pp. 5887-5890, vol. 17, No. 24.
International Search Report and Written Opinion, PCT Application No. PCT/US2013/032466.
Hiramatsu, Mineo et al. Carbon Nanowalls. Wien: Springer-Verlag, 2010, ISBN 978-3-211-99717-8, pp. 1-161.
Nien, Po-Chin et al., Electroanalysis, Jul. 2006, pp. 1408-1415, vol. 18, No. 13-14.
Rout, Chandra Sekhar et al., Applied Physics Letters, Sep. 2010, vol. 97, No. 13, 133108.
Bhuv Ana, Thiruvelu et al., Applied Materials & Interfaces, Mar. 2010, pp. 644-648, vol. 2, No. 3.
Shao, Yuyan et al., Electroanalysis, May 2010, pp. 1027-1036, vol. 22, No. 10.
International Search Report and Written Opinion, PCT Application No. PCT/US2012/051008.
Suenaga, K. et al., Synthesis of Nanoparticles and Nanotubes with Well-Separated Layers of Boron Nitride and Carbon, Science, Oct. 1997, pp. 653, vol. 278.
Liao, Lei et al., Multiwall Boron Carbonitride/Carbon Nanotube Junction and Its Rectification Behavior, Institute of Physics, American Chemical Society, 2007, pp. 9562-9653, vol. 129, No. 31.
Golberg, Dmitri et al., Boron Nitride Nanotubes and Nanosheets, American Chemical Society, 2010, pp. 2979-2993, vol. 4, No. 6.
Anupam, K. et al., Experimental Investigation of a Single-Bed Pressure Swing Adsorption Refrigeration System Towards Replacement of Halogenated Refrigerants, Chemical Engineering Journal, Elsevier, 2011.
Myers, A. L. et al. Adsorption in Porous Materials at High Pressure: Theory and Experiment, Langmuir, 2002, vol. 18.
Gallego, Nidia et al., Carbon Foams for Thermal Management, International Seminar on Advanced Applications for Carbon Materials, 2003, 41, 1461.
Voevodin, A. A. et al., Growth and Structure of Fullerene-like CNx thin films produced by pulsed laser ablation of Graphiet in Nitrogen, Journal of Applied Physics, 2002, pp. 4980-4988, vol. 92, No. 9.
Barros, E. B. et al., Raman Spectroscopy of Graphitic Foams, Physical Review, 2005, pp. 165422.
Thomsen, C. and S. Reich, Double Resonant Raman Scattering in Graphite, Physical Review Letters, 2000, pp. 5214-5217, vol. 85, No. 24.
Arutyunyan, N. R. et al., Incorporation of Boron and Nitrogen in Carbon Nanomaterials and its Influence on Their Structure and Opto-Electronical Properties, Carbon, Elsevier, 2012, pp. 791-799, vol. 50.
Jhi, S. and Young-Kyun Kwon, Hydrogen Adsorption on Boron Nitride Nantubes: A Path to Room-Temperature Hydrogen Storage, Physical Review, 2004, pp. 245407, vol. 69.
Raidongia, Kalyan et al., Synthesis, Structure and Properties of Mesoporous B/C/N Microspheres, Z. Anorg. Alleg. Chem., 2010 pp. 30-35.
Zhi, C., Y. Bando , C. Tang , H. Kuwahara , D. Golberg , Adv. Mater. 2009, 21, 2889.
Kim, D. H., E. Byon, S. Lee, J. K. Kim, H. Ruh, Thin Solid Films 2004, 447-448, 192.
Gago, R., I. Jimenez, J. M. Albella, Thin Solid Films 2000, 373, 277.
Tsai, P. C., Surf. Coat. Technol. 2007, 201, 5108.
Blase, X., J.-C. Charlier, A. D. Vita, R. Car, X. Blase , J.-C. Charlier, A. D. Vita, R. Car, Appl. Phys. Lett. 1997, 70, 197.
Li, B., Z. Lei, X. Zhang , Z. Huang , Catal. Today 2010, 158 , 515.
Kletta, J., R. Hardyb , E. Rominec , C. Wallsa , T. Burchella , Carbon 2000 , 38 , 953.
Kustov, L. M., I. M. Sinev , Russ. J. Phys. Chem. A 2010 , 84 ,1676.
Portehault, D., C. Giordano , C. Gervais , I. Senkovska , S. Kaskel , C. Sanchez , M. Antonietti , Adv. Fund. Mater. 2010 , 20 , 1827.
Burke, A., C. Brown, W. Bowling, J. Glaub, D. Kapsch, C. Love, R. Whitaker, W. Moddeman, Surf. Interface Anal. 1988, 11, 353.
Zhuge, F., Z. G. Ji , H. P. He , Z. Z. Ye , L. P. Zhu , J. Cryst. Growth 2008, 310 , 3869.
Hubacek, M., T. Sato , J. Solid State Chem. 1995, 114 , 258.
Leong, K. C., H. Y. Li , L. W. Jin , J. C. Chai , J. Heat Transf. 2011 , 133, 060902.
Wang, R. Z., J. P. Jia, Y. H. Zhu, Y. Teng, J. Y. Wu, J. Cheng, Q. B. Wang, J. Solar Energy Eng. 1997, 119, 214.
Cacciola, G., G. Restuccia , L. Mercadante , Carbon 1995 , 33 , 1205.
Deng, J., R. Z. Wang , G. Y. Han , Process Energy Combustion Sci. 2011 , 37 , 172.
Artiles, M. et al. "Graphene-based hybrid materials and devices for biosensing," Adv Drug Delivery Reviews, vol. 63, No. 14, Jul. 25, 2011, pp. 1352-1360.
Yang, W. et al. "Carbon Nanomaterials in Biosensors: Should you Use Nanotubes or Graphene?" Angew Chem Int Ed., vol. 49, No. 12, Mar. 15, 2010, pp. 2114-2138.
Shang et al., "Catalyst-Free Efficient Growth, Orientation and Biosensing Properties of Multiayer Graphene Nanoflake films with Sharp Edge Planes," Adv. Funct. Mater., vol. 18, No. 21, Nov. 10, 2008, pp. 3506-3514.
Kang X. et al., "Glucose Oxidase-Graphene-Chitosan Modified Electrode for Direct Electrochemistry and Glucose Sensing," Biosens Bioelectric., vol. 25, No. 4, Dec. 15, 2009, pp. 901-905.
European Search Report for related PCT/US2012/051008, dated Jul. 2, 2015.

(56) References Cited

OTHER PUBLICATIONS

Wu, H. et al., "Glucose Biosensor based on Immobilization of Glucose Oxidase in Platinum nanoparticles/graphene/chiosan nanocomposite film," Talanta, 2009, pp. 403-406.
Paul, R., S. N. Das, S. Dalui, R. N. Gayen, R. K. Roy, R. Bhar, A. K. Pal, J. Phys. D: Appl. Phys. 2008, 4 , 055309.

\* cited by examiner

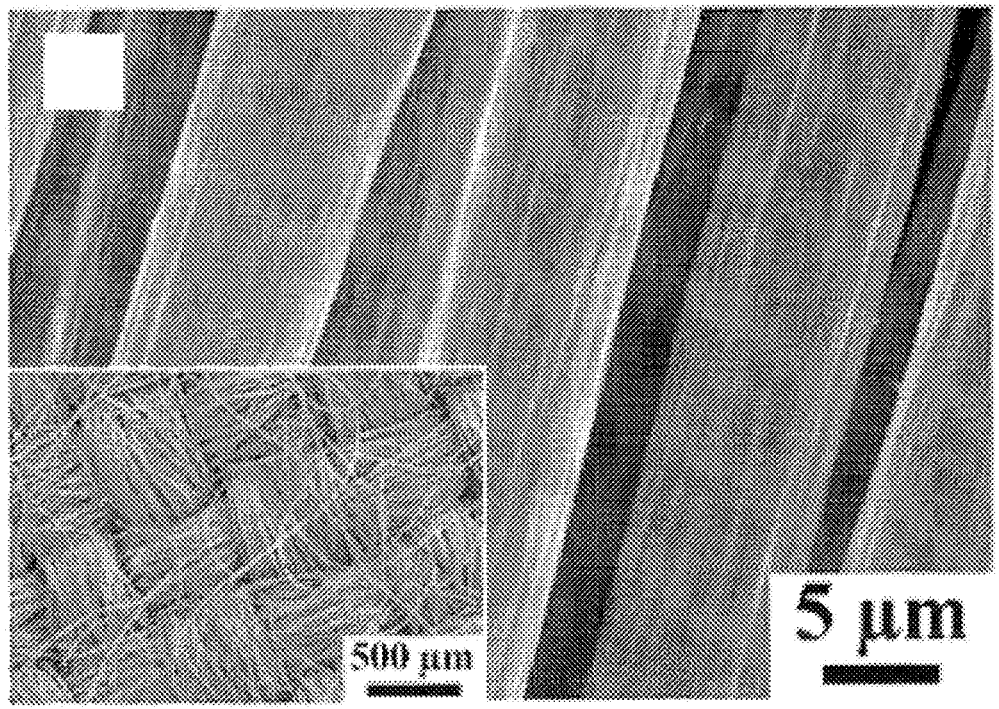
FIG. 3-2a
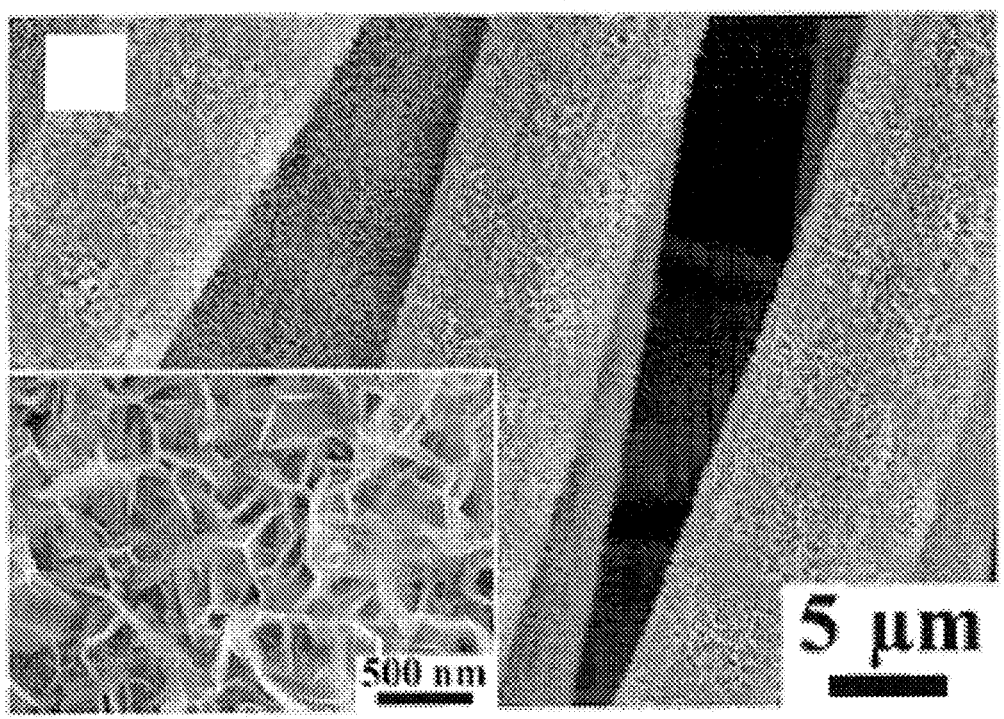
FIG. 3.2b

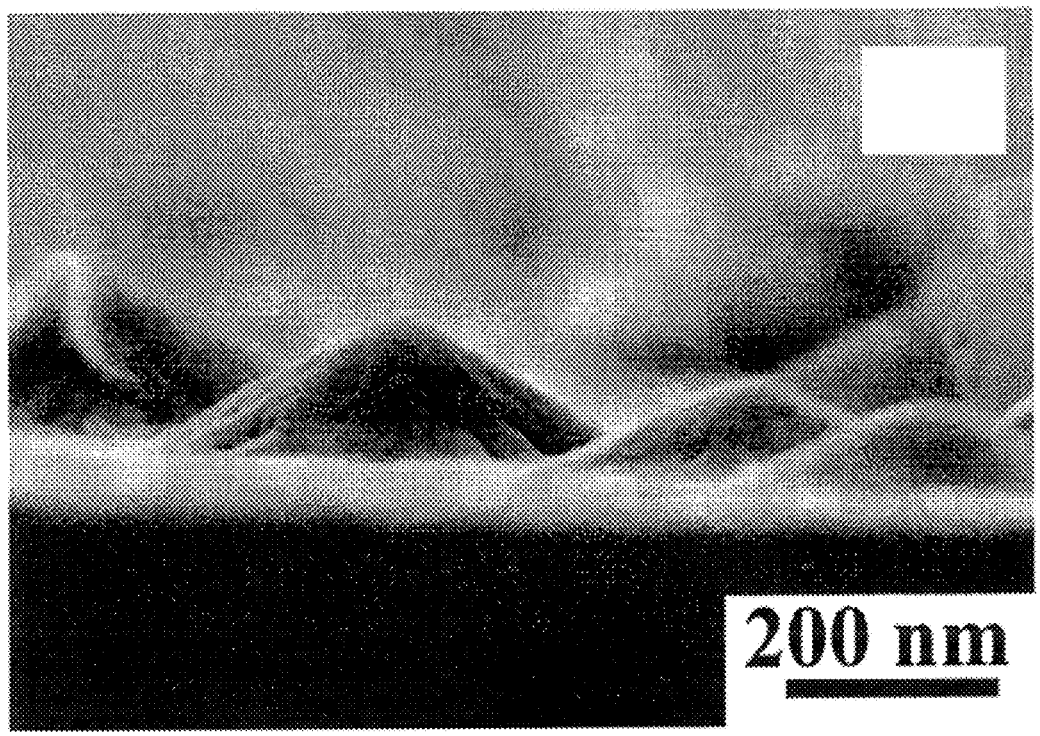
FIG. 6-3.1a
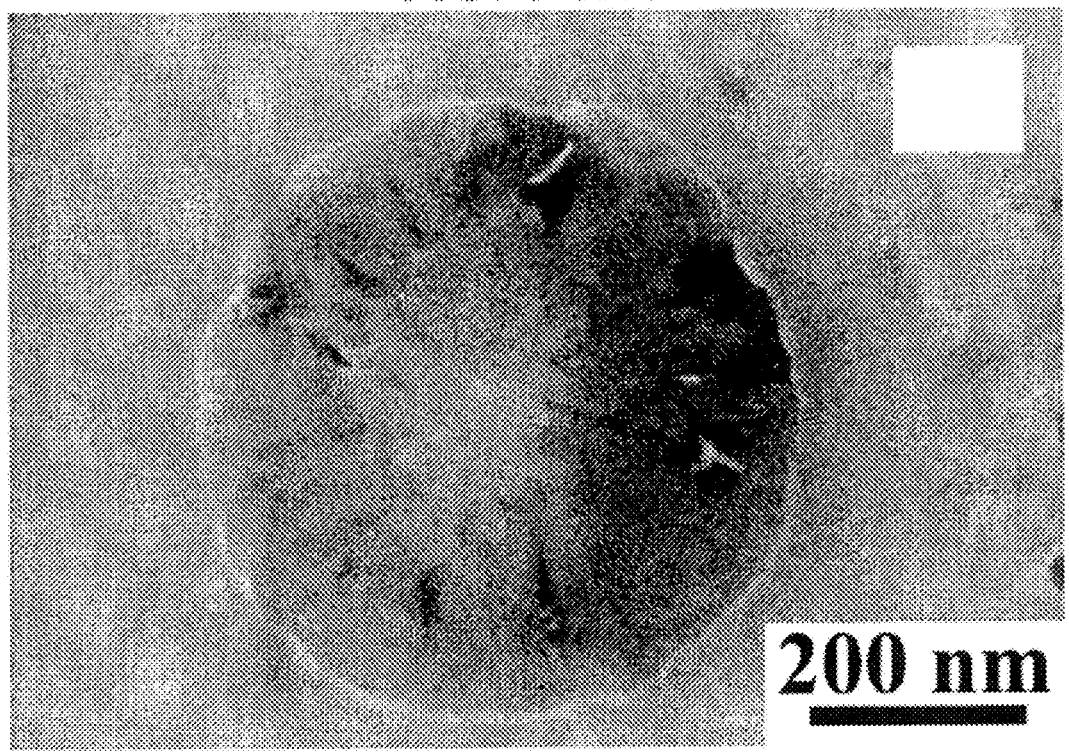
FIG.6-3.1b

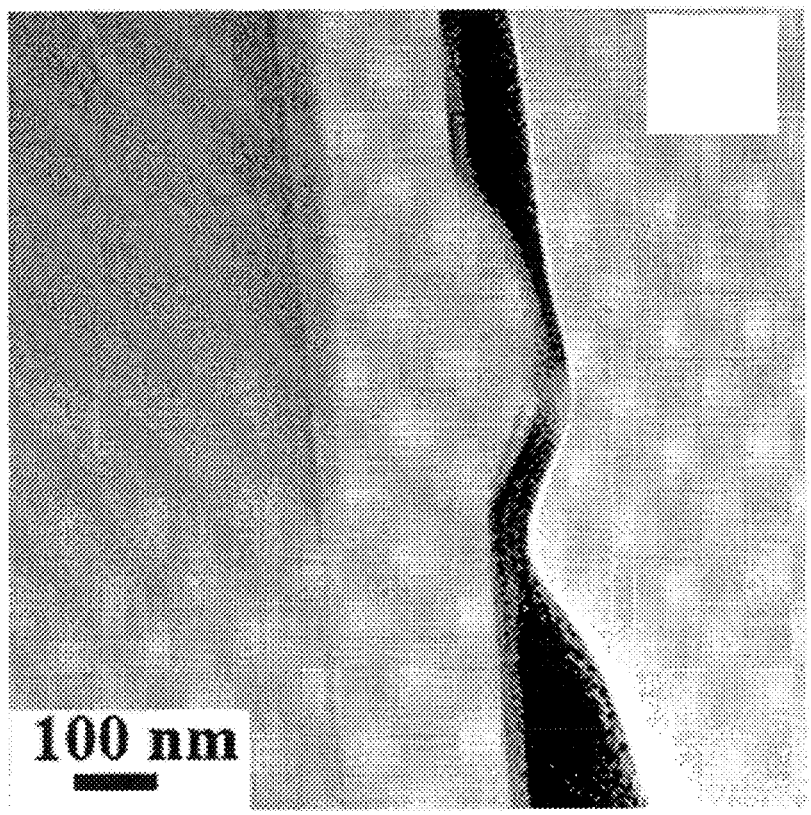
FIG. 6-3.2a
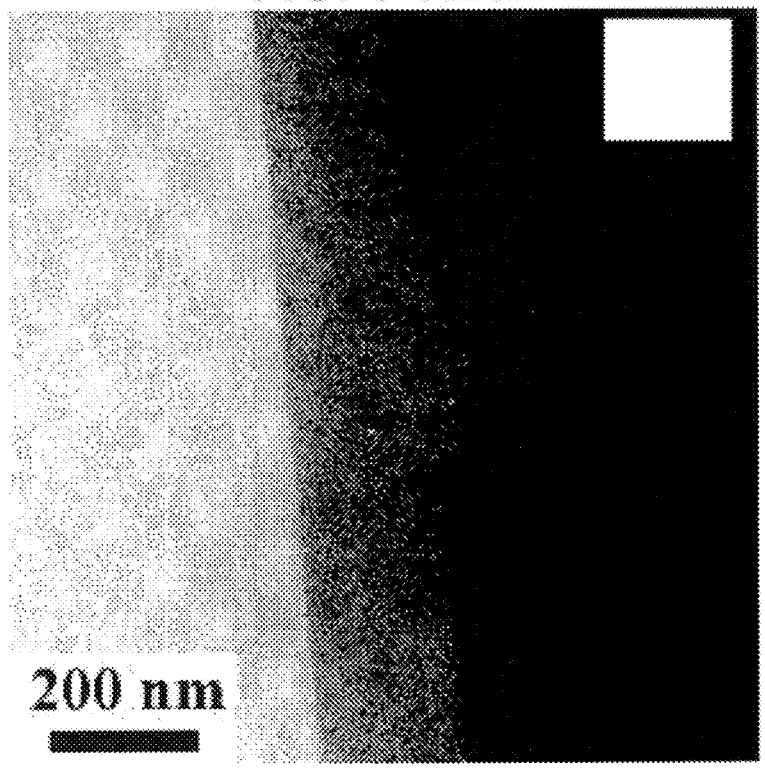
FIG. 6-3.2b

FIG. 6-3.2c

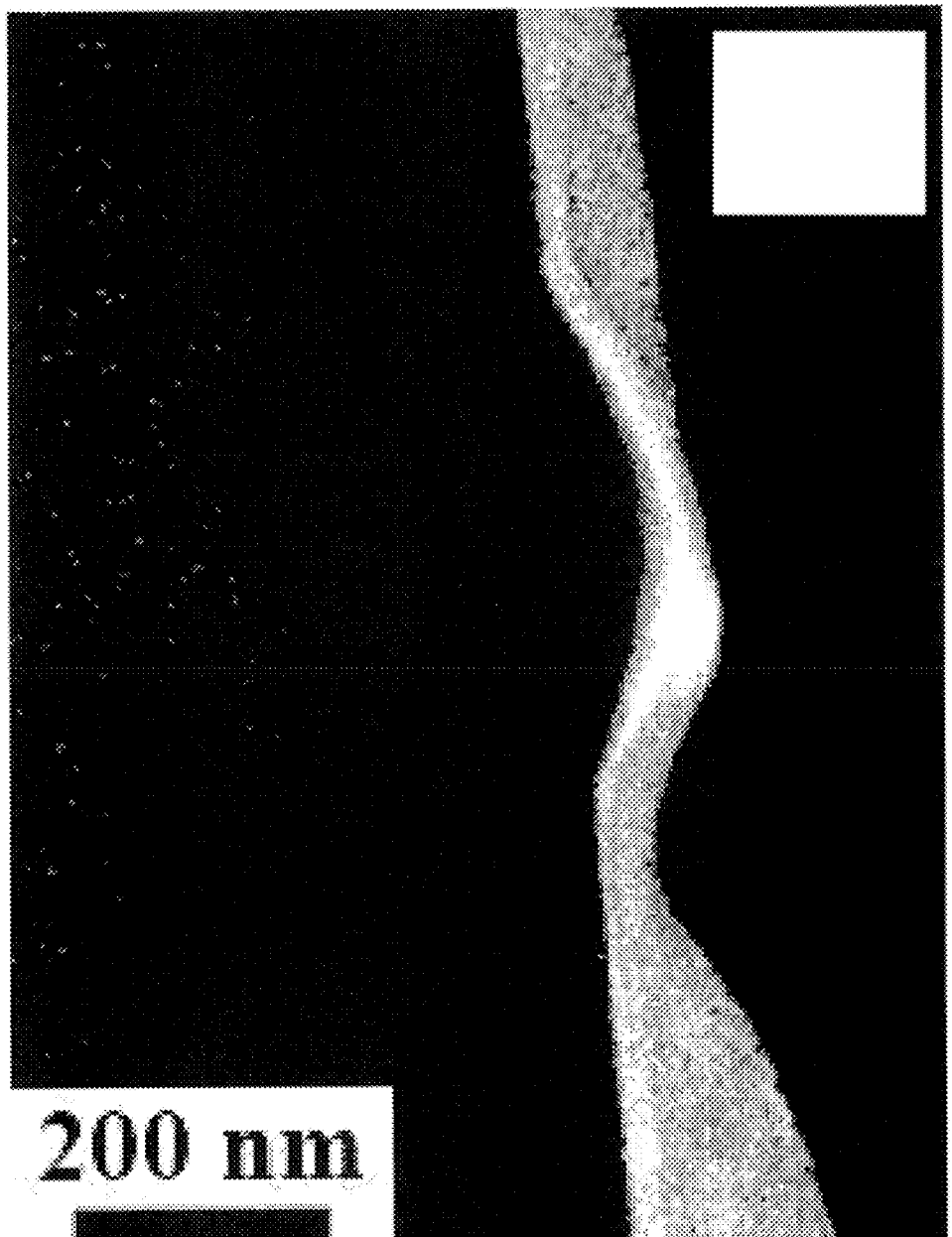
FIG. 6-3.2d

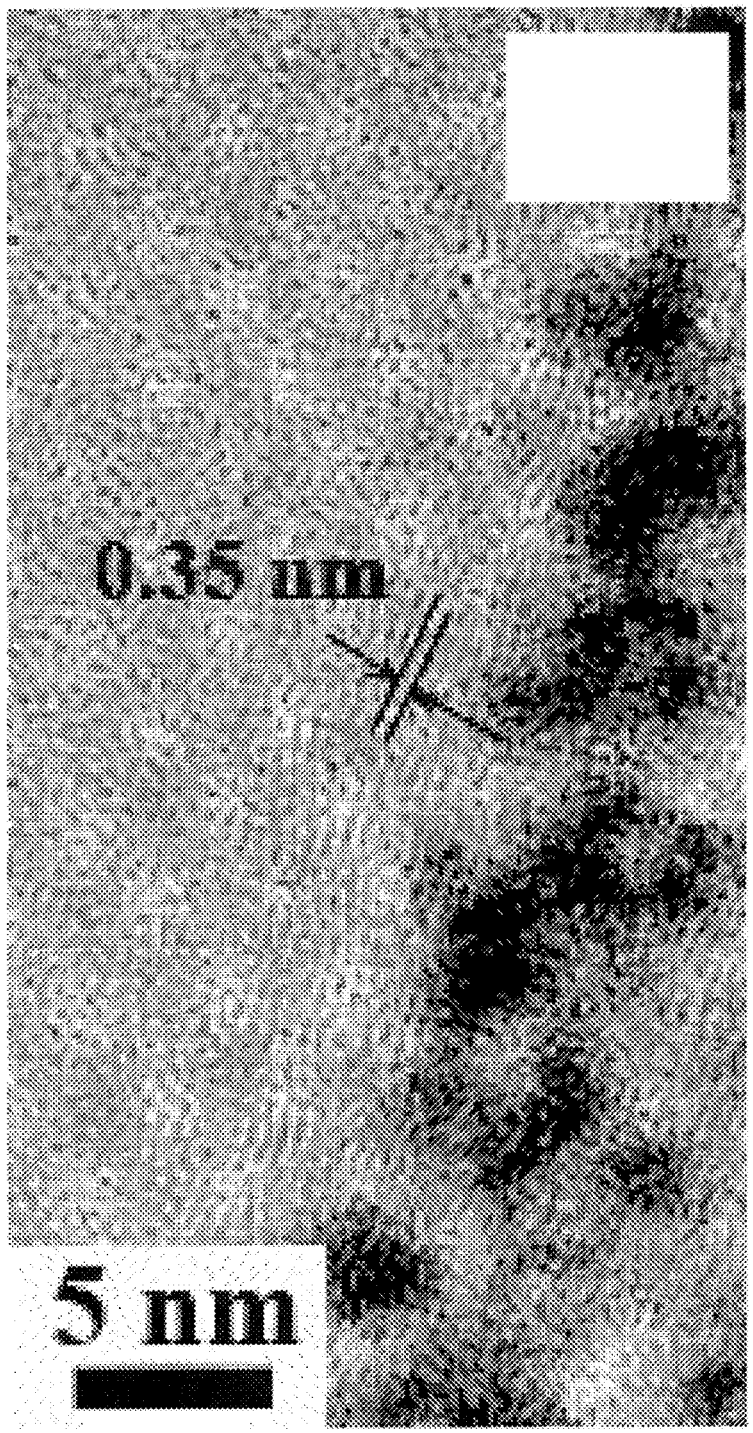
FIG. 6-3.2e

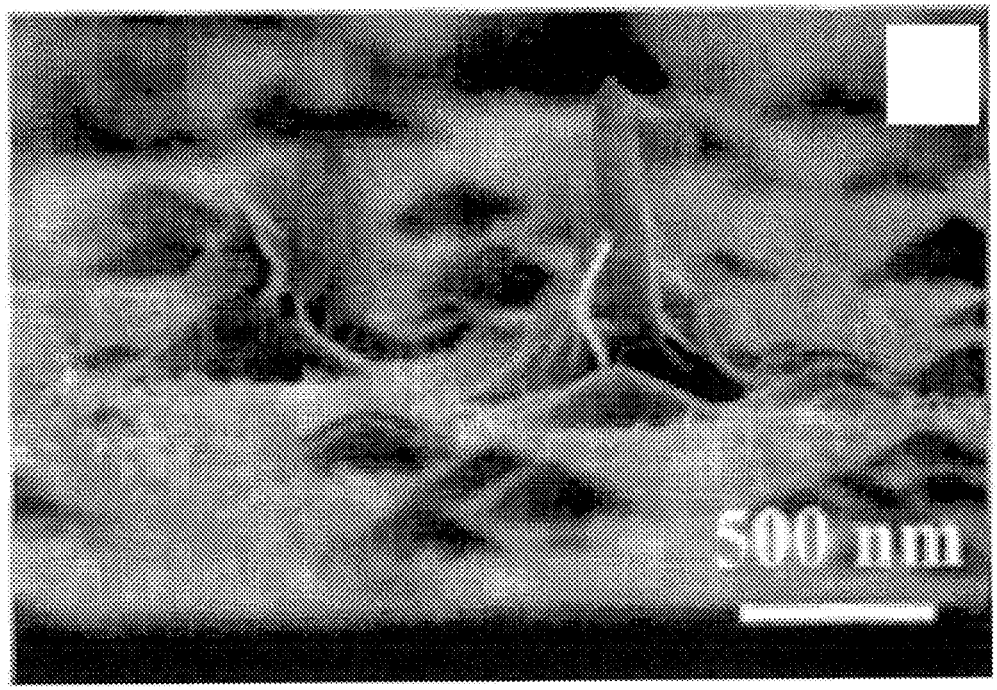
FIG. 6-3.3a
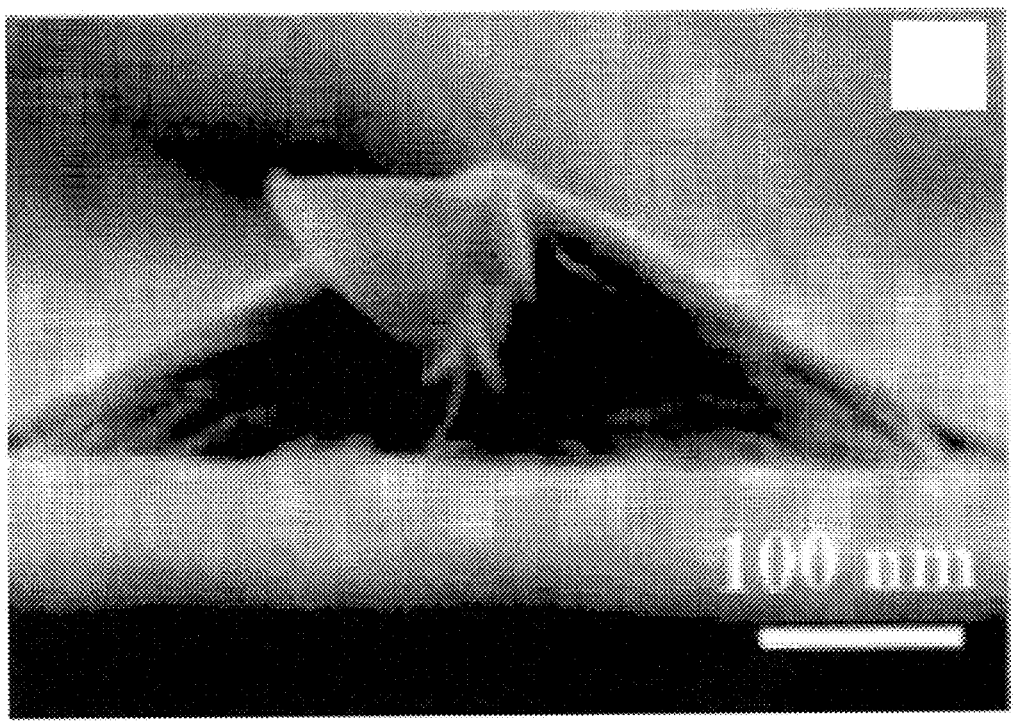
FIG. 6-3.3b

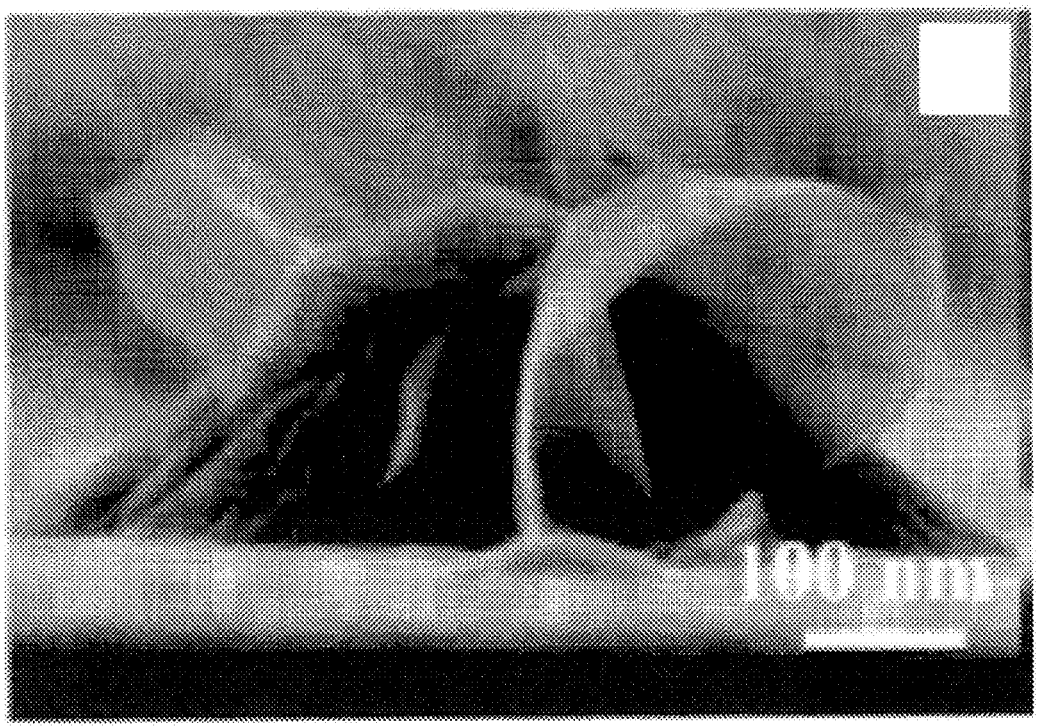
FIG. 6-3.3c
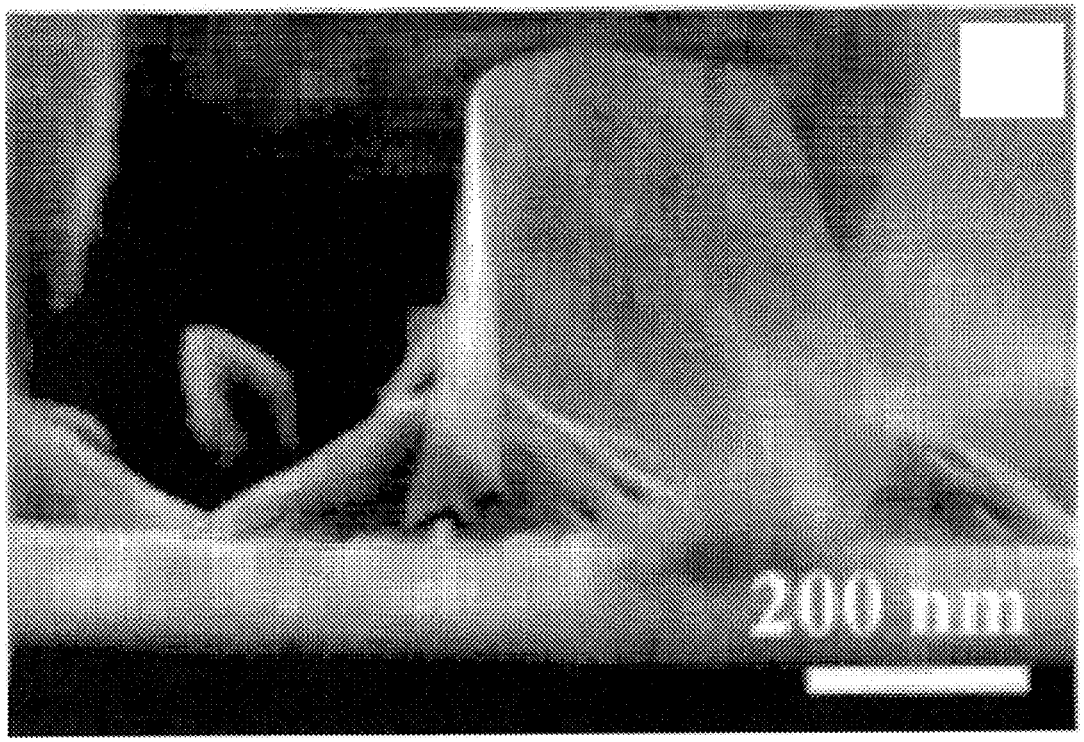
FIG. 6-3.3d

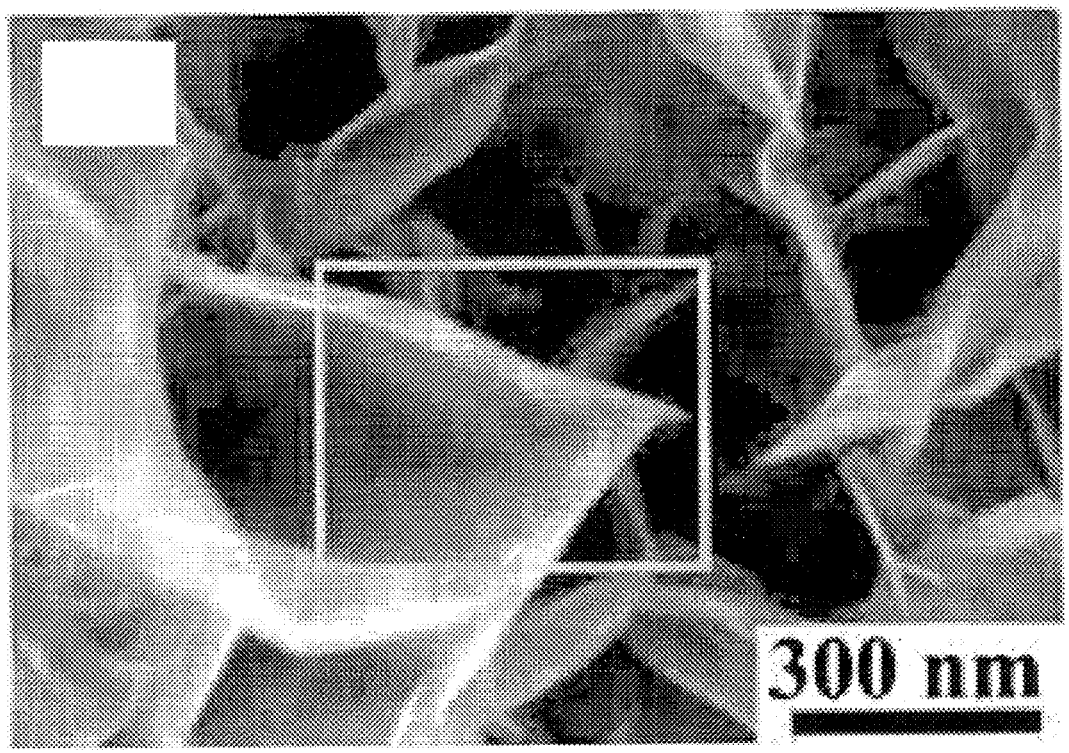
FIG. 6-3.6a
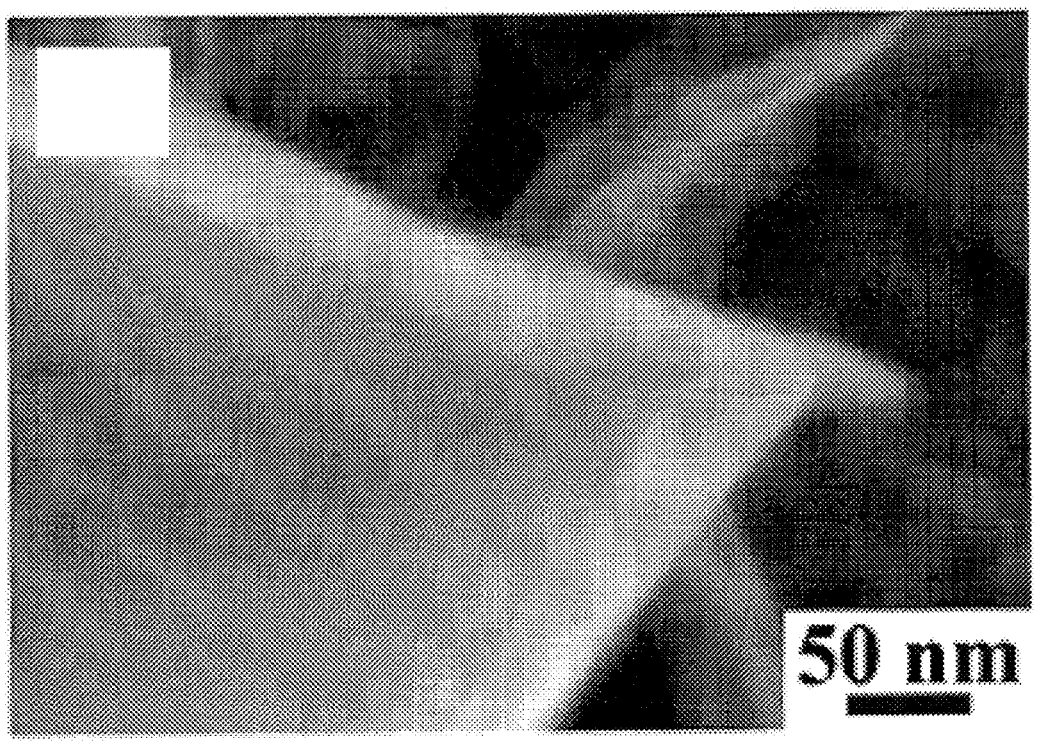
FIG. 6-3.6b

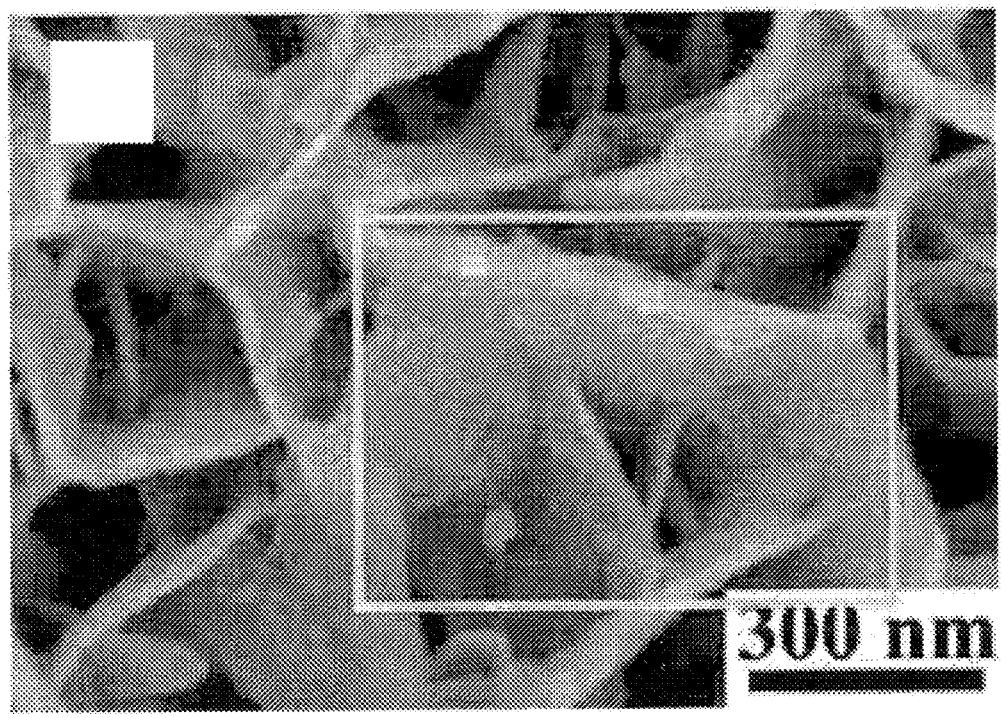
FIG. 6-3.6c
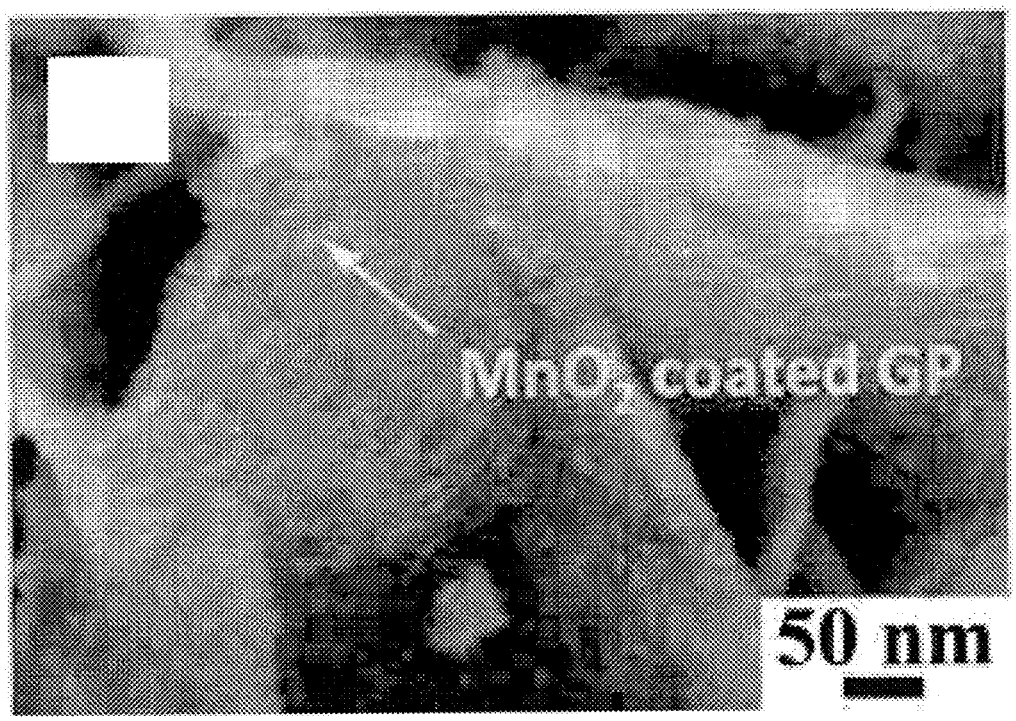
FIG. 6-3.6d

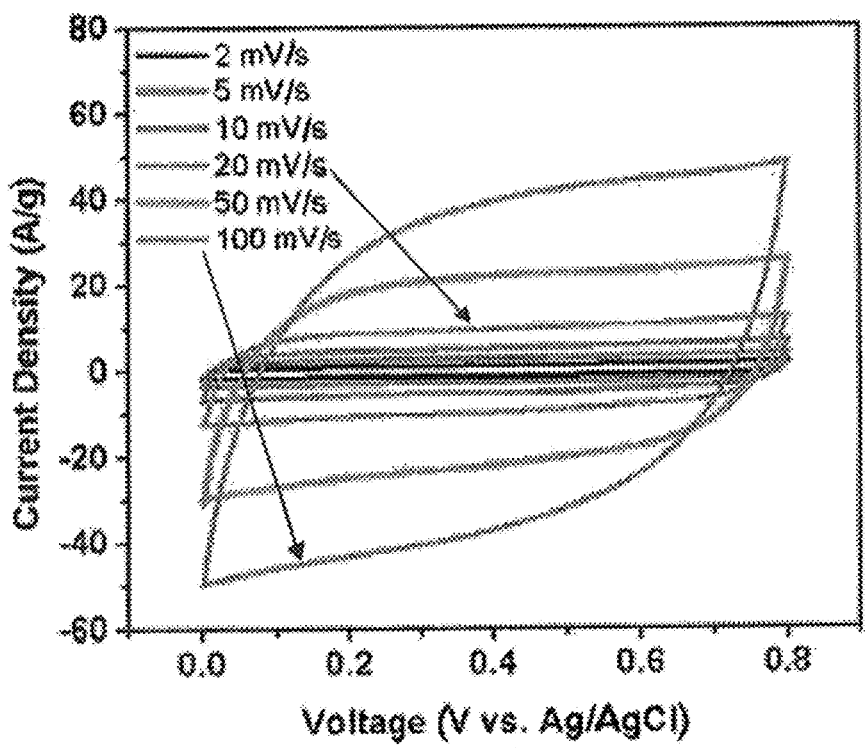
FIG. 6-3.7a
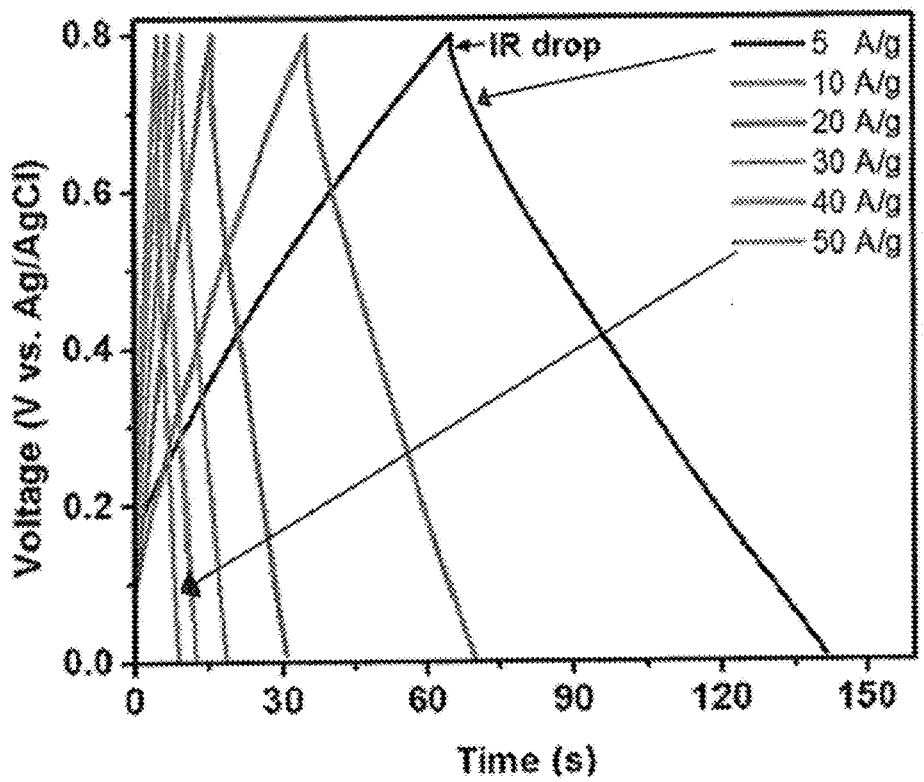
FIG. 6-3.7b

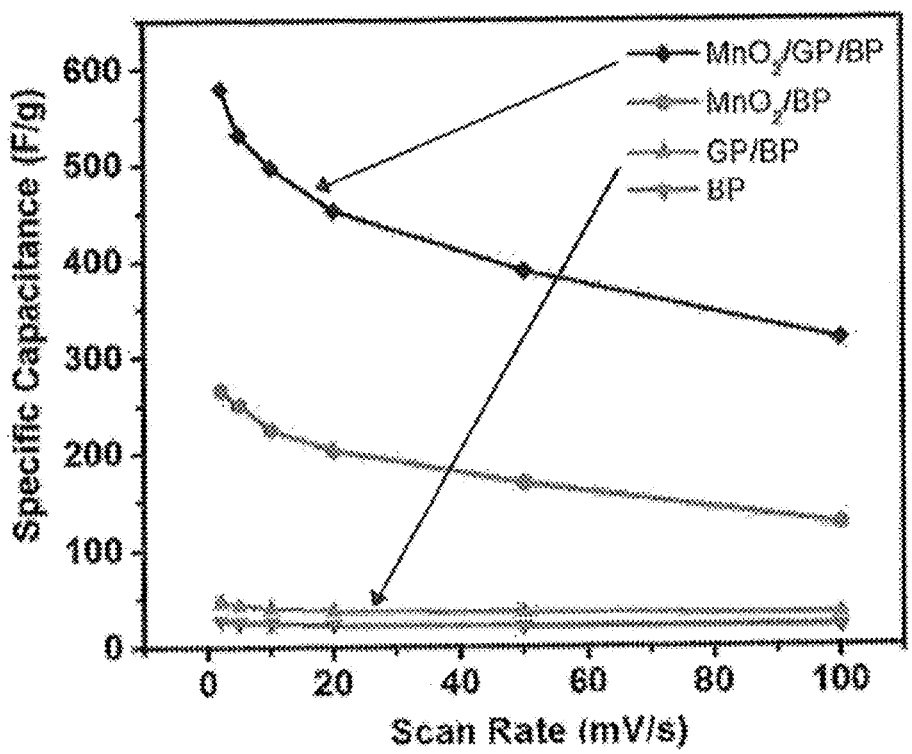
FIG. 6-3.7c
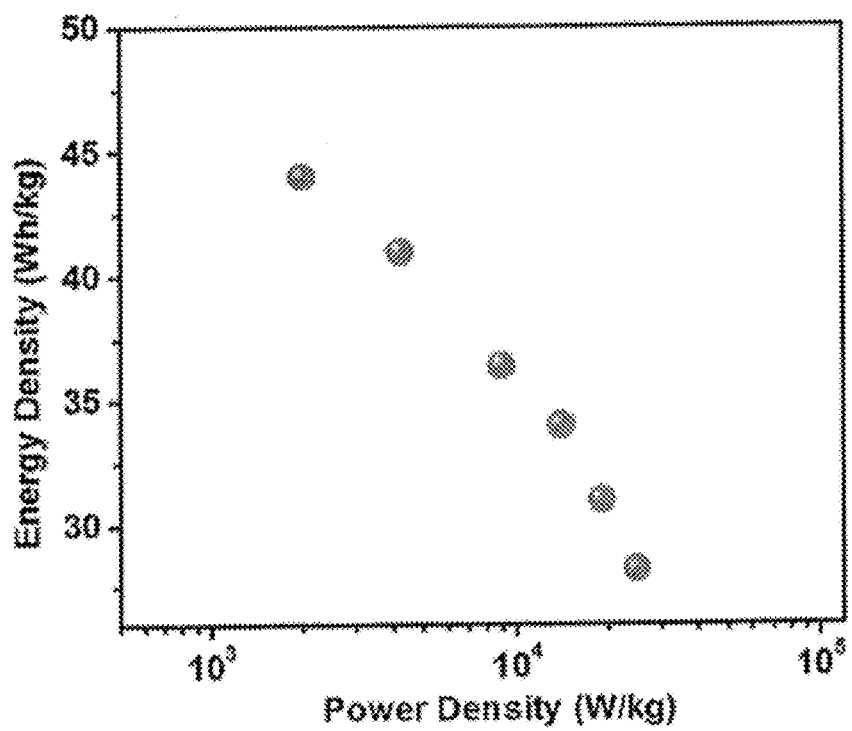
FIG. 6-3.7d

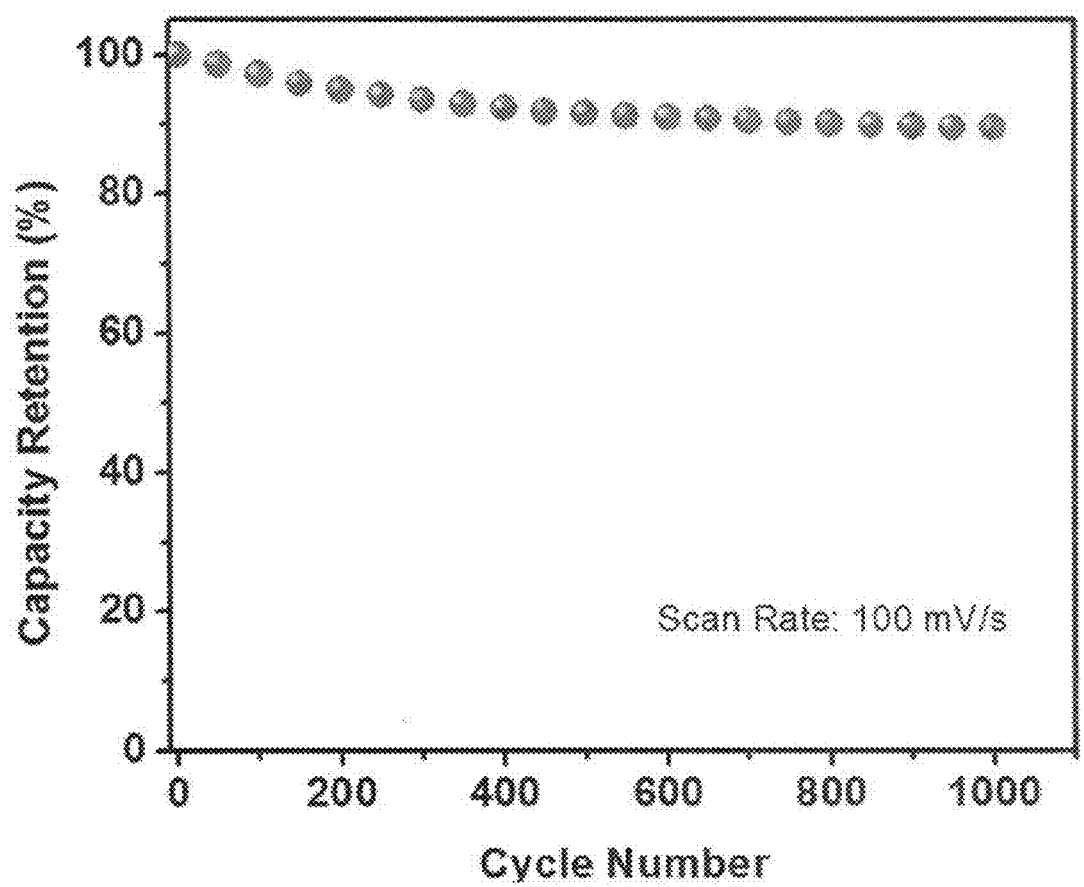
Fig. 6-3.7f

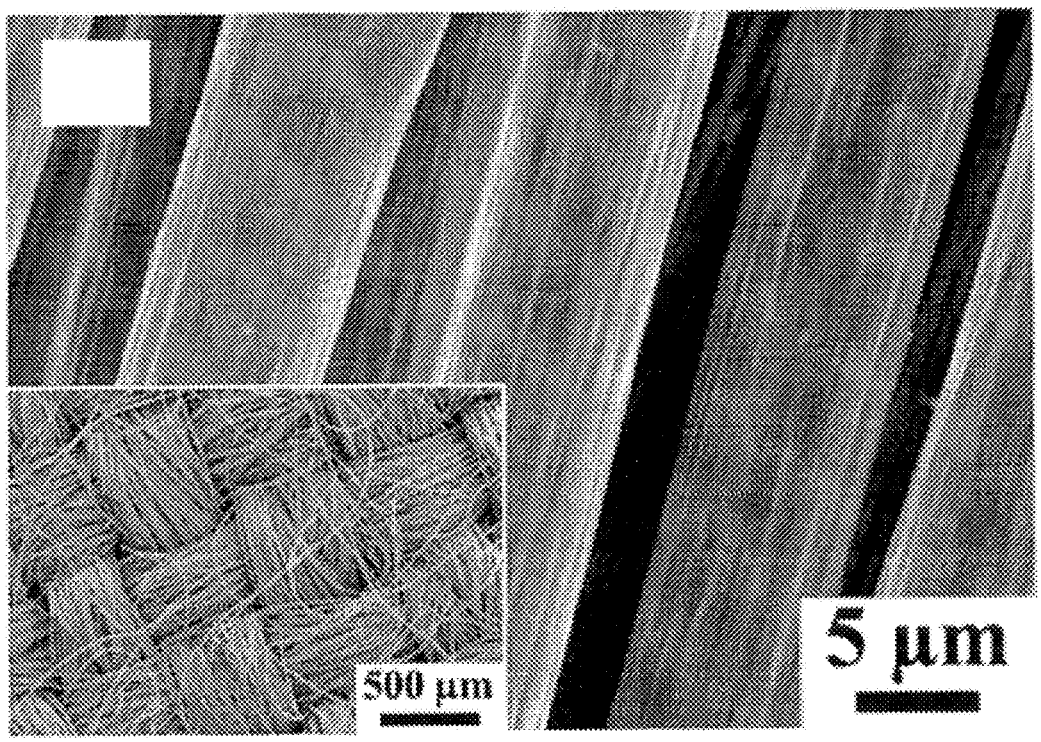
FIG. 6-3.9a
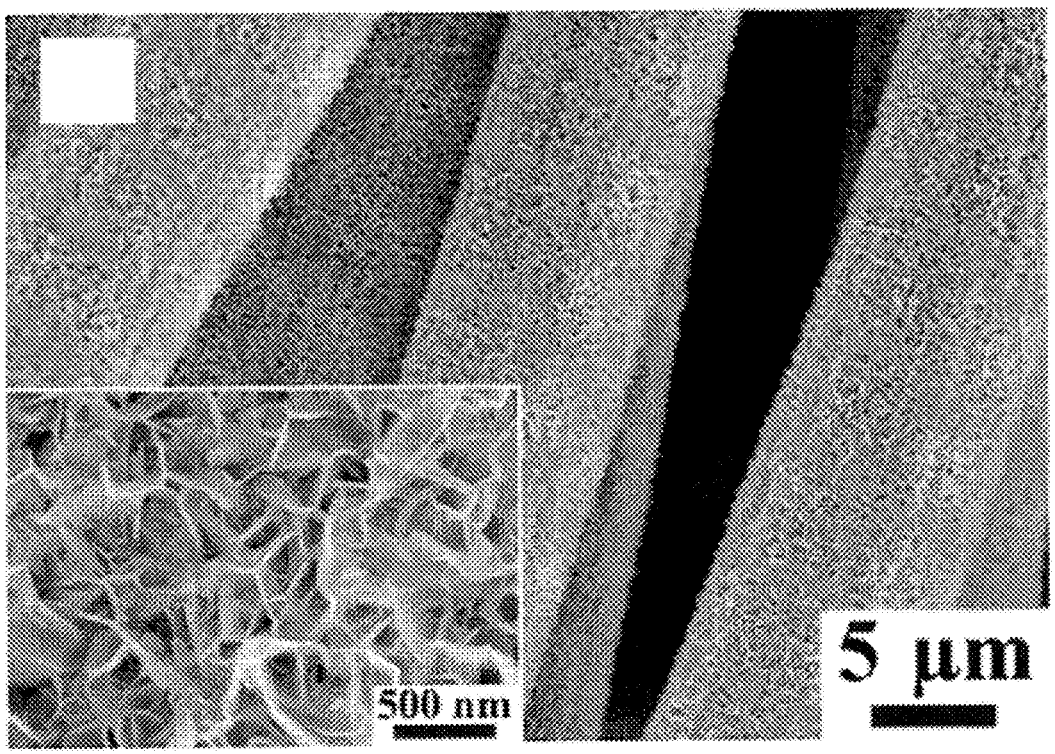
FIG. 6-3.9b

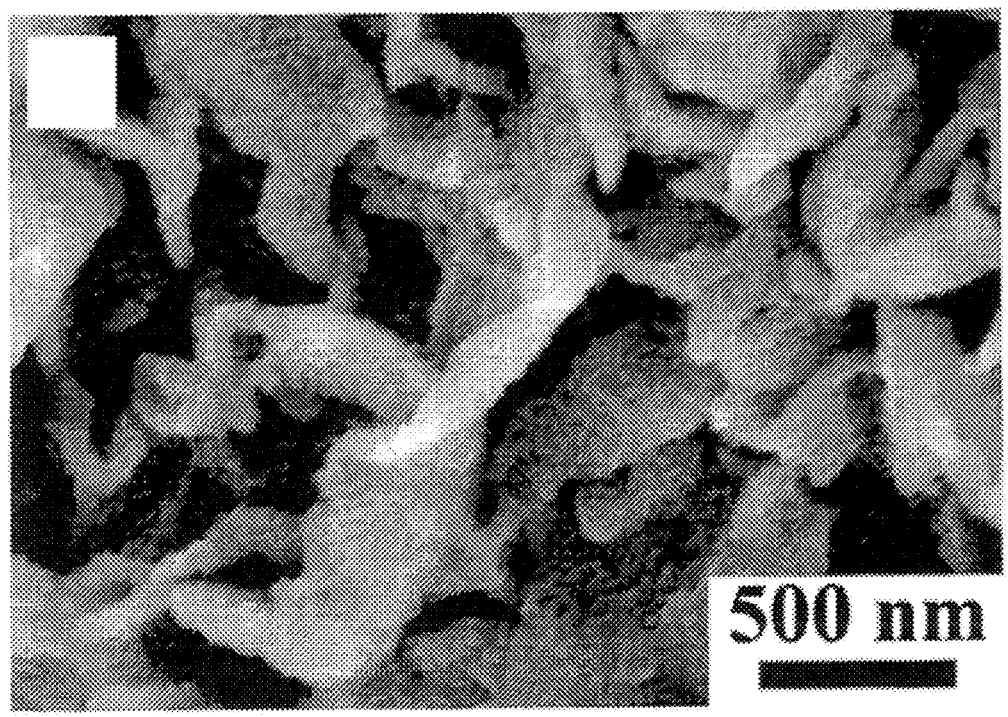
FIG. 6-3.9c
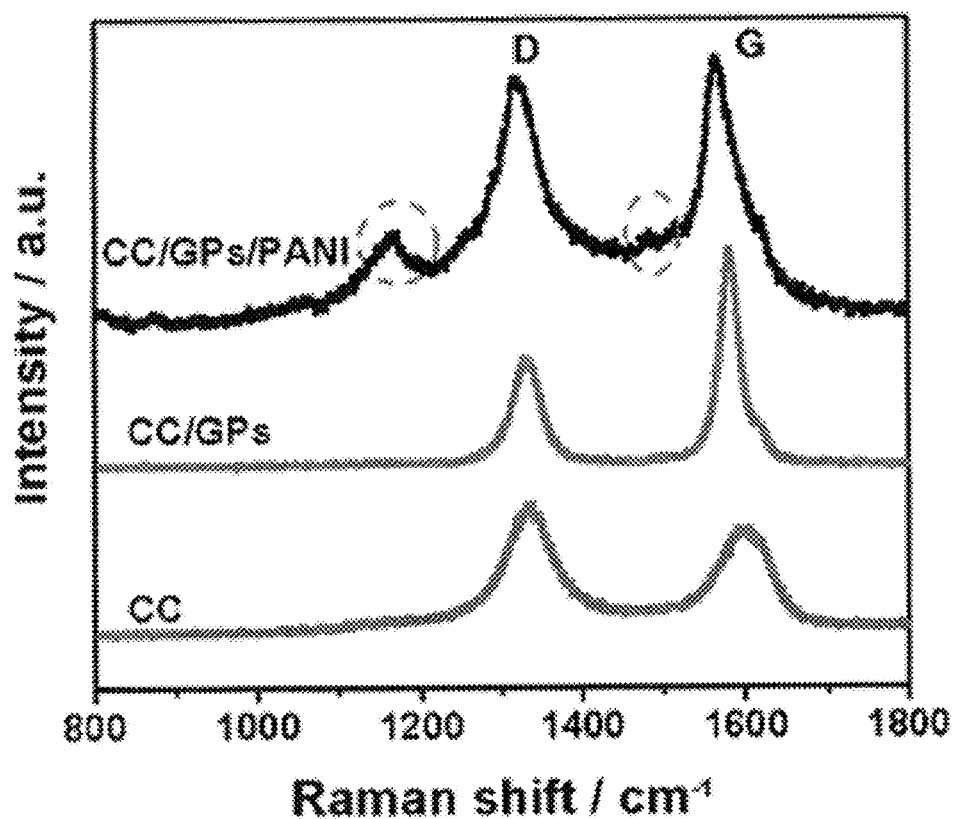
FIG. 6-3.9d

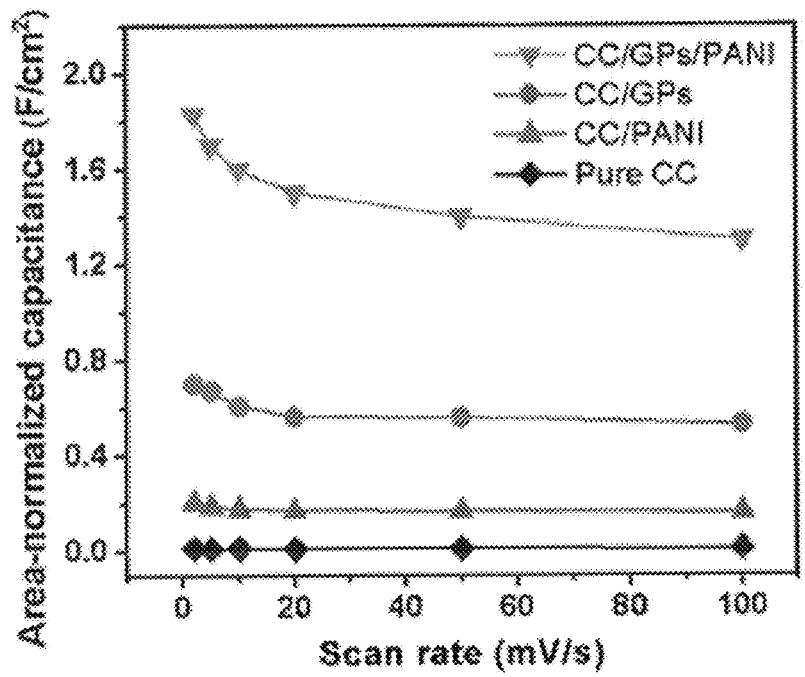
FIG. 6-3.10a
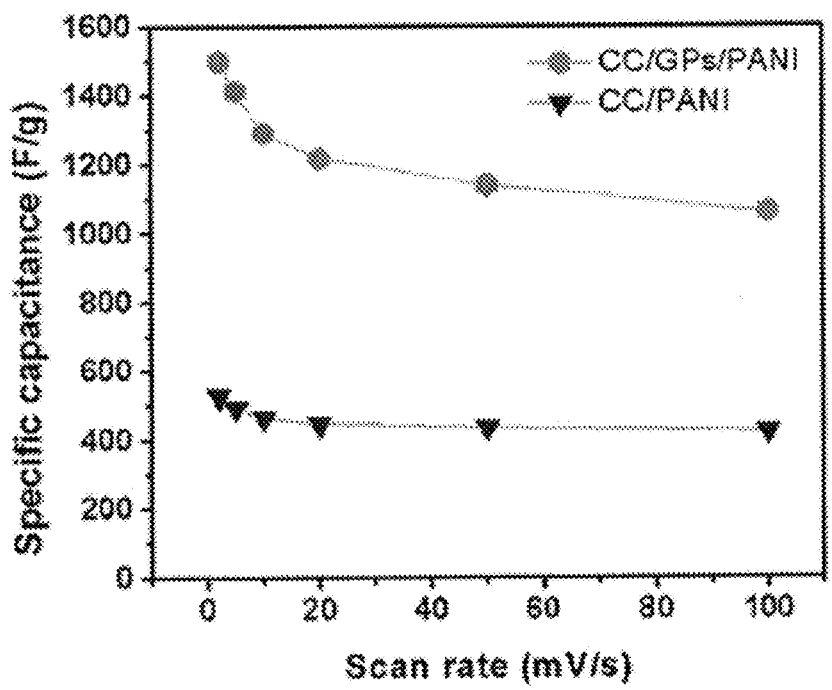
FIG. 6-3.10b

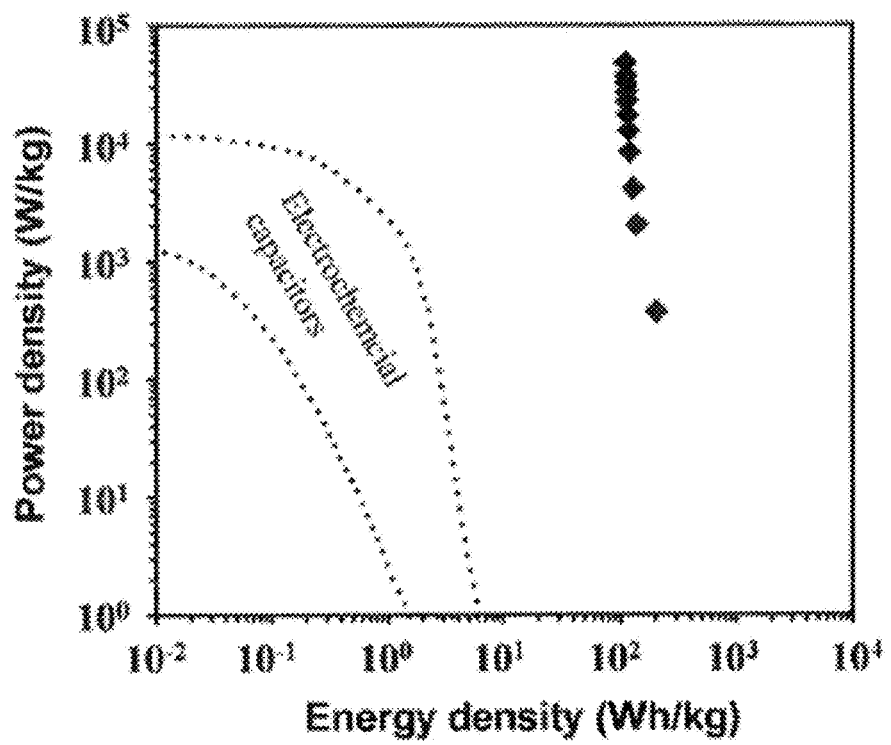
FIG. 6-3.10c
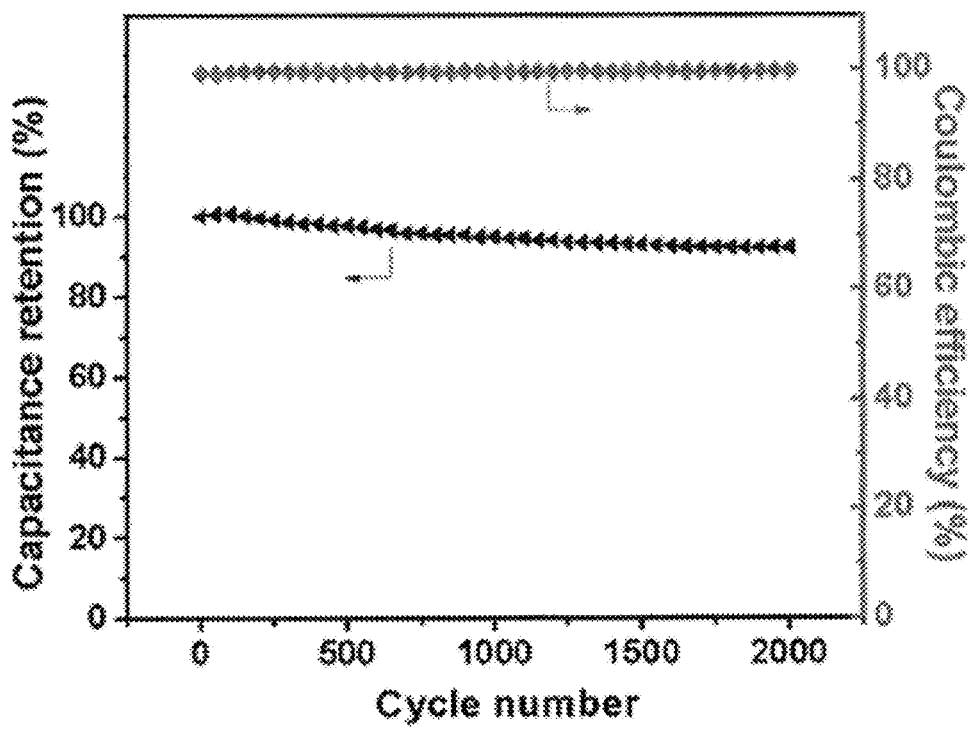
FIG. 6-3.10d

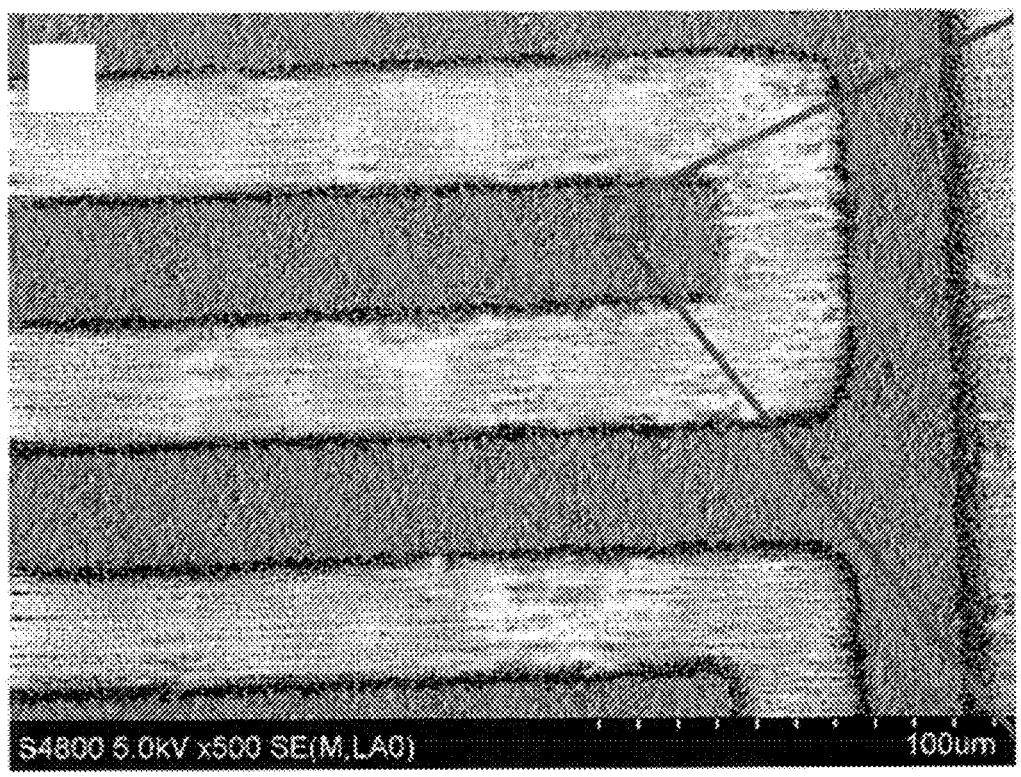
FIG. 6-4.1a
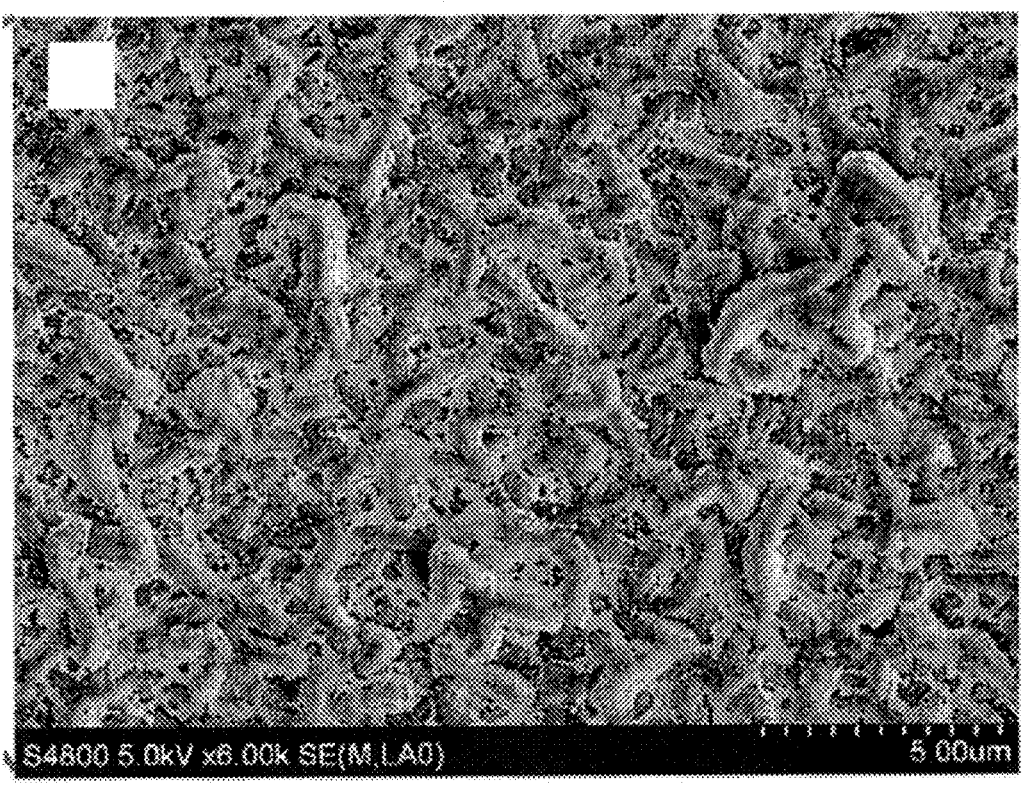
FIG. 6-4.1b

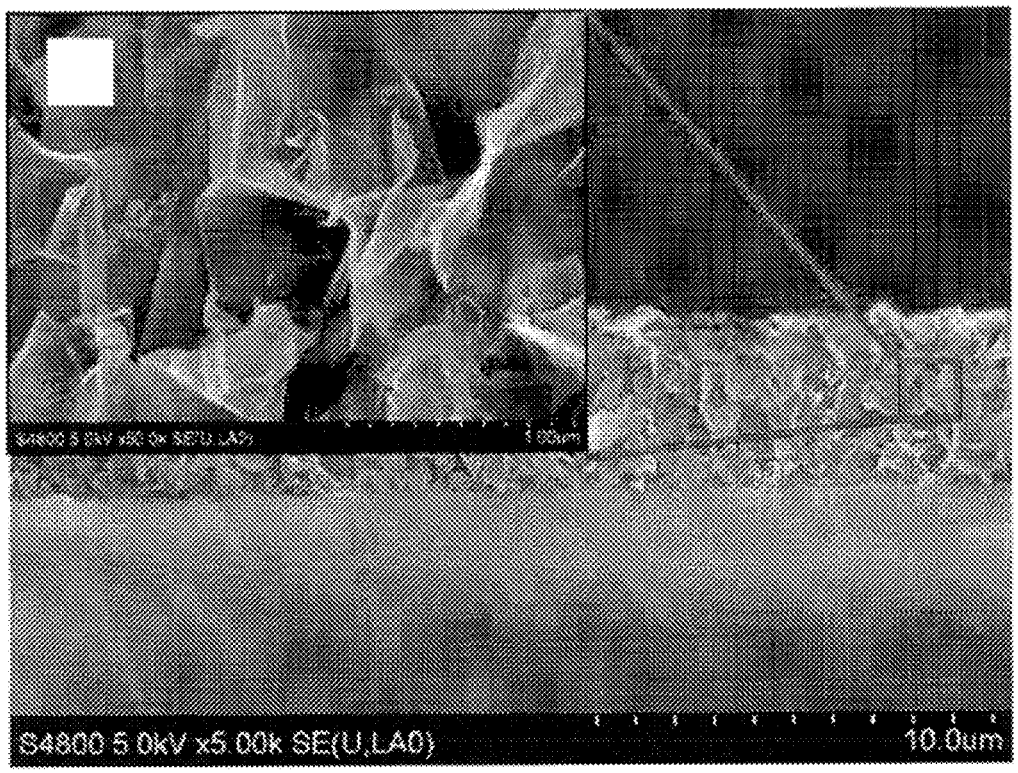
FIG. 6-4.1c
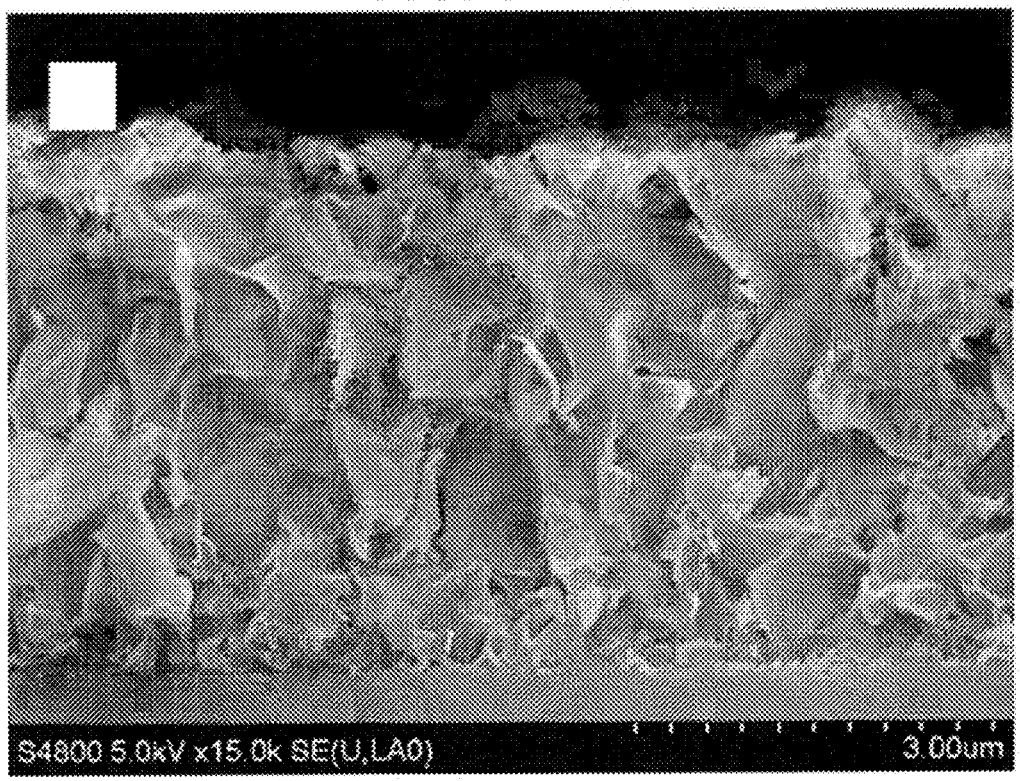
FIG. 6-4.1d

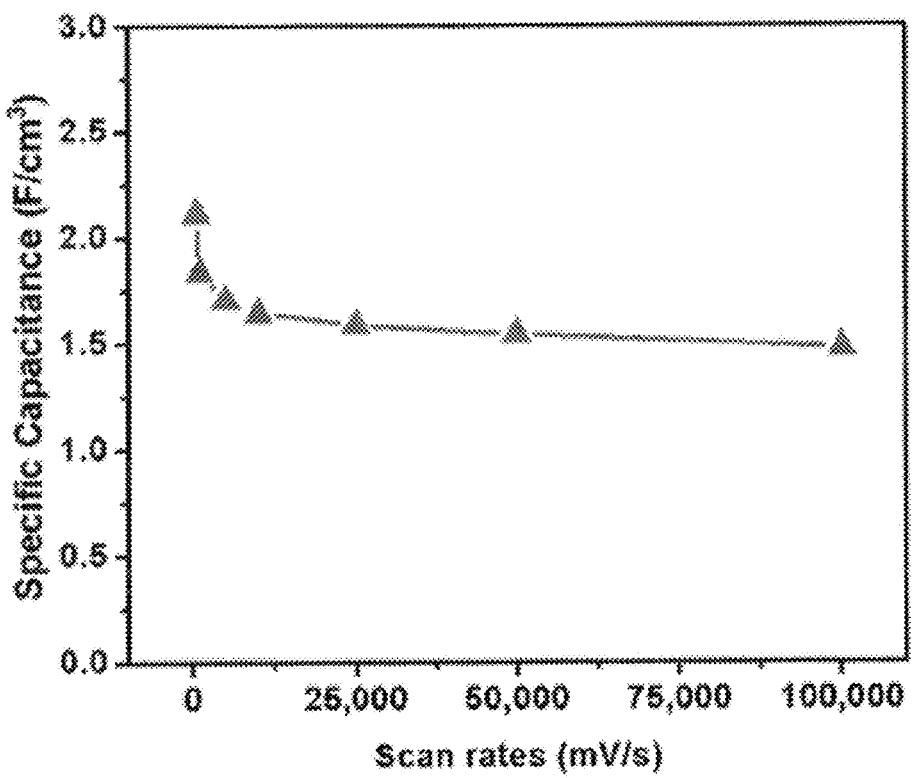
FIG. 6-4.3a
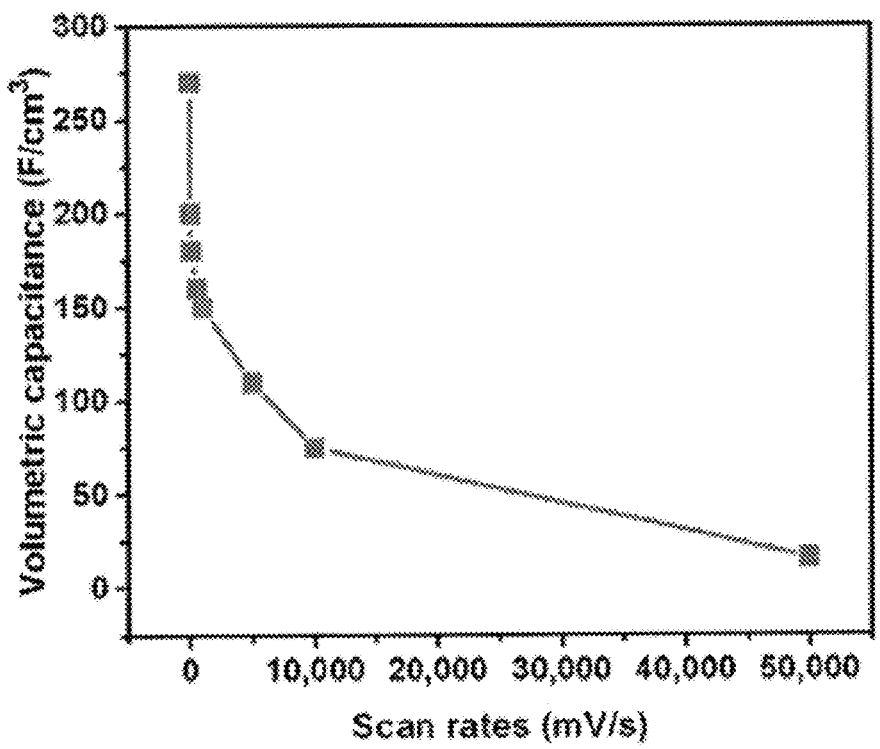
FIG. 6-4.3b

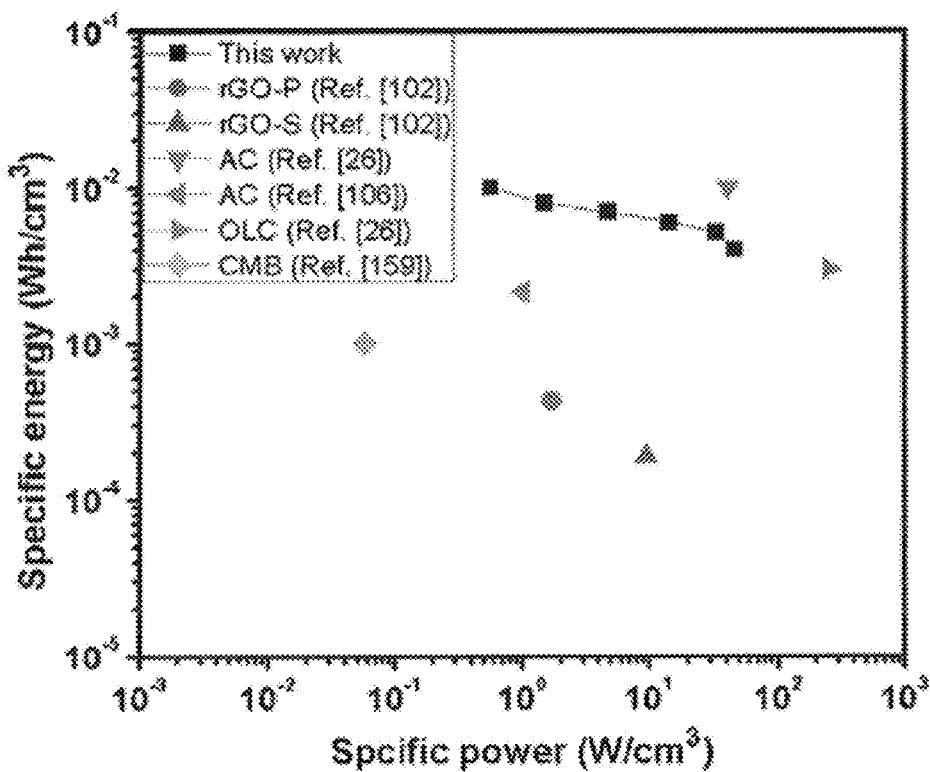
FIG. 6-4.3c
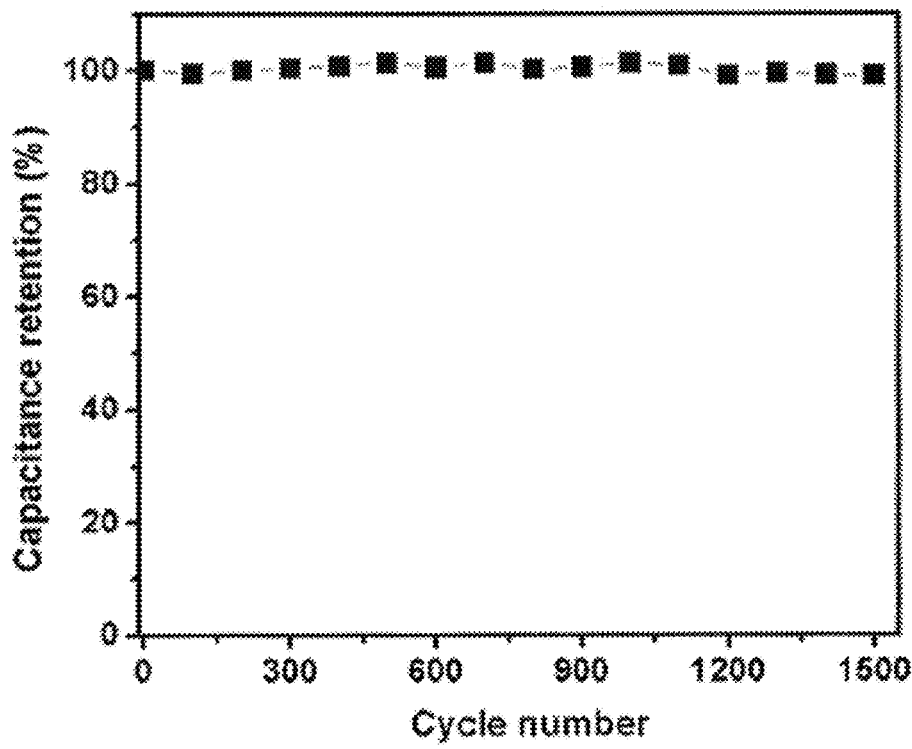
FIG. 6-4.3d

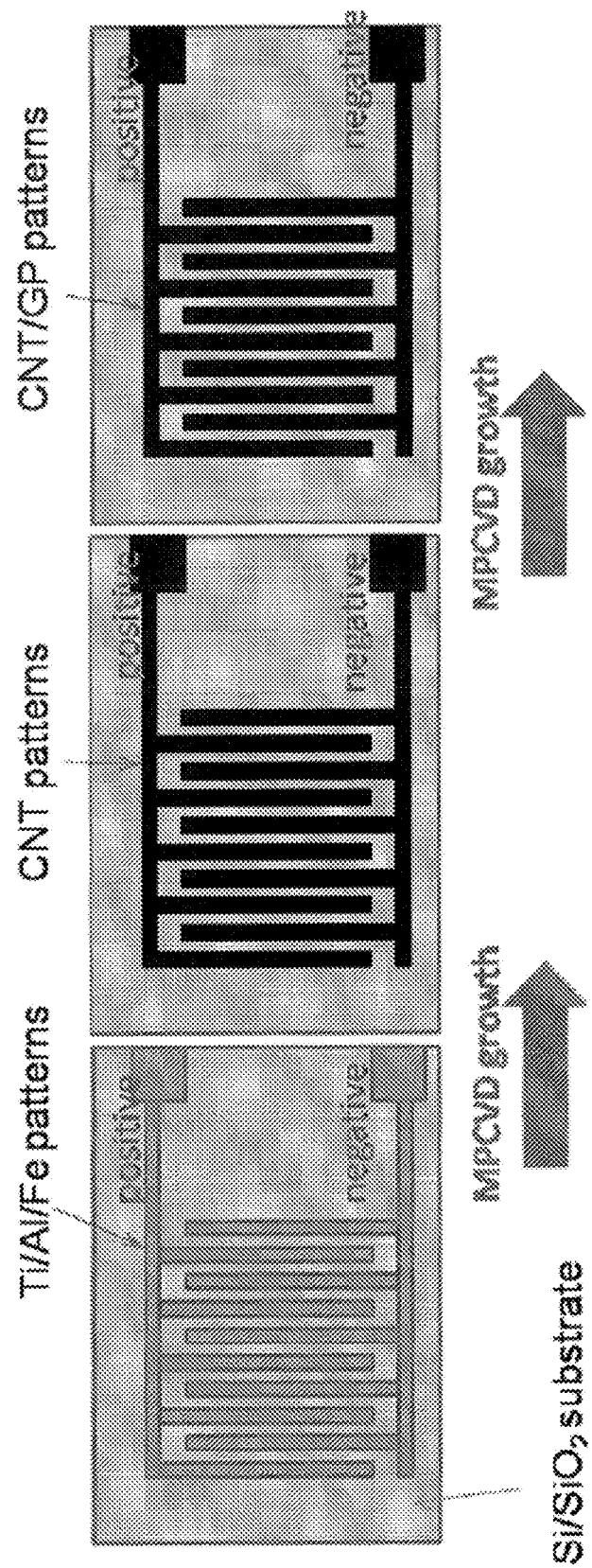
FIG. 6-4.4

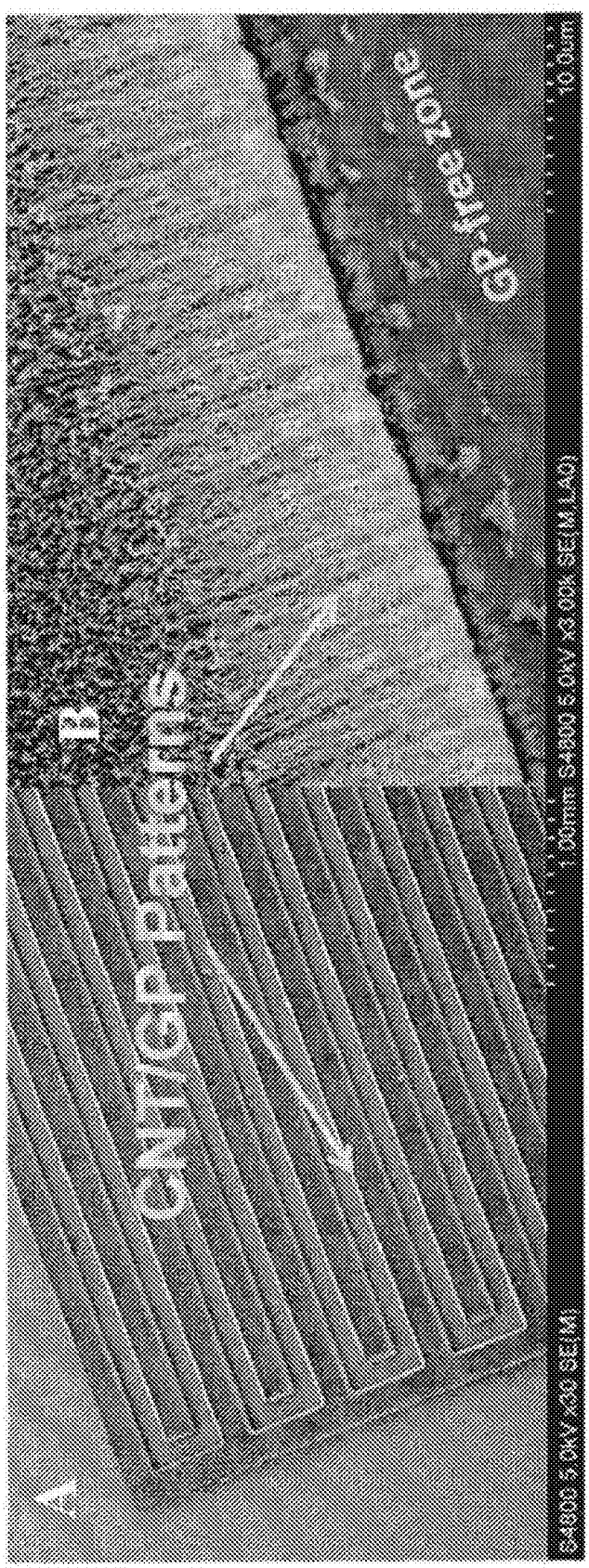
FIG. 6-4.5a,b

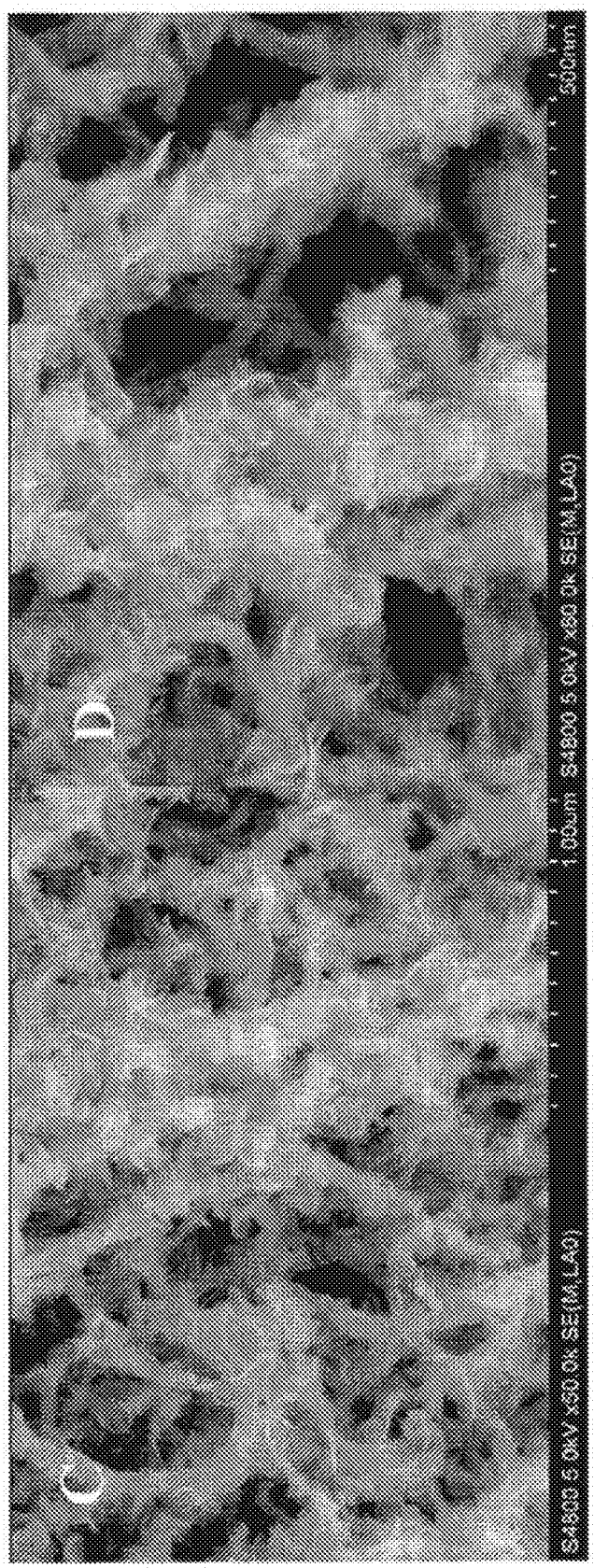
FIG. 6-4.5c, d

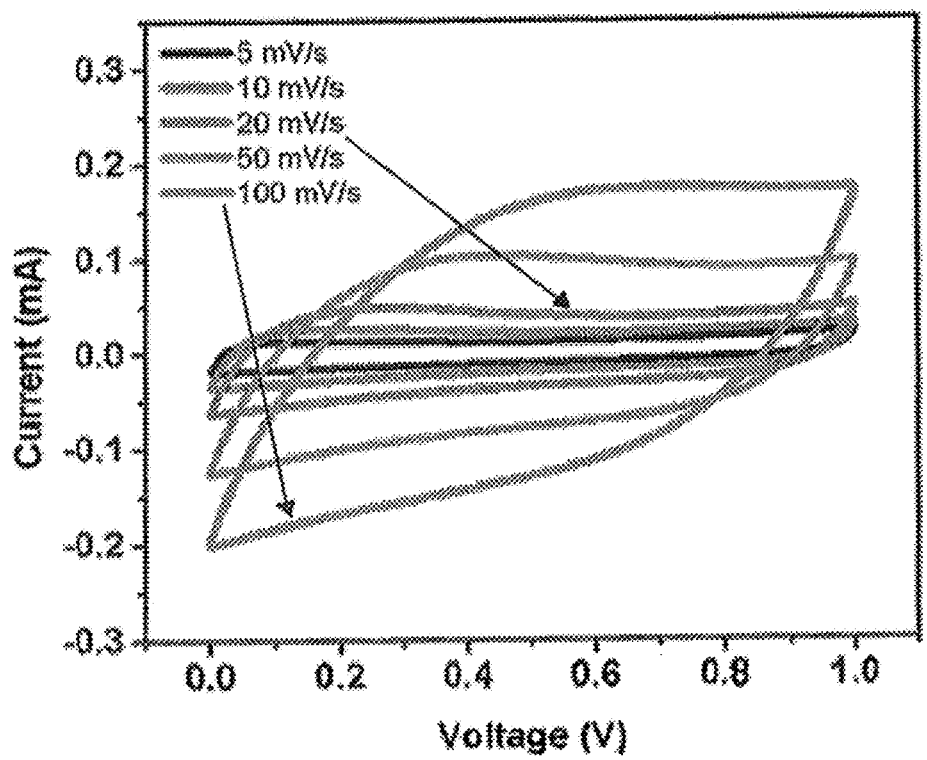
FIG. 6-4.6a
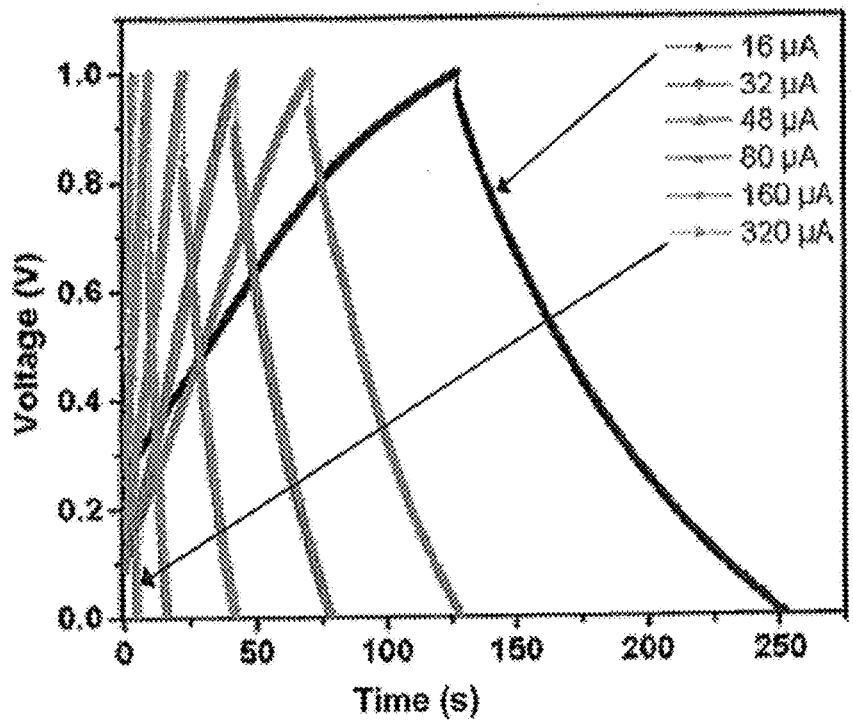
FIG. 6-4.6b

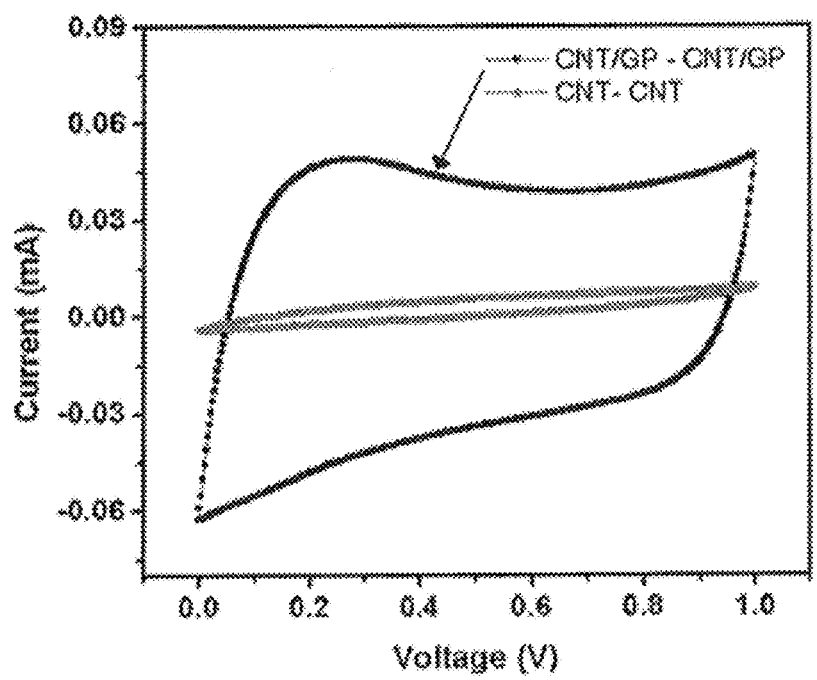
FIG. 6-4.6c
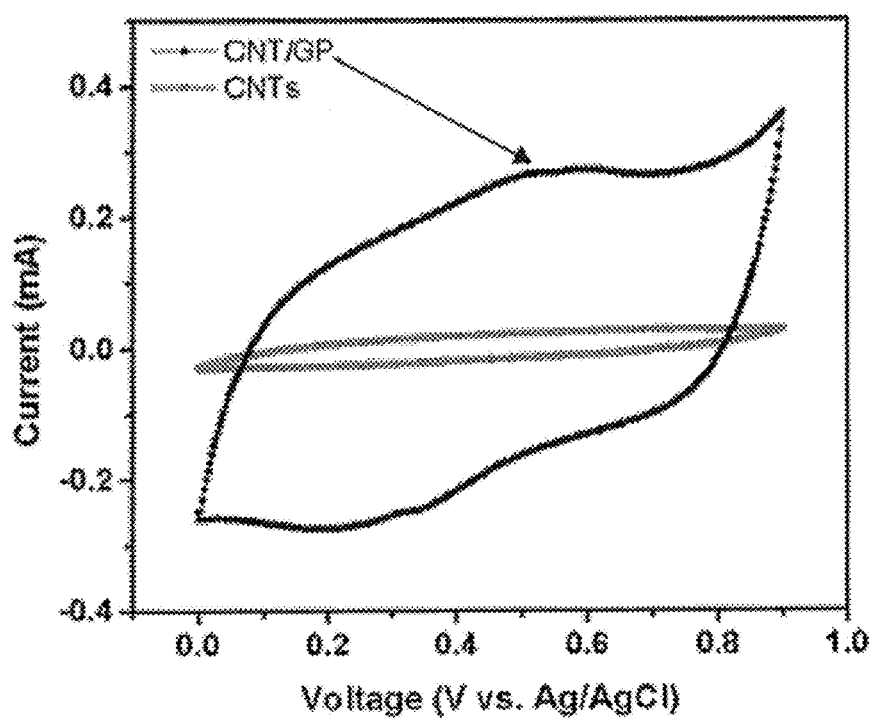
FIG. 6-4.6d

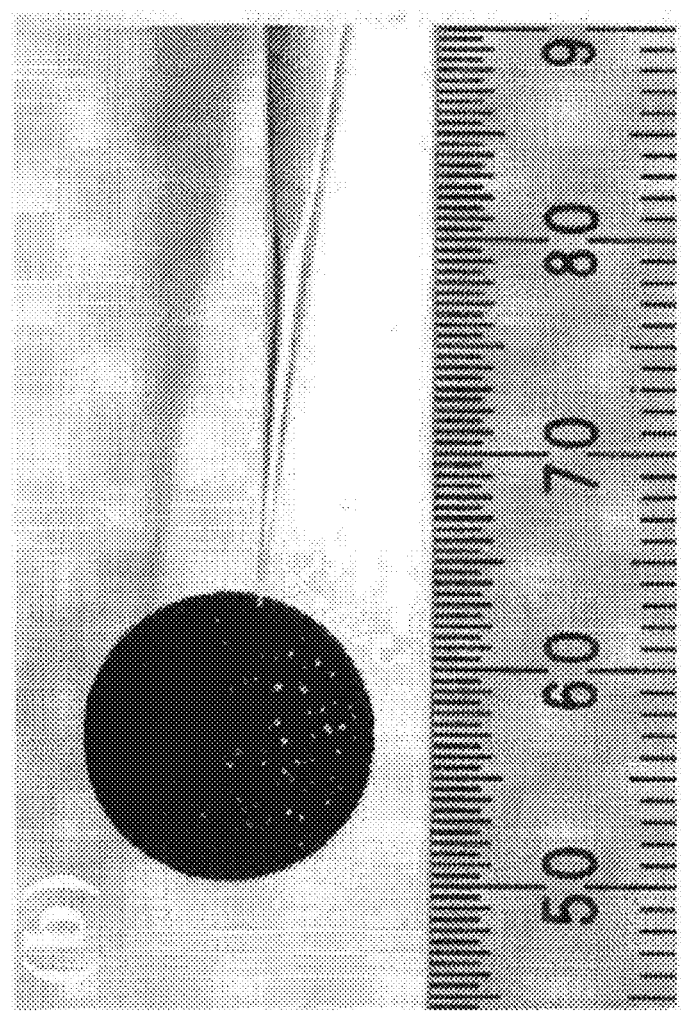
FIG. 6-4.7b
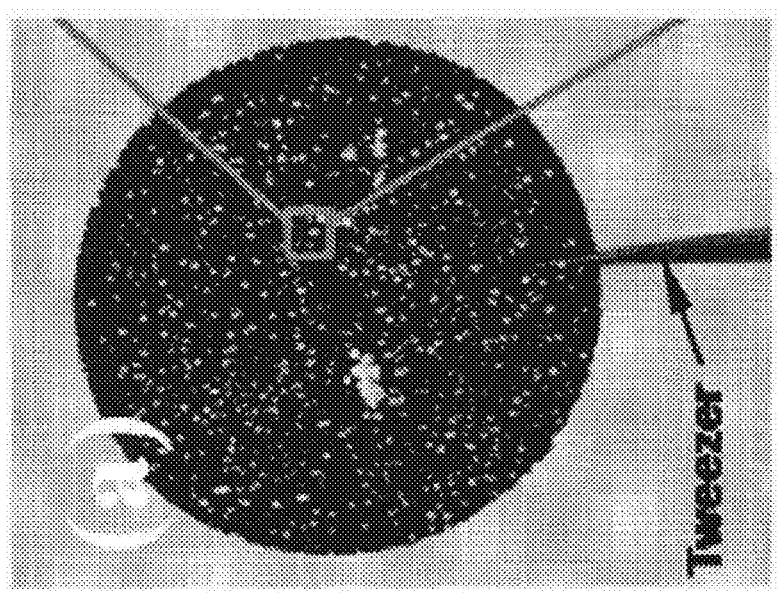
FIG. 6-4.7a

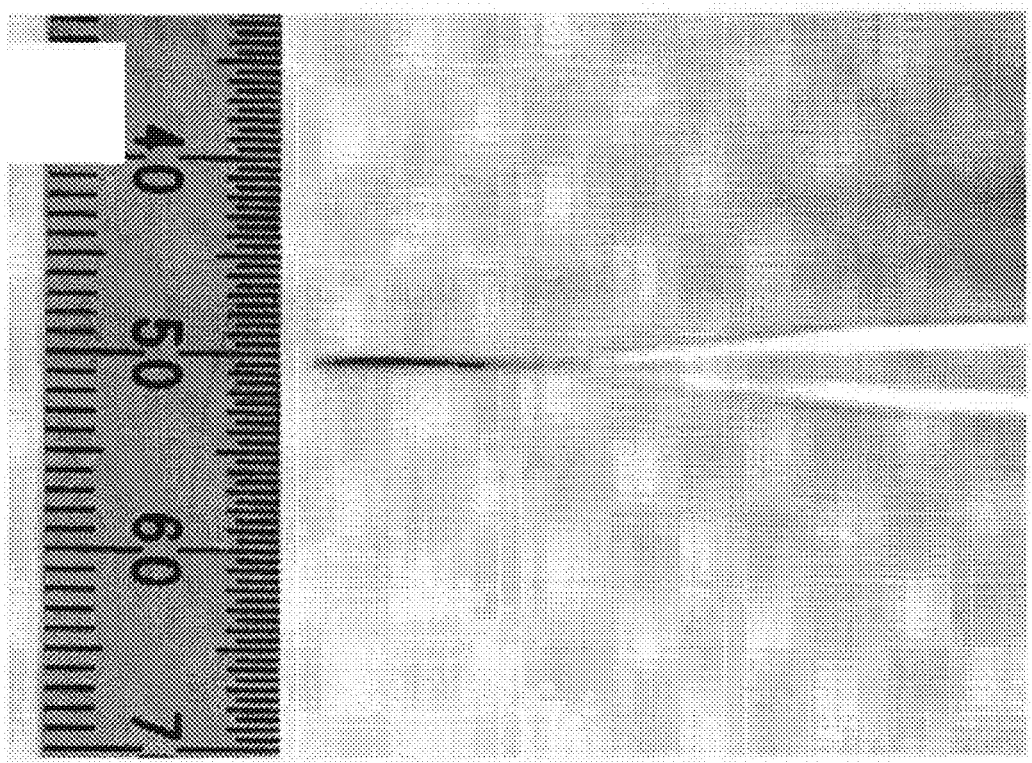
FIG. 6-4.7c
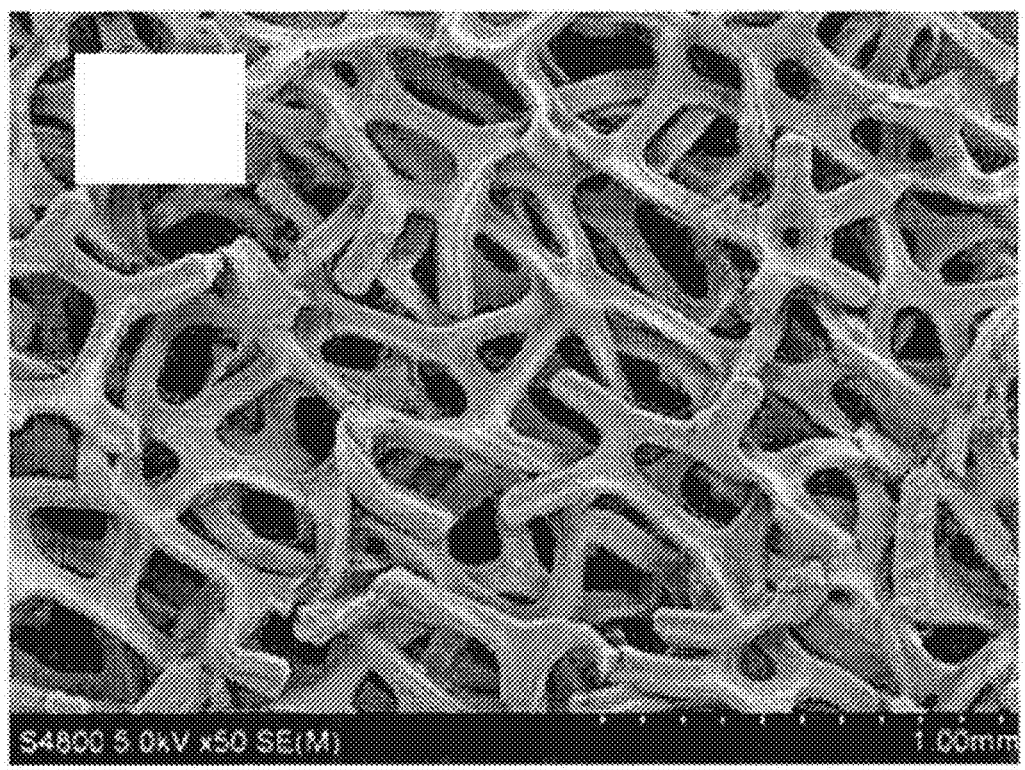
FIG. 6-4.7d

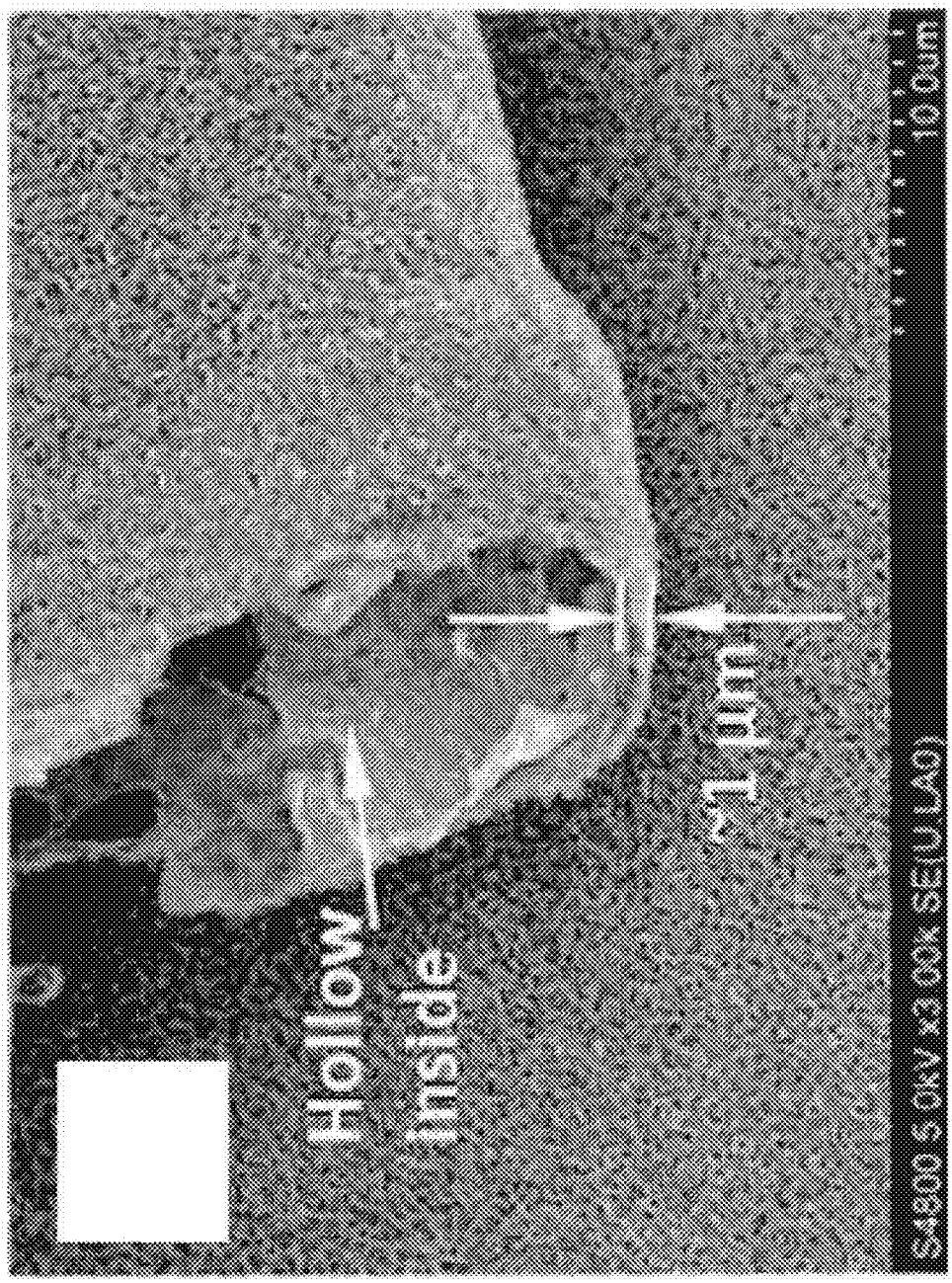
FIG. 6-4.7e

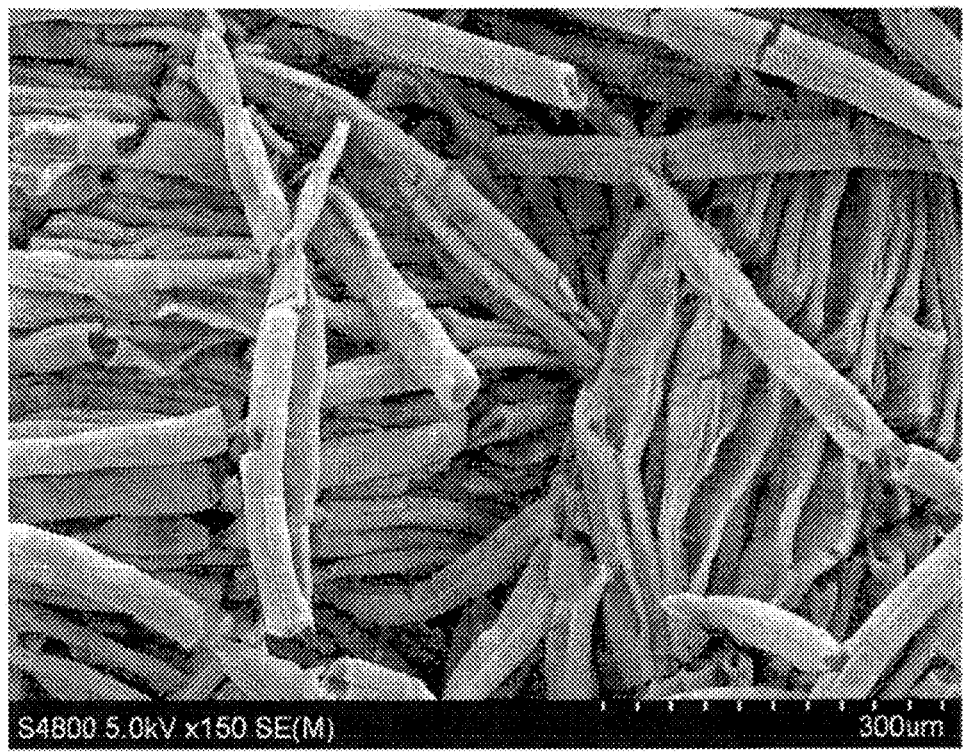
FIG. 6-4.8a
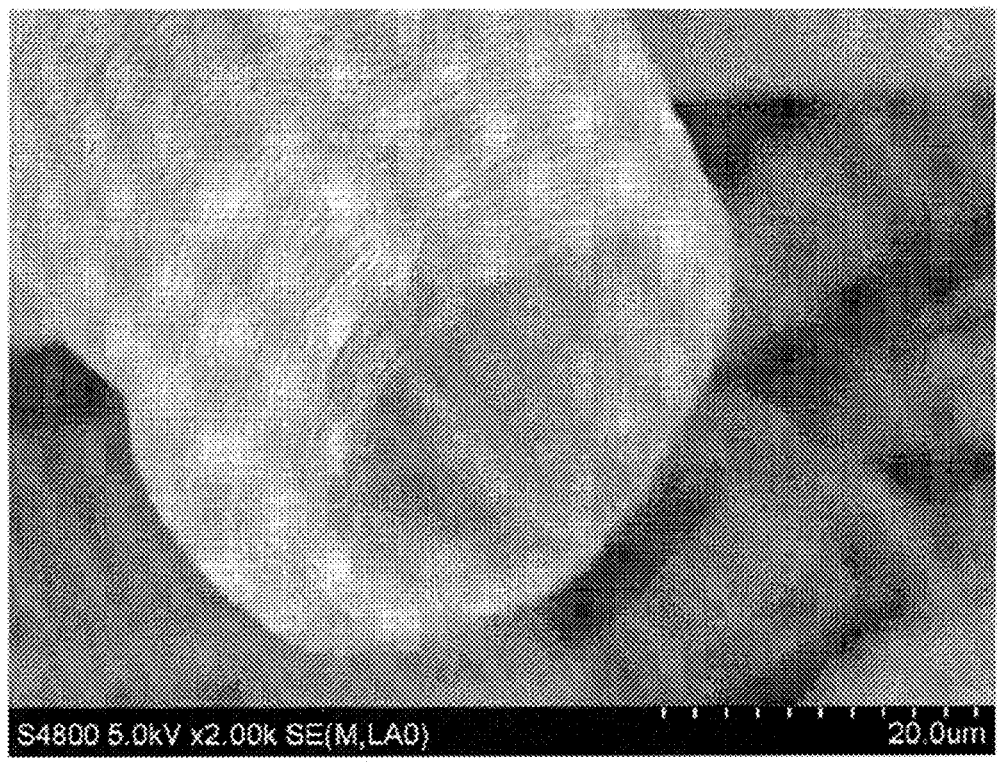
FIG. 6-4.8b

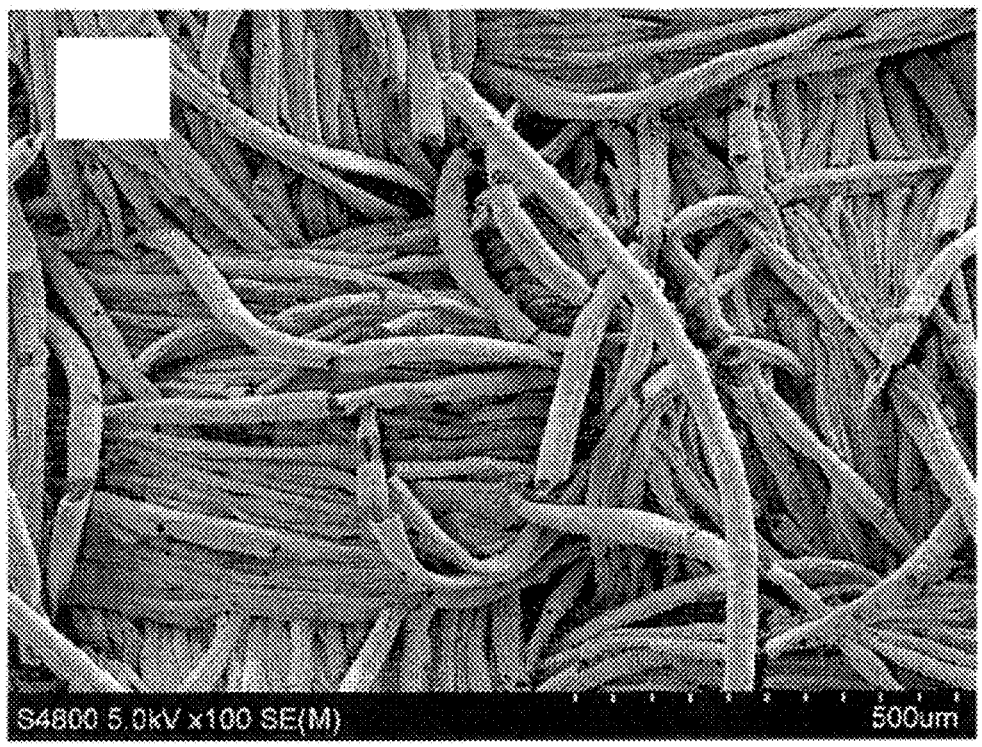
FIG. 6-4.9a
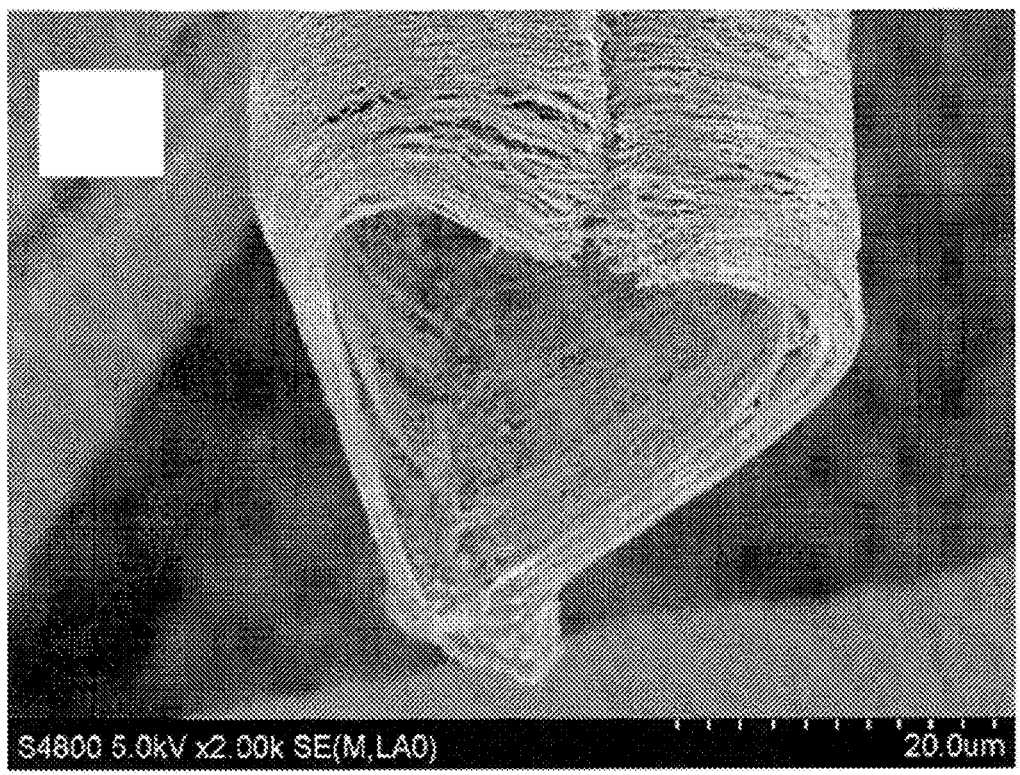
FIG. 6-4.9b

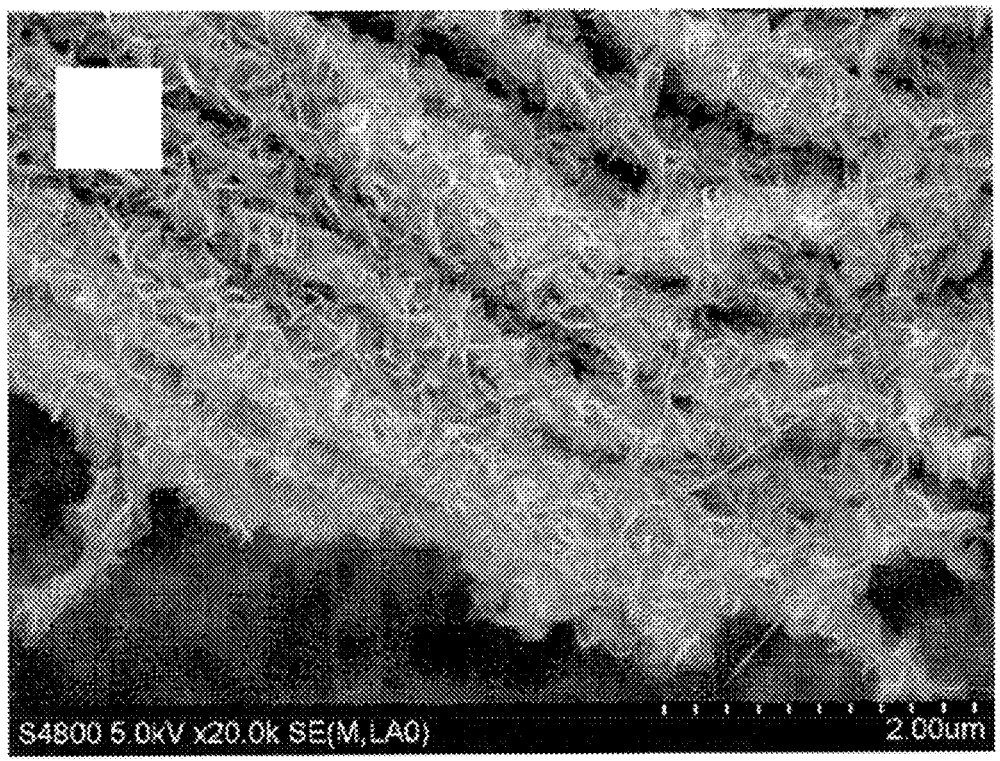
FIG. 6-4.9c
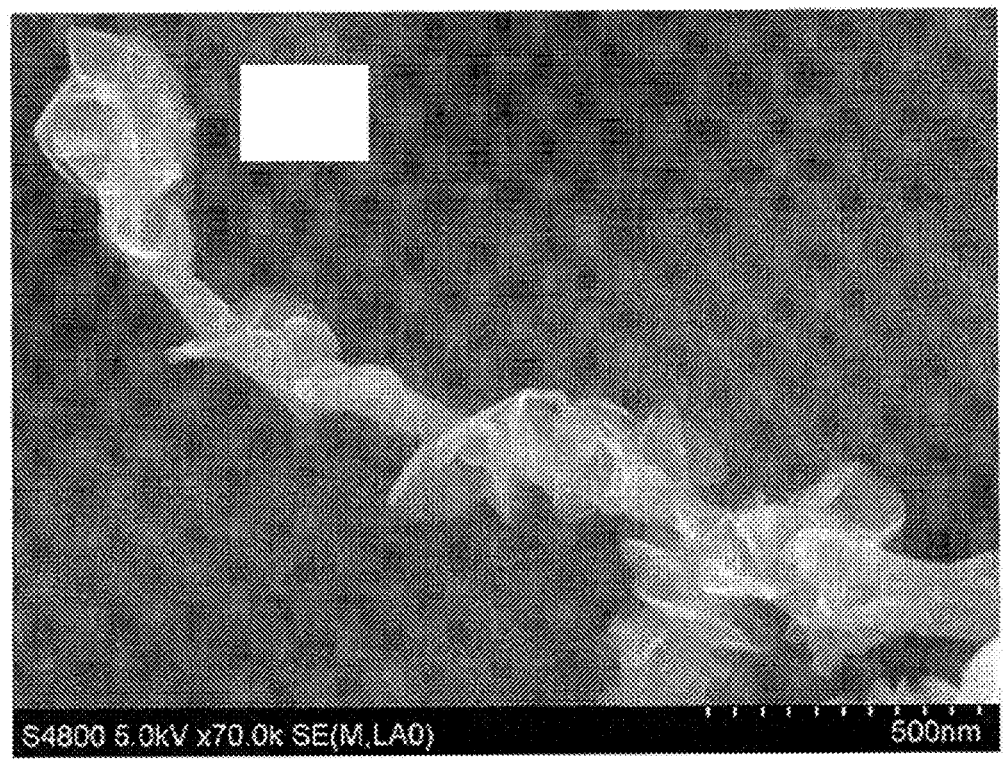
FIG. 6-4.9d

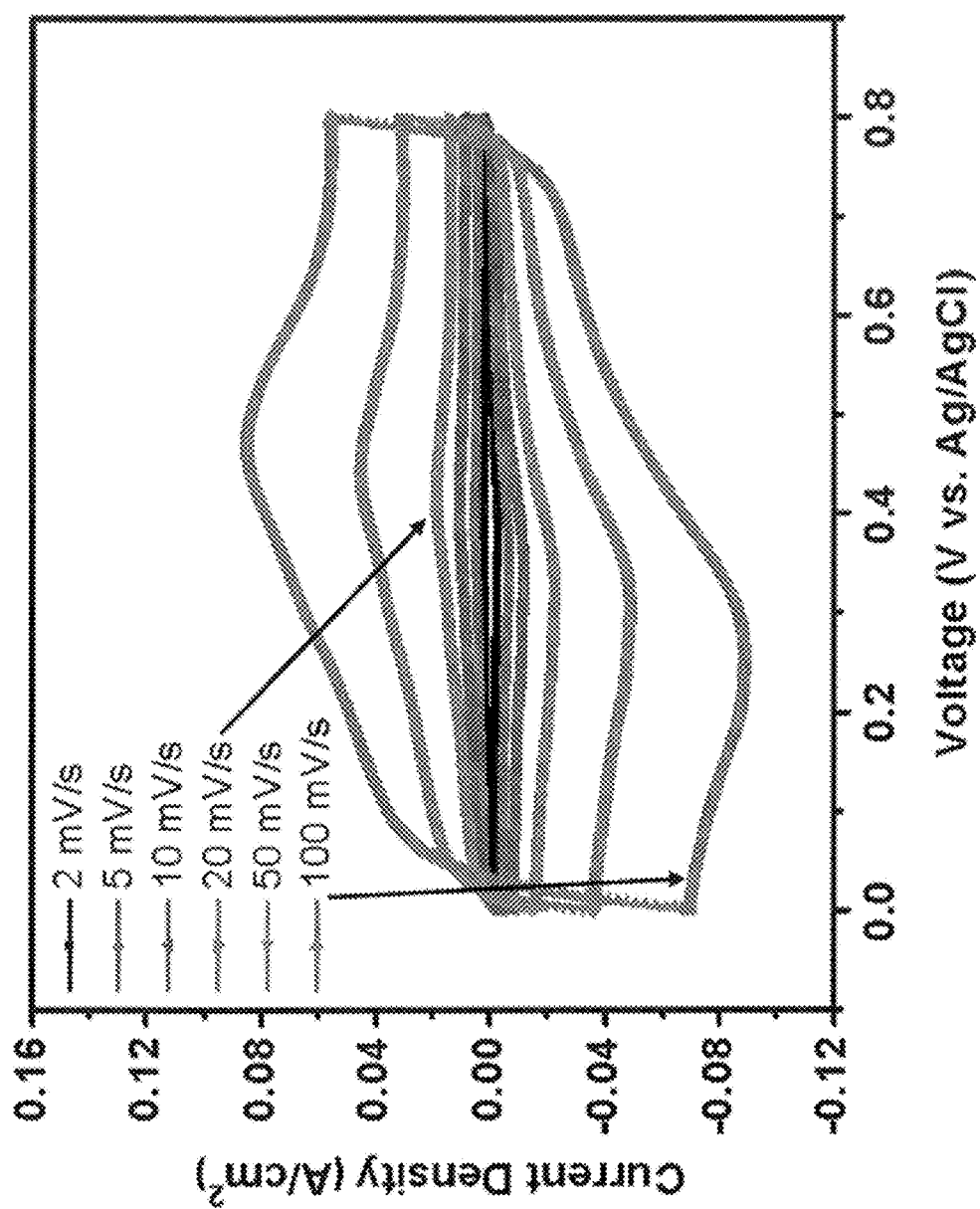
FIG. 6-4.10

MODIFIED GRAPHITIC ELECTRODES FOR ELECTROCHEMICAL ENERGY STORAGE ENHANCEMENT

CROSS REFERENCE TO RELATED APPLICATION

This application is a continuation of the parent PCT Application No. PCT/US13/32446 filed Mar. 15, 2013, which claims benefit of priority to U.S. Provisional Application No. 61/644,717 filed May 9, 2012, and U.S. Provisional Application No. 61/723,757 filed Nov. 7, 2012, and is also a continuation-in-part of the parent PCT Application No. PCT/US12/51008 filed Aug. 15, 2012, which further claims benefit of priority to U.S. Provisional Application No. 61/523,646 filed Aug. 15, 2011, the disclosures of which are incorporated herein by reference.

STATEMENT REGARDING FEDERALLY SPONSORED RESEARCH

This invention was made with government support under grant number FA9550-12-1-0037 awarded by the Air Force Office of Scientific Research. The government has certain rights in the invention.

BACKGROUND OF THE INVENTION

Nanostructures have recently been utilized in a variety of bio-sensing applications due to their enhanced surface area, precise biomolecule-electrode connections, and enhanced delivery of application agents. In the realm of electrochemical sensing, conductive nanostructures immobilized on electrodes enhance electrocatalytic behavior due to quantum confinement and may exhibit properties including more favorable Faradic-to-capacitive current ratios, higher current densities, and faster mass transport by convergent diffusion than their larger micro/macro electrode counterparts. In order to increase biosensor current output to measurable levels, large arrays of nanostructures (i.e., nanoelectrode arrays [NEAs]), have been immobilized on electrode surfaces. These NEA biosensors, fabricated with various nanostructures (e.g., nanowires, nanotubes, and nanocrystals) have shown promising results, displaying high sensitivities and fast response times.

Recently developed graphene petal nanosheets, with reactive edge planes similar to oriented pyrolytic graphite (HOPG) or vertically oriented CNTs, can be grown directly on a variety of surfaces without the need for metal catalysts—creating a nanostructured surface well suited for integration into numerous electrochemical sensing applications.

Various biofunctionalization techniques have been developed to immobilize biorecognition agents onto electrode surfaces including covalent binding through self-assembled monolayers (SAMs), non-covalent membranes, and electrodeposition with conductive polymers. Each biofunctionalization technique has advantages. Self-assembled monolayers provide a covalent link to the biorecognition agent and electrode surface. Non-covalent membranes can be rapidly assembled on electrode surfaces. Poly(3,4-ethylenedioxythiophene) (PEDOT and sometimes referred to as PEDT) is an electrically conductive polymeric material that can be utilized in biosensor interfaces due to its biocompatibility, stability, and high conductivity. Mixtures of the monomer 3,4-ethylenedioxythiophene (EDOT) and Poly (styrene-sulfonate) (PSS) are soluble in aqueous environments and can be controllably electrodeposited onto conductive surfaces. Furthermore PEDOT displays high stability with aqueous electrolytes. This high electrochemical stability, owing to inherent dioxyethylene bridging groups, makes PEDOT well suited for enzyme immobilization.

Water soluble molecules can also be incorporated into the PEDOT matrix during electropolymerization. PEDOT has been used as an enzyme immobilization matrix for use in glucose and cholesterol amperometric biosensing applications.

Carbon nanomaterials (e.g., carbon nanotubes, nanospheres, nanohorns, nanoplates, nanoparticles) have attracted considerable research attention due to their unique properties and potential applications. Transition metals such as Fe and Ni have been traditionally viewed as important catalysts for sp2 carbon growth since they enable rapid dissociation of carbon-rich molecules to form metal-carbon alloys that precipitate carbon through a vapor-liquid-solid mechanism. Two dimensional graphene in the form of single-layer graphene (SLG) or few layer graphene (FLG) has been the particular focus of much recent research because of its unique electronic properties.

In contrast to the production of conformal sheets of SLG or FLG, small crystalline graphitic petals (GPs), or carbon nanowalls (or nanosheets) containing a few layers of grapheme have interesting industrial applications because they grow roughly perpendicular to a substrate and dramatically increase the surface area from which they grow. The GPs are thin, containing only a few graphitic layers, and can be catalyst free, suggesting they might be a source of free-standing graphitic material. Various methods have been reported to grow GPs in the past decade, among which microwave plasma-enhanced chemical vapor deposition (MPCVD) is particularly common. GPs can be used for field emission enhancement, hydrogen storage, sensors, nanocomposites and as a growth template for nanostructures of different materials.

In order to satisfy the requirements of today's increasingly multifunctional portable electronic devices, sustainable and renewable power sources, such as supercapacitors and batteries, are designed and fabricated in the trend of being small, thin, lightweight, environmentally friendly and even flexible. Electrochemical capacitors (ECs), also known as supercapacitors or ultracapacitors, with the merits of high power density, fast power delivery or uptake and excellent cycle stability, have become some of the most promising candidates for next-generation high-performance power devices.

Due to high theoretical capacities, electrically conducting polymers (ECPs), such as polyaniline (PANI), polypyrrole (PPy), and polythiophene (PTP), are commonly used as pseudocapacitive materials to further increase the energy and power density. Among them, PANI gains particular interests in the past 30 years because of its high theoretical specific capacitance (2000 F/g), high degree of processability and chemical stability in air, as well as its fairly high conductivity and favorable electrochemical cycling characteristics. In addition, PANI can also be synthesized in different morphologies (e.g., films, nanofibers, arrays) on different substrates. Despite of the high theoretical specific capacitance, ref. indicates that the current experimental value is far less than the theoretical one, because of the limited mass transport rates of anions and relatively low PANI conductivities. Therefore, it is essential to coat PANI on templates with a high specific surface area to fully exploit its electrochemical capacitive properties. Various porous carbon materials (e.g., carbon cloth, activated carbon, mesoporous carbon, and carbon nanotubes) were used as conductive templates.

Graphene, a new member of carbon nanomaterials with unique properties, was also combined with PANI to fabricate composites by in situ chemical or electrochemical polymerization, and self-assembly. In the most of the previous work, reduced graphene oxide was used as templates or supports for PANI nanostructures. Free-standing chemically converted graphene/PANI nanofiber paper-like composite was synthesized through vacuum filtration of suspensions of the two components. The composite shows a specific capacitance of 210 F/g and 160 F/cm$^3$ but with a poor cycling life (21% loss at 3 A/g after 800 cycles). Reduced graphene nanosheets/PANI composite was synthesized using in situ polymerization in the graphene nanosheet suspension and a specific capacitance of 1046 F/g (based on GNS/PANI composite) was obtained at a scan rate of 1 mV/s. However, the specific capacitance shows a significant loss at 100 mV/s (~50%) compared with that at 1 mV/s in the presence of conducting agent and binding materials.

Graphene nanosheets (nanowalls), or graphitic petals (GPs), containing a few layers of graphene and growing roughly perpendicularly to a substrate over a large surface area, are the ideal candidates for electrochemical energy storage applications, due to high specific area and high electrical conductivity. They were previously synthesized on different substrates, such as Ni foil and carbon cloth, for electrochemical energy storage application. The unique sharp edges of GPs greatly increase charge storage as compared with that of designs that rely on basal plane surfaces. Density functional theory analysis shows the presence of these edges affects not only the reactivity of the carbon material toward the adsorption of Li atoms but also their diffusion properties. Up to date, utilization of this highly conductive and unique GP structure as a nanotemplate to further exploit the electrochemical properties of the pseudocapacitive materials (e.g., conducting polymer) has rarely been reported, not to mention the applications of these composite electrodes in flexible two-terminal devices.

While in the application level of supercapacitors, all-solid-state and flexible supercapacitor devices, based on polymer gel electrolyte, have recently aroused particular interests in this research field because of their obvious advantages in environmental friendliness, flexibility, cost and versatility in comparison with many currently employed counterparts. The advantages of paper-like supercapacitors in structure design over conventional supercapacitor device configuration (a separator sandwiched between two electrodes sealed in liquid electrolyte) have been well addressed. However, the specific capacitance and high power properties of the former flexible solid-state devices still needs to be further improved.

SUMMARY OF THE INVENTION

One aspect of the present invention pertains to an apparatus including a substrate having a surface. Other embodiments include a plurality of carbon mounds located on the surface. Still other embodiments pertain to a plurality of graphitic petals, each petal growing from a corresponding one of said mounds.

Another aspect of the present invention pertains to a method for depositing carbon on a surface. Some embodiments include providing a substrate having an outer surface. Yet other embodiments include depositing carbon on a roughened outer surface. Still other embodiments include growing a graphitic petal from the carbon on the roughened surface.

Yet another aspect of the present embodiment pertains to a method for depositing carbon on a surface. Some embodiments include providing a substrate having a first layer of a first material on top of a second layer of a second material, the first layer having an outer surface. Other embodiments include diffusing a third gaseous material through the first layer. Yet other embodiments exposing the substrate during said diffusing to an electrical field. Still other embodiments include depositing a fourth material containing carbon on the outer surface.

Another aspect of the present embodiment pertains to a biosensor. Some embodiments include an electrode. Yet other embodiments include a silica based wafer, multilayered petal nanosheets supported by the wafer, and platinum nanoparticles supported by the nanosheets. Still other embodiments include an enzyme and poly(3,4-ethylenedioxythiophene) electrodeposited on the electrode.

Still another aspect of the present invention pertains to a method of producing a biosensor. Some embodiments include providing an electrode comprising a silica based wafer, petal nanosheets supported by the wafer, and electrodepositing platinum nanoparticles on the nanosheets. Still other embodiments include electrodepositing an enzyme and poly(3,4-ethylenedioxythiophene) on the electrode.

Yet another aspect of the present invention pertains to a supercapacitor. Some embodiments include a carbon nanotube substrate. Yet other embodiments include graphitic petal structure supported by the substrate, and manganese dioxide supported by the graphitic petal structure.

Factors influencing the formation and structure of graphitic petals grown by microwave plasma-enhanced chemical vapor deposition on oxidized silicon substrates are investigated through process variation and materials analysis. Unlike the spatially homogeneous growth mechanisms reported elsewhere, some graphitic petals are found to grow at an accelerated rate, often growing ~20 times faster than other petals located only a fraction of a micrometer away. Using scanning electron microscopy and atomic force microscopy, the rapid growth rate of these fast-growing petals is attributed to the formation of nanoscale cones. Electron energy loss spectroscopy reveals that the formation of these nanoscale cones is associated with a localized roughening of the oxidized silicon substrate. Raman spectroscopy and transmission electron microscopy are used to confirm the graphitic nature of the as-grown petals. Also, a simple scribing method can be used to control both the location and formation of petals on flat Si substrates.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

Some of the figures shown herein may include dimensions. Further, some of the figures shown herein may have been created from scaled drawings or from photographs that are scalable. It is understood that such dimensions, or the relative scaling within a figure, are by way of example, and not to be construed as limiting.

FIG. 1-1a illustrates field emission scanning electron microscopy (FESEM) micrographs of a GPN electrode grown by microwave plasma chemical vapor deposition (MPCVD) on a Titanium (Ti) coated silicon substrate. Inset shows a magnified view.

FIG. 1-1b discloses raman spectra of the GPNs displaying an intensity increase in the D peak after $O_2$ plasma etch.

FIG. 1-1c shows cyclic voltammograms created by scanning the potential between −0.2 V and 0.6 V at a scan rate of 100 mV/s versus a Ag/AgCl reference electrode in 4 mM $Fe(CN)_6^{3-}$ and 1 M $KNO_3$.

FIG. 1-1d displays a hydrogen peroxide ($H_2O_2$) calibration plot displaying amperometric sensing of $H_2O_2$ oxidation in 20 mL of phosphate buffered saline (PBS) (pH 7.4) via a 3-electrode electrochemical set-up with a working potential of 500 mV. Incremental $H_2O_2$ concentration increases of 10 μM are injected into the test vial while a working potential of 500 mV is applied between the GPN and Pt auxiliary electrodes. Inset portrays a bar graph of $H_2O_2$ sensitivity of the GPN electrode before and after the oxygen plasma etch.

FIGS. 1-2a through 1-2f illustrate characterization of the platinum nanoparticle modified graphene petal nanosheet (PtNP-GPN) electrodes before enzyme immobilization.

FIGS. 1-2a through 1-2e illustrate field emission scanning electron microscopy (FESEM) micrographs of PtNPs electrodeposited on GPNs.

FIG. 1-2a illustrates FESEM micrographs of PtNPs electrodeposited on GPNs with current pulses (500 ms) of 312 μA) used to electrodeposit Pt nanoparticles of distinct size and density onto the GPNs.

FIG. 1-2b illustrates FESEM micrographs of PtNPs electrodeposited on GPNs with current pulses (500 ms) of 625 μA) used to electrodeposit Pt nanoparticles of distinct size and density onto the GPNs.

FIG. 1-2c illustrates FESEM micrographs of PtNPs electrodeposited on GPNs with current pulses (500 ms) of 1.25 mA) used to electrodeposit Pt nanoparticles of distinct size and density onto the GPNs.

FIG. 1-2d illustrates FESEM micrographs of PtNPs electrodeposited on GPNs with current pulses (500 ms) of 2.5 mA used to electrodeposit Pt nanoparticles of distinct size and density onto the GPNs.

FIG. 1-2e illustrates FESEM micrographs of PtNPs electrodeposited on GPNs with current pulses (500 ms) of 5.0 mA used to electrodeposit Pt nanoparticles of distinct size and density onto the GPNs.

FIG. 1-2f shows a bar graph displaying the $H_2O_2$ sensitivity of the GPN electrode before and after oxygen plasma etch and the PtNP-GPN electrodes. Errors bars show standard deviation for 3 different experiments.

FIG. 1-3a illustrates a tilted cross-sectional schematic illustrating the GOx/PEDOT biofunctionalized PtNP-GPN glucose biosensor with adjacent magnified view portrayal of GOx immobilized on a single PtNP. Glucose binds within the GOx enzymatic pocket producing $H_2O_2$ while consuming $O_2$.

FIG. 1-3b displays glucose calibration plots of the Pt-GPN biosensors. Pt electrodeposition current pulses of 312 μA, 625 μA, 1.25 mA, 2.5 mA, and 5.0 mA portray the dynamic current response for a glucose concentration range of 5-60 mM by 5 mM aliquots.

FIG. 1-3c shows linear glucose sensing range with linear regression analysis and coefficient of determination ($R^2$) corresponding to FIG. 3b.

FIG. 1-3d discloses glucose calibration plots for a glucose concentration range of approximately 0.01 mM to approximately 26.65 mM: (1) by incremental glucose concentration steps of 10 μM within the glucose concentration range of 10-50 μM, (2) by incremental glucose concentration steps of 100 μM within the glucose concentration range of 100-500 μM, (3) by incremental glucose concentration steps of 1 mM within the glucose concentration range of 1-5 mM, (4) by an incremental glucose concentration step of 2.5 mM within the glucose concentration range of 5-7.5 mM, (5) by an incremental glucose concentration step of 5 mM within the glucose concentration range of 7.5-17.5 mM, and (5) by a glucose concentration step of 10 mM above the glucose concentration of 17.5 mM.

FIG. 1-3e shows linear glucose sensing range and coefficient of determination ($R^2$) corresponding to FIG. 3d.

FIG. 1-4a illustrates glucose sensing ranges of the Pt-GPN glucose biosensors. Pt electrodeposition current pulses of 312 μA, 625 μA, 1.25 mA, 2.5 mA, and 5.0 mA are compared to glucose levels found in urine, blood, tears, and saliva.

FIG. 1-4b displays biosensor lifetime measurements where the glucose sensitivity for each distinct Pt-GPN glucose biosensor was monitored over a period of 5 weeks.

FIG. 1-4c discloses selectivity test demonstrating minimal interference from 100 μM aliquots of uric acid (UA), acetaminophen (AP), and ascorbic acid (AA) and successful detection of glucose (5 mM) within the backdrop of said electroactive, interfering species for the Pt-MGPN glucose biosensor (Pt electrodeposition of 2.5 mA).

FIG. 2-1. Schematic diagram of the MPCVD chamber illustrating the approximate location of the oxidized silicon substrate with respect to the plasma.

FIG. 2-2. Surface morphologies of etched $SiO_2$/Si after the hydrogen plasma etching before GP growth, (a) $SiO_2$/Si boundary showing an advancing etch front (arrow indicated), (b) A magnified image of the etch front.

FIG. 2-3. AFM images of a micrometer-size EOS feature on the etched $SiO_2$ Si substrate, (a) Top-view (b) 3-dimensional, perspective view. Trenches or fissures in the EOS feature are apparent.

FIG. 2-7. Top-view FESEM images of GPs grown for 15 min in a plasma power of 700 W. (a) Top-view of a cluster of ~12 nanoscale cones. One nanocone supports the growth of a GP which resembles the letter 'P'. (b) A region of the substrate where smaller GPs are found in close proximity to cones where larger GPs emerge, (c) and (d) The nucleation and growth of GPs with a distribution of sizes from the same nanocone.

FIG. 2-8. Raman spectra of GPs prepared for 1 min, 5 min and 15 min.

FIG. 2-9. (a) A TEM image of an as-grown GP. (b) A high-resolution TEM image of the GP.

FIG. 2-10. GP growth for different durations (a) 1 min of growth, when carbon deposits form nanoislands across the surface of the substrate, (b) 7 min of growth, when large GPs emerge from nanoscale cones, (c) 10 min of growth, when the coexistence of the smaller and larger GPs appears and (d) 20 min of growth, when a full coverage of GPs fills the surface of the substrate.

FIG. 2-11. Top-view FESEM images of GPs prepared on the oxidized silicon substrates at (a) 700 W, (b) 300 W both for 7 min.

FIG. 2-12. Controlled formation of nanocones and GPs by a simple scratch on a silicon substrate with a 500-nm-thick oxide layer, (a) A low magnification image illustrating three scratched lines, (b) A top-view high magnification image of the boxed region of (a). The confined growth of GP is evident, (c) Evidence for nanocone growth, (d) A cross-sectional SEM image of a substrate cleaved perpendicular to a scratched line. The image shows a reduced oxide layer thickness, the presence of nanocones, and the growth of GPs.

FIG. 3-1. Schematic illustration of CC/GPs/PANI nanostructures as high-performance EC electrodes. The synthesis process involves two steps: (I) uniform and large-area coverage of GPs on highly conductive CC substrate by MPCVD method; (II) Controlled and conformal PANI nanoscale thin layer coating on CC/GP substrates by electropolymerization method.

FIG. 3-2. Structural characterization of CC/GPs/PANI hybrid composite. (A) SEM images of pure carbon cloth (inset, lower magnification); (B) SEM images of a fully GP covered CC substrate, (inset, a high magnification of GPs) (C) A high magnification of conformal PANI coating on GP surfaces. (D) Raman characterization of pure CC, CC/GPs and CC/GPs/PANI.

FIG. 3-3. Electrochemical performances of the CC/GPs/PANI electrodes. (A) Both the mass specific capacitance and area-normalized specific capacitance as a function of electrochemical polymerization time at 2 mV/s for CC/GPs/PANI electrode. (B) CV curves of the hybrid CC/GPs/PANI composite electrode (5 min of PANI electropolymerization) at different scan rates of 2, 5, 10, 20, 50 and 100 mV/s with potential windows ranging from 0 to 0.8 V vs. Ag/AgCl in 1 M $H_2SO_4$ aqueous electrolyte. (C) The comparison of area-normalized specific capacitance of Pure CC, CC/GPs, CC/PANI and CC/GPs/PANI at different scan rates. (D) The comparison of mass specific capacitance for both pure CC and CC/GP substrates.

FIG. 3-4. Galvanostatic constant-current charge/discharge performance of CC/GPs/PANI hybrid composite electrode. (A) Galvanostatic constant-current charge/discharge performances are evaluated for the CC/GPs/PANI hybrid electrode at different constant-current densities. (B) Specific capacitances of the CC/GPs/PANI hybrid electrode at different constant-current densities. (C) Ragone plot of the estimated specific energy and specific power at various charge/discharge rates (current densities). The dashed line region for electrochemical capacitors was cited from previous references. (D) Charge/discharge cycling test at the current density of 10 $mA/cm^2$, showing ~7% loss in capacitance after 2000 cycles.

FIG. 3-5. Electrochemical performances of the two-terminal highly flexible supercapacitors. (A) Schematic illustration of all-solid state highly flexible CC/GPs/PANI supercapacitors based on PVA-$H_2SO_4$ polymer gel electrolyte. (B) Galvanostatic charge/discharge performances of as-prepared all-solid-state supercapacitors. (C) Comparison of the specific energy and power density (per $cm^3$ of stack) of typical electrolytic capacitors, batteries, commercial supercapacitors and as-prepared devices in a Ragone plot. (D) Charge/discharge cycling test at the current density of 5 $mA/cm^2$, showing ~10% loss after 1000 cycles. (E) CV curves at 5 mV/s for the supercapacitor group from 0 V to 2.5 V in both normal and bent conditions. The overlapping CV curves of the two situations indicate the excellent mechanical properties of the device under flexible testing conditions. (F) Digital pictures that show three highly flexible devices in series, wrapped around a glass rod (inset), to light a green light-emitting-diode well.

FIG. 4-1. SEM images of (a) graphitic petals, (b) A magnified image of graphitic petals showing smooth surfaces, (c) $MnO_2$ coated on graphitic petals, (d) A magnified image of uniform MnO2 coating on graphitic petals.

FIG. 4-2. (a) Cyclic voltammetry curves of the $MnO_2$/GP/BP composites at different scan rates in 1 M $Na_2SO_4$ aqueous electrolyte, (b) Cyclic voltammetry curves of BP, GP/BP, $MnO_2$/BP, and $MnO_2$/GP/BP at 10 mV/s. (c) Specific capacitances of $MnO_2$/GP/BP (black), $MnO_2$/BP (red), GP/BP (dark cyan) and BP (blue) at different scan rates, (d) Charge/discharge curve of $MnO_2$/GP/BP at different current densities, (e) Ragone plot of the estimated specific energy and specific power at various current densities, (f) Capacity retention of $MnO_2$/GP/BP as a function of cycle number.

FIG. 4-3. (a) Schematic diagram of $MnO_2$ clusters and graphene (top view); (b) Electronic density of states under compressive/tensile stresses (c) The comparative electronic density of states of graphene, $MnO_2$ and $MnO_2$/graphene; (d) Iso-electronic charge contour plot shown at a particular plane (indicated by the yellow line from the top view in (a), perpendicular to the graphene plane and along a zig-zag direction) with electronic charge distribution at $MnO_2$/graphene interface.

FIG. 5-2 A uniform and large-area coverage of GPs on flexible CC substrates.

FIG. 5-3 SEM morphology of PANI coated on CC/GPs for different electropolymerization time: (a) 5 min, (b) 10 min, and (c) 20 min.

FIG. 5-4 Current vs. time during PANI electropolymerization process for both pure CC and CC/GP substrate.

FIG. 5-5 (A) Galvanostatic constant-current charge/discharge curves of the CC/GPs/PANI electrode at higher current densities. (B) IR drop of the CC/GPs/PANI electrode in 1 M $H_2SO_4$ electrolyte.

FIG. 5-6 (A) CV curves at 5 mV/s of a single flexible supercapacitor device base on CC/GPs/PANI electrode with polymer gel as electrolyte; (B) normal (C) bent and (D) twisted conditions.

FIG. 6-3.1. FESEM images of nanoscale cones observed in the middle regions of the substrate after a growth time of 15 min for a plasma power of 700 W. (a) Side-view; (b) top-view FIG. 6-3.2. High resolution TEM and EELS characterization of a thin slice cut from a nanocone. (a) A bright field TEM image of a thin slice taken across a nanocone. Elemental mapping shows the spatial distribution of mapped elements, (b)-(d) Silicon, oxygen, and carbon maps, respectively, (e) HRTEM image of the $SiO_2$/C interface of the nanocone indicates the graphitic nature of the C layers with an interlayer distance of 0.35 nm. The dark spots in the image correspond to a Pt protection layer deposited during sample preparation.

FIG. 6-3.3. Side-view FESEM images of GPs grown for 15 min in a plasma with a power of 700 W. (a) Nanoscale cones at low magnification that illustrate the localized, rapid growth of a few GPs as well as smaller, surroundings GPs which grow at a considerable slower rate, (b) An FESEM image of a large GP emerging radially from a single nanoscale cone, (c) A GP growing in the shape of a nano horn, (d) A large, thin GP emerging from a nanocone.

FIG. 6-3.6. SEM images of (a) graphitic petals, (b) A magnified image of graphitic petals showing smooth surfaces, (c) $MnO_2$ coated on graphitic petals, (d) A magnified image of uniform $MnO_2$ coating on graphitic petals.

FIG. 6-3.7. (a) Cyclic voltammetry curves of the $MnO_2$/GP/BP composites at different scan rates in 1 M $Na_2SO_4$ aqueous electrolyte, (b) Charge/discharge curve of $MnO_2$/GP/BP at different current densities, (c) Specific capacitances of $MnO_2$/GP/BP (black), $MnO_2$/BP (red), GP/BP (dark cyan) and BP (blue) at different scan rates, (d) Ragone plot of the estimated specific energy and specific power at various current densities, (f) Capacity retention of $MnO_2$/GP/BP as a function of cycle number.

FIG. 6-3.9. (A) SEM images of pure carbon cloth (inset, lower magnification); (B) SEM images of a fully GP covered CC substrate, (inset, a high magnification of GPs) (C) A high magnification of conformal PANI coating on GP surfaces. (D) Raman characterization of pure CC, CC/GPs and CC/GPs/PANI.

FIG. 6-3.10. (A) The comparison of area-normalized specific capacitance of Pure CC, CC/GPs, CC/PANI and CC/GPs/PANI at different scan rates. (B) The comparison of mass specific capacitance for both pure CC and CC/GP substrates. (C) Ragone plot of the estimated specific energy and specific power at various charge/discharge rates (current densities). The dashed line region for electrochemical capacitors was cited from previous references. (D) Charge/discharge cycling test at the current density of 10 mA $cm^2$, showing approximately 7% loss after 2000 cycles.

FIG. 6-4.1. (A) SEM image of etched GP electrode patterns; (B) A higher magnification of the GP electrodes coated with Ti/Au; (C) A low-magnification SEM image (side view) and a higher magnification of the GP patterned electrodes, indicating that the electrode has a uniform thickness of 4 micro-meter. (D) The boundaries of GP layers nesting on each other are marked (see red dots), demonstrating the 3D structures and sharp edges.

FIG. 6-4.3. Electrochemical characterization of GP-based micro-supercapacitors. (A) Specific capacitances vs. scan rates before electrochemical oxidation. (B) Specific capacitances vs. scan rates after electrochemical oxidation for 30 min. (C) Ragone plots of Ragone plot energy density vs. power density for as-prepared micro-supercapacitors in aqueous electrolytes and the up-to-date reported values of different electrode materials in organic electrolytes. (D) Cyclic stability of as-prepared GP-based micro-supercapacitors.

FIG. 6-4.4. Schematic of growth process of CNT/GP patterns for micro-supercapacitor application.

FIG. 6-4.5. SEM characterization of CNT/GP structures on Si/$SiO_2$ substrates. (A) SEM characterization of inter-digitated CNT/GP patterned electrodes for micro-supercapacitors at a low magnification. (B) A tilted SEM image of a CNT/GP electrode. (C) A top view of CNT/GP electrode. (D) A side view of CNT/GP electrode.

FIG. 6-4.6. Electrochemical Characterization of CNT/GP micro-supercapacitors. (A) shows the cyclic voltammetry curves of patterned CNT/GP electrodes at different scan rates. (B) charge/discharge curves of CNT/GP-CNT/GP electrodes at different current densities (C) Comparative CV curves of micro-supercapacitors based on CNT-CNT and CNT/GP-CNT/GP electrodes at a scan rate of 20 mV/s. (D Comparative CV curves of CNT and CNT/GP electrodes at a scan rate of 20 mV/s in a three-electrode system.

FIG. 6-4.7. Free-standing GP foam after removing Ni foam, (a)-(c) optical image of free-standing GP foam, (d) and (e) SEM images of GP foam at a low and high magnification.

FIG. 6-4.8. (a) CC micro-conduits on carbon cloth at a lower magnification, (b) A CNT micro-conduit at higher magnification.

FIG. 6-4.9. (a) CNT/GP micro-conduit on CC at a low magnification, (b) A CNT/GP micro-conduit with a heart shape, (c) A CNT/GP micro-conduit at higher magnification, (d) CNT/GP at a high magnification.

FIG. 6-4.10. Cyclic voltammetry characterization of CNT/GP micro-conduit electrodes.

FIG. 7 shows an exemplary method for forming electrodes and for generating a corresponding lithium ion cell.

FIG. 8 shows a schematic representation of a lithium ion cell according to at least one embodiment.

FIG. 9 shows a magnified image of a B-C-N modified carbon nanotube-based electrode.

FIG. 10 shows an exemplary chemical structure for $C_2BN$.

FIG. 11 shows a graph of discharge capacity as a function of charge-discharge cycle for electrodes formed by different methods.

DESCRIPTION OF THE PREFERRED EMBODIMENT

Figures 1, 1A:
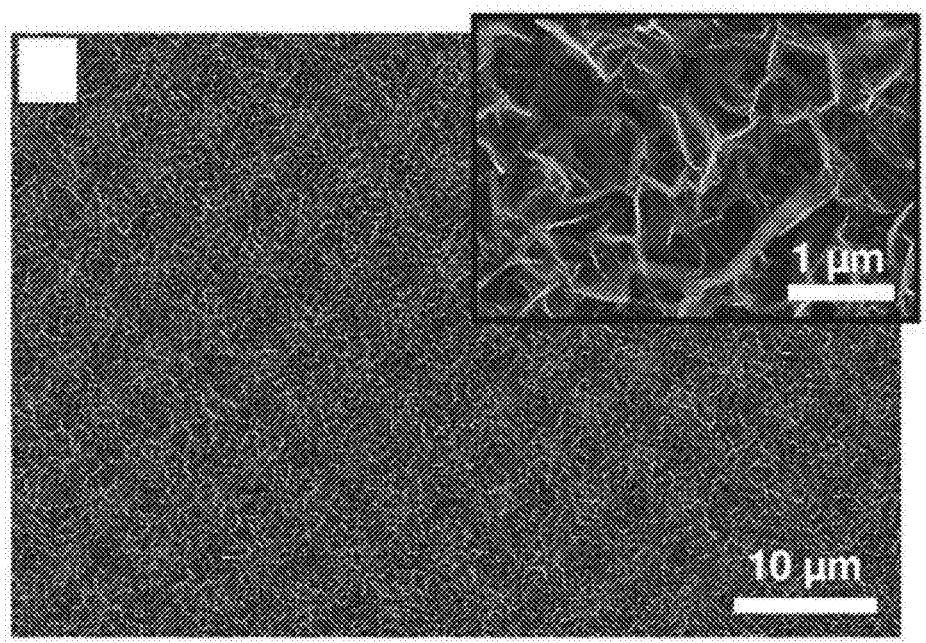
FIGS. 1-1a through 1-1c illustrate characterization of the graphene petal nanosheets (GPN) electrodes before and after exposure to an oxygen plasma etch.
Figures 1, 1B:
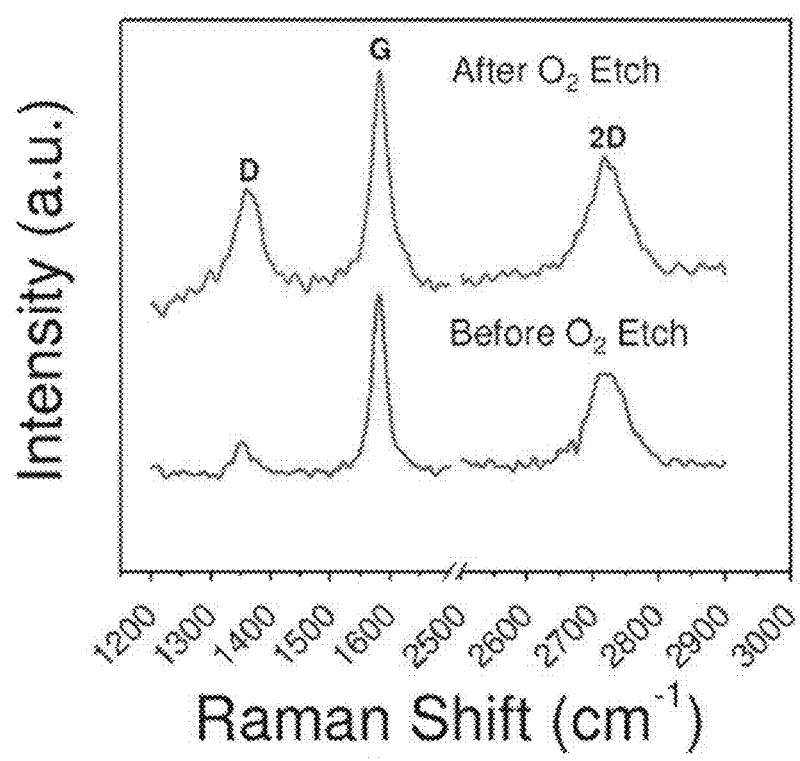
Figures 1, 1C:
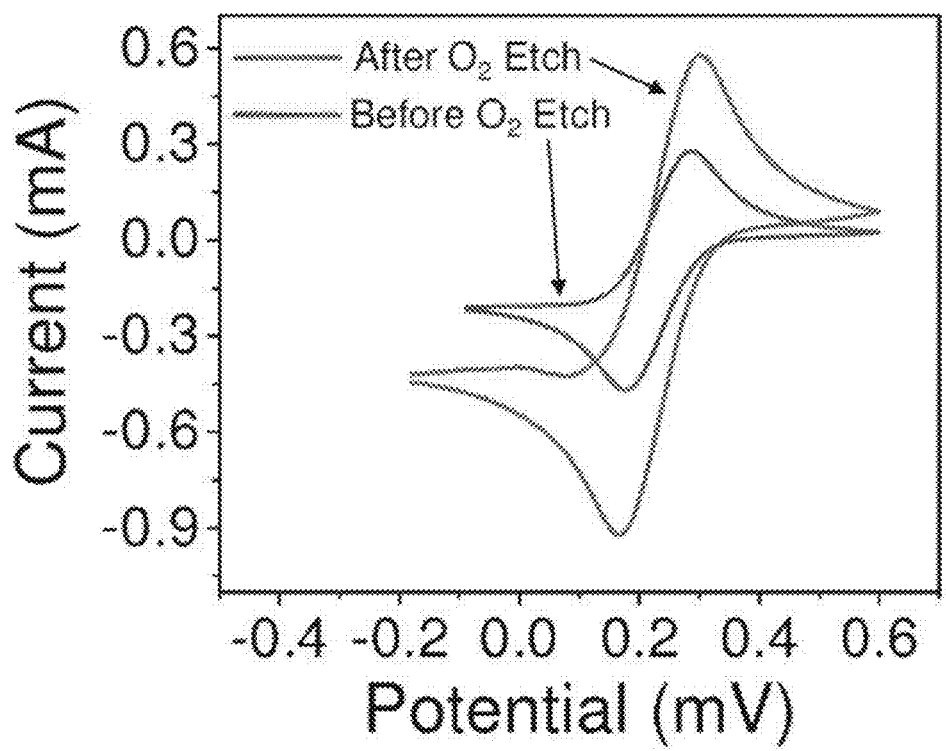
Figures 1, 1D:
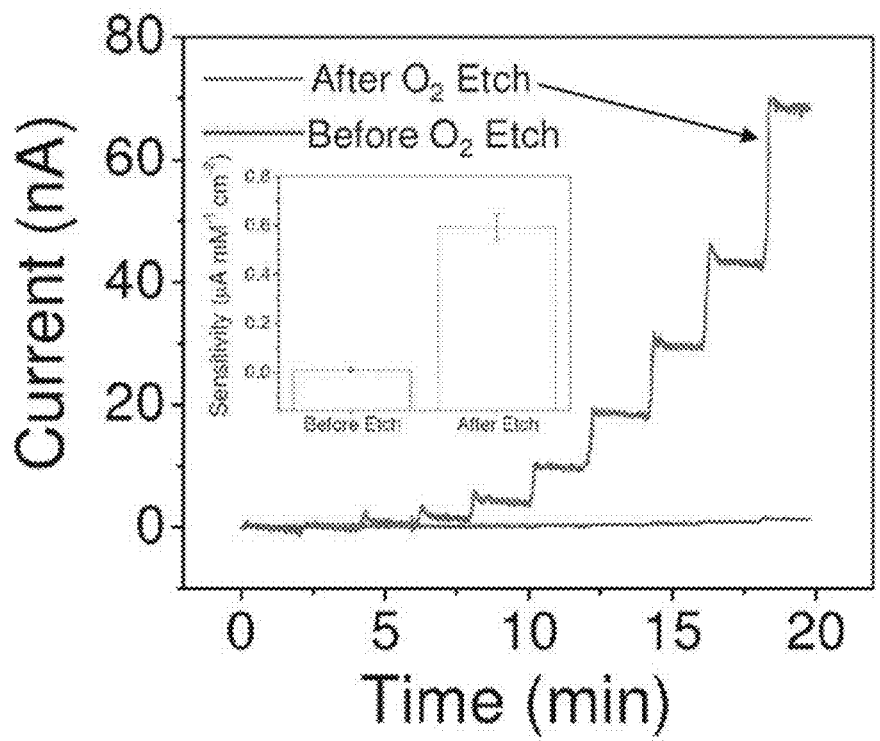

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated.

Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples only, and further, unless otherwise noted, are approximate values, and should be considered as if the word "about" prefaced each quantity. Further, with discussion pertaining to a specific composition of matter, that description is by example only, and does not limit the applicability of other species of that composition, nor does it limit the applicability of other compositions unrelated to the cited composition.

What will be shown and described herein, along with various embodiments of the present invention, is discussion of one or more tests that were performed. It is understood that such examples are by way of examples only, and are not to be construed as being limitations on any embodiment of the present invention.

One embodiment of the present invention pertains to a nanostructured biosensor that addresses some of the limitations that nanoelectrode array biosensors currently face. In lieu of lithography/etch back fabrication techniques, porous templates, or metal catalyst driven carbon nanotube arrays, one embodiment includes the growth of multilayered graphene petal nanosheets (GPNs) on a silicon wafer through a chemical vapor deposition technique. The GPNs act as a conductive template for subsequent Pt nanoparticle electrodeposition. An electrodeposition process is used to grow platinum nanoparticles (PtNPs) along the graphene petal edges and planes to enhance electrochemical performance. The size and density of the PtNPs are manipulated to improve the biosensor sensitivity and dynamic sensing range. A sensor biofunctionalization protocol is used to electrodeposit an enzyme with the electrically conductive polymer Poly(3,4-ethylenedioxythiophene) (PEDOT) onto the electrode surface. In order to benchmark the performance against other biosensors, the enzyme glucose oxidase (GOx) (perhaps the most widely studied enzymatic biosensing paradigm since its inception from Clark and Lyons in 1962), is encapsulated within the PEDOT matrix for subsequent amperometric glucose sensing. The optimized PtNP-GPN glucose biosensor performance proves to be exemplary with strong glucose sensitivity even after 5 weeks of use, minimal interference from endogenous electroactive species (i.e., ascorbic acid, uric acid, and acetaminophen) typically found in human serum samples, and a low detection limit and wide linear sensing range that improves upon the performance of glucose biosensors previously reported in the literature.

In one embodiment a monolithic layer of GPNs were grown across a Ti coated silicon substrate through a microwave plasma chemical vapor deposition technique. The petals grow across the surface of the electrode—protruding a distance of approximately 500 nm from the surface (FIG. 1-1). The 1-10 nm thickness of the petals (as measured by a Veeco atomic force microscope) is consistent with previous reported morphologies corresponding to 5-25 graphene layers. In an effort to increase the electroactive nature of the GPN electrodes and improve subsequent PtNP deposition, the GPN electrodes were exposed to a 30 second oxygen plasma etch. The effects of this etching process were characterized with Raman spectroscopy, ferricyanide cyclic voltammetry, and amperometric hydrogen peroxide ($H_2O_2$) sensing. Improvements can be attributed to the $O_2$ plasma etch generating defects and oxygenated species on the superficial graphene layers. The generated defects render the graphene surface more electroactive than the untreated, superficial basal planes, while newly formed oxygenated species alter the electrode nature from hydrophobic to hydrophilic—enhancing the ability of electrolyte to impregnate the carbon surface.

The Raman spectra of the GPNs before and after the oxygen plasma etch is shown in FIG. 1-1 b. The Raman spectra display a D band near 1350 $cm^{-1}$, a G band near 1580 $cm^{-1}$, and a 2D band near 2700 $cm^{-1}$. The D peak, which is a disorder induced peak, arises only in the presence of defects. The peak intensity ratio (both $I_D/I_G$ and $I_{2D}/I_G$) and the shape and full width at half maximum (FWHM) of the 2D peak have been used to characterize single and few layer graphene. The relative intensity of the G peak and the 2D peak ($I_{2D}/I_G\sim0.5$) and the FWHM of the 2D peak [FWHM(2D)=64] indicate that the petals are likely made up of only a few layers of graphene sheets. The oxygen plasma etch results in an increase in the $I_D/I_G$ ratio, (from 0.17 to 0.48), thus indicating increased defects in the plasma treated GPN. These defects created through plasma etching assist in subsequent nanoparticle deposition by serving as nanoparticle nucleation sites.

The heterogeneous electron transfer (ET) rate of carbon based electrodes is highly dependent upon electrode surface structure. In the case of $sp^2$ hybridized carbon in graphene, the rate of ET is enhanced at exposed edge planes or defect sites in lieu of the basal plane surface. In order to quantify the ET rate of the GPN electrodes, ferricyanide cyclic voltammetry before and after the oxygen plasma etch was performed while the separation between the anodic and cathodic peak currents ($\Delta E_P$) was measured (FIG. 1-1 c). As illustrated in FIG. 1-1 c, cyclic voltammetry measurements were taken by immersing the electrodes in 4 mM $Fe(CN)_6^{3-}$ and 1 M $KNO_3$ and scanning the potential between −0.2 V and +0.6 V at a scan rate of 100 mV/s versus a Ag/AgCl reference electrode. The $\Delta E_P$ values for these scan rates fall between 110 and 135 mV which are a marked improvement to the electron transfer kinetics of ferricyanide for basal plane pyrolytic graphite electrodes ($\Delta E_P$=360-596) that have been exposed to air for over 30 minutes and compare quite similarly to the $\Delta E_P$ values reported for edge plane pyrolytic MWCNTs ($\Delta E_P$=109-137) held under similar conditions. Thus the GPN electrodes exhibit an ET rate that is well suited for electrochemical sensing. Furthermore, the peak anodic current ($Ip_a$) more than doubles from 0.28±0.5 mA to 0.58±0.5 after the plasma $O_2$ etch—indicating an enhancement in the electro-reactivity of the electrode.

Finally the GPN electrodes were electrochemically characterized by testing their sensitivity to hydrogen peroxide ($H_2O_2$)—the measurable electroactive species byproduct of oxidase enzymes including GOx. Amperometric $H_2O_2$ testing was first performed via a 3 electrode set-up, were the GPN electrode was biased with 500 mV against a Pt wire auxiliary in 20 mL of phosphate buffered saline (PBS: pH 7.4) while Ag/AgCl acted as the reference electrode. $H_2O_2$ calibration plots are created by adding aliquots of $H_2O_2$ with increasing concentration into the test vial while the solution is continuously stirred (500 rpm) (FIG. 1-1 d). The effect of the plasma etching is clearly noticeable as the sensitivity to $H_2O_2$ increases from 0.015 mA $mM^{-1}$ $cm^{-2}$ to 0.595 mA $mM^{-1}$ $cm^{-2}$ before and after etching respectively.

In an effort to increase the electro-reactivity of the GPN electrodes, Pt nanoparticles of varying size and density are electrodeposited onto the GPNs (FIGS. 2a-2e). Pt nanoparticles are electrodeposited through a current pulse technique with a similar 3-electrode set-up discussed below. Five distinct currents are used to create five Pt-GPN electrodes with Pt nanoparticles of differing size and density. Current pulses of 312 μA initiate nanoparticle growth along the GPN ridge lines with an average nanoparticle width of (46±5) nm. The ridgeline nanoparticles grow to (86±5) nm at 625 μA current pulses while nanoparticles (<20 nm) began to form on each petal face. Ridgeline nanoparticles begin to coalesce at current pulses of 1250 μA with average widths of (100±10) nm while petal face nanoparticles (<20 nm) begin to become more apparent. At 2500 μA current pulses the petal tips are generally coated with Pt nanoparticles (<10 nm in width) extending from ridgeline nanoparticles (width of (100±25) nm) while all visible petal faces now contain an array of nanoparticles (<20 nm). At 5000 μA current pulses the Pt ridgelines have now expanded in width to (300±50) nm while the petal face nanoparticles have grown to (35±10) nm. Thus by changing the pulse deposition current the Pt nanoparticle size, density, and morphology can be altered. These distinct Pt nanoparticle characteristics have significant and unique impacts on subsequent $H_2O_2$ and glucose sensing.

Figures 1, 2, 2A:
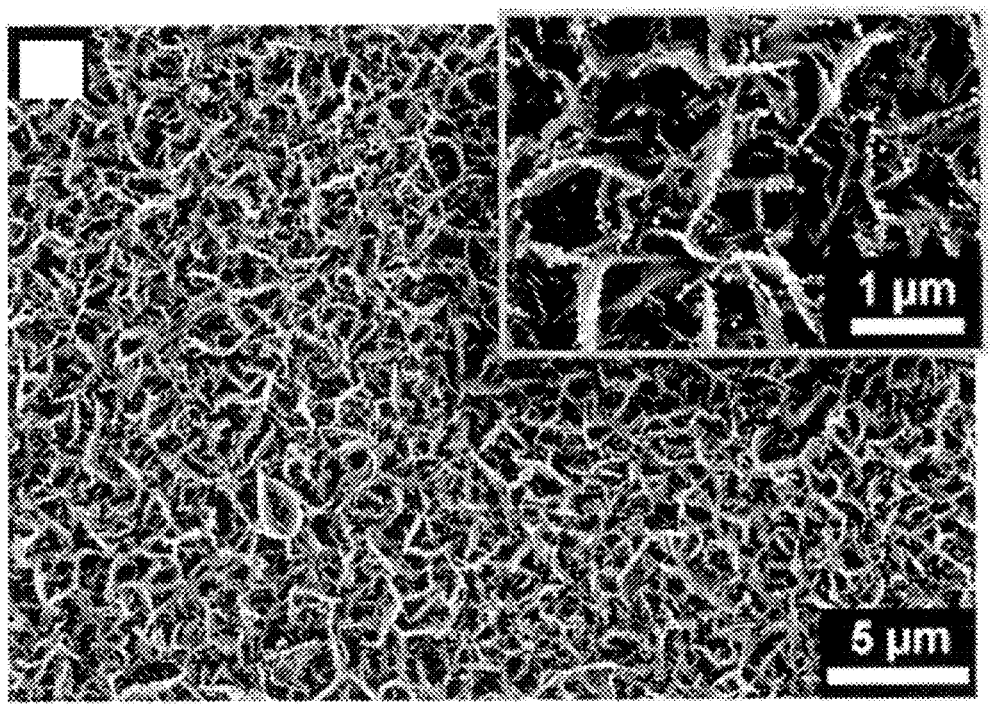
Figures 1, 2, 2B:
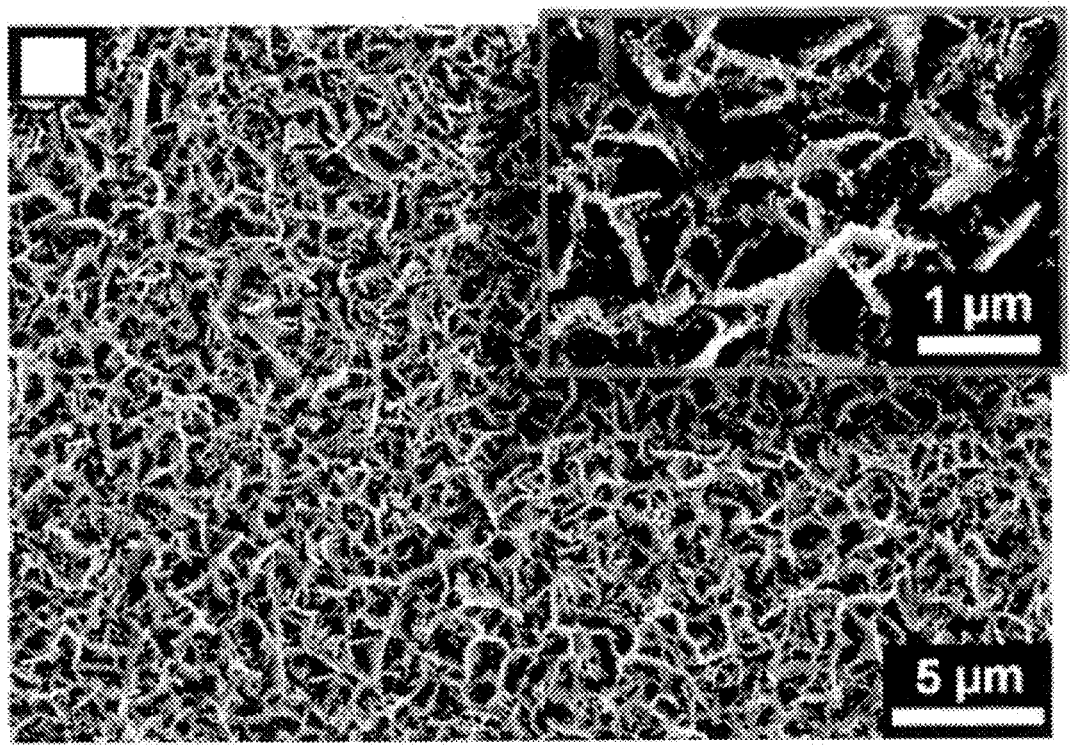
Figures 1, 2, 2C:
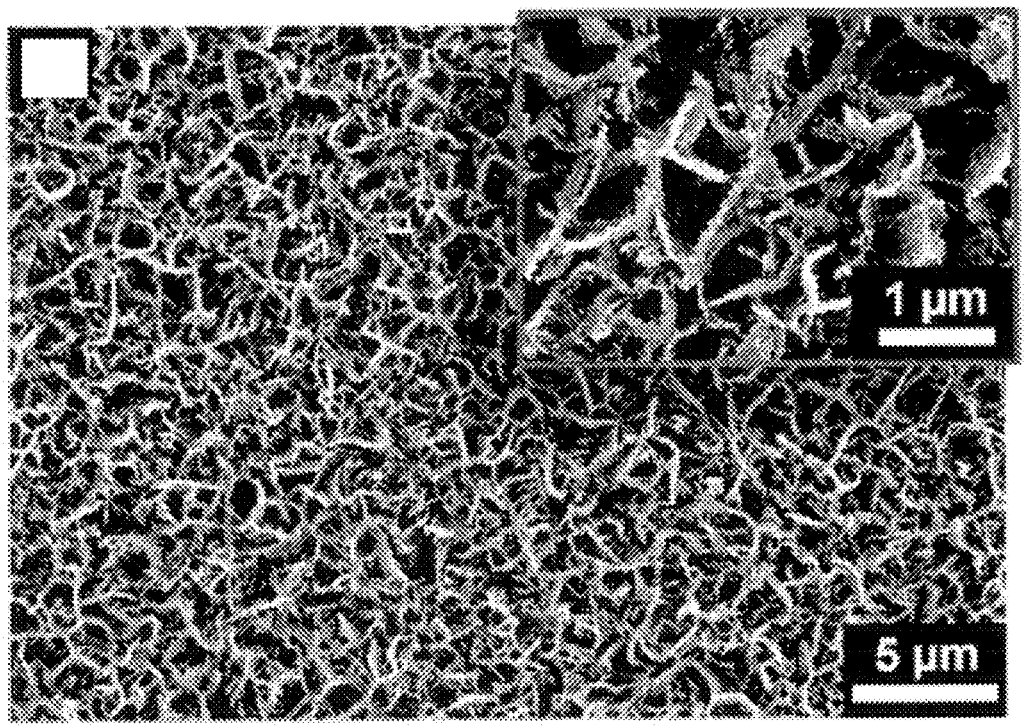
Figures 1, 2, 2D:
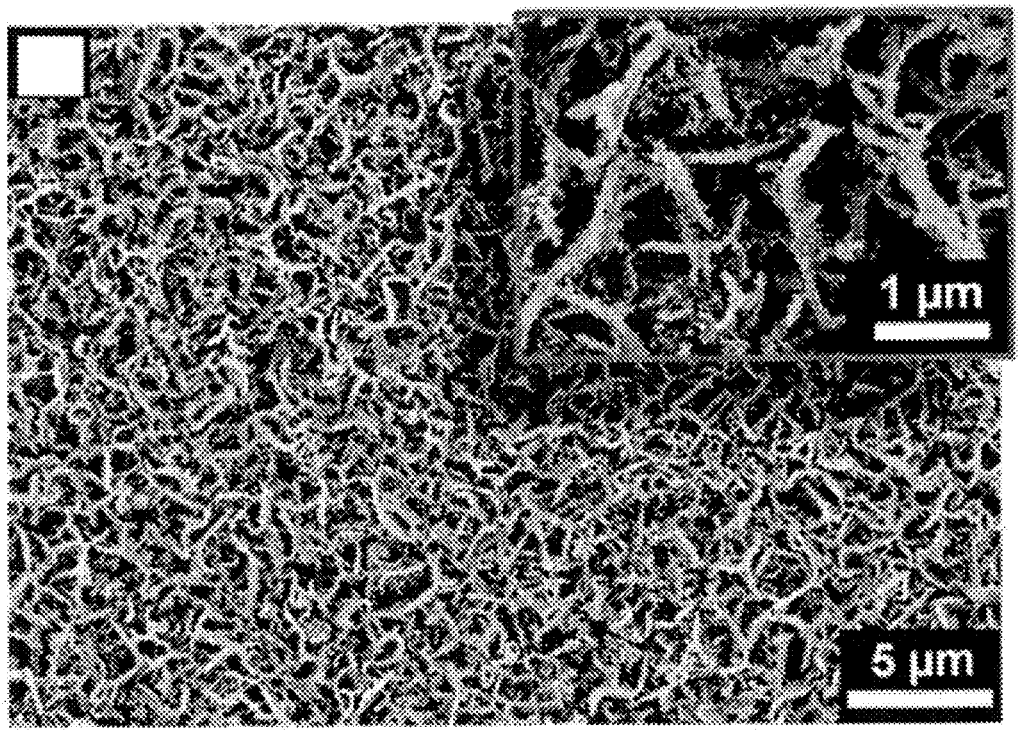
Figures 1, 2, 2E:
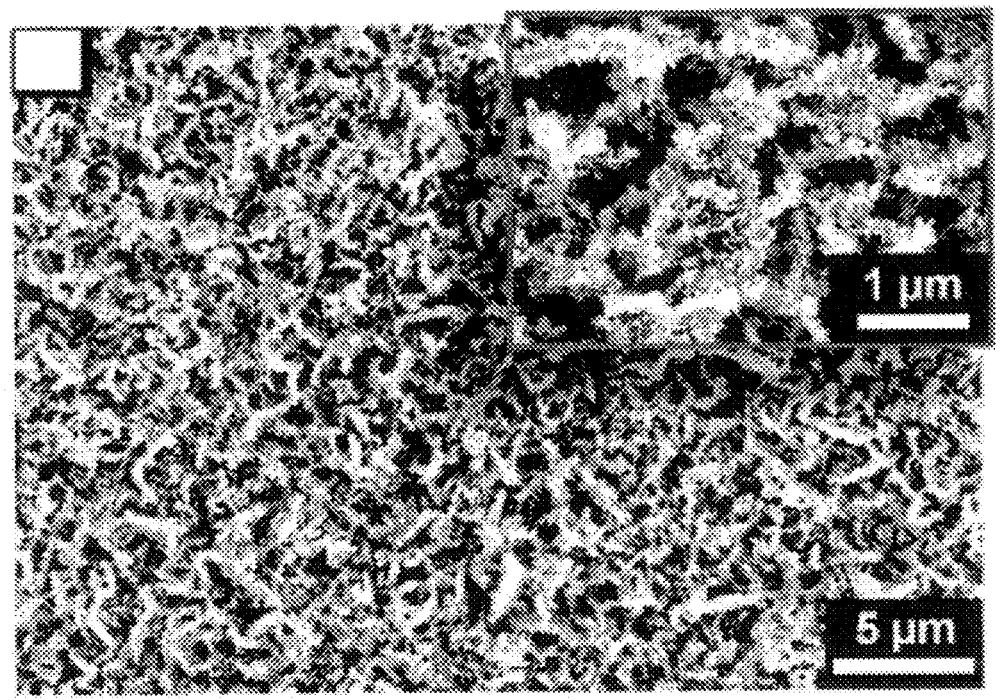
Figures 1, 2, 2F:
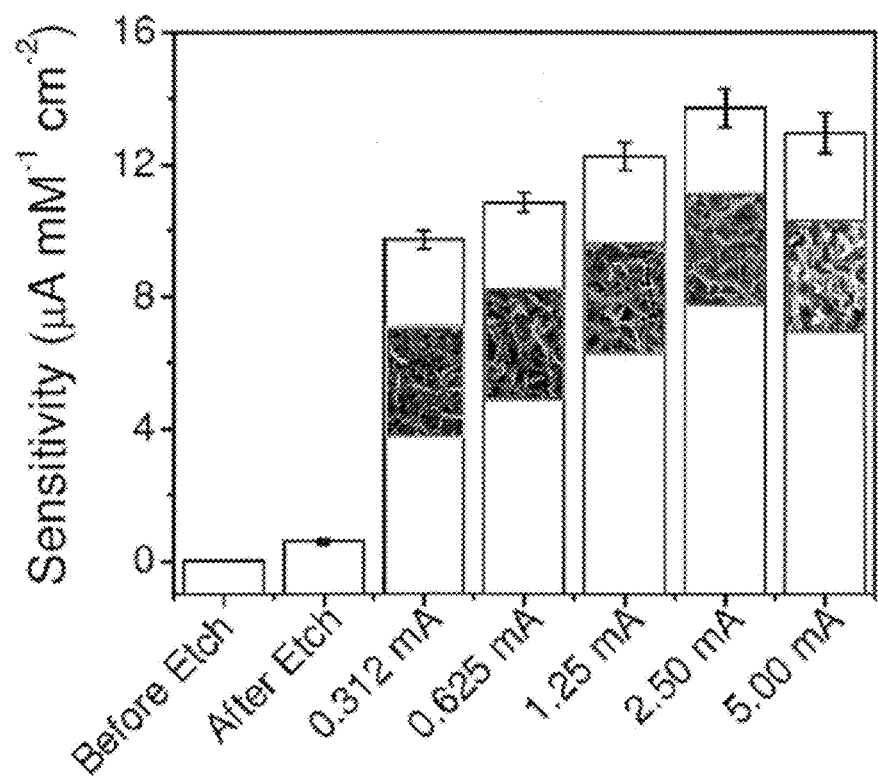

As with the GPN electrodes, the 5 distinct Pt-GPN electrodes were electrochemically characterized by testing their sensitivity to $H_2O_2$ (FIG. 1-2f).

Amperometric $H_2O_2$ calibration plots were performed in the same manner as mentioned previously with a working potential of 500 mV. The $H_2O_2$ sensitivity of the GPN electrode is enhanced with the introduction of Pt as the sensitivity jumps from 0.595 mA mM$^{-1}$ cm$^{-2}$ (GPN electrode after oxygen plasma etch) to 9.71 mA mM$^{-1}$ cm$^{-2}$, an increase of more than 16 fold, after Pt electrodeposition with 312 µA current pulses. The $H_2O_2$ sensitivity continues to increase for higher Pt electrodeposition current pulse until a maximum sensitivity of 13.7 mA mM$^{-1}$ cm$^{-2}$ is reached for the Pt-GPN biosensor with 2.50 mA current pulses. The $H_2O_2$ sensitivity decreases to 12.9 mA mM$^{-1}$ cm$^{-2}$ for Pt-GPN biosensor with 5.0 mA current pulses. As a supplementary control experiment, Pt was electrodeposited onto planar highly ordered pyrolytic graphite (HOPG) at the same conditions (2.5 mA current pulses, 250 cycles) as the optimized Pt-MGPN electrode. The $H_2O_2$ sensitivity of the optimized Pt-MGPN was nearly 5 times as great as the Pt-HOPG electrode—illustrating the enhanced sensitivity of MGPNs over conventional carbon-based substrates.

Figures 1, 2, 3, 3A:
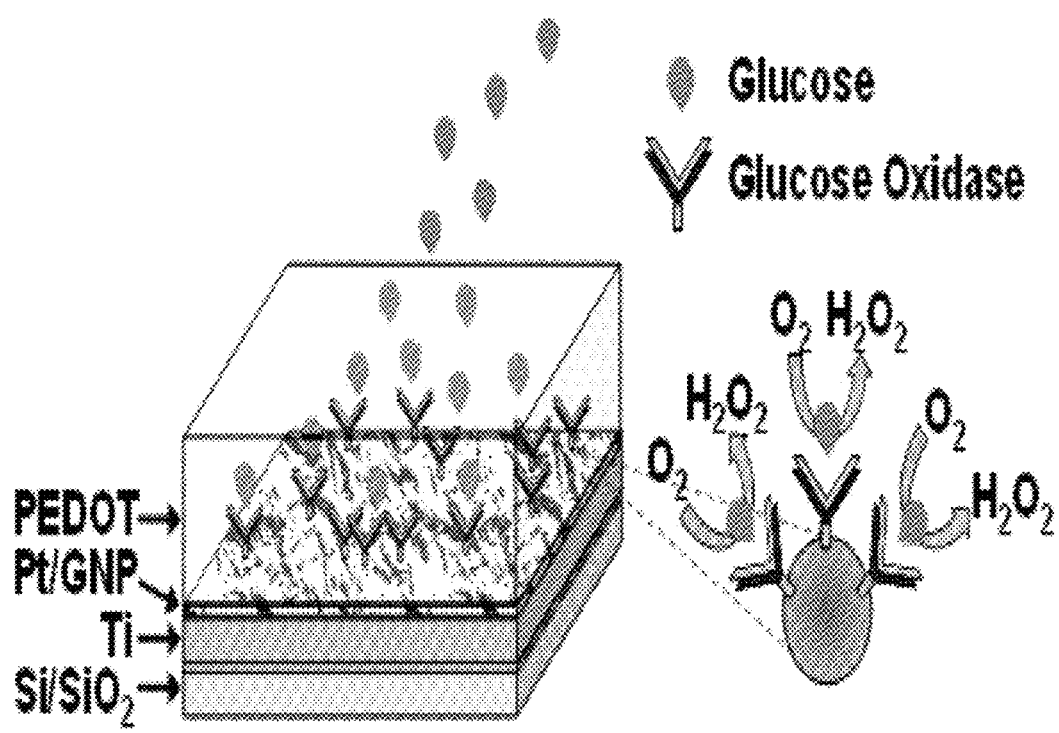

In order to convert the PtNP-GPN electrodes into enzymatic biosensors, the enzyme GOx is mixed with the conductive polymer PEDOT and subsequently electrodeposited onto the electrode surface. During electrochemical glucose sensing, glucose is broken down by GOx into hydrogen peroxide ($H_2O_2$) and is subsequently oxidized at the electrode surface, producing measurable current signal (Eq. 1 & 2). A schematic portraying the biofunctionalized PtNP-GPN glucose biosensors as well as the enzymatic function of GOx is illustrated in FIG. 3a.

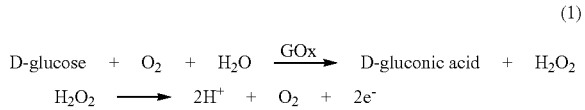

$$\text{D-glucose} + O_2 + H_2O \xrightarrow{\text{GOx}} \text{D-gluconic acid} + H_2O_2 \quad (1)$$

$$H_2O_2 \longrightarrow 2H^+ + O_2 + 2e^-$$

Amperometric glucose sensing is carried out in the same 3-electrode set-up and working potential (500 mV) as the amperometric $H_2O_2$ testing. Amperometric glucose calibration plots for all 5 PtNp-GPN biosensors were created by adding successive aliquots of increasing concentrations of glucose and measuring the corresponding steady-state signal response, typically achieved within 5 seconds (FIGS. 3b-3e). The glucose sensitivity for the Pt-GPN biosensors and linear sensing range of the PtNp-GPN glucose biosensors follow similar trends found in the amperometric $H_2O_2$ testing where values continue to increase for higher Pt electrodeposition current pulses until a maximum sensitivity (0.24 µA mM$^{-1}$ cm$^{-2}$) and linear sensing range (0.01-50 mM) is reached for the PtNp-GPN biosensor with 2.50 mA current pulses (FIGS. 3a-3e and FIG. 4). The glucose detection limit (S/N=3, signal-to-noise ratio of 3) and linear sensing range of the optimized Pt-GPN biosensor is listed and compared to glucose biosensors comprised of similar materials including graphene, carbon nanotubes, and PtNPs (Table 1).

TABLE 1

Electrochemical biosensor performance comparison of glucose biosensors based upon, graphene/graphite, carbon nanotubes, and metallic nanoparticles.

| Biosensor | Base Material | Detection Limit (µM) | Sensing Range (mM) | Ref. |
|---|---|---|---|---|
| GOx-PEDOT/PtNP/GPNs | Graphene/Graphite | 0.3 | 0.01-50 | this disclosure |
| GOx-Nafion-Pt-xGnPs | Graphene/Graphite | 1 | 1-20 | 52 |
| Ppy-GOx-Gn | Graphene/Graphite | 3 | .002-.040 | 53 |
| GOx-CNx-MWCNTs | Carbon Nanotubes | 10 | .02-1.02 | 54 |
| GOx-Fc-MWCNTs | Carbon Nanotubes | 3 | .012-3.8 | 55 |
| GOx-HRP-Ppy-SWCNT | Carbon Nanotubes | 0.5 | .012-3.8 | 56 |
| GOx-Nafion/AuNPs-MWCNTs | Carbon Nanotubes | 20 | 0.05-22 | 57 |
| GOx-PtNPs-SWCNTs | Carbon Nanotubes | 0.5 | 0.005-5 | 58 |
| GOx-PtNps-CNTs/TiO$_2$ | Carbon Nanotubes | 5.7 | 0.006-1.5 | 59 |
| GOx-aligned-SWCNTs | Carbon Nanotubes | 80 | up to 30 | 25 |
| GOx/AuNWs-CS | Metallic Nanoparticles | 5 | .01-10 | 60 |
| GOx-CS-IL/AuNPs | Metallic Nanoparticles | 1.5 | 0.003-9 | 61 |
| GOx-CS-Nafion-AuNPs | Metallic Nanoparticles | 2.7 | .005-2.4 | 62 |

Figures 1, 2, 3, 3B:
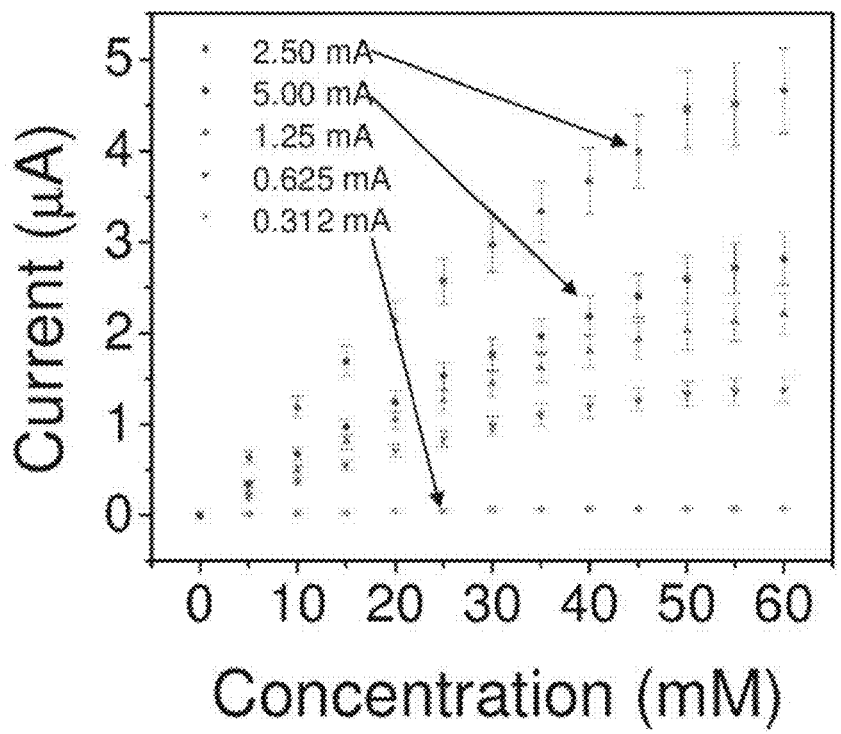
Figures 1, 2, 3, 3C:
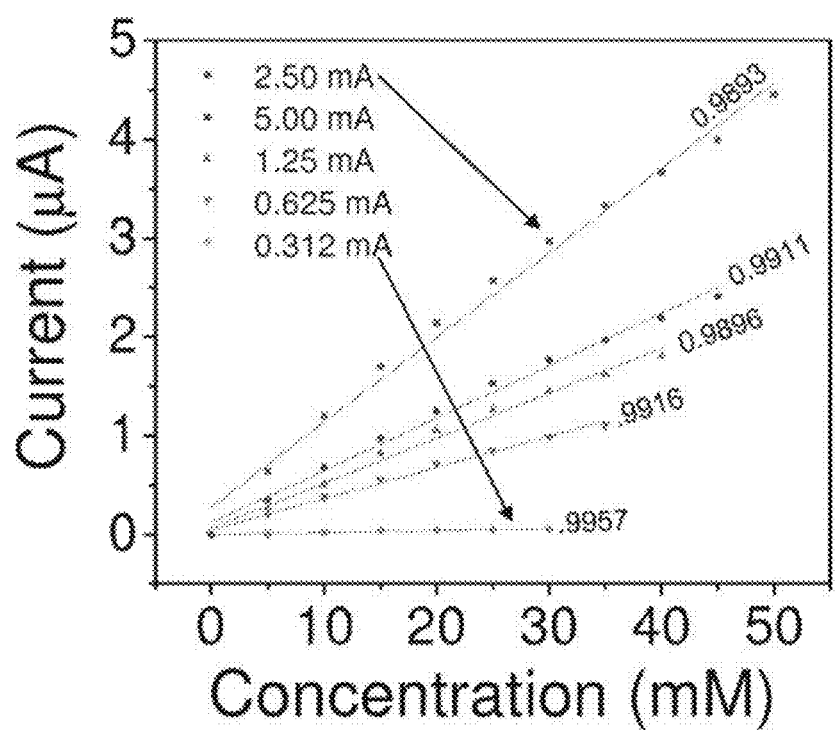

(GOx)—glucose oxidase, (xGnPs)—exfolidate graphite nanoplatelets, (Gn)—graphene, (Ppy)—polypyrrole, (MWCNT)—multi-walled carbon nanotubes, (SWCNT)—single-walled carbon nanotube, (PtNPs)—platinum nanoparticles, (AuNPs)—gold nanoparticles, (AuNWs)—Aunanowires, (CNx-MWCNTs)—nitrogen doped multi-walled carbon nanotubes, (Fc)—ferrocenecarboxaldehyde, (HRP)—horseradish peroxidase, (CS)—chitosan, (IL)—ionic liquid The sensing range of the optimized Pt-GPN biosensor was wider respectively then other nanostructured biosensors reported in the literature. Furthermore, the linear sensing range of the Pt-GPN biosensor not only enables glucose sensing within the physiological range for blood glucose found within healthy patients with blood glucose within the range of approximately 3.6 mM and approximately 7.5 mM (65 mg/dL-135 mg/dL) and diabetic patients with blood glucose within the range of approximately 1.1 mM and approximately 20.8 mM (20 mg/dL-350 mg/dL); it enables glucose sensing in saliva, tears, and urine as well—opening the door for unique glucose sensing paradigms were glucose levels from distinct human serums could be monitored simultaneously (FIG. 4a).

The durability of GOx/PEDOT electrodeposition technique was validated by performing glucose biosensing measurements over a 5 week period. Between weekly testing, the sensors were stored within a capped Petri dish with no refrigeration—mimicking off-the-shelf storage typical of home blood glucose monitoring systems. The sensitivity of the optimized Pt-GPN biosensor retained more than 75% of its sensitivity even after 5 weeks of testing—demonstrating the robust nature of the enzyme immobilization protocol with cyclic testing and storage (FIG. 4b).

The glucose selectivity of the PtNP-GPN glucose biosensors was tested by sensing glucose within three known electroactive species (uric acid (UA), acetaminophen (AP), and ascorbic acid (AA)), commonly found in human serum samples. A glucose concentration of 5 mM (which corresponds to a typical human blood glucose level) electrochemically monitored after the addition of 100 µM aliquots of AP, UA, and AA exhibits minimal interference from endogenous electroactive species as illustrated by FIG. 4c.

A glucose concentration of 5 mM was electrochemically monitored for all 5 sensors after physiological relevant concentrations (1 μM) of UA, AP, and AA were added to the test vial according to previous inference testing protocols. The percent ratio of current response for interfering substance to glucose is presented in Table 2. The Pt-GPN glucose biosensors that were created with respective Pt current pulses of 625 μA, 1.25 mA, and 2.5 mA maintain a minimal current response of UA, AP, and AA. Furthermore, the biosensor retains more than 75% of its sensitivity even after 5 weeks of use and storage at room temperature (~25° C.)

Various embodiments of the present invention pertain to the use of graphene petal nanosheets (GPNs) in an electrochemical biosensing application. The emergence of GPN is in its infancy within the research literature, but initial research has begun to uncover favorable electrochemical properties stemming from the exposed petal tips that exhibit the fast ET rates typically found in graphitic edge planes. Various embodiments include the concept of using the GPNs as templates for Pt nanoparticle growth to enhance the electro-reactivity of the petals and in effect present a nanoelectrode array fabrication protocol that eliminates the complexity of traditional NEA design that typically includes anodic alumina or polycarbonate templates and/or multi-step lithography steps. These Pt nanoparticle GPNs outperform conventional planar Pt nanoparticle/HOPG in terms of $H_2O_2$ sensitivity (~5:1 respectively), thus demonstrating the impact nanostructured, three dimensionally arrayed MGPNs fused with Pt nanoparticles can exhibit in electrochemical sensing.

The link between electrode nanostructuring and enzymatic biosensing sensitivity remains relatively unexplored in the literature. Various embodiments of the present invention illustration how Pt nanoparticle size, morphology, and density can modulated to improve the linear sensing range and the detection limit of the enzymatic biosensors. Some embodiments widen the glucose sensing range into the physiological concentration levels found in urine, tears, and saliva in addition to blood. Furthermore, the electrodeposition of GOx with PEDOT onto the PtNP modified GPNs enables robust glucose sensing with minimal interference for over one month from endogenous electroactive species commonly found in human serum samples. The results of the selectivity experiments can be explained in part by the electrodeposited PEDOT layer. The electrodeposition of PEDOT at high concentrations (>=1 mA) as performed in this work can over-oxidize carbon atoms on the polymer backbone—transforming the PEDOT polymer chain charge from positive to partially negative. Thus the electrodeposited PEDOT tends to repel negatively-charged electrochemical interferents (e.g., ascorbic and uric acid) due to electrostatic repulsion during electrochemical biosensing.

The bottom-up growth of GPNs on a silicon wafer, electrodeposition of Pt nanoparticles, and electrodeposition of enzyme encapsulated within the conductive polymer PEDOT are all scalable fabrication techniques that can be potentially integrated into a wide array of electronic devices. This highly sensitivity biosensing platform should be quite versatile as the GOx can be interchanged with other enzymes such as glutamate oxidase, lactate oxidase, and alcohol oxidase for the advancement of basic research and in-field biosensing associated with neurological disorders, patient trauma, food quality, and next generation bio-ethanol fuel technologies. Furthermore, various inventive embodiments incorporate these fabrication protocols into lab-on-a-chip platforms where the GPNs, PtNPs, and respective enzymes can all be electrodeposited onto distinct microelectrodes for multi-plexed biosensing purposes.

Using immobilized glutamate oxidase allows the testing of glutamate levels for the diagnosis and treatment of Alzheimer's disease, Parkinson's disease, and epilepsy. The technology can also be employed in a wide range of non-medical fields. Examples include incorporation of acetylcholinesterase enzyme to detect organophosphorus pesticides in agricultural applications, polyphenol oxidase to detect the presence of phenolic pollutants in environmental applications, and organophosphorus hydrolase to detect nerve-agents for national defense. The platform represents an enabling technology for the detection of miniscule quantities of a wide variety of analytes.

Various embodiments discussed above were fabricated using methods that will now be described. A thin film of Ti (100 nm) is e-beam evaporated onto an oxidized silicon wafer [P <100> Si (5 μm), $SiO_2$ (500 nm)] at a base pressure of 5.0×10−7 Torr. The metalized wafer is diced with a diamond-blade dicing saw (Disco DAD-2H/6) into equally-sized electrodes (0.35 cm$^2$) after a thin film of AZ1518 photoresist is spun and hard baked (10 min at 120° C.) unto the wafer to protect the surface during cutting operation. After wafer dicing, the electrodes are solvent cleaned with acetone, methanol, and isopropyl alcohol and subsequently dried under a gentle stream of $N_2$ gas to remove the photoresist and debris before GPN Synthesis.

The growth of the GPNs is carried out by microwave plasma chemical vapor deposition (MPCVD) with a SEKI AX5200S MPCVD reactor. The Ti coated silicon electrodes are elevated 6 mm above a 5.1 cm diameter molybdenum puck, placed inside the MPCVD reactor chamber and heated to 700° C. in a hydrogen ambient by a 3.5 kW radio-frequency power supply at a pressure of 30 Torr. A hydrogen plasma is generated over the sample via a 5 kW ASTeX AX2100 microwave generator, while methane ($CH_4$) gas, the acting precursor for GPN growth, is pumped into the chamber for 10 minutes at a flow rate of 10 SCCM. The hydrogen plasma decomposes the methane gas to permit monolithic GPN growth across the entire surface of the electrode (FIG. 1-1 a).

In an effort to improve the electroactive nature of the GPNs, the GPN electrode was exposed to an $O_2$ plasma etch within a Plasma Tech Reactive Ion Etch (RIE). The GPN electrode was placed inside the vacuum chamber of the reactor and pumped down to a base pressure of 0.1 mTorr to eliminate/minimize contaminating species that may have been introduced into the chamber during loading. $O_2$ was introduced into the chamber at a flow rate of 50 SCCM and the chamber pressure was adjusted to 60 mTorr. A $O_2$ plasma was generated over the GPN electrode for 30 seconds by setting the RF generator to the 100 W power setting.

A 3 electrode electrochemical set-up (BASi Epsilon Three-Electrode Cell Stand—potentiostat) where the GPNs acted as the working electrode, Pt gauze as the auxiliary electrode, and Ag/AgCl as the reference electrode were dipped within a plating bath consisting of 4 mM $H_2PtCl_6.6H_2O$ (Sigma Aldrich 206083) and 0.5 M $Na_2SO_4$ (Fluka 71960) to electrodeposit Pt nanoparticles onto the GPN electrodes. Current pulses (500 ms) of 312 uA, 625 uA, 1.25 mA, 2.5 mA and 5.0 mA were utilized in cycles of 250 to manipulate the size and density of Pt nanoparticles deposited on the GPNs.

Glucose oxidase is first mixed with Poly(3,4-ethylenedioxythiophene) (PEDOT) before it is electrodeposited onto the PtNP-GPN electrodes. The GOx/PEDOT solution is created by first mixing 0.1 M poly(styrenesulfonate) in $H_2O$.

Next, 0.03 M 3,4-ethylenedioxythiophene (Sigma Aldrich 483028) is added to the mixture while the solution is agitated. The enzyme glucose oxidase (GOx) (Sigma Aldrich G7141) is next added to the mixture in a concentration of 2 mg/ml. The subsequent PEDOT/GOx solution is electrodeposited onto each Pt-GPN electrode via constant current pulses of 1 mA that are applied between the working electrode (Pt-GPN) and auxiliary electrode (Pt gauze) for 500 cycles.

Although PEDOT has been tested, shown, and described in various embodiments of the present invention, other embodiments anticipate the use of any conductive polymers or, intrinsically conducting polymers, including any organic polymers that conduct electricity. Such compounds typically have metallic conductivity or can be semiconductors, and are organic materials. They can offer high electrical conductivity and preferably do not show similar mechanical properties to other commercially available polymers. The electrical properties can be fine-tuned using the methods of organic synthesis and by dispersion techniques. In one embodiment this enzyme could be glucose oxidase and the conductive polymer could be PEDOT which is produced by mixing poly(styrenesulfonate) in $H_2O$ and then adding M 3,4-ethylenedioxythiophene to the mixture while the solution is agitated. Then enzyme is added to this mixture before electrodeposition.

All electrochemical testing was performed in a 3 electrode set-up (BASi Epsilon Three-Electrode Cell Stand—potentiostat) where the GPN or PtNp-GPN electrodes acted as the working electrode, a Pt wire as the auxiliary electrode, and Ag/AgCl as the reference electrode. Amperometric hydrogen peroxide ($H_2O_2$) and glucose sensing experiments were performed in phosphate buffered saline (PBS, 0.1 M pH 7.4) at a working potential of 500 mV under constant stirring (500 rpm) with a 0.5 cm (length) magnetic stir bar while successive increasing concentration aliquots of said target analyte were pipetted into the testing vial. The Pt-GPN biosensors act as small electrochemical dipstick were the sensor region of the electrode (0.35 $cm^2$) is submerged in the testing solution and the other end is electrically wired to the potentiostat.

Raman spectroscopy was performed using T64000 system by Horiba Scientific. All the spectra were collected at room temperature using a laser excitation at 488 nm wavelength. The laser power was 2 mW and a 50× objective lens was used.

A S-4800 Hitachi microscope was utilized at a power setting of 5.0 kV to obtain all field emission scanning electron microscopy (FESEM) micrographs. No additional processing steps were required before image analysis.

Taking advantage of the high aspect ratio of the GPs and by varying the growth time, it is possible to identify a mechanism that explains the rapid growth of GPs from nanocones. There are at least two possible sources for C, leading to two different growth processes of the GPs: (i) a rapid growth mechanism from the top of a GP which is dominated by C species from the decomposition of $CH_4$, and (ii) a slower growth from the side of a GP which is governed by the precipitation and diffusion of carbon atoms from the substrate, forming multiple layers and thus allowing the GPs to grow in thickness as well as vertical height. There is also an inherent self-limiting aspect to the growth process. When smaller petals merge to form a larger interconnected network, the resultant petal structure forms an electrostatic equipotential surface, reducing the effect of the inhomogeneous, local electric field distribution, leading to a more uniform growth of GPs.

It is possible to develop techniques to control and confine the growth of GPs on flat substrates. Such a processing step is useful if the desirable properties of this high surface area form of C are to be utilized in practical applications. Controlling the rapid growth of GPs can be achieved by producing localized rough regions on a flat Si wafer. One way to accomplish this goal is to create a pattern of lines scratched into a $SiO_2$ layer. In this study, these lines were produced using a simple scribing tool. After scratching the oxide layer and subjecting the substrate to MPCVD growth conditions, highly localized regions of GPs were in fact observed to grow in patterned lines on the flat substrate. Complex patterns can be generated at the nanoscale using a diamond tip mounted to a microcantilever rastered across a substrate by a controller operating a contact mode AFM. A simple patterning technique will allow the controlled growth of GPs on oxidized silicon substrates for many promising practical applications.

The schematic diagram of the chamber is shown in FIG. 2-1. In brief, the plasma source consists of a 2.45 GHz frequency microwave power supply with variable power. Oxidized silicon wafers (p-type <111>) with different thicknesses of $SiO_2$ top layers were used as substrates. Unless otherwise stated, the substrate dimension in these experiments is 1×1 $cm^2$. The substrates, elevated 15 mm above a 55-mm-diameter Mo puck by ceramic spacers, were subjected to MPCVD conditions of $H_2$ (50 sccm) and $CH_4$ (10 sccm) as the primary feed gases at 30 Torr total pressure. The GP growth time varied from 30 s to 30 min to produce samples at different stages of growth. The substrates were initially exposed to hydrogen plasma for approximately 6 min, during which the plasma power gradually increased from 300 W to 700 W. At a plasma power of 300 W, visible plumes appeared at each corner of the substrate because of the high localized electric field. When plasma power increased to 700 W, the size of plumes increased, and eventually they coalesced to cover the entire substrate. This plasma is sufficient to heat the samples from room temperature up to ~1100° C., as measured by a dual-wavelength pyrometer (Williamson PRO 92). After introducing $CH_4$, the measured temperature decreases slightly to ~1000° C. To better understand the formation of the nanoscale cones, a lower plasma power (300 W) was used during GP growth for some experiments.

A Hitachi S-4800 field emission scanning electron microscope (FESEM) operated at 5 kV was used to study sample surface morphology. A FEI Titan 80-300 operated at 300 kV was utilized for a high-resolution transmission electron microscopy (HRTEM) to characterize structure of the as-grown GPs, as well as substrate/oxide and oxide/GP interfaces. The same instrument was equipped with Gatan imaging filter (GIF Tridiem, model 863), which allows acquisition of elemental mapping images via electron energy loss spectroscopy (EELS). TEM samples for GP structure analysis were prepared by scratching a sample surface with a razor blade to remove deposited material into a vial with acetone followed by ultrasonic bath treatment for several minutes, after which a drop of obtained suspension was put onto a lacey carbon 300 mesh copper TEM grid. For interface analysis, cross-sectional TEM samples were prepared by a focused ion beam (FIB) lift-out technique in a FEI Nova 200 dual beam SEM/FIB system equipped with a Klöcke™ nanomanipulator.

AFM imaging studies of bare $SiO_2$/Si substrates after etching by the hydrogen plasma were performed with a Veeco Dimension 3100 scanning probe microscope (SPM) using a NS-IV controller in tapping mode with a Pt—Ir coated Si tip (spring constant=1-5 N/m and resonant frequency=75 kHz). Raman characterization was performed with an Xplora spectrometer (Horiba Jobin Yvon Inc.) with a fixed laser excitation wavelength of 532 nm, power of 2.5 mW, spot size of 600 nm, and magnification of 100×.

Before GP growth, the effect of the hydrogen plasma on the substrates was investigated in order to understand the role, if any, of hydrogen plasma pretreatment prior to GP growth. As-received Si/SiO$_2$ substrates with a 500-nm-thick SiO$_2$ layer were etched in hydrogen plasma for approximately 6 min without introducing CH$_4$ into the chamber, corresponding to a null growth time. FIG. 2-2 shows FESEM images of the etched substrates. A gray-scale contrast boundary is evident in FIG. 2-2(a) located at the corner edge of the substrate and demarcates a region that has been significantly etched (darker region) as compared to the substrate's center (lighter region), where substrate etching occurs at a slower rate. FIG. 2-2(b) shows a close-up of the boundary between the dark and light regions. At the boundary, the lateral size of the localized etched oxidized silicon (EOS) features range from tens of nanometers to several micrometers. These EOS features were further studied using AFM imaging. FIG. 2-3 shows the results of parallel AFM studies which reveal a local roughening of the substrate with identifiable nanoscale trenches or fissures emanating in a roughly radial direction from a central point. AFM images of several EOS features indicate that the overall height can be a few hundred nanometers above the surrounding substrate.

The formation of these localized EOS features is directly attributed to exposure to the hydrogen plasma. The edge of the substrate couples to the plasma, producing a region with an enhanced electric field, causing the formation of a plasma sheath. The nature of the sheath depends on various parameters including the geometry of the substrate, its position inside the chamber, ionizing species in the plasma, the background pressure, and the plasma power. As shown in FIG. 2-1, the substrate is electrically isolated from ground, and hence acts as an electrically floating object immersed in the plasma. During hydrogen plasma etching, two processes occur in parallel. The first is an erosion of material from the SiO$_2$/plasma interface, causing a gradual reduction of the SiO$_2$ thickness. The second process is the diffusion of hydrogen atoms from the plasma through the oxide layer, causing an aggregation of H at the Si/SiO$_2$ interface. The localized trench-like surface morphologies observed in FIGS. 2-2 and 2-3 are assumed to result from reactions such as

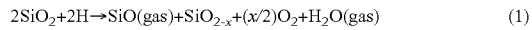

$$2SiO_2+2H \rightarrow SiO(gas)+SiO_{2-x}+(x/2)O_2+H_2O(gas) \quad (1)$$

which describes a process in which hot SiO and H$_2$O vapor escape from the SiO$_2$ substrate, causing a localized swelling across the surface. This reaction accelerates in regions where the electric field is relatively high (e.g., the edge of an oxidized silicon substrate) and gradually consumes the substrate as the etch front moves away from the substrate edges. Because of the release of SiO and H$_2$O vapor, radial-like trenches or fissures dominate the surface of EOS features. Because of the local electric field gradient from the edge to the center of the substrate, hydrogen plasma etching will be less prevalent in the middle regions of the substrate. As a result, EOS features of nanometer size with lower densities may predominate for short etch times. Upon introduction of a carbon source (methane) to the plasma, carbonaceous material will deposit on the substrate and undergo subsequent surface diffusion. The nanoscale trenches in the EOS features will efficiently trap diffusing carbon atoms, thus forming preferential sites for carbon aggregation. Carbon aggregation, along with direct carbon deposition onto the EOS regions, becomes one process for nucleation of fast growing GPs.

Focusing on GPs grown in the middle region of the oxidized silicon substrate enables a better understanding of the GP growth mechanism. A SiO$_2$/Si substrate with a 500-nm-thick SiO$_2$ top layer was placed inside the MPCVD chamber, and the plasma power was slowly ramped from 300 W to 700 W before introducing CH$_4$ at a flow rate of 10 seem to initiate GP growth for 15 min at a plasma power of 700 W. FIG. 3-1 shows tilted side-view and top-view SEM images from the middle region of the substrate subjected to these conditions. The emergence of nanoscale cone-like features with diameters ranging from 50 nm to a few 100 nm is evident.

Elemental mapping and HRTEM characterization (see FIG. 3-2) elucidate the chemical composition and structure of these nanocones. FIG. 3-2(a)-(d) contains a bright field TEM image, silicon map, oxygen map and carbon map, respectively, of a thin slice cut from a representative nanocone. The silicon map in FIG. 3-2(b) shows the extent of the silicon substrate used in these experiments. The oxygen map in FIG. 3-2(c) shows the extent of the SiO$_2$ layer, indicating that the core of the nanocone is SiO2.

The original SiO$_2$ layer thickness was 500 nm. After hydrogen plasma etching and roughening, the SiO$_2$ layer is reduced to roughly 150 nm in thickness. The carbon map in FIG. 3-2(d) shows a thin (~20 nm) carbon film conformally covering the surface of the sample. Interestingly, a bright region observed on the nanocone (marked by an arrow) indicates a locally enhanced concentration of carbon atoms. This bright region indicates where the rapid growth of a GP is likely to occur. Further HRTEM characterization of the SiO$_2$/C interface layer (FIG. 3-2(e)) confirms that the carbon film covering the surface of the nanocone is graphitic with interlayer spacing of 0.35 nm. The black smudges seen in FIG. 3-2(e) are Pt nanoparticles used to attach the sample during sample preparation.

The chemical composition of nanocones caused by the plasma etching may be based on the starting chemical composition of the substrate. Furthermore, a ~20 nm thick C layer conformally coats the SiO$_2$ nanocone and shows evidence for the formation of graphitic layers. All these findings are consistent with the conclusion that nanocones form preferential sites for C aggregation and lead to the rapid growth of GP at later stages.

The growth of GPs has been studied on oxidized silicon substrates which initially have a 500-nm-thick SiO$_2$ layer. In what follows, the GPs that grow for 15 min under a plasma power of 700 W are studied in further detail. FIG. 3-3 shows side-view FESEM images of GPs emerging from nanoscale cones. The growth is non-uniform across the substrate since the GPs are found to emerge from select regions of a few nanoscale cones. Contributing factors to this highly inhomogeneous growth environment are local electric fields, varying carbon deposition rates, and microscopic cone geometry. It seems clear that once conditions are favorable for GP growth, rapid emergence of a localized GP can result.

FIG. 3-3(a) shows nanoscale cones and GPs at a relatively large scale. FIG. 3-3(b)-(d) shows FESEM images of individual nanoscale cones from which GPs emerge. In FIG. 3-3(b), a GP grows along a radial direction from the cone axis. FIG. 3-3(c) shows a GP in the shape of a horn growing from a nanoscale cone decorated with visible trenches or fissures. The conical horn GP has a subtended interior cone angle of approximately 60°. The outer edge of the horn is not smooth, but faceted. FIG. 3-3(*d*) shows that a GP can be thin enough (less than 1 nm) to be semi-transparent in an FESEM.

FIG. 2-7 shows top-view FESEM images of rapidly growing GPs emerging from individual nanoscale cones. These images demonstrate that the rapidly growing GPs are confined to the cones. Slower growing GPs appear primarily in the flat areas between the nanocones. Some cones are decorated with a few large GPs, while others show a distribution of GP sizes.

Raman spectroscopy is often used to characterize the graphitic nature of the GPs. Within this context, three particular Raman peaks are useful. The D band at 1350 $cm^{-1}$ is known to result from various types of defects and anomalies of transverse optical vibrations near the K-point. The G peak at 1580 $cm^{-1}$ arises because of the doubly degenerate zone center E2g mode. The 2D band at 2700 $cm^{-1}$ is due to intervalley zone-boundary transverse optical phonon scattering. This peak consists of multiple sub-peaks and is difficult to analyze quantitatively if there are more than 5 graphitic layers.

FIG. 2-8 shows the Raman data from GPs for different growth times of 1 min, 5 min and 15 min. The $I_D/I_G$ and $I_{2D}/I_G$ ratios calculated from FIG. 2-10 for 5 min of growth are 0.38 and 0.65, respectively; those for 15 min of growth are 0.25 and 0.56, respectively. The decreasing presence of defects with growth time suggests that increasingly graphitic GPs are produced over time.

The atomic structures of the GPs were also investigated using HRTEM. FIG. 2-9(*a*) shows a representative TEM image of as-grown GPs. The left-most edge of this micrograph provides evidence for thin nanosheets. FIG. 2-9(*b*) shows a HRTEM image of a cross-section through a thin GP. The micrograph indicates that the petal is comprised of between 4 and 7 layers of graphene with a planar lattice spacing of approximately 0.35 nm.

In order to understand the nucleation and growth mechanism of GPs further, identical substrates were studied after different growth times in 700 W plasma (1, 7, 10, 20 min), keeping other parameters the same. Top-view FESEM images in FIG. 2-10 reveal the evolution of nanoscale comes and GPs throughout the growth process. FIG. 2-10(*a*) shows the substrate after 1 min of growth, when carbon deposits form nanoislands across the surface of the substrate; the same situation is observed in the case of growth for 30 s (not shown here). No GPs are observed for these short times, but the nanoislands are thought to be nucleation sites of GPs on Si substrates. FIG. 2-10(*b*) shows the emergence of GPs after 7 min of growth. Large GPs emerge from individual nanoscale cones. FIG. 2-10(*c*) shows the substrate after 10 min of growth. The co-existence of the smaller and larger GPs is now evident. FIG. 2-10(*d*) shows the substrate after 20 min of growth, when coverage of GPs fills the entire surface of the substrate.

These images support a mechanism whereby the oxidized silicon substrate is roughened by plasma etching while carbon is deposited on the substrate. Carbon diffuses across the substrate while preferential trapping occurs in localized EOS features. This leads to preferential GP growth from nanoscale cones during the initial stages of the growth process. As time increases, carbon diffusion across the entire substrate feeds the growth of GPs everywhere on the substrate, leading to a dense coverage of GPs.

To understand the influence of plasma power in the formation of GPs, experiments were performed in which the plasma power was varied, while fixing all other growth conditions. FIG. 2-11 shows top-view FESEM images of the GPs observed with two different plasma powers (300 W, 700 W) but the same growth time (7 min). As expected, GPs decorage the nanoscale cones (see the marked boundaries of a nanocones in FIG. 2-11 (*a*)) for a plasma power of 700 W. However, no nanoscale cones are observed on the substrates (even at the edge of the substrates) when the plasma power is reduced to 300 W (see FIG. 2-11 (*b*)). The fact that no nanoscale cones were observed for low plasma power suggests that plasma power intensity is an important factor in the formation of the nanoscale cones.

The plasma power directly influences two growth parameters: i) the final temperature of the substrate and ii) the intensity of electric field above the substrate. A low plasma power results in a lower temperature on the surface, which reduces the diffusion rate of the carbon atoms and thus reduces the growth rate of GPs. Evidently, the lower power also reduces the possibility of forming nanoscale cones. A low electric field leads reduces hydrogen plasma etching, which in turn hinders EOS formation and thus the formation of well-defined nanoscale cones. Eventually, GPs grow from the irregular and roughened $SiO_2$ surface due to the partial etching produced by the low-power hydrogen plasma, as shown in FIG. 2-11 (*b*).

Similar experiments have been performed on different substrates such as Ti/Si, Ni foil, and Cu foil in order to investigate whether similar nanocone formation occurs. Although all substrates produced GPs, no nanoscale cones were observed on these substrates (even for a high plasma power of 700 W) during early-stage GP growth. We conclude that the silicon dioxide layer and the high plasma power are primarily responsible for the formation of these nanoscale cone features.

The local growth of GPs is largely uncontrolled in the present process, occurring at random locations across a substrate. Different GPs grow at different rates, even though separated one from another by a fraction of a micrometer. To take advantage of the GP material properties, improved control of the growth process is needed. To this end, we highlight three processes that are all important to GP growth:

I. Carbon species that are directly adsorbed onto the outermost edge of GPs are helpful for rapid GP growth. This process uses an enhanced electric field in the plasma, due in part to the high aspect ratio of the GPs. Direct deposition of carbon material onto a petal edge and incorporation into an emerging petal allows for rapid GP vertical growth.

II. Carbon can also fall directly onto the substrate due to decomposition of CH in the plasma. While the rate of carbon deposition may be uneven due to a variety of factors (e.g., a shadowing effect produced by larger growing petals (see FIG. 2-7(*b*)), the deposited carbon will randomly diffuse until a GP nucleation site is encountered.

III. Carbon may be continually etched by the plasma, either from the uppermost edge of a GP or from the substrate itself. This point emphasizes the diversity of phenomena caused by the presence of hydrogen: i) as an etchant to remove amorphous carbon, ii) as a promoter of crystalline graphite by removing secondary nuclei that might interfere with GP growth, and iii) by eliminating cross-linking of carbon at free edges of growing GPs, thus preventing excessive edge thickening.

Expanding on Eq. (1), the following chemical reactions may occur on a nanoscale cone at elevated local temperatures:

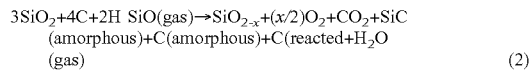

$$3SiO_2 + 4C + 2H\ SiO(gas) \rightarrow SiO_{2-x} + (x/2)O_2 + CO_2 + SiC$$
(amorphous)+C(amorphous)+C(reacted+$H_2O$
(gas)   (2)

In writing Eq. (2), subtle differences in C atoms present and distinguish between amorphous (unreacted) C and C that has reacted to form a variety of species such as C clusters and C nanoparticles. Analysis of the XPS spectrum collected as a function of deposition time clearly indicates a three-step process in which first a SiC layer is formed on the silicon, followed by an amorphous carbon layer which is then subsequently covered by few-layer graphene flakes. Throughout the process, the presence of SiC is important because it serves as a catalyst that facilitates the growth of carbon, either through precipitation and/or SiC decomposition.

GPs originate from the unreacted C species only, since once reacted to form C clusters, the C will exhibit a reduced diffusion coefficient. The local environment encountered by unreacted C is capable (under the proper set of conditions) of transforming amorphous carbon to ordered, graphitic-like carbon sheets that take the form of GPs. During the initial period of growth on an oxidized Si substrate, GPs grow rapidly from nanoscale cones.

Wherever nanoscale cones are formed, a very local enhanced decomposition of hydrocarbons into deposited C results, possibly due to the local enhancement of the electric field. Because C accumulate more rapidly on the conical structures as compared to flat regions of the substrate, the likelihood increases that precipitated C self-assembles on substrate features that promote multiple sets of graphitic planes that then rapidly emerge as vertically oriented GPs.

These insights suggest that by controlling the formation of nanopeaks, the rapid emergence of graphitic features can be patterned onto flat substrates in a prescribed way. One way to control the growth and formation of nanocones is to intentionally roughen a silicon substrate by inscribing a scratch in the 500-nm-thick oxide layer. The scratch will provide many sites that will seed the rapid growth of GPs.

FIG. 2-12 displays top-view and side-view FESEM images of a scratched substrate in an attempt to produce the controlled growth of nanocones and GPs. FIG. 2-12(a) shows three lightly scribed scratches in a Si substrate at low magnification after 6 min of growth at 700 W plasma power. FIG. 2-12(b) shows a magnified top-view image of one scratched area in FIG. 2-12(a) (indicated by the rectangular box) where preferential GP growth is evident. FIG. 2-12(c) is a magnified image of FIG. 2-12(b) showing that the GPs are seeded by the formation of nanocones (see arrow). FIG. 2-12(d) is a typical cross-sectional FESEM image of a wafer edge that was produced by cleaving the substrate perpendicular to a scratched line. FIG. 2-12(d) indicates a reduced oxide layer thickness in the scratched area of ~250 nm after the hydrogen plasma etching during the growth process. Cross-sectional SEM images of other scratched lines reveal reduced oxide layer thicknesses in the range of 150 to 300 nm. The roughened surfaces in these cross-sectional images further corroborate the contention that GPs grow from nanocones, in agreement with the top-view SEM characterization in FIG. 2-12(c). Further experiments show that preferential GP growth is confined to all scratched lines we have tested to date.

Factors influencing the formation and structure of graphitic petals (GPs) grown by microwave plasma-enhanced chemical vapor deposition on oxidized silicon substrates are investigated through process variation and materials analysis. Some graphitic petals are found to grow at an accelerated rate, often growing approximately 20 times faster than other petals located only a fraction of a micrometer away. Using scanning electron microscopy and atomic force microscopy, the rapid growth rate of these fast-growing petals is attributed to the formation of nanoscale cones in the plasma etched S1O2 layer (see FIG. 3.1). Electron energy loss spectroscopy reveals that the formation of these nanoscale cones is associated with a localized roughening of the oxidized silicon substrate a process that depends on plasma power. Raman spectroscopy and transmission electron microscopy are used to confirm the graphitic nature of the as-grown petals. Insights gained into the growth mechanism of these graphitic petals suggest a simple scribing method can be used to control both the location and formation of petals on flat Si substrates. Experiments performed to test this hypothesis show that controlled petal growth can be achieved, a development that enables an exploitation of the graphitic petal properties in many practical applications.

Elemental mapping and high-resolution transmission electron microscopy (HRTEM) characterization (see FIG. 3.2) elucidate the chemical composition and structure of these nanocones. FIGS. 3.2a-d disclose a bright field TEM image, silicon map, oxygen map and carbon map, respectively, of a thin slice cut from a representative nanocone. The silicon map in FIG. 3.2b shows the extent of the silicon substrate used in these experiments. The oxygen map in FIG. 3.2c shows the extent of the $SiO_2$ layer, indicating that the core of the nanocone is $SiO_2$. The original $SiO_2$ layer thickness was 500 nm. After hydrogen plasma etching and roughening, the $SiO_2$ layer is reduced to roughly 150 nm in thickness. The carbon map in FIG. 3.2d shows a thin (approximately 20 nm) carbon film conformally covering the surface of the sample. Interestingly, a bright region observed on the nanocone (marked by an arrow) indicates a locally enhanced concentration of carbon atoms. This bright region indicates where the rapid growth of a GP is likely to occur. Further HRTEM characterization of the $SiO_2$/C interface layer (FIG. 3.2e) confirms that the carbon film covering the surface of the nanocone is graphitic with interlayer spacing of 0.35 nm. The black smudges seen in FIG. 3.2e are Pt nanoparticles used to attach the sample during sample preparation.

FIG. 3.3 shows side-view FESEM images of GPs emerging from nanoscale cones after 15 min of growth under a plasma power of 700 W. FIG. 3.3a shows nanoscale cones and GPs at a relatively large scale. FIGS. 3.3b-d show FESEM images of individual nanoscale cones from which GPs emerge. In FIG. 3.3b, a GP grows along a radial direction from the cone axis. FIG. 3.3c shows a GP in the shape of a horn growing from a nanoscale cone decorated with visible trenches or fissures. The conical horn GP has a subtended interior cone angle of approximately 60°. The outer edge of the horn is not smooth, but clearly faceted. FIG. 3.3d shows that a GP can be thin enough (less than 1 nm) to be semi-transparent in an FESEM.

Yet another embodiment pertains to a hybrid manganese dioxide/graphitic petal structure on carbon nanotube substrates to achieve high specific capacitance, energy density, power density, and long cycle life for flexible supercapacitor application. Vertical nanoscale graphitic petals were prepared by microwave plasma chemical vapor deposition on commercial carbon nanotube substrates and subsequently coated with a thin layer of $MnO_2$. The thickness is controlled by the immersion time. An immersion time of 40 minutes was arbitrarily chosen in our study. We think this gives a $MnO_2$ coating of 5-10 nanometers thick.

To make composites suitable for electrochemical electrodes, prior to $MnO_2$ coating or electrochemical measurement, concentrated $H_2SO_4$ and $HNO_3$ (volume ratio 3:1) were used to functionalize the surface of GPs at 50° C. for 2 hours in an oven. The samples were then washed by deionized water and dried at 100° C. overnight. A neutral precursor solution (~pH 7) for the $MnO_2$ coating process was prepared by mixing 0.1 M $Na_2SO_4$ (Alfa Aesar) and 0.1 M $KMnO_4$ (Alfa Aesar) solutions. The GPs grown on BP were immersed into the solution, which was kept at 80° C. in an oven for 40 min. The loading amount can be easily controlled by adjusting the immersion time. The sample was then rinsed with deionized water and subsequently annealed at 200° C. for 3 hours using a hotplate in air. The mass of coated $MnO_2$ was calculated from the weight difference before and after the coating process.

The graphitic petal/carbon nanotube architecture without any binder provides an efficient scaffold for maximizing the electrochemical performance of $MnO_2$. A specific capacitance (based on the mass of $MnO_2$) of 579 F/g is obtained at a scan rate of 2 mV/s in 1 M $Na_2SO_4$ aqueous electrolyte. The energy density and power density at 50 Ag are 28.2 Wh/kg and 24.5 kW/kg (with a maximum value of 114 kW/kg), respectively. In addition, the composite electrode shows long-term cyclic stability (less than 10% decrease of specific capacitance after 1000 cycles). Such behavior indicates that the $MnO_2$/graphitic petal/carbon nanotube composite is a promising electrode material for high-performance supercapacitors. Density functional theory indicates that coating of $MnO_2$ on the surface of GPs enhances the conduction path of the electron transport during the charge/discharge process.

SEM images of GPs synthesized by MPCVD are shown in FIG. 3.6a. The petals extend approximately 500 nm out from the BP surface, and the typical span width of a single unwrinkled 2-D grain ranges from 100 nm to 500 nm. The thickness of a GP layer can reach several nanometers, corresponding to less than 50 graphene layers. A magnified image of one petal marked by the rectangular box in FIG. 3.6a is shown in FIG. 3.6b, revealing the smooth surfaces of the GPs. These surfaces provide accessible sites for $MnO_2$ coating. The crumpled structures of the vertical graphene sheets with both sides exposed to $MnO_2$ precursor solution can provide large specific area for coating. FIG. 3.6c shows the morphology of $MnO_2$ coated on GPs. FIG. 3.6d contains a magnified image of the area marked by the rectangular box in FIG. 3.6c, showing a thin uniform layer of $MnO_2$ on the smooth GP surfaces, even on the smaller petals. FIG. 3.7a shows the cyclic voltammetry (CV) curves of the $MnO_2$/GP/BP composites at scan rates of 2, 5, 10, 20, 50, 100 mV/s in 1 M $Na_2SO_4$ aqueous solution with potential windows ranging from 0 to 0.8 V. The constant-current charge/discharge curves of the as-prepared $MnO_2$/GP/BP hybrid structure at different current densities are shown in FIG. 3.7b. The charge/discharge curves display a symmetric shape, indicating that the structure has a good electrochemical capacitive characteristic. FIG. 3.7c shows comparative specific capacitances of BP, GP/BP, $MnO_2$/BP and $MnO_2$/GP/BP calculated from CV curves at voltage scan rates from 2 to 100 mV/s. At a scan rate of 2 mV/s, the specific capacitance of the $MnO_2$/GP/BP hybrid composite reaches 579 F/g (based on the mass of pristine $MnO_2$). At a high scan rate of 100 mV/s, the specific capacitance of $MnO_2$/GP/BP still remains close to 320 F/g, which is comparable to the rate performance reported elsewhere. However, for the same $MnO_2$ coating time, the specific capacitance of $MnO_2$/BP is only about 266 F/g (based on pristine $MnO_2$) at 2 mV/s (see FIG. 3.7c). The superior rate capability of $MnO_2$/GP/BP composites demonstrates the advantages of this new architecture of GP/BP as a highly conductive scaffold for maximizing the utilization of the practical electrochemical performance of $MnO_2$. Since previous studies show that only a thin layer of $MnO_2$ is involved in the charge storage process, the specific capacitance of $MnO_2$ coated on the supporting GP/BP can be further improved by optimizing the thickness of coated $MnO_2$ layer. FIG. 3.7d shows the Ragone plot for the $MnO_2$/GP/BP structured electrode at different current densities. At a high current density of 50 A/g, the calculated energy density is 28.2 Wh/kg, and the average power density is 24.5 kW/kg. The maximum power density, calculated from $V^2/4RM$, is found to be 114 kW/kg. These values are higher than the reported energy density (14.8 Wh/kg) and power density (2.5 kW/kg) of electrodeposited $MnO_2$ films on BP substrates, suggesting that as-prepared composite is a promising electrode material for supercapacitors.

Another embodiment pertains to the design and fabrication of a hybrid three-dimensional nanoarchitecture by electropolymerizing aniline monomers into a nanometer-thick conformal polyaniline (PANI) film on graphitic petals (GPs) that are directly grown on highly conductive carbon cloth (CC) through microwave plasma enhanced chemical vapor deposition (MPCVD) for flexible supercapacitor application. The hybrid CC/GPs/PANI electrodes yield greatly improved capacitive performance with a high specific capacitance of approximately 2000 F/g (based on PANI mass), close to the theoretical capacitance, and a large area-normalized specific capacitance of approximately 2.5 $F/cm^2$ (equivalent to a volumetric capacitance of approximately 230 $F/cm^3$) at 1 A/g. The hybrid electrodes also exhibit an rate capability with an energy density of 109.9 Wh/kg and a maximum power density of 265.1 kW/kg at a high current density of 100 A/g, respectively, and long-term cycling stability (approximately 7% loss of its initial capacitance after 2000 cycles), with a coulombic efficiency of approximately 99.8%. Moreover, all-solid-state flexible supercapacitors based on the hybrid CC/GPs/PANI electrodes are also fabricated, which show beneficial electrochemical properties, outperforming the reported all-solid-state flexible supercapacitors up to date. Such improved performance indicate that the hybrid nanocomposite electrodes can be used for supercapacitors.

FIG. 3.9A shows the morphology and microstructure of pure carbon cloth at low (FIG. 3.9A inset) and high magnifications. The diameter of a carbon fibre in the carbon cloth is approximately 9 microns. The surface of a carbon fibre is relatively smooth. FIG. 3.9B displays the morphology and microstructure of GPs fully covering carbon fibres at low and high (FIG. 3.9B inset) magnifications. GPs are grown approximately 500 nm out from the carbon fibre surface and the typical span width of a single unwrinkled two-dimensional (2-D) plane ranges from 100 nm to 500 nm. The thickness of the 2-D GP plane can reach several nanometers, corresponding to less than 50 graphene layers. TEM characterizations of such GPs on carbon fibers indicates that the fiber-petal transition is continuous which facilitates electron transport at the interface between carbon fibers and GPs. The diameter of a carbon fibre decorated with GPs does not change noticeably.

FIGS. 3.9B (inset) and 3.9C are comparative SEM images of GPs before and after electrochemical polymerization. Apparently, before the electrochemical polymerization, 2-D unwrinkled GP surfaces are thin and smooth; however, after electrochemical polymerization for 5 min, PANI are conformally coating GP surfaces, making them rougher and relatively thicker. The PANI mass can be easily adjusted by controlling the electrochemical polymerization time. FIG. 3.9D shows comparative Raman spectroscopy of CC, CC/GPs and CC/GPs/PANI. Apart from the D and G bands in the Raman spectroscopy of CC/GPs/PANI hybrid materials, another two new representative peaks (circle indicated), indexed at 1167 $cm^{-1}$ and 1468 $cm^{-1}$, are due to the presence of PANI structure, corresponding to C—H vibrations in quinoid/phenyl groups and semiquinone radical cation structure in PANI.

FIG. 3.10A displays the comparison of area-normalized specific capacitance of Pure CC, CC/GPs, CC/PANI and CC/GPs/PANI at different scan rates. Electrochemical polymerization time for both CC/PANI and CC/GPs/PANI electrodes are 5 min. Pure CC contributes negligible area-normalized specific capacitance to the electrodes (0.01 $F/cm^2$ at a scan rate of 2 mV/s). After decorating GPs on CC by PECVD method, the area-normalized specific capacitance of the composite electrode reaches 0.7 $F/cm^2$ at a scan rate of 2 mV/s and decreases slightly with increasing scan rate. In order to demonstrate the structures of GPs in the electrochemical charge storages in some embodiments, a pure CC is electrochemically coated with PANI for comparison with the hybrid composite electrode of CC/GPs/PANI with the same PANI electropolymerization time (5 min). At a scan rate of 2 mV/s, the area-normalized specific capacitance of CC/GPs/PANI reaches 1.84 $F/cm^2$, approximately one order of magnitude higher than that of CC/PANI (0.19 $F/cm^2$). At a scan rate of 100 mV/s, the area-normalized capacitance remains 71%, higher than the reported value in reduced graphene oxide/PANI electrodes containing binder (approximately 50% retention at 100 mV/s), indicating beneficial rate capabilities of the hybrid CC/GPs/PANI electrode.

To find out how GP structures affect the efficiency of PANI in the pseudocapacitive reactions with acidic electrolyte, FIG. 3.10B shows the comparison of mass specific capacitance based only on PANI for both pure CC and CC/GP substrates. Apparently, PANI coated on CC/GP substrates has much higher mass specific capacitance than that on pure CC substrates. At a scan rate of 2 mV/s, the mass specific capacitance of PANI is approximately 3 times as high as that on pure CC, indicating that the unique GP structures play a synergetic role utilizing PANI in electrochemical reactions. FIG. 3.10C shows the Ragone plot for the CC/GPs/PANI composite electrode at the potential window of 0.8 V in 1 M $H_2SO_4$ aqueous electrolyte. The energy density decreases from 202.2 to 109.9 Wh/kg, while the maximum power density increases from 118.5 to 265.1 kW/kg, as the galvanostatic charge/discharge current increased from 1 to 100 A/g. FIG. 3.10D shows the specific capacitance retention of the CC/GPs/PANI hybrid electrode as a function of charge/discharge cycling numbers. The composite electrode showed approximately 7% loss in the capacitance after 2000 charge-discharge cycles, indicating excellent long-term stability. Coulombic efficiency of the hybrid electrode is approximately 99.8%, indicating high efficiency of the rapid electron-transfer for charge storage and delivery.

FIG. 3-5A shows the schematic illustration of all-solid state highly flexible CC/GPs/PANI supercapacitors based on PVA-$H_2SO_4$ polymer gel electrolyte. Galvanostatic charge/discharge performances were carried out on an individual flexible device in FIG. 3-5B, which shows that charge/discharge curves of a CC/GPs/PANI paper-like supercapacitor at different constant current densities ranging from 1 A/g to 50 A/g. Comparison of the specific energy and power density (per $cm^3$ of stack) of typical electrolytic capacitors, supercapacitors and batteries in a Ragone plot is shown in FIG. 3-5C. It compares the performance of our all-solid-state flexible device with the current various kinds of state-of-the-art commercial energy storage devices. The CC/CPs/PANI based supercapacitor exhibit energy densities of up to 3.38 mWh/$cm^3$, a value that reaches the upper range of the lithium thin-film battery and almost approximately 10 times as high as that of the commercial 3.5V/25-mF supercapacitor. The cycling life tests over 1000 cycles for the CC/GPs/PANI hybrid electrode at a current density of 5 mA/$cm^2$ were carried out using constant current galvanostatic charge/discharge cycling techniques in the potential windows from 0 to 0.8 V, as shown in FIG. 3-5D. Approximately 10% loss in capacitance after 1000 cycles and coulombic efficiencies of the hybrid electrode of approximately 99.5% were measured for the device, indicating a relatively good stability and high efficiency of the rapid electron-transfer for charge storage and delivery. To show the practical application of highly flexible and all-solid-state paper-like supercapacitors, we prepared three supercapacitor units (each size approximately 0.5 cm×approximately 2.0 cm) in series to light a green light-emitting-diode (LED, the lowest working potential is 1.5 V). The as-prepared supercapacitor group shows no performance degradation when in highly flexible conditions, as shown in FIG. 3-5E. CV curves of the supercapacitor group (scanning from 0 V to 2.5 V) in both normal and bend conditions almost overlaps, indicating the highly flexibility of the device. FIG. 3-5F demonstrated that three highly flexible devices in series, wrapped around a glass rod (inset), were used to light a green LED well. After being charged at 2.5 V for 15 min, the highly flexible device could light the LED very well for more than 30 min.

Symmetric micro-supercapacitors can include several-micrometer-thick layer graphitic petals, synthesized by micro-wave plasma enhanced chemical vapor deposition and patterned by conventional optical lithography and reactive ion etching techniques on oxidized silicon substrate. High charge/discharge rates up to 100,000 mV/s, three orders of magnitude higher than conventional supercapacitors, have been measured for the microdevices in 1 M $H_2SO_4$ aqueous electrolyte. After electrochemical oxidation of the graphitic petals, a high volumetric capacitance of approximately 270 F/$cm^3$ (equivalent to an area-normalized capacitance of 108 mF/$cm^2$) was calculated at a scan rate of 20 mV/s, two orders of magnitudes higher than before the electrochemical oxidation, while still maintaining high charge/discharge rates. The micro-meter sized device exhibited an energy density of 4 mWh/$cm^3$ (approximately 1.6 Wh/$cm^2$) and a power density of 48 W/$cm^3$ (approximately 192 mW/$cm^2$) at a current of 100 μA and excellent cyclic stability (1% capacitance loss after 1,500 cycles).

FIG. 4.1A shows SEM images of the GP micropatterns with Ti/Au coated on the top of the surfaces. The SEM images show that the width of the electrodes and the gap between are 30 μm and 35 μm, respectively. FIG. 4.1 B displays a magnified SEM image of micro-patterns, showing that Ti/Au metal films are coated on the surface of the GPs. FIG. 4.1 C shows side-view SEM images of GP micropatterns at a low magnification and a high magnification (inset). The thickness of the GP micro-electrodes is approximately 4 μm. The inset image shows the morphology of the GP structures with sharp edges. The thickness of the first layer of CNWs is typically limited to several micrometers generally <3 µm because of the restricted intrinsic electric field strength across the sheath region. The thickness of the two dimensional (2D) carbon nanowalls (or the first carbon nanowalls layer) to reach approximately 2 µm. In order to achieve 3D GP growth, apart from the first 2D GP layer growth, a second growth was carried out by MPCVD after functionalizing the first 2D layer with —O⁻ or —COO⁻ groups by oxidizing them in 2 M $HNO_3$ at 95° C. for 6 h. In this process, 3D GP networks can be easily synthesized by a one-step method because of the unique setup during the growth process (elevated substrates). The thickness of the GP electrode can be controlled by the growth time and plasma power. 3D GP networks comprise many GP layers nesting on each other, demonstrated by the boundaries of the GP layers outlined in FIG. 4.1 D.

FIG. 4.3A shows specific capacitances vs. scan rates (as high as 100,000 mV/s) of GP-based micro-supercapacitors before electrochemical oxidation. The volumetric capacitances calculated for GP electrodes in 1 M $H_2SO_4$ electrolyte is higher than the reported values (1.3 $F/cm^3$) for OLCs in 1 M $Et_4NBF_4$/anhydrous propylene carbonate. After electrochemical oxidation of the graphitic petals, a high volumetric capacitance of approximately 270 $F/cm^3$ (equivalent to an area-normalized capacitance of 108 $mF/cm^2$) was calculated at a scan rate of 20 mV/s (see FIG. 4.3B), two orders of magnitudes higher than before the electrochemical oxidation, while still maintaining high charge/discharge rates. At 10,000 mV/s, the volumetric capacitance of the micro-device remains 75 $F/cm^3$. FIG. 4.3C shows the Ragone plot energy density versus power density for as-prepared micro-supercapacitors and the up-to-date reported values for different materials—rGO in both sandwich (rGO-S) and planar (rGO-P) structures, ACs, OLCs and carbon micro-beads (CMBs) in organic electrolytes. Noticeably, the volumetric power and energy densities of GP-based micro-supercapacitors with aqueous electrolytes are comparable to or even higher than up-to-date micro-supercapacitors with organic electrolytes, indicating the potential of using such structures in electrodes for micro-power application. FIG. 4.3D shows the micro-supercapacitors exhibits good cyclic stability (1% capacitance loss after 1,500 cycles).

CNTs, particularly vertical aligned CNT arrays (VCNTs), exhibit usefulness as supercapacitor electrode materials. Therefore, new fabrication techniques are still needed to achieve high ordered CNT array electrodes with excellent horizontal electronic properties and mechanical robustness. In this disclosure, GPs were selectively grown on CNT patterns for micro-supercapacitor electrode application. The uniqueness of the GP strengthening CNT vertical arrays overcomes the problems: (1) GPs intercalate CNTs arrays, further reduces the contact resistance between CNTs and also improves contacts between CNTs and bottom metal layers. (2) GPs enhance the mechanical robustness of the VCNT arrays and the orientation of VCNT arrays maintains when wetted by electrolytes, which facilitates ion diffusion during charge and discharge process. (3) GPs further increase surface area of the electrodes and thus increases specific capacitances. The schematic of fabrication process of GP/CNTs are showing in FIG. 4.4.

Before the growth, Ti/Al/Fe tri-layer catalysts (30/10/5 nm) were deposited on Si/SiO₂ wafer by Vecco thermal evaporator at a base pressure of $1.0×10^{-7}$ Torr. Then the substrates are loaded on a 55-mm-diameter Mo puck in the MPCVD chamber. During the growth of the CNT micro-conduits, $H_2$ (50 sccm) and $CH_4$ (10 sccm) were introduced as gas sources, with a pressure of 10 Torr total pressure. The plasma power during the growth was 300 W and the substrates were heated to 800° C. The CNT growth time in this work was 30 min.

For the selective growth of GPs on CNTs, as-prepared CNT patterns on Si/SiO₂ substrates, elevated 15 mm above a 55-mm-diameter Mo puck by ceramic spacers, were subjected to the same MPCVD system with a condition of $H_2$ (50 sccm) and $CH_4$ (10 sccm) as the primary feed gases at 30 Torr total pressure. The GP growth time was 6 min. The plasma power is 500 W during the growth process. This plasma is sufficient to heat the samples from room temperature up to approximately 1100° C., as measured by a dual-wavelength pyrometer (Williamson PRO 92).

FIG. 4.5A shows SEM characterization of interdigitated CNT/GP patterned electrodes for micro-supercapacitors at a low magnification. The spaces between two adjacent electrodes are 100 µm and GP-free zones. FIG. 4.5B shows a tilted SEM image of a CNT/GP electrode. FIGS. 4.5C and 4.5D are a top-view and side-view SEM images of CNT/GP electrodes, respectively.

FIG. 4.6 shows the electrochemical characterization of CNT/GP patterned electrodes for micro-supercapacitors. FIG. 4.6A shows the cyclic voltammetry curves of patterned CNT/GP electrodes at different scan rates in 1 M $H_2SO_4$ aqueous electrolyte. FIG. 4.6B shows the charge/discharge curves of CNT/GP-CNT/GP electrodes at different current densities. FIG. 4.6C displays comparative CV curves of micro-supercapacitors based on CNT-CNT and CNT/GP-CNT/GP electrodes at a scan rate of 20 mV/s. FIG. 4.6D displays comparative CV curves of CNT and CNT/GP electrodes at a scan rate of 20 mV/s in a three-electrode system (Ag/AgCl as a reference electrode). Both FIGS. 4.6C and 4.6D show that decorations of GP on arrays significantly reduces the internal resistances, making the CV curves more rectangular.

Materials, facilities and experiments: Ni foam (MTI Corp., thickness: 1.6 mm, purity>99.99%, surface density: 350±30 g/m^2 and porosity: ≥95%) was used as a 3-D template to grow GPs in a MPCVD system. Before the growth, the Ni foam was compressed (700 LBs press force, Fairweather, model: HIP 1-β) from 1.6 mm to 110 µm in order to couple well with hydrogen plasma. The Ni foam substrate, with a diameter of 12 mm, was elevated 17 mm above a Mo puck by ceramic spacers. The sample was subjected to MPCVD conditions of $H_2$ (50 sccm) and $CH_4$ (10 sccm) as the primary feed gases at 20 Torr total pressure. The plasma power was 500 W. The growth time was 30 min. The Ni foams covered with graphite petals were immersed in a PMMA solution (4 wt % in ethyl lactate), and then baked at 180 C for 30 min. The samples were then put into a 3M HCl solution at 80° C. for 5 h to completely dissolve the nickel to obtain GP foam-PMMA composite. Finally free-standing GP foams were obtained by dissolving the PMMA with hot acetone at 55° C. SEM images of free-standing GP foams (see FIGS. 4.7*a-c*) after removing Ni templates can be seen as in FIGS. 4.7*d* and 4.7*e*. GP ligaments can be as thin as 1 µm with a hollow channel inside (See FIGS. 4.7*e*).

Ti/Al/Fe tri-layer catalysts (30/10/5 nm) were deposited on carbon cloth substrates by Vecco thermal evaporator at a base pressure of $1.0×10^{-7}$ Torr. Then the substrates are loaded on a 55-mm-diameter Mo puck in the MPCVD chamber. During the growth of the CNT micro-conduits, $H_2$ (50 sccm) and $CH_4$ (10 sccm) were introduced as gas sources, with a pressure of 10 Torr total pressure. The plasma power during the growth was 300 W and the substrates were heated to 800° C. After 10 min of growth, CNTs are growing on the surface of carbon microfibers in the shape of conduits, with an outer diameter of 30-40 μm, as shown in FIGS. 4.8a and 4.8b.

For the growth of GPs on CNT micro-conduits, as-prepared CNT/CC substrates, elevated 15 mm above a 55-mm-diameter Mo puck by ceramic spacers, were subjected to the same MPCVD system with a condition of $H_2$ (50 sccm) and $CH_4$ (10 sccm) as the primary feed gases at 30 Torr total pressure. The GP growth time was 25 min. The plasma power is 500 W during the growth process. This plasma is sufficient to heat the samples from room temperature up to approximately 1100° C., as measured by a dual-wavelength pyrometer (Williamson PRO 92). FIG. 4.9 displays the SEM images of GPs grown on surfaces of CNTs. FIG. 4.9a shows CNT/GP micro-conduits on CC substrates at a lower magnification. The shape of CNT/GP micro-conduit is similar to CNT conduit on CC. FIG. 4.9b displays a CNT/GP micro-conduit in a heart shape. FIGS. 4.9c and 4.9d show GPs decorating CNT structures at a higher magnification. The typical span width of a single unwrinkled 2-D plane ranges from 100 nm to 200 nm. The thickness of the 2-D GP planes can reach several nanometers, corresponding to less than 50 graphene layers. CNT/GP micro-conduit consists of a lot of tree-branch structures, in which CNTs serves as a branchlet and GPs as leaves as illustrated in FIG. 4.9d.

There are several aspects of CNT micro-conduits decorated by GP structure: (1) GPs increase the specific areas of the CNT structure. (2) GPs improve the mechanical properties of CNT micro-conduits by intercalating CNT tightly together. The enhanced mechanical robustness of these CNT/GP micro-conduits was demonstrated by using concentrated acid to modify the CNT/GP micro-conduit surfaces. After concentrated acid treatment ($H_2SO_4$:$HNO_3$ volume ratio=3:1) at 40° C. for 3 hours, the CNT/GP micro-conduit structure still maintains. (3) GPs further improve the electron conductivity of the conduit and reduce contact resistance between CNTs.

Cyclic voltammetry characterization of CNT/GP micro-conduit electrodes with different scan rates in a three-electrolyte system is shown in FIG. 4.10. A specific capacitance of as high as 0.8 F/cm$^2$ at 2 mV/s was achieved, indicating that the hybrid electrodes are ideal candidates as electrodes for electrochemical supercapacitors and lithium ion batteries.

Hybrid manganese dioxide/graphitic petal structures grown on carbon nanotube substrates are shown to achieve high specific capacitance, energy density, power density, and long cycle life for flexible supercapacitor applications. Vertical nanoscale graphitic petals were prepared by microwave plasma chemical vapour deposition on commercial carbon nanotube substrates and subsequently coated with a thin layer of $MnO_2$. The graphitic petal/carbon nanotube architecture without any binder provides an efficient scaffold for maximizing the electrochemical performance of $MnO_2$. A specific capacitance (based on the mass of $MnO_2$) of 580 F/g is obtained at a scan rate of 2 mV/s in 1 M $Na_2SO_4$ aqueous electrolyte. The energy density and power density at 50 Ag are 28 Wh/kg and 25 kW/kg, respectively. In addition, the composite electrode shows long-term cyclic stability (less than 10% decrease in specific capacitance after 1000 cycles) while maintaining a small internal resistance. Parallel density functional studies were performed to investigate the stability and electronic structure of the $MnO_2$/graphene interface.

Electrochemical capacitors (ECs), known as supercapacitors or ultracapacitors, with high power density, fast power delivery and long cycle life, promise to complement or even replace batteries in energy storage applications such as uninterruptible back-up power supplies, load-leveling, portable electronics, hybrid electronic vehicles and renewable energy systems. To achieve high power and high energy density, suitable electrode materials should undergo fast reversible redox reactions. Metal oxides {e.g., $MnO_2$, $RuO_2$, VO, $Fe_2O_3$) offer high pseudocapacitance through fast and reversible redox reactions near the surface of active materials. Because of its high specific capacitance (720 F/g), $RuO_2$ is one of the most promising candidates for ECs. $MnO_2$, with low cost, low toxicity, and most importantly high theoretical specific capacitance (~1370 F/g) has attracted much attention as a pseudocapacitive electrode material. However, its poor electric conductivity ($10^{-5}$-$10^{-6}$ S/cm) and its tendency to function capacitively in thin surface layers create practical challenges to realizing its high theoretical capacitance.

Carbon materials {e.g., carbon nanotubes, carbon fibres, activated carbon, graphene) are useful as supercapacitor electrodes due to high specific area, high conductivity and low mass density. Among these, vertical graphene nanosheets or graphitic petals (GPs) are useful as active electrode materials in ECs. However, to date, this highly conductive and two-dimensional (2-D) carbon nanosheet structure as a nanotemplate has not yet been systematically studied and optimized to exploit the electrochemical properties of the pseudocapacitive materials {e.g., metal oxide).

Various embodiments of the present invention pertain to the EC performance of vertical GPs grown by microwave plasma chemical vapor deposition (MPCVD) on flexible commercial buckypaper (BP). The BP provides a light, flexible, and mechanically robust substrate for GP growth. This substrate, when coated with a thin $MnO_2$ layer, forms an architecture referred to as a $MnO_2$/GP/BP composite electrode. The GP/BP architecture offers an effective scaffold for exploiting the electrochemical behavior of $MnO_2$, realizing high energy and power density characteristics for electrochemical supercapacitor applications.

The formation of petals in one embodiment uses a plasma environment. Briefly, the plasma source consists of a 2.45 GHz frequency microwave power supply with variable power. Commercial buckypaper (Nanocomp Technologies, Inc., USA), washed in 6 M $HNO_3$ for 15 min to eliminate the residuals and surfactant before GP growth, was used as substrates to grow GPs. The substrates, elevated 9 mm above a Mo puck by ceramic spacers, were subjected to MPCVD conditions of $H_2$ (50 sccm) and $CH_4$ (10 sccm) as the primary feed gases at 30 Torr total pressure. The substrates were initially exposed to hydrogen plasma for approximately 2 min, during which the plasma power gradually increased from 300 W to 600 W. The GP growth duration was 20 min. The typical dimensions of the samples were 15 mm×5 mm.

To make GP/BP composites suitable for electrochemical electrodes prior to $MnO_2$ coating or electrochemical measurement, concentrated $H_2SO_4$ and $HNO_3$ (volume ratio 3:1) were used to functionalize the surface of GPs at 50° C. for 2 hours in an oven. The samples were then washed in deionized water and dried at 100° C. overnight. A neutral precursor solution (pH 7) for the $MnO_2$ coating process was prepared by mixing 0.1 M $Na_2SO_4$ (Alfa Aesar) and 0.1 M $KMnO_4$ (Alfa Aesar) solutions. The GPs grown on BP were immersed into the solution, which was kept at 80° C. in an oven for 40 min. The loading amount was controlled by adjusting the immersion time. The sample was then rinsed with deionized water and subsequently annealed at 200° C.

for 3 hours using a hotplate in air. The mass of coated $MnO_2$ was calculated from the weight difference before and after the coating process. The loading amount of $MnO_2$ in this study is approximately 110 μg, measured using a microbalance with an accuracy of 1 μg.

The electrochemical performance of the $MnO_2$/GP/BP hybrid structure was evaluated using a BASi Epsilon electrochemical system (Bioanalytical Systems Inc., Indiana, USA). The standard three-electrode cell consisted of Ag/AgCl as the reference electrode, Pt mesh as the counter electrode and the synthesized composite sample as the working electrode. A 1 M $Na_2SO_4$ solution served as the electrolyte at room temperature. Scan rates of 2, 5, 10, 20, 50, and 100 mV/s were employed for cyclic voltammetry, and charge/discharge measurements were carried out at different current densities of 5, 10, 20, 30, 40 and 50 A/g. Long-term cyclic stability of the composite electrodes was evaluated repeatedly at 100 mV/s for 1000 cycles. A potential window in the range from 0 to 0.8 V was used in all measurements. A Hitachi S-4800 field emission scanning electron microscope (FESEM) was used to image the surface morphology of all the samples.

Throughout this study, multiple samples were prepared under identical conditions to test for reproducibility of the processing conditions. CV data acquired from the multiple samples could be reproduced to within ±5%.

To understand the electronic structure of the $MnO_2$/GP composite large clusters of (4×2) $MnO_2$ were simulated on a graphene supercell (6×6) using density function theory (DFT). Although in real cases the $MnO_2$ structure displays diverse conformations with edge- and corner-sharing $MnO_6$ possessing various pore sizes within the range of approximately 0.19 nm to approximately 0.46 nm, with a distribution of Mn cations among the network of oxygen atoms, we employed the simplest configuration. $MnO_2$ forms many different crystallographic structures. The different structures are characterized by atomic-scale pores (also called tunnels) which penetrate throughout the material. Electronic structure calculations were carried out by DFT with the plane-wave self-consistent field (PWSCF) code. The generalized gradient approximation (GGA) was implemented to estimate the exchange correlation energy of electrons. Ultrasoft pseudopotentials were used to represent the interaction between ionic cores and valence electrons. Kohn-Sham wave functions were represented with a plane-wave basis using an energy cutoff of 40 Ry and charge density cutoff of 240 Ry. A uniform mesh of k points (5×5×1) was taken for integration over the Brillouin zone.

SEM images of GPs synthesized by MPCVD are shown in FIG. 4-1 *a*. The petals extend approximately 500 nm from the BP surface, and the typical span width of a single unwrinkled 2-D petal ranges from 100 nm to 500 nm. The thickness of a GP can reach several nanometers, corresponding to less than 50 graphene layers. A magnified image of one petal marked by the rectangular box in FIG. 4-1 *a* is shown in FIG. 4-1 *b*, revealing the smooth surfaces of the GPs. These surfaces provide easily accessible sites for $MnO_2$ coating. The crumpled structures of the vertical graphene sheets with both sides exposed to $MnO_2$ precursor solution offer large specific area for coating. FIG. 4-1 *c* shows the morphology of $MnO_2$ coated on GPs. FIG. 4-1 *d* contains a magnified image of the area marked by the rectangular box in FIG. 4-1 *c*, clearly showing a thin uniform layer of $MnO_2$ on the smooth GP surfaces, even on the smaller petals.

Previous studies suggest that $MnO_4^-$ ions can be reduced spontaneously to $MnO_2$ on the surface of carbon nanotubes by oxidizing exterior carbon atoms via the following redox reaction:

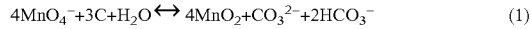

$$4MnO_4^- + 3C + H_2O \leftrightarrow 4MnO_2 + CO_3^{2-} + 2HCO_3^- \quad (1)$$

A similar mechanism applies here in the case of $MnO_2$ coating on GP surfaces. Reduction of permanganate ion ($MnO_4^-$) to $MnO_2$ on carbon is pH-dependent. Neutral pH solution leads to thin films of $MnO_2$, while acidic solution can result in large agglomerated $MnO_2$ particles. Consequently, the thin film of $MnO_2$ coated on GPs can be attributed to the neutral electrolyte used in this disclosure.

FIG. 4-2*a* shows cyclic voltammetry (CV) curves of the $MnO_2$/GP/BP composites at scan rates of 2, 5, 10, 20, 50, 100 mV/s in 1 M $Na_2SO_4$ aqueous solution with potential windows ranging from 0 to 0.8 V. The advantages of the unique electrochemical behaviours of $MnO_2$/GP/BP electrodes are apparent in FIG. 4-2*b* which shows a comparison of CV curves for BP, GP/BP, $MnO_2$/BP and $MnO_2$/GP/BP at a fixed scan rate of 10 mV/s. The shapes of these curves are quasi-rectangular, indicating the presence of electrical double-layer capacitance and pseudocapacitance. The $MnO_2$-coated GP/BP architecture involves redox reactions in the cyclic voltammetry tests as Mn atoms are converted into higher/lower (IV/III) oxidation states. These conversions are induced by intercalation/extraction of $H_3O^+$ or alkali cations ($Na^+$) to/from the $MnO_2$ outer layer. The mechanism of this reaction can be expressed as the following reaction:

$$(MnO_2)_{surface} + X^+ + e^- \leftrightarrow (MnOOX)_{surface}$$

$$(X^+ = Na^+ \text{ or } H_3O^+) \quad (2)$$

The average specific capacitance from CV curves was determined by the following formula:

$$C = \frac{1}{2sM(V_h - V_l)} \int_{V_l \to V_h \to V_l} I(V) dV \quad (3)$$

where C is the specific capacitance in F/g, s is the scan rate in V/s, M is the mass of the added $MnO_2$ to the electrodes in g, $V_h$ and $V_l$ are high and low potential limits of the CV tests in V, I is the instantaneous current on CV curves, and V is the applied voltage (V). The specific capacitance of BP at a scan rate of 2 mV/s calculated from the CV curves is 27 F/g, which is comparable to reported values for CNTs. The specific capacitance of GP/BP (based on total mass of the two components) calculated at 2 mV/s is 47 F/g, which is approximately 70% higher than that of bare BP. The same improvement (~70%) was also observed in $H_2SO_4$ electrolyte, indicating an inherent improvement in specific capacitance after GP growth on BP. This result is attributed to an increase in the specific area after growing GPs on the BP substrate coupled with electric field enhancement introduced by the sharp edges of the GPs.

The specific capacitance of the $MnO_2$/GP/BP composites was calculated based on the mass of pristine $MnO_2$ for the following reasons: (1) The surface of carbon was coated with $MnO_2$; consequently, the carbon materials would participate weakly in the charge storing process as charge is primarily stored at the outer layer of $MnO_2$ through a Faradic reaction. (2) The specific capacitances of BP and GP/BP are mainly of the electrostatic double-layer type and are far smaller than the specific capacitance of $MnO_2$ caused by Faradic redox reactions, making it reasonable to calculate the specific capacitance based on the mass of pristine $MnO_2$.

FIG. 4-2*c* shows comparative specific capacitances of BP, GP/BP, $MnO_2$/BP and $MnO_2$/GP/BP calculated from CV curves at voltage scan rates from 2 to 100 mV/s. At a scan rate of 2 mV/s, the specific capacitance of the $MnO_2$/GP/BP hybrid composite reaches 580 F/g (based on the mass of pristine $MnO_2$). At a high scan rate of 100 mV/s, the specific capacitance of $MnO_2$/GP/BP still remains close to 320 F/g, which is comparable to the rate performance reported by others. However, for the same $MnO_2$ coating time, the specific capacitance of $MnO_2$/BP is only about 266 F/g (based on pristine $MnO_2$) at 2 mV/s (see FIG. 4-2*c*). The superior rate capability of $MnO_2$/GP/BP composites demonstrates the advantages of this new architecture of GP/BP as a highly conductive scaffold for maximizing the utilization of the practical electrochemical performance of $MnO_2$. Since previous studies show that only a very thin layer of $MnO_2$ is involved in the charge storage process, the specific capacitance of $MnO_2$ coated on the supporting GP/BP can likely be further improved by optimizing the thickness of coated $MnO_2$ layer.

Constant-current charge/discharge curves of the as-prepared $MnO_2$/GP/BP hybrid structure at different current densities are shown in FIG. 4-2*d*. The charge/discharge curves display a symmetric shape, indicating that the structure has a good electrochemical capacitive characteristic. The specific capacitance derived from galvanostatic (GV) tests can be calculated from the following formula:

$$C = \frac{I_d}{Mv} \quad (4)$$

where $I_d$ is the discharge current in A, and $v$ is the slope of the discharge curve after the initial potential drop associated with the cell internal resistance (IR drop). The specific capacitances derived from the discharge curves agree well with the results calculated from CV measurements. At 5 A g, the calculated specific capacitance is 493 F/g, which is almost identical to the specific capacitance 497 F/g calculated at 10 mV/s, corresponding to an average current density close to 5 A/g (see FIG. 4-2*b*).

The energy density E (in Wh/kg) and the power density P (in kW/kg) are important parameters to characterize the electrochemical performance of supercapacitors. In this disclosure, these quantities were calculated by:

$$E = \frac{CV^2}{2M} \quad (5)$$

$$P = \frac{E}{\Delta t} \quad (6)$$

where V is the applied voltage in volts and $\Delta t$ is the discharge time in seconds. FIG. 3.7*d* shows the Ragone plot for the $MnO_2$/GP/BP structured electrode at different current densities. At a high current density of 50 A g, the calculated energy density is 28 Wh/kg, and the average power density is 25 kW/kg. These values are more promising than reported energy densities (14.8 Wh/kg) and power densities (2.5 kW/kg) of electrodeposited $MnO_2$ films on BP substrates. Various embodiments of the present invention include $MnO_2$/GP/BP composites as electrode material in supercapacitor applications.

Cycle lifetime is a factors in supercapacitor applications. Typical issues facing $MnO_2$-based electrodes in aqueous electrolyte include: mechanical expansion of $MnO_2$ during ion insertion/desertion processes, $MnO_2$ film detachment from electrode surfaces, and Mn dissolution into electrolyte. A cyclic stability test over 1000 cycles for the $MnO_2$/GP/BP structured electrode at a scan rate of 100 mV/s was carried out in a potential window ranging from 0 to 0.8 V. FIG. 3.7*f* shows the specific capacitance retention as a function of cycle number. The composite electrode shows less than 10% loss in specific capacitance after 1000 charge/discharge cycles, indicating good capacity retention.

DFT simulations can help to elucidate the fundamental properties at interfaces between $MnO_2$ and graphene, particularly in terms of lattice stability and electronic structure of the composite. A schematic diagram of $MnO_2$ clusters and graphene (top view) is shown in FIG. 4-3*a*. In this configuration, constrained relaxation was carried out (only atomic positions of the $MnO_2$ are allowed to relax, with initially relaxed graphene). The $MnO_2$/GP composite is relaxed with energy converged to less than 2 kcal/mol. The formation energy of the composite is calculated to be 128 kcal/mol, suggesting covalent bonding between $MnO_2$ and graphene. During the charge/discharge process, we expect the composite to undergo compressive/tensile stresses. To mimic the phenomena, we have simulated the structure with various pressure values in the supercell. From the electronic density of states, the composite exhibits metallic behaviour (finite density of states at $E_F$) in both cases, and this metallic state changes little with different stresses as shown in FIG. 4-3*b*, where different negative/positive pressures are used to mimic compressive/tensile stresses. The comparative electronic density of states of graphene, $MnO_2$ and $MnO_2$/graphene (the most stable structure) are shown in FIG. 4-3*c*.

The low interfacial resistance achieved in the $MnO_2$/GP/BP electrode is a matter of interest, and we use the results of DFT calculations to provide further insight into this result. The iso-electronic charge contour plot drawn in FIG. 4-3(*d*) is a two-dimensional cut of the charge density in a vertical plane that contains the yellow line drawn parallel to the zig-zag direction as shown in FIG. 4-3(*a*). This vertical plane was chosen to highlight the redistribution of charge from the graphene layer toward the oxygen atoms in $MnO_2$. Further iso-electronic contour plots in different planes are provided in the supplementary information. From these plots, we infer that charge transfer at the graphene-$MnO_2$ interface is facilitated by the oxygen atoms in the $MnO_2$ complex, providing some understanding for the low interfacial resistance experienced by electron transport through the composite interface. Without this conduction channel, charge transfer would be reduced, making the composite less suitable for supercapacitor applications.

A new structure of $MnO_2$/GP/BP has been demonstrated for flexible supercapacitor electrodes, showing promising electrochemical behavior. The GP/BP architecture without any binder provides an efficient scaffold for maximizing the practical electrochemical performance of $MnO_2$, realizing high specific capacitance, rate capability and long-term cycle life, high energy density and high power density. The metallic nature of the $MnO_2$/GP composite provides a facile conduction path for electron transport in the charge/discharge process. These results suggest that such a $MnO_2$/GP/BP architecture may be practically useful for next generation high-performance supercapacitors.

Another embodiment of the present invention includes a hybrid three-dimensional nanoarchitecture by electropolymerizing aniline monomers into a nanometer-thick conformal polyaniline (PANI) film on graphitic petals (GPs) that are directly grown on highly conductive carbon cloth (CC) through microwave plasma enhanced chemical vapor deposition (MPCVD) for flexible supercapacitor applications. The hybrid CC/GPs/PANI electrodes yield greatly improved capacitive performance with a high specific capacitance of ~2000 F/g (based on PANI mass), close to the theoretical capacitance, and a large area-normalized specific capacitance of ~2.5 F/cm$^2$ (equivalent to a volumetric capacitance of ~230 F/cm$^3$) at 1 A/g. The hybrid electrodes also exhibit an excellent rate capability with an energy density of 109.9 Wh/kg and a maximum power density of 265.1 kW/kg at a high current density of 100 A/g, respectively, and an outstanding long-term cycling stability (~7% loss in its initial capacitance after 2000 cycles), with a coulombic efficiency of ~99.8%. Moreover, all-solid-state flexible supercapacitors based on the hybrid CC/GPs/PANI electrodes are also fabricated, which show beneficial electrochemical properties, outperforming the reported all-solid-state flexible supercapacitors to date.

Some embodiments pertain to the fabrication of a novel hybrid nanoarchitecture by electropolymerizing aniline monomers into a nanometer-thick PANI film and conformally coating it on GPs that are directly grown on highly conductive carbon cloth through MPCVD method. Such unique 3D porous networks, without any binder, not only allow large loading of active electrode materials but also facilitate easy access of electrolytes to the electrodes. In 1 M $H_2SO_4$ aqueous electrolyte, CC/GPs/PANI electrodes yield greatly improved capacitive performance with a specific capacitance of 1502 F/g (~2000 F/g at a current density of 1 A/g) at 2 mV/s (5 min of PANI electropolymerization), ~3 times as high as that of CC/PANI and an area-normalized specific capacitance of ~2.5 F/cm$^2$ (equivalent to a volumetric capacitance of ~230 F/cm$^3$) at 1 A g, ~10 times as high as that of CC/PANI, outperforming many other currently available carbon-based electrodes. Such rationally designed ECs also exhibited ultrahigh energy and power densities and excellent cycling performance. To demonstrate their promising applications as flexible power sources, all-solid state and paper-like flexible supercapacitors based on CC/GPs/PANI were also fabricated, exhibiting excellent electrochemical properties, and demonstrated to light a LED. A nanoscale electrode based on such highly conductive, porous and 3D frameworks can provide breakthroughs for designing future multifunctional ECs.

As-prepared GPs serve as highly graphitic and conductive templates, which PANI films were subsequently coated conformally on by electropolymerization of aniline monomers. Schematic illustrations of such novel hybrid CC/GPs/PANI nanostructures are shown in FIG. 3-1. This strategy has several advantages: (1) Macroscopically, 3D carbon cloth would provide a flexible and highly conductive substrate and create channels for fast and effective electrolyte ion transport. (2) Highly graphitic and conductive GPs would largely increase the specific surface of the electrodes and provide a direct path for the electrons transport. The sharp edges of GPs would not only largely increase the charge storage but also speed up the ion diffusion due to lower energy barriers. (3) A nanoscale thin layer of PANI would enable a fast, reversible farad is reaction and provide a short ion diffusion path.

The novel 3D nanostructure was achieved in one embodiment by two-step methods. First, carbon cloth substrates, elevated 9 mm above a Mo puck by ceramic spacers, are subjected to MPCVD conditions of $H_2$ (50 sccm) and $CH_4$ (10 sccm) as the primary feed gases at 30 Torr total pressure for 25 min. SEM images in FIG. 3-2A show the morphology and microstructure of pure carbon cloth at low (inset) and high magnifications. The diameter of a carbon fibre in the carbon cloth is approximately 9 microns. The surface of a carbon fibre is relatively smooth. FIG. 3-2B display the morphology and microstructure of GPs fully covering carbon fibres at low and high (inset) magnifications. These GPs uniformly cover CC substrate in a large scale, providing a basis for large-scale fabrication process (see FIG. 5-2). GPs are grown approximately 500 nm out from the carbon fibre surface and the typical span width of a single unwrinkled two-dimensional (2-D) grain ranges from 100 nm to 500 nm. The thickness of the 2-D GP plane can reach several nanometers, corresponding to less than 50 graphene layers. TEM characterizations of such GPs on carbon fibers in our previous work indicates that the fiber-petal transition is continuous which facilitates electron transport at the interface between carbon fibers and GPs. The diameter of a carbon fibre decorated with GPs does not change noticeably. The thickness of CC/GPs sample grown in this condition is measured to be approximately 110 microns. These GPs on carbon cloth are highly hydrophobic and can benefit from further acid treatment.

Second, electropolymerization process is carried out on a CC/GP sample impregnated with 20 mL solution containing 0.05 M aniline monomers in 0.5 M $H_2SO_4$ at 0.8 V versus Ag/AgCl reference electrode. After the polymerization, the as-prepared composite was washed in deionized water and then dried at 80° C. over 2 hours. The adsorbed aniline monomers on the both surfaces of a vertical GP will be electropolymerized to form PANI. The sharp edges of GPs maintains well after the decoration of PANI. FIGS. 3-2B (inset) and 3-2C are comparative SEM images of GPs before and after electrochemical polymerization. Apparently, before the electrochemical polymerization, 2-D unwrinkled GP surfaces are thin and smooth; however, after electrochemical polymerization for 5 min, PANI are conformally coating GP surfaces, making them rougher and relatively thicker. The PANI mass can be easily adjusted by controlling the electrochemical polymerization time. PANI will become thicker after electropolymerization for longer time. The mass of PANI in the composite is estimated from the total Faradic charge consumed in the electropolymerization reaction, assuming an average of 2.5 electrons per aniline monomer in emeraldine.

Raman spectroscopy is often used to characterize graphene based materials. The D band at 1350 cm$^{-1}$ is known to result from various types of defects and anomalies of transverse optical vibrations near the K-point. The G peak at 1580 cm$^{-1}$ arises because of the doubly degenerate zone center $E_{2g}$ mode. FIG. 3-2D shows comparative Raman spectroscopy of CC, CC/GPs and CC/GPs/PANI. Apart from the D and G bands in the Raman spectroscopy of CC/GPs/PANI hybrid materials, another two new representative peaks (circle indicated), indexed at 1167 cm$^{-1}$ and 1468 cm$^{-1}$, are due to the presence of PANI structure, corresponding to C—H vibrations in quinoid/phenyl groups and semiquinone radical cation structure in PANI.

Electrochemical polymerization time ranging from 0, 30 s, 2 min, 5 min, 8 min, 10 min to 15 min is used to study the influence of PANI mass on comprehensive electrochemical properties including specific capacitance based on active material and also the overall area-normalized capacitance of the nanocomposite electrode.

FIG. 3-3A shows both the mass specific capacitance and area-normalized specific capacitance as a function of electrochemical polymerization time at 2 mV/s for CC/GPs/

PANI electrode. When the electropolymerization process only lasted for 30 s, aniline monomers polymerization on the graphene surfaces was not enough, consequently only part of PANI covered the surface of GPs, giving high mass specific capacitance based on the mass of PANI, while in fact part of the capacitance comes from the electric double layer contribution. Meanwhile the area-normalized specific capacitance reaches 1.1 F/cm$^2$, higher than that of CC/GP electrode (0.7 F/cm$^2$). PANI coated on mesoporous carbon monolith carbonized from mesophase pitch at 1000° C. can have a high specific capacitance of 2200 F/g (based on PANI mass), with a significant contribution coming from electric double layer capacitance [9]. This may be because of the hydrophobic properties of carbon monolith after carbonization of mesophase pitch at high temperature, giving rise to nonuniform coverage of PANI on the electrode surface. Moreover, inflexible carbon monolith substrate will limit its practical applications. PANI mass increases and the specific capacitance based on PANI significantly decreases as electropolymerization time prolongs. The overall area-normalized specific capacitance of the composite electrode gradually increases, reaches a saturation when electropolymerization time is 5 min and eventually reaches approximately to 2 F/cm$^2$ at a scan rate of 2 mV/s when electropolymerization time is 15 min.

As PANI polymerization time prolongs, more and more PANI will participate in the electrochemical reactions, leading to more pseudocapacitance and consequently higher area-normalized specific capacitance. However, due to the limited ion transport in inner part of active material when PANI is thick and relatively low electrical conductivity, only the outer layer of PANI can be utilized in pseudocapacitive reactions, giving rise to relatively low mass specific capacitance and also the saturation of overall area-normalized specific capacitance. To make a balance between efficiency of PANI utilization and overall area-normalized specific capacitance, we choose electropolymerization time as 5 min for the further discussions in the work.

FIG. 3-3B shows the cyclic voltammetry (CV) curves of the hybrid CC/GPs/PANI composite electrode (5 min of PANI electropolymerization) at different scan rates of 2, 5, 10, 20, 50 and 100 mV/s with potential windows ranging from 0 to 0.8 V vs. Ag/AgCl in 1 M H$_2$SO$_4$ aqueous electrolyte. Redox peaks ($C_1/A_1$, $C_2/A_2$ and $C_3/A_3$) from the CV curves indicate the presence of pseudocapacitive PANI. Redox transitions between a semiconducting state (leucoemeraldine form) and a conducting state (polaronic emeraldine form) are responsible for peaks $C_1/A_1$, and the Faradaic transformation of emeraldine pernigraniline initiates the redox peaks $C_2/A_2$. Peaks $C_3/A_3$ have been attributed to the formation/reduction of bipolaronic pernigraniline. It is also noted that the cathodic peaks ($C_2$) shift positively and the anodic peaks ($A_2$) shift negatively with the increment of potential sweep rates, which is because of the increment of the resistance in the electrodes.

FIG. 3-3C displays the comparison of area-normalized specific capacitance of Pure CC, CC/GPs, CC/PANI and CC/GPs/PANI at different scan rates. Electrochemical polymerization time for both CC/PANI and CC/GPs/PANI electrodes are 5 min. Pure CC contributes negligible area-normalized specific capacitance to the electrodes (0.01 F/cm$^2$ at a scan rate of 2 mV/s). After decorating GPs on CC by PECVD method, the area-normalized specific capacitance of the composite reaches 0.7 F/cm$^2$ at a scan rate of 2 mV/s and decreases slightly with increasing scan rate. In order to compare structures of GPs in the electrochemical charge storages, a pure CC is electrochemically coated with PANI for comparison with the hybrid composite electrode of CC/GPs/PANI with the same PANI electropolymerization time (5 min). At a scan rate of 2 mV/s, the area-normalized specific capacitance of CC/GPs/PANI reaches 1.84 F/cm$^2$, approximately one order of magnitude higher than that of CC/PANI (0.19 F/cm$^2$). At a scan rate of 100 mV/s, the area-normalized capacitance remains 71%, higher than the reported value in reduced graphene oxide/PANI electrodes containing binder (approximately 50% retention at 100 mV/s), indicating the rate capabilities of the hybrid CC/GPs/PANI electrode.

Figures 1, 2, 3, 3D:
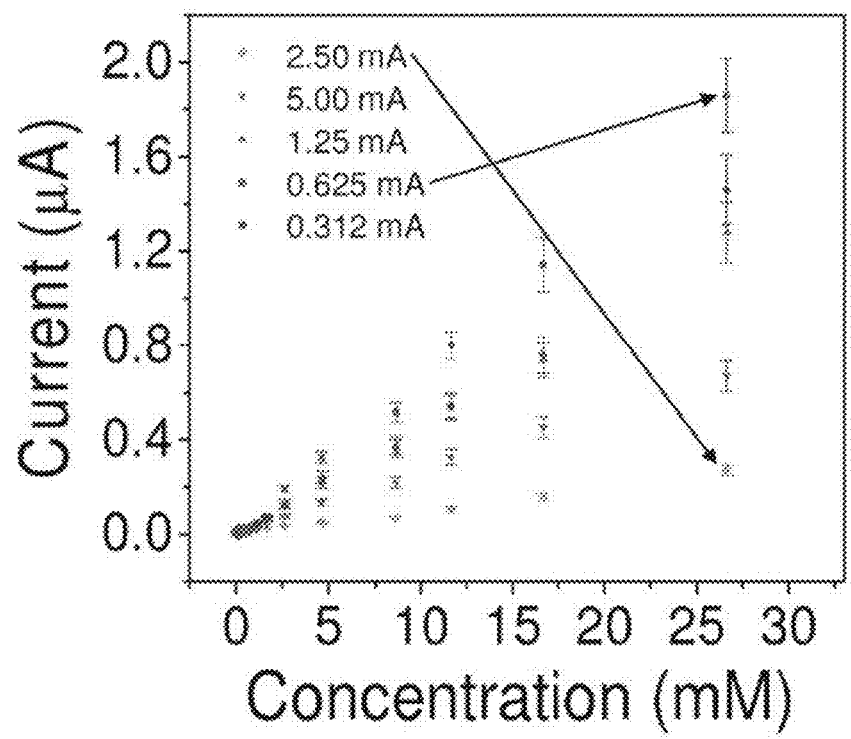
Figures 1, 2, 3, 3E:
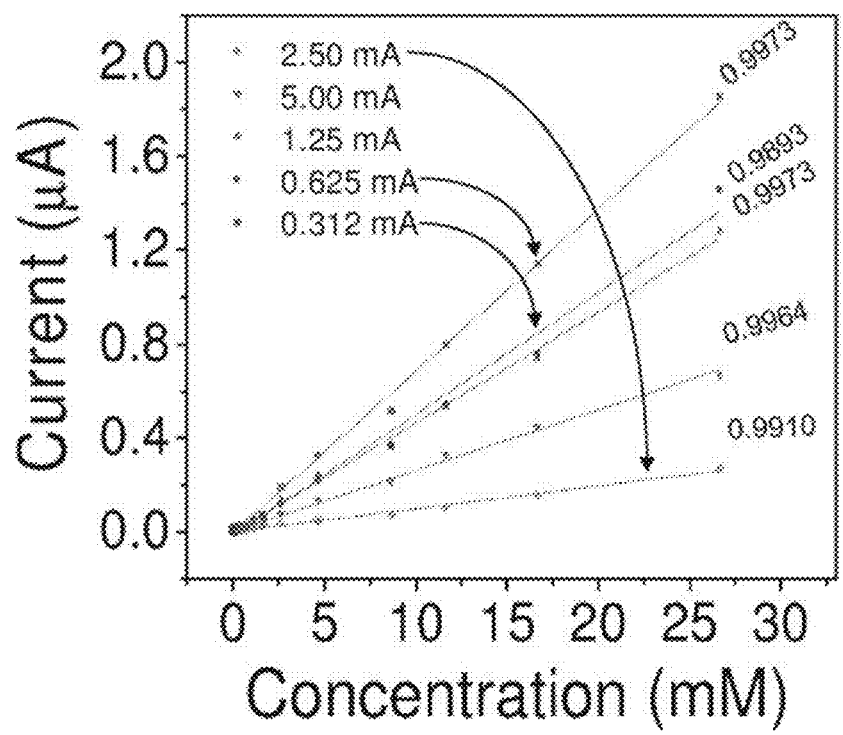
Figures 1, 2, 3, 4, 4A:
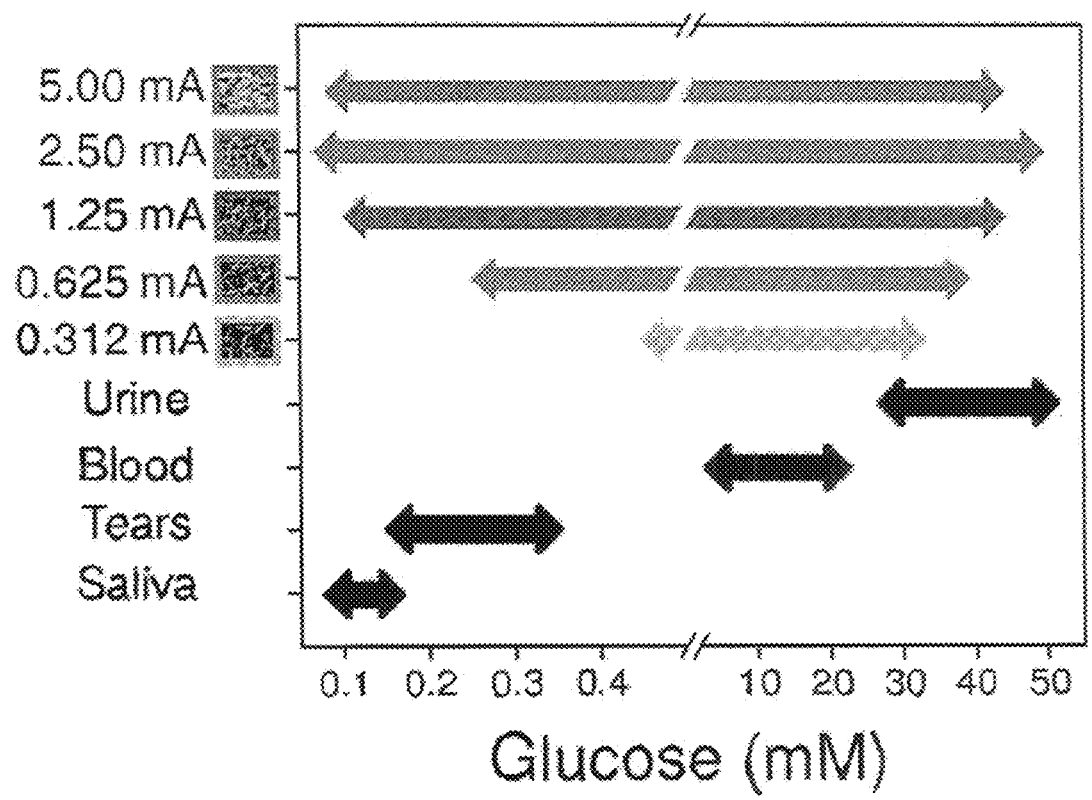
Figures 1, 2, 3, 4, 4B:
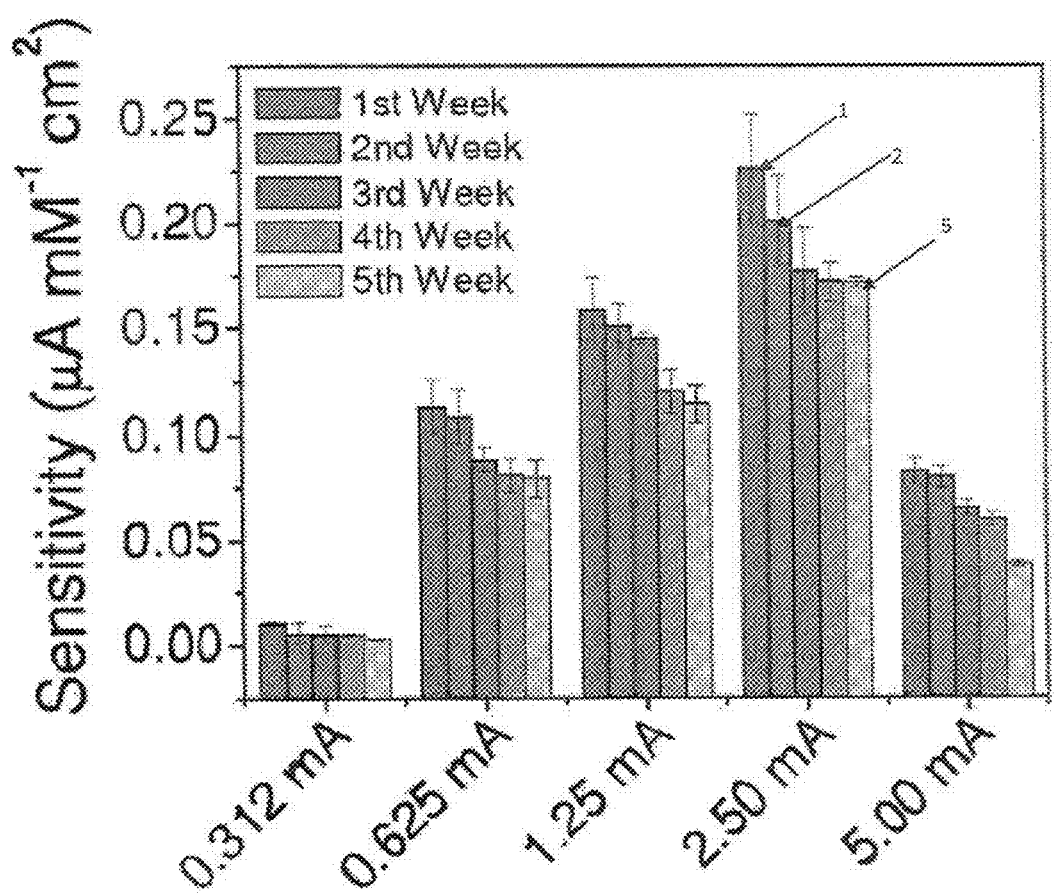
Figures 1, 2, 3, 4, 4C:
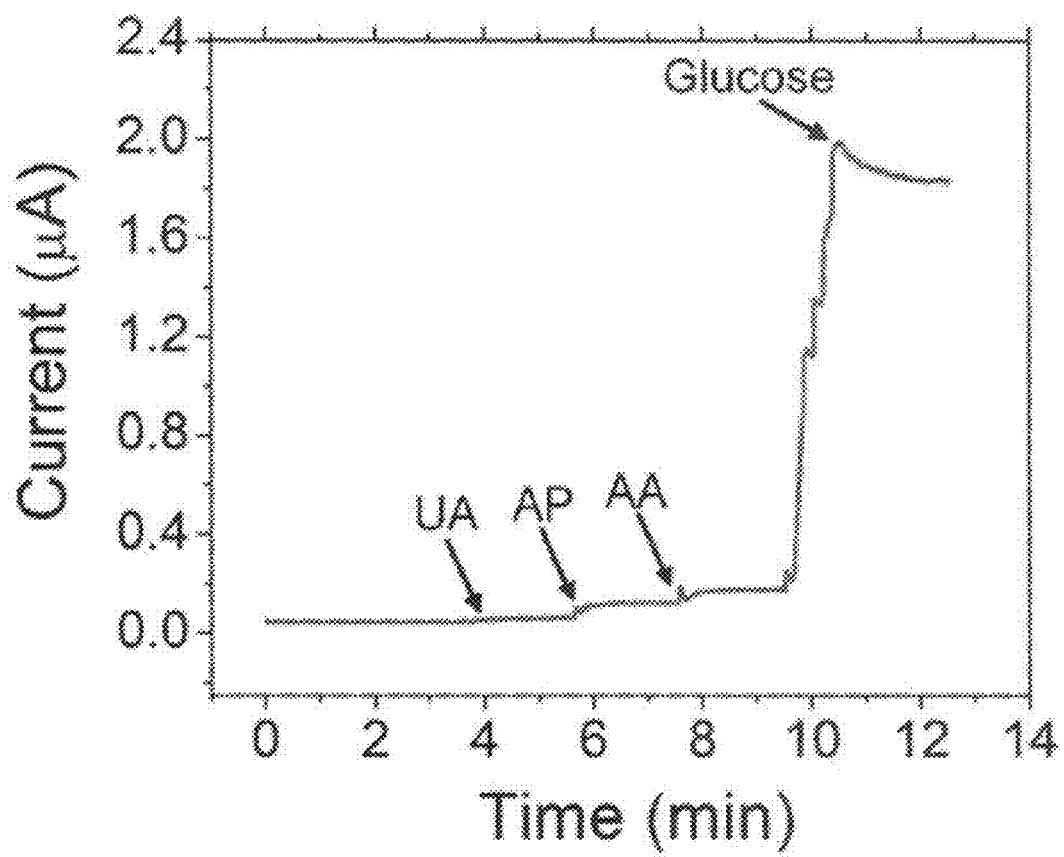

FIG. 3-3D shows the comparison of mass specific capacitance based only on PANI for both pure CC and CC/GP substrates. Apparently, PANI coated on CC/GP substrates has much higher mass specific capacitance than that on pure CC substrates. At a scan rate of 2 mV/s, the mass specific capacitance of PANI is approximately 3 times as high as that on pure CC, indicating that the unique GP structures play a synergetic role utilizing PANI in electrochemical reactions. This synergetic role of GPs can be attributed the following advantages: 1) vertical graphene nanosheets allow PANI to be coated on both sides of the GP surfaces, further increasing the specific area. 2) moreover, based on the prior work and analysis, we believe that the sharp edges of GP further enhance the local electric field, allowing more charges to be stored along the edges; sharp edges will also affect the ion diffusion paths on the GP/PANI surfaces. SEM images indicate that the edges maintained after coating with PANI.

Rate capability is one factor for evaluating the power applications of supercapacitors. Galvanostatic constant-current charge/discharge performances are evaluated for CC/GPs/PANI hybrid electrode at different constant-current densities, ranging from 1 A/g up to 100 Ag based on the mass of PANI. The charge/discharge cycling curves have a symmetric nature, indicating that the composite has a good electrochemical capacitive characteristic and superior reversible redox reaction. This symmetric nature of the CC curves can be maintained even at a low density of 1 A/g, as shown in FIG. 3-4A. Charge/discharge curve of the hybrid electrode at higher current densities can be seen from supporting information FIG. 5-5, in which the IR drop at higher current densities can be seen.

The mass specific capacitance and area-normalized specific capacitance derived from the discharging curves at different charge/discharge rates (current densities) are shown in FIG. 3-4B. At a constant current density of 1 A/g, the calculated mass specific capacitance is 1998 F/g, close to the theoretical capacitance of PANI and the area-normalized specific capacitance is approximately 2.56 F/cm$^2$, corresponding to a volumetric charge storage of ~237 F/cm$^3$, which is higher than those reported values so far. The highest area-normalized capacitance for PAN1/carbon based electrodes is reported to be 1.8 F/cm$^2$. Reduced graphene oxide paper coated with PANI show a volumetric charge storage of 135 F/cm$^3$ and 160 F/cm$^3$. PANI electropolymerized on stainless steel is reported with a area-normalized capacitance of 0.9 F/cm$^2$ at a deposit charge of 2.35 C/cm$^2$. Volumetric capacitances of PANI-based electrodes are usually higher than those of carbon nanotubes (<16 F/cm$^3$), graphene paper (64 F/cm$^3$), carbide-derived carbon (61-90 F/cm$^3$) and activated carbons (<50 F/cm$^3$). Both mass specific capacitance and area-normalized capacitance decrease relatively fast at low current densities and then stay stable at high current densities. At 100 A/g, the mass specific capacitance can still be as high as ~1200 F/g and area-normalized capacitance 1.5 F/cm$^2$, which are consistent with the values calculated using CV curves.

Specific energy and power densities are the two factors for evaluating the power applications of electrochemical supercapacitors. An electrochemical supercapacitor can provide high energy density or high specific capacitance at high charging-discharging rates. The internal resistance which can be determined from the initial voltage drop of the discharge curves is also an important factor affecting the maximum power of the device. At a current density of 100 A/g, the $VI_R$ is approximately 0.12 V, corresponding to a low internal resistance of 2.5 SI This demonstrates the reduced charge-transfer resistance of the CC/GPs/PANI hybrid electrode. FIG. 3-4C shows the Ragone plot for the CC/GPs/PANI composite electrode at the potential window of 0.8 V in 1 M $H_2SO_4$ aqueous electrolyte. The energy density decreases from 202.2 to 109.9 Wh/kg, while the maximum power density increases from 118.5 to 265.1 kW/kg, as the galvanostatic charge/discharge current increased from 1 to 100 A g.

Figures 1, 3:
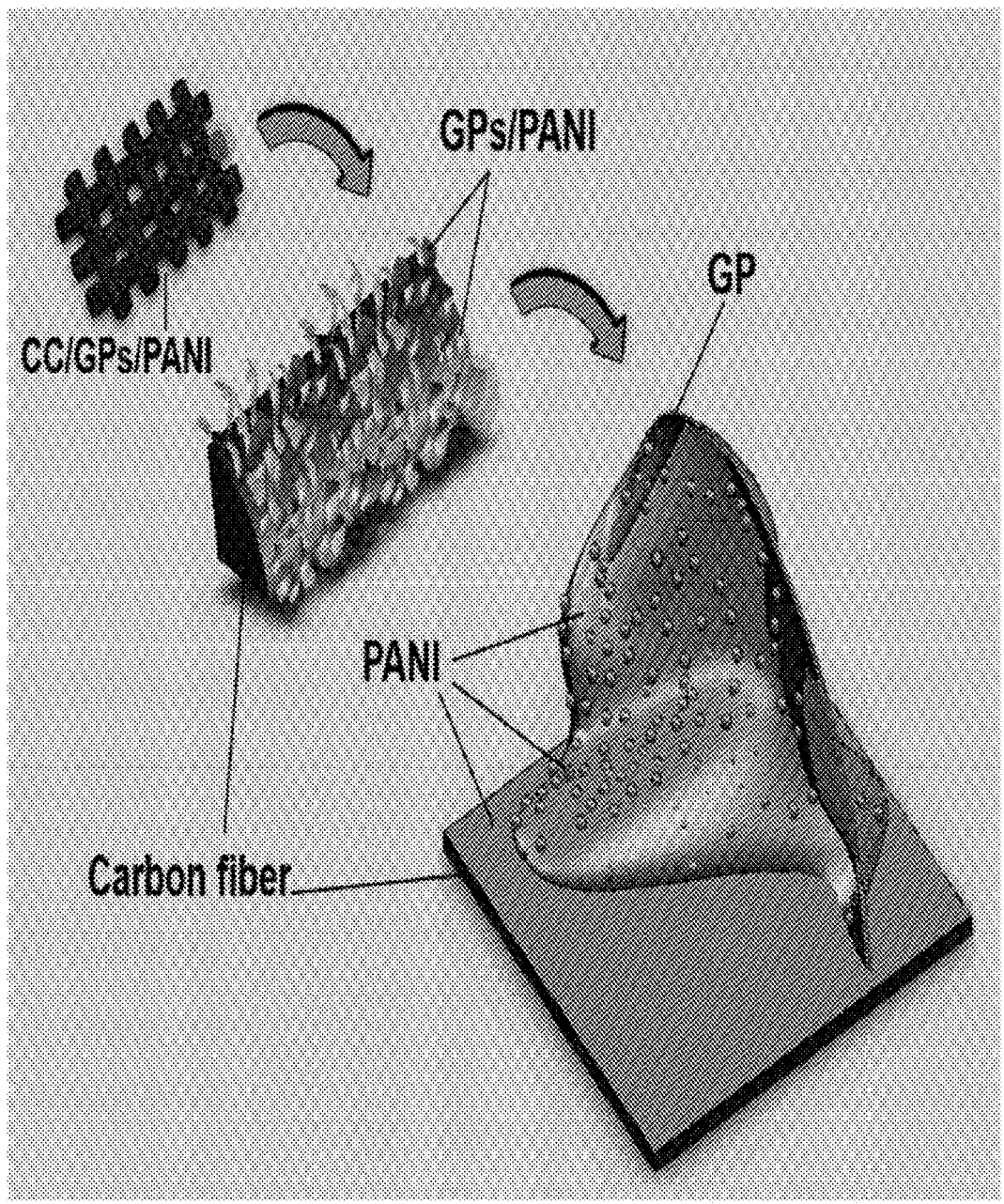
Figures 2C, 3:
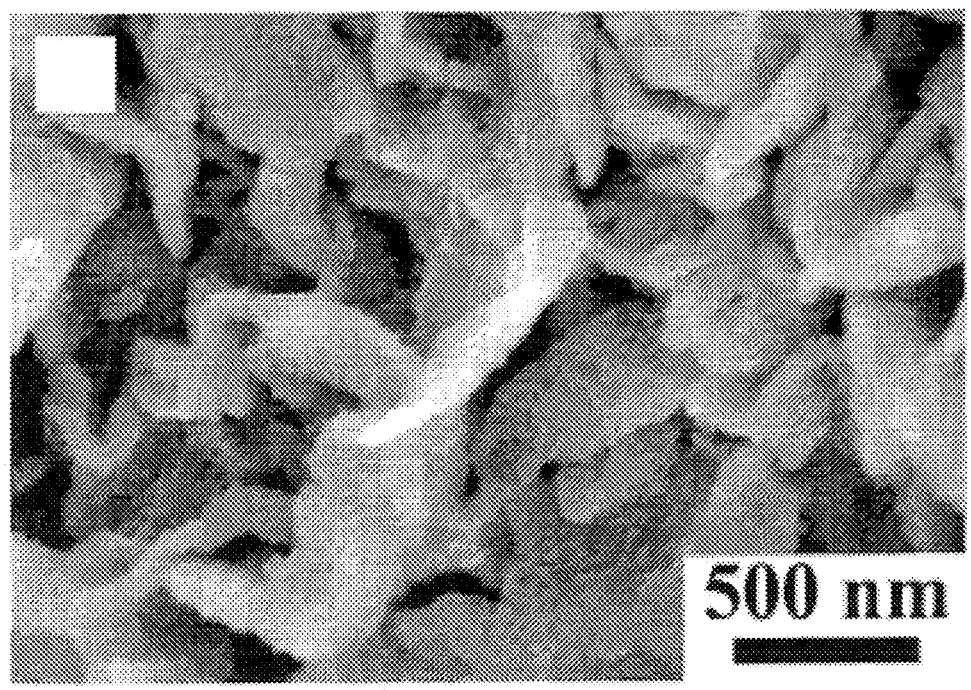
Figures 2D, 3:
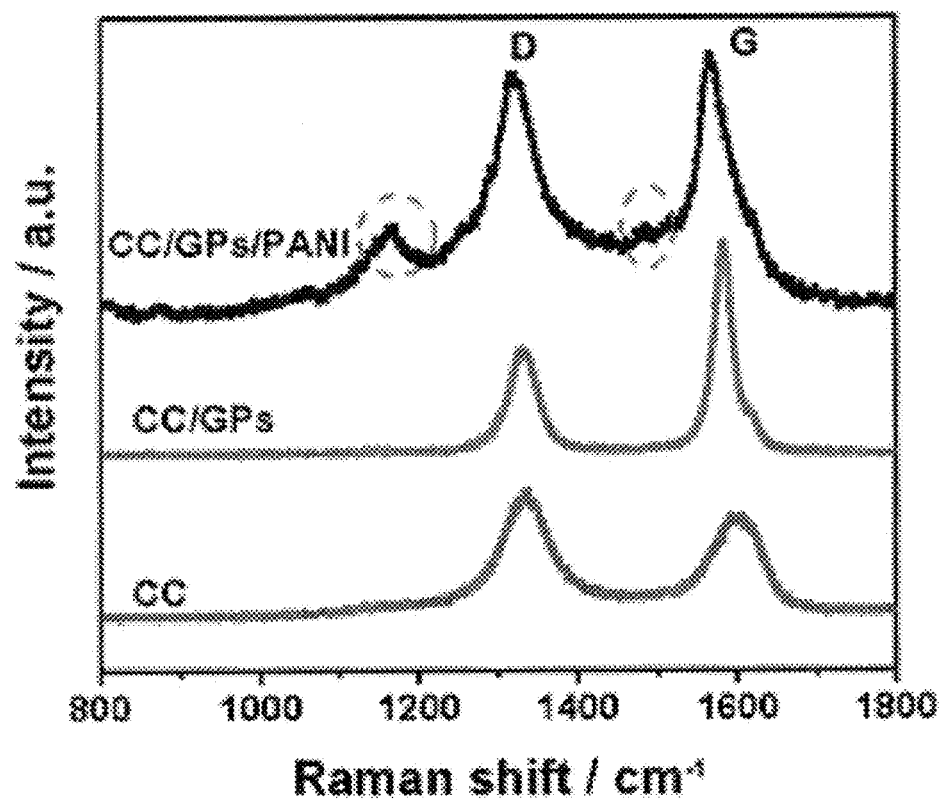
Figures 3, 3A:
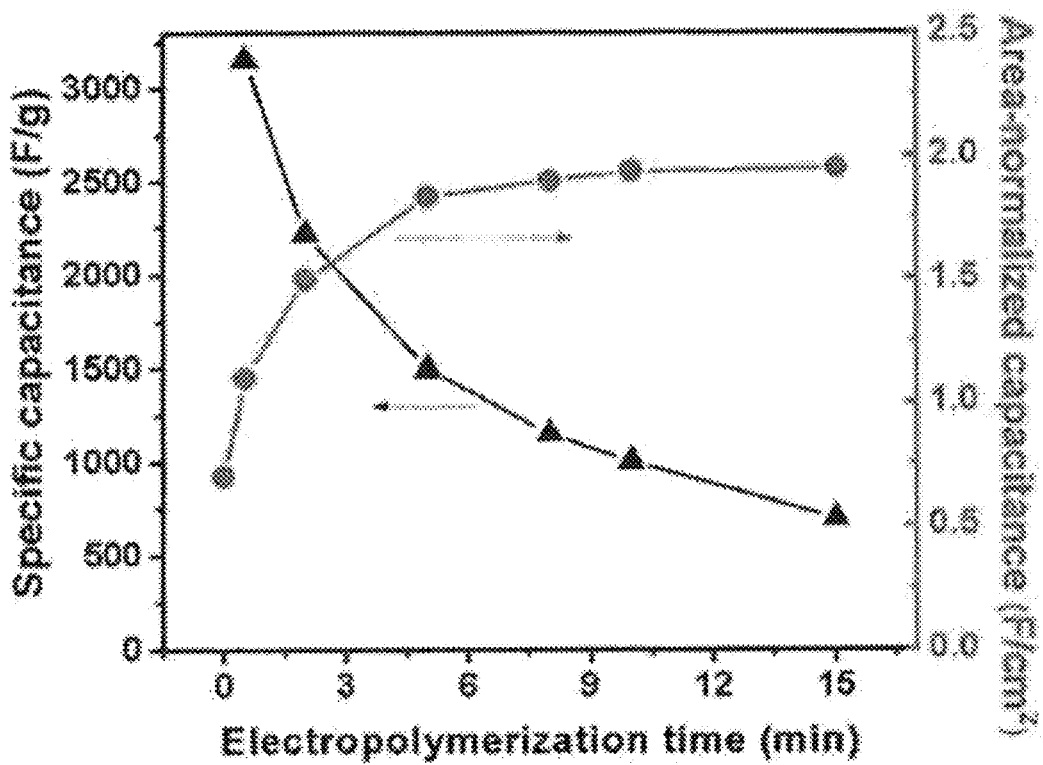
Figures 3, 3B:
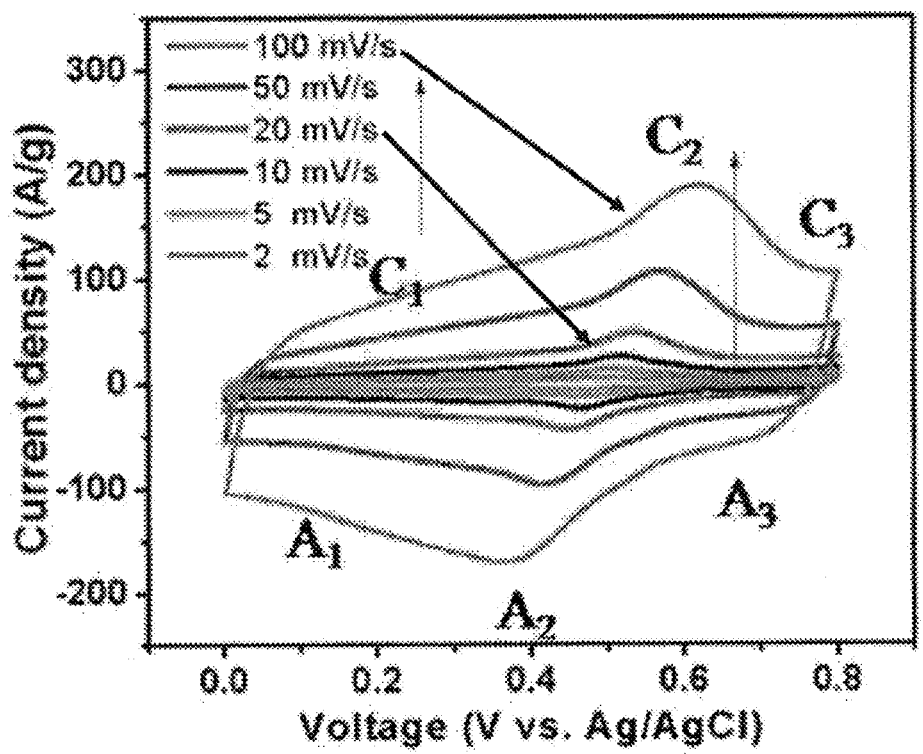
Figures 3, 3C:
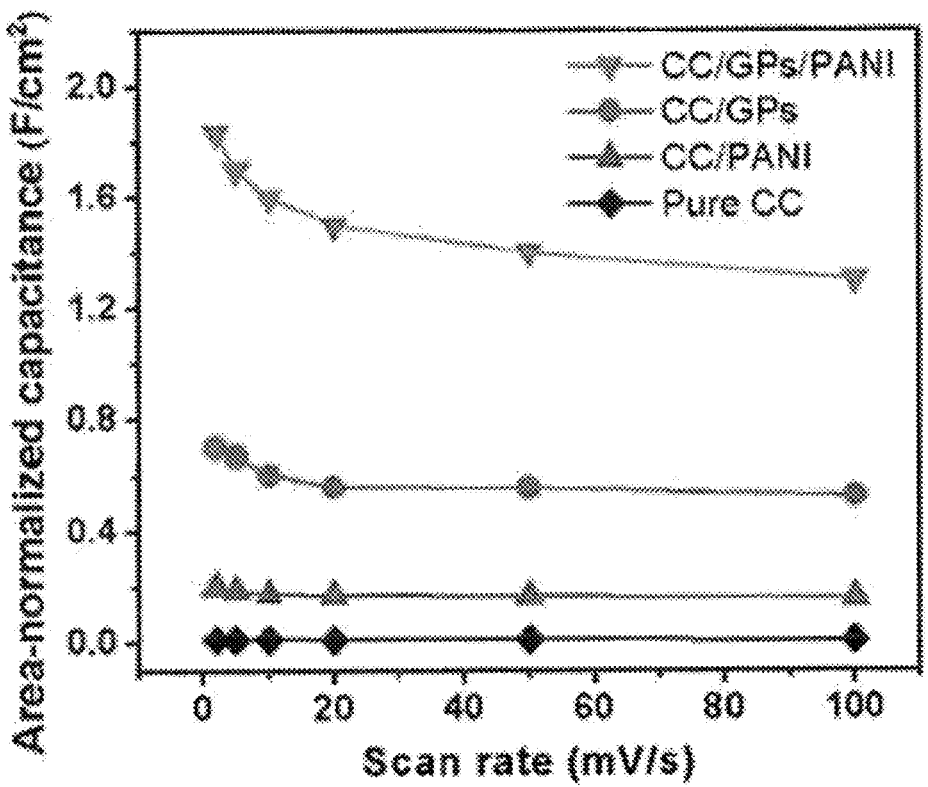
Figures 3, 3D:
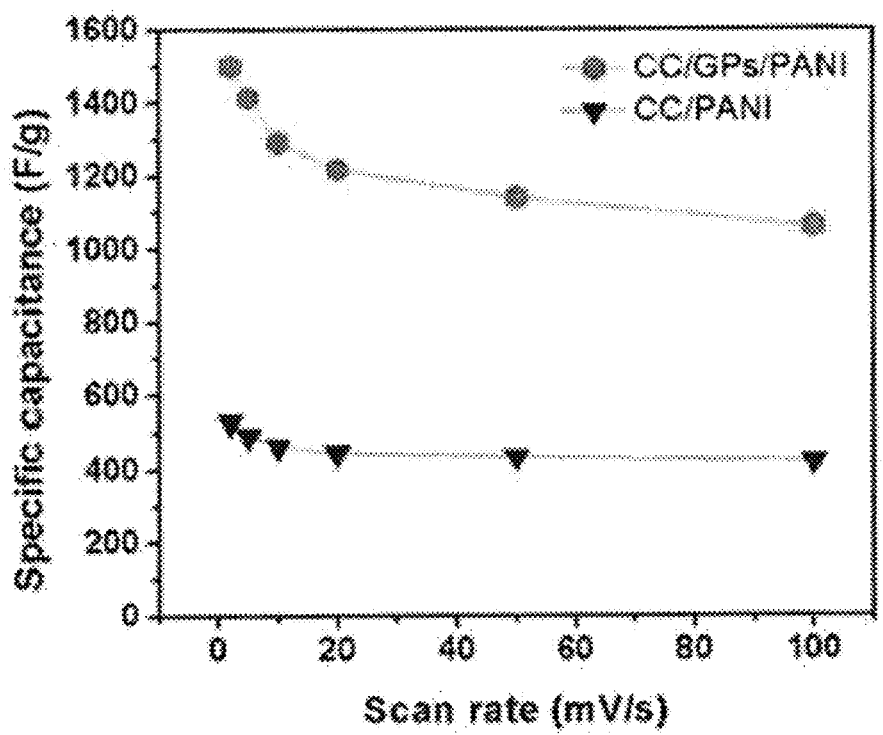
Figures 3, 4, 4A:
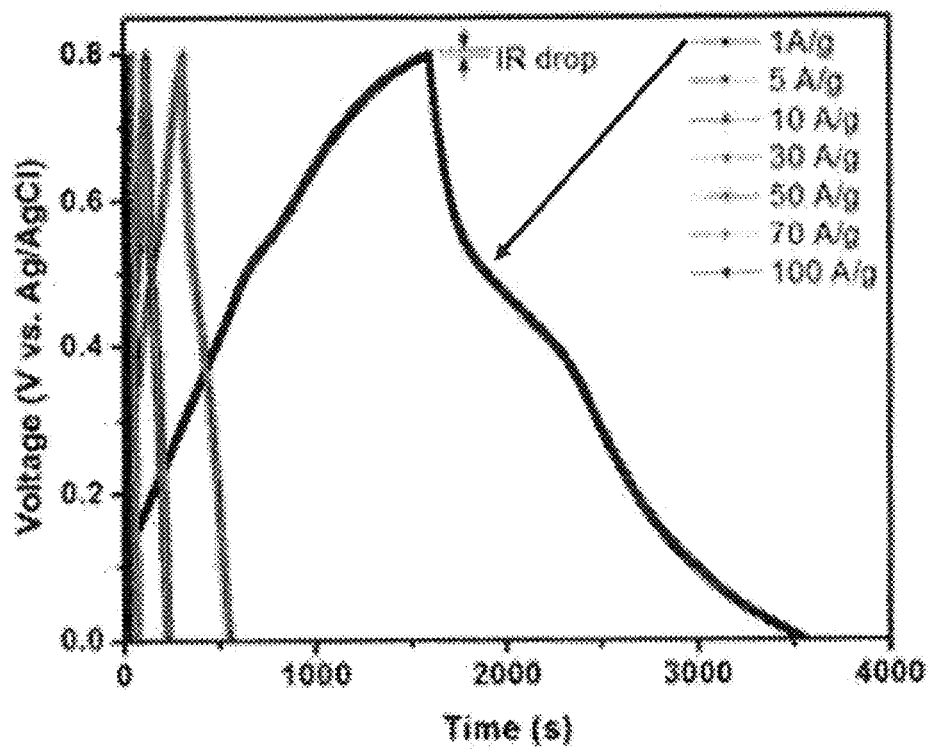
Figures 3, 4, 4B:
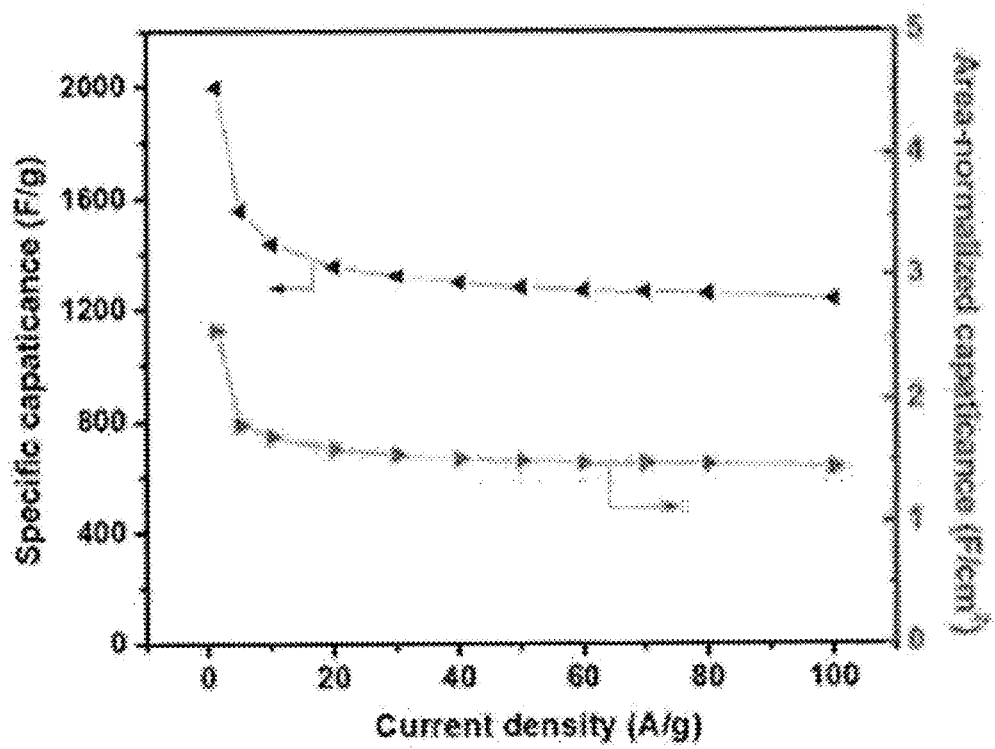
Figures 3, 4, 4C:
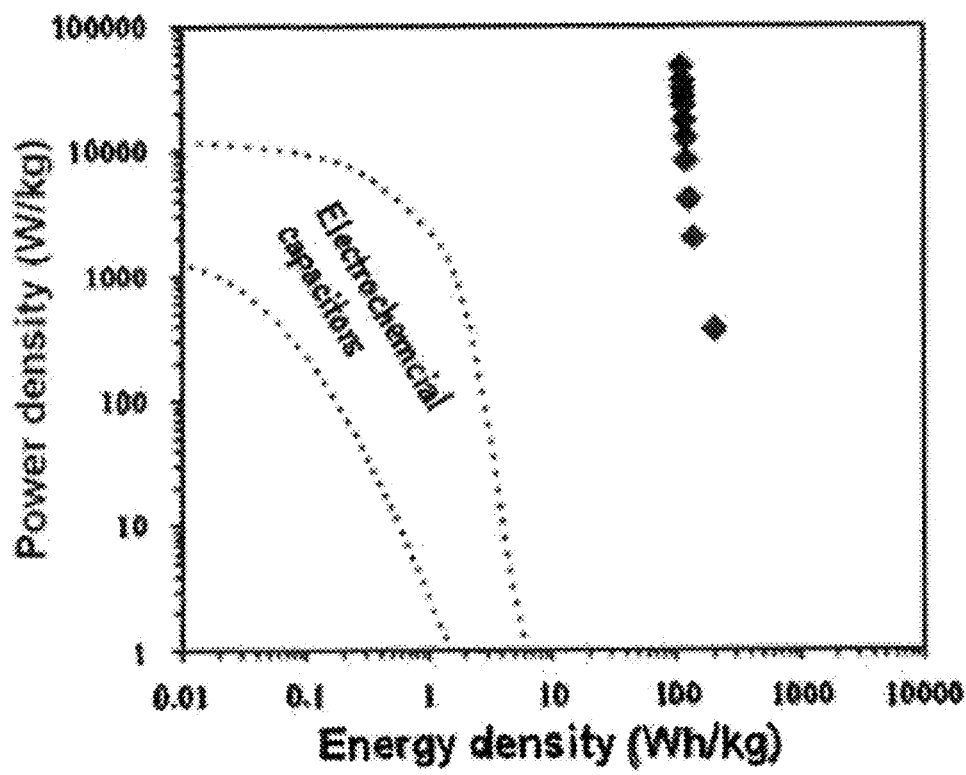
Figures 3, 4, 4D:
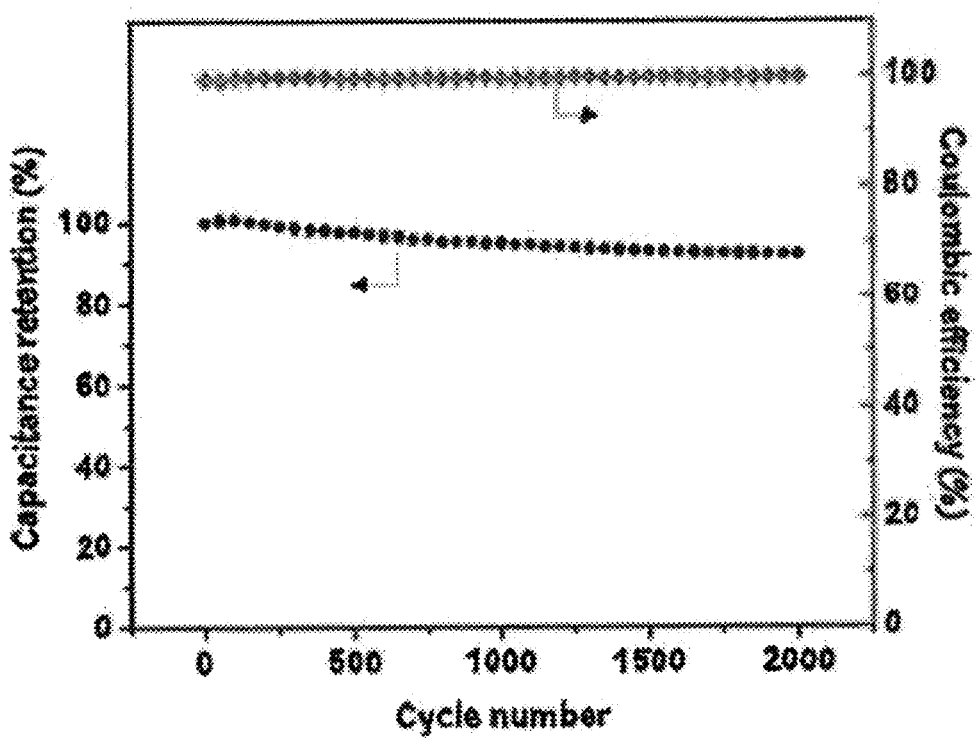
Figures 3, 4, 5, 5A:
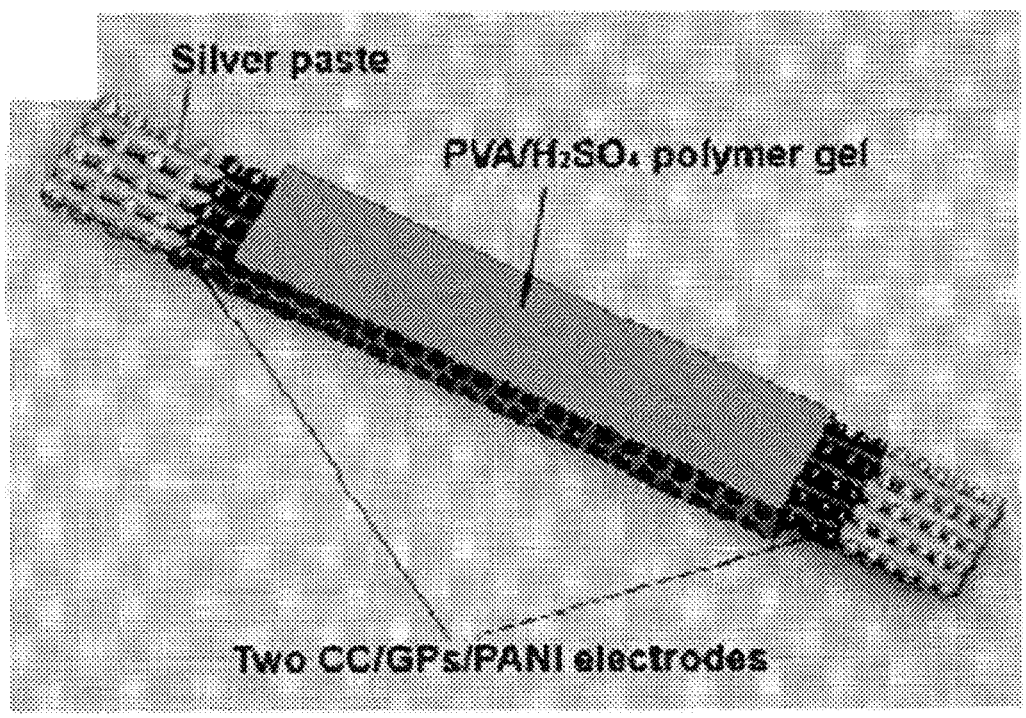
Figures 3, 4, 5, 5B:
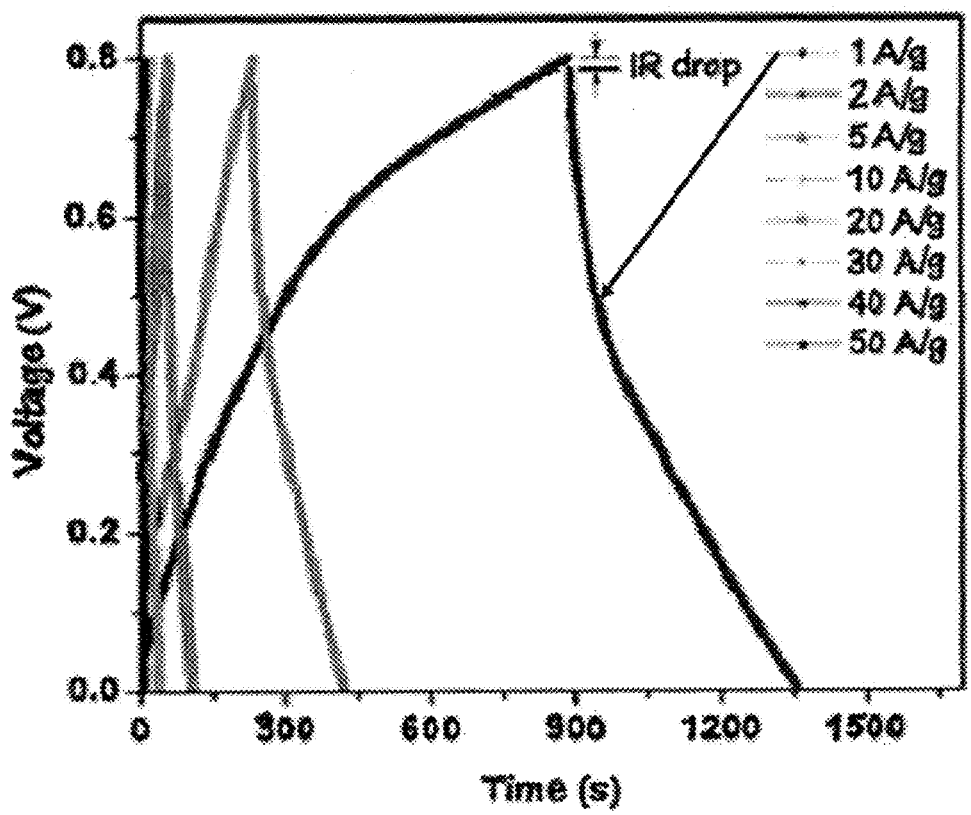
Figures 3, 4, 5, 5C:
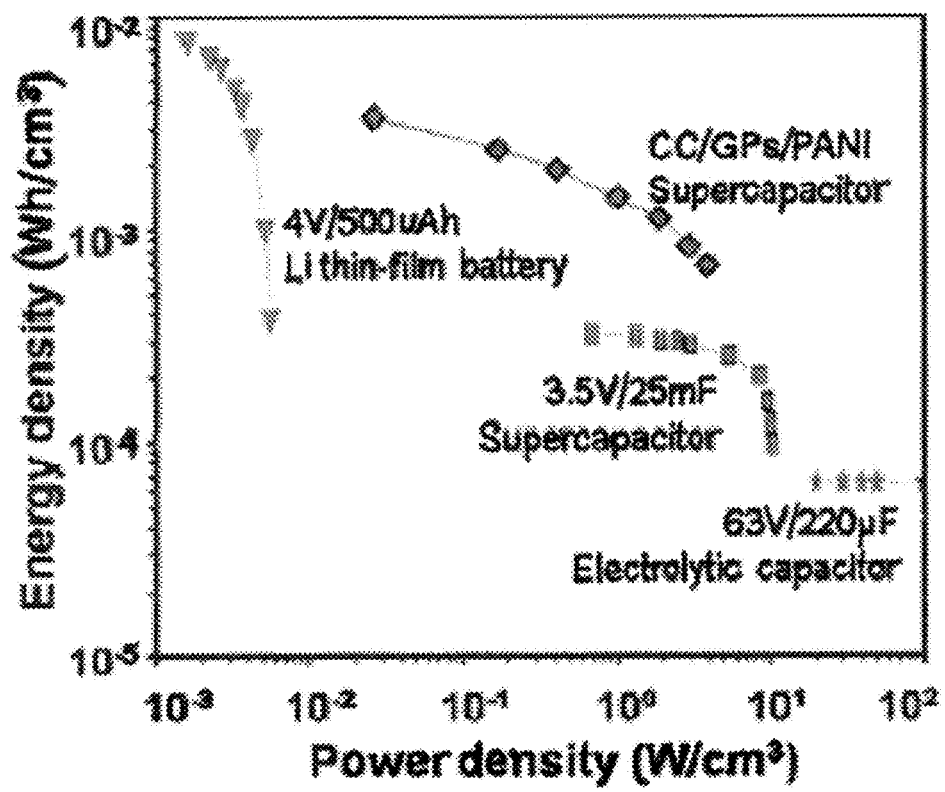
Figures 3, 4, 5, 5D:
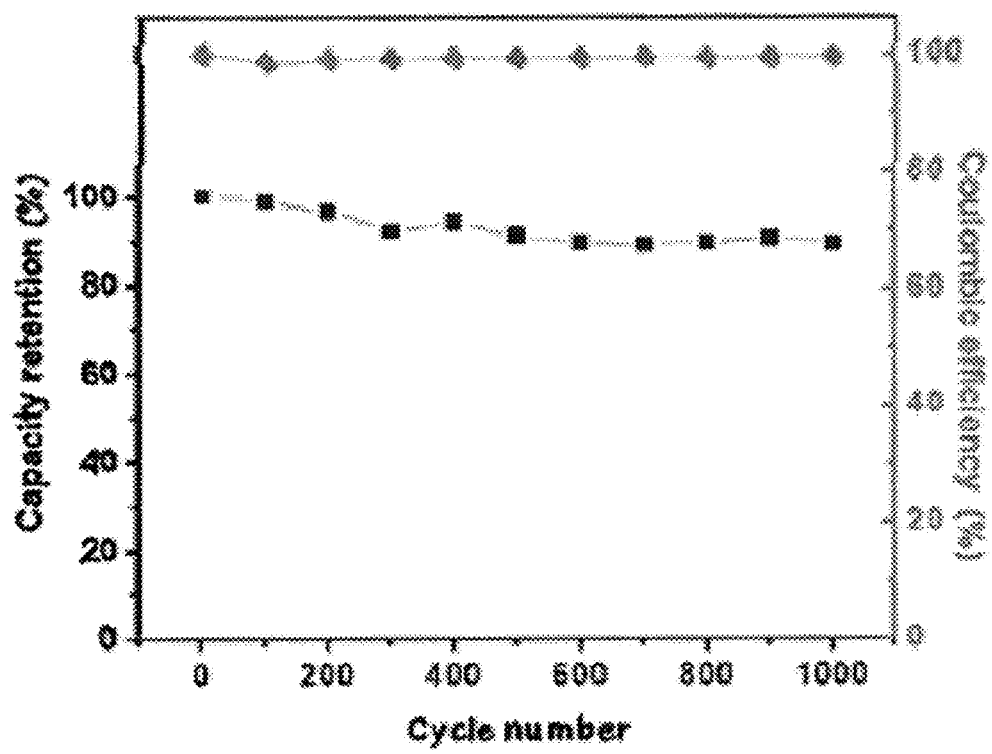
Figures 3, 4, 5, 5E:
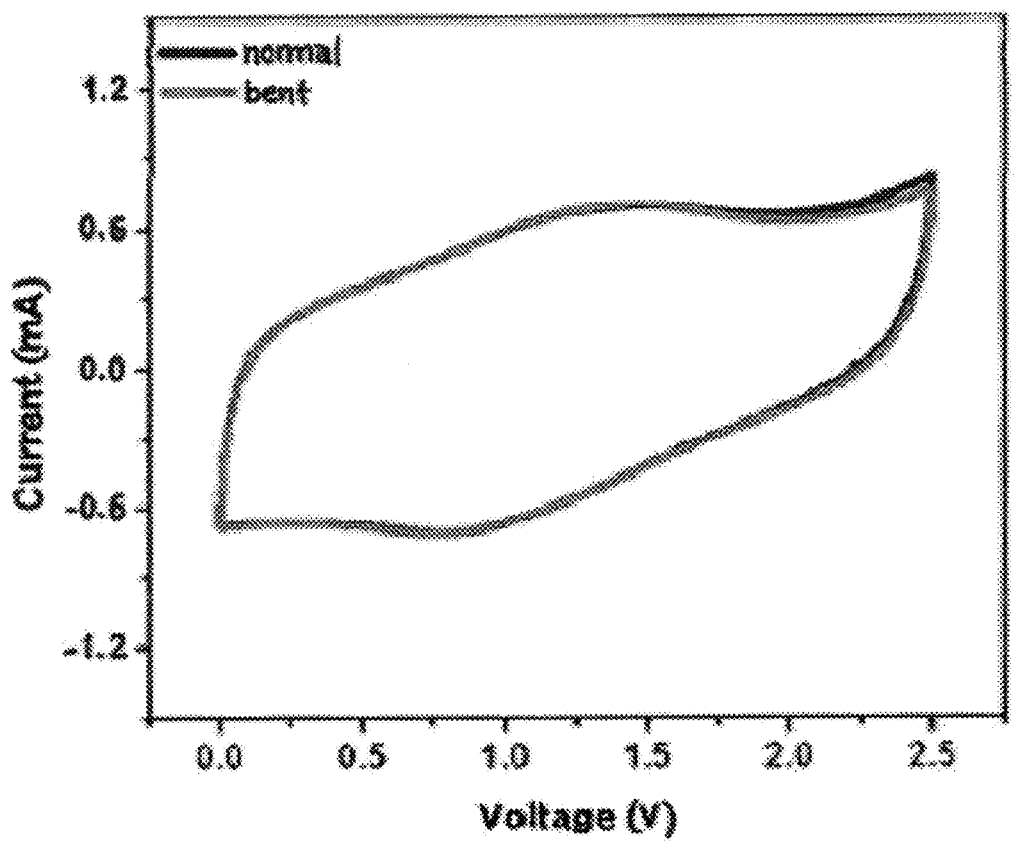
Figures 3, 4, 5, 5F:
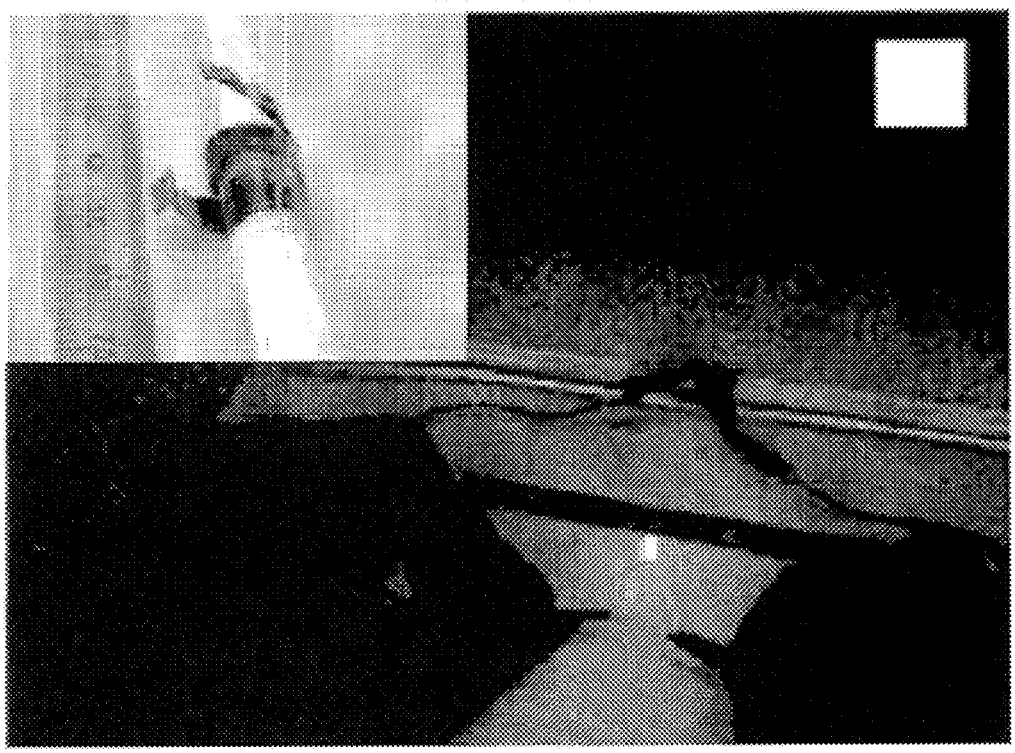
Figures 1A, 4:
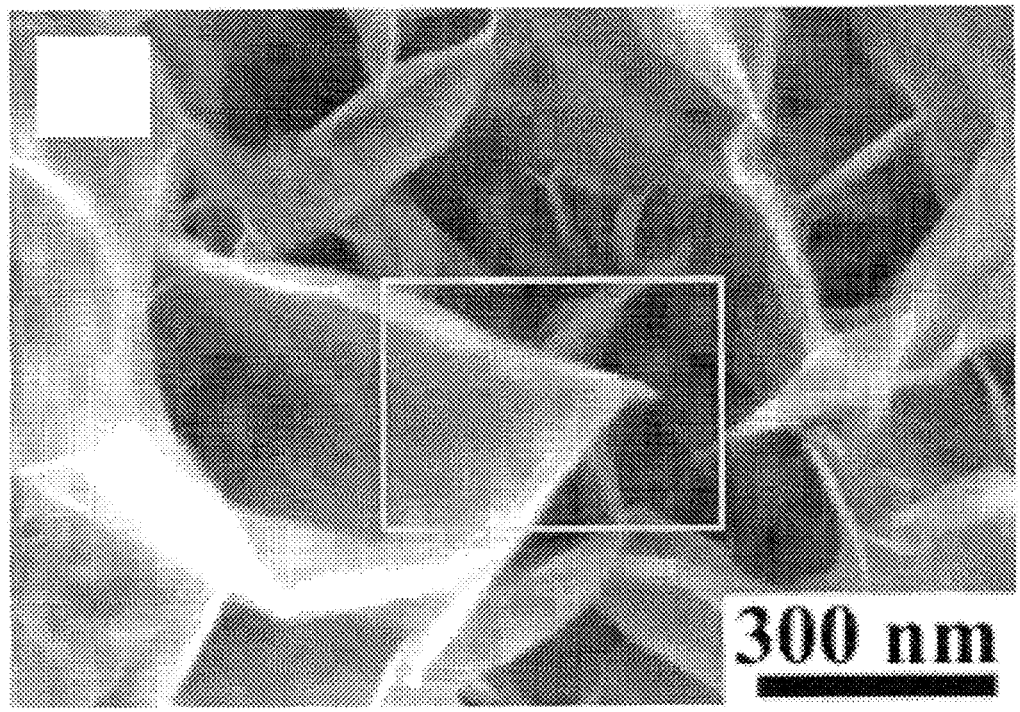
Figures 1B, 4:
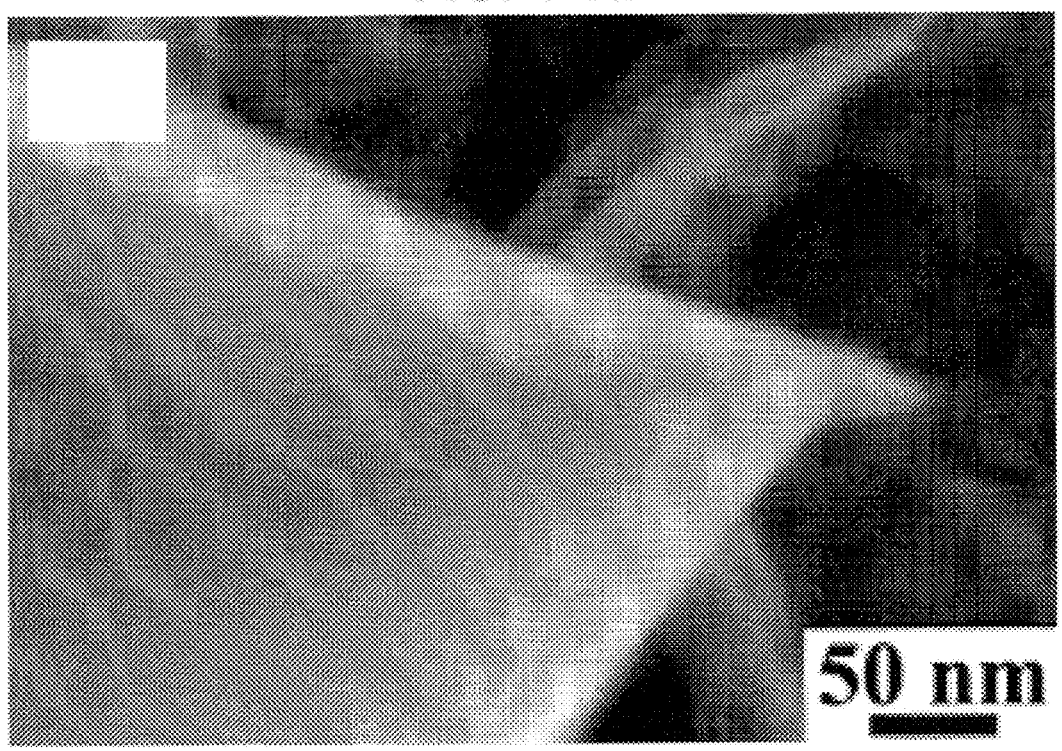
Figures 1C, 4:
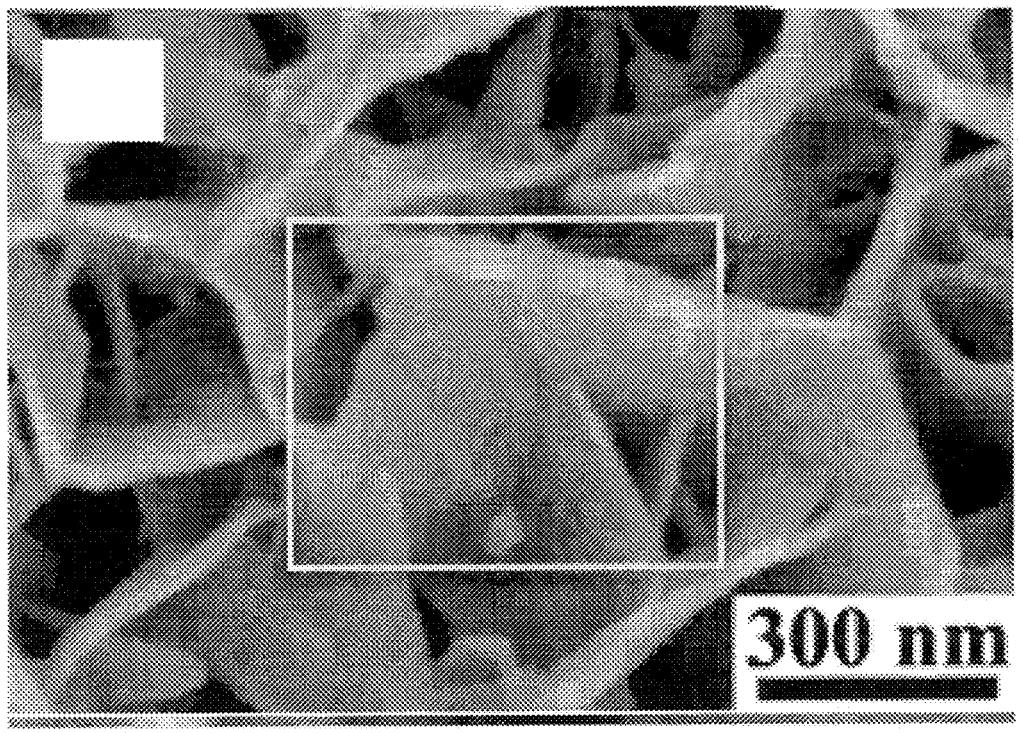
Figures 1D, 4:
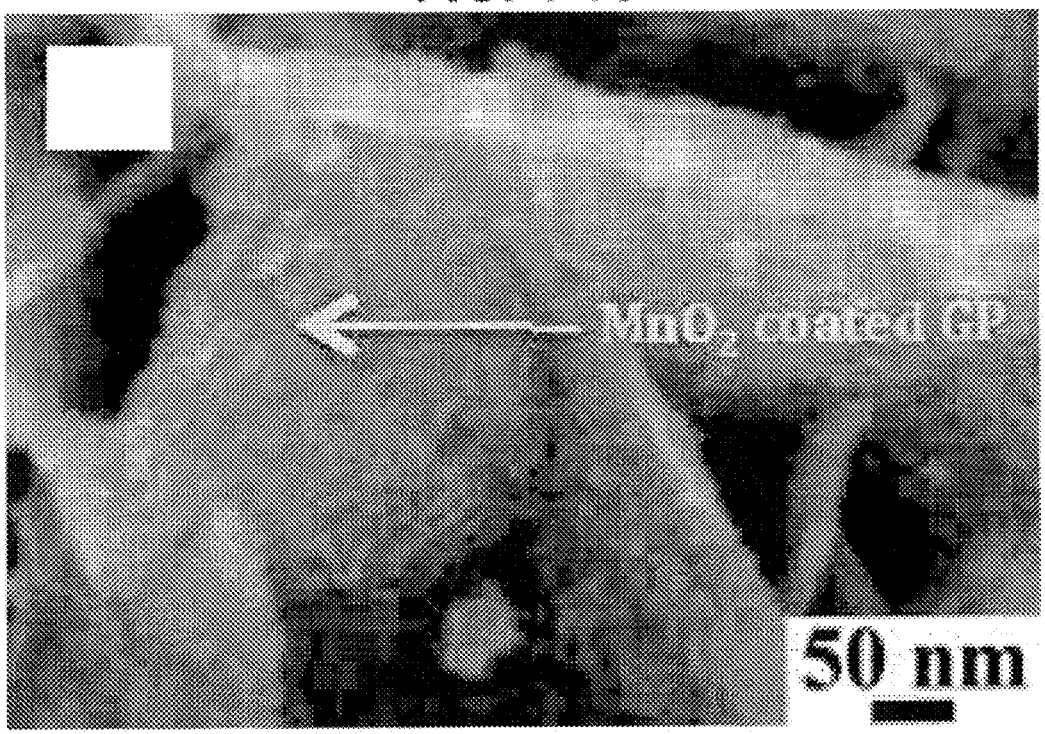
Figures 2, 4:
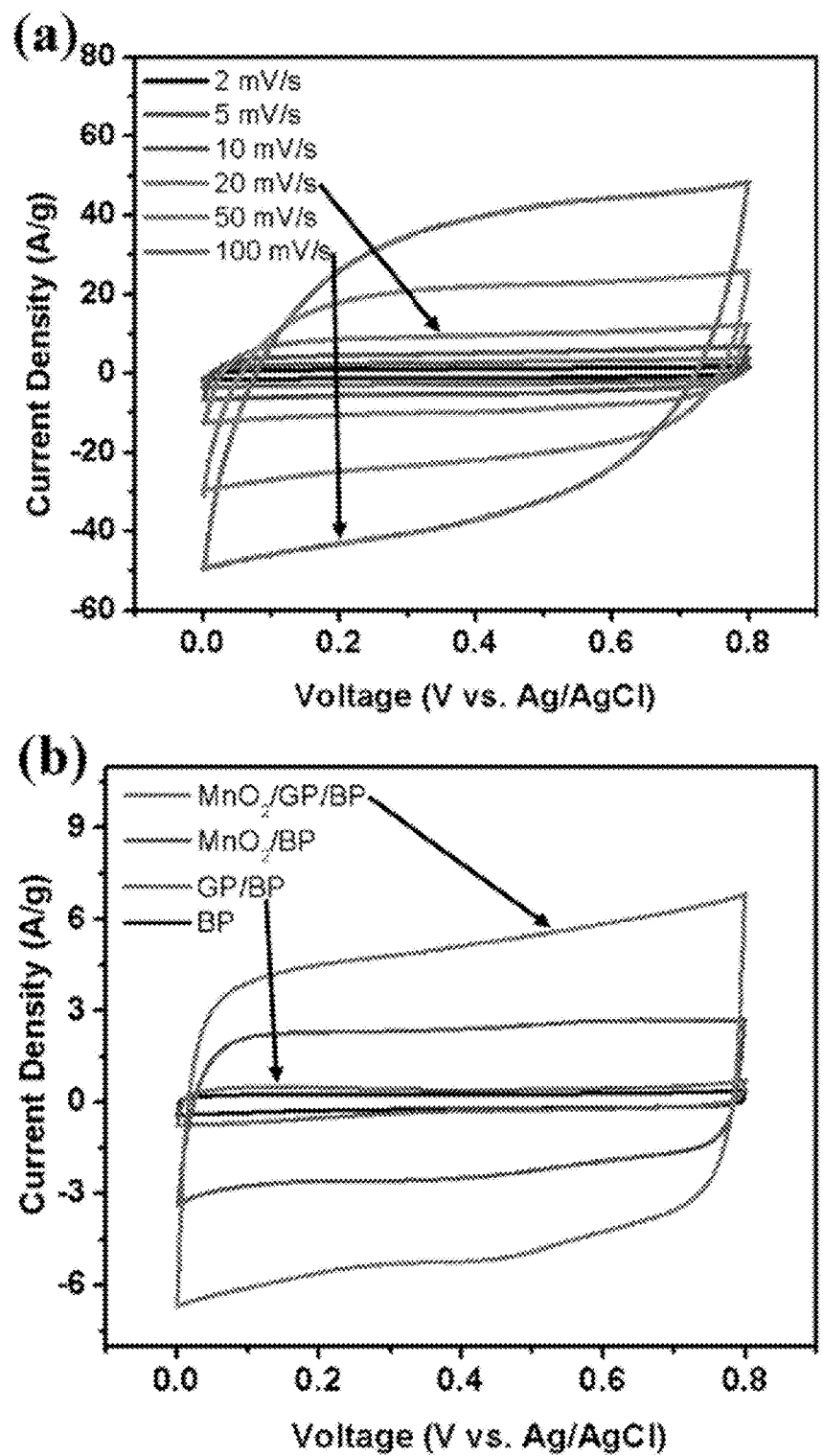
Figures 2, 4:
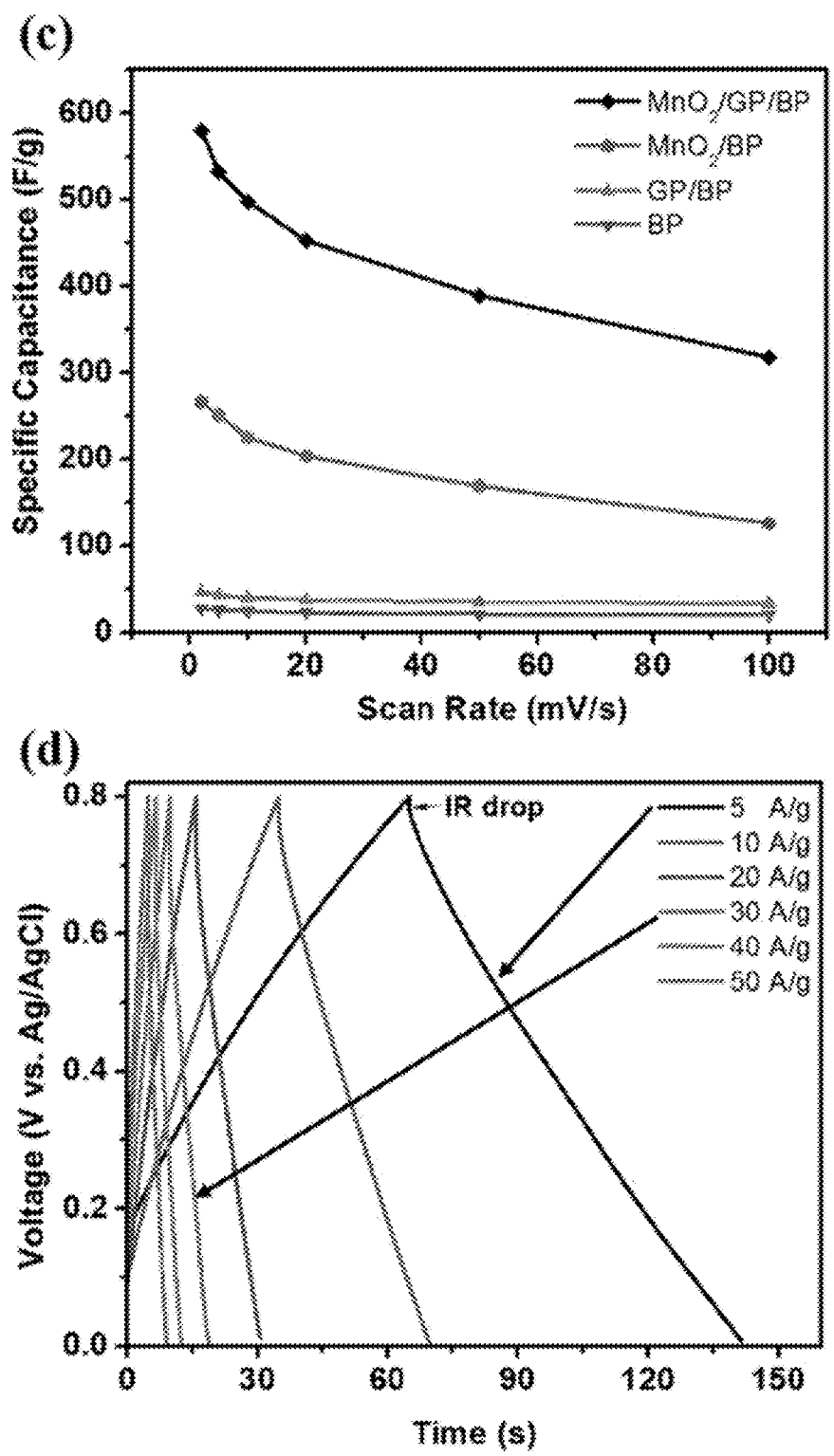
Figures 2, 4:
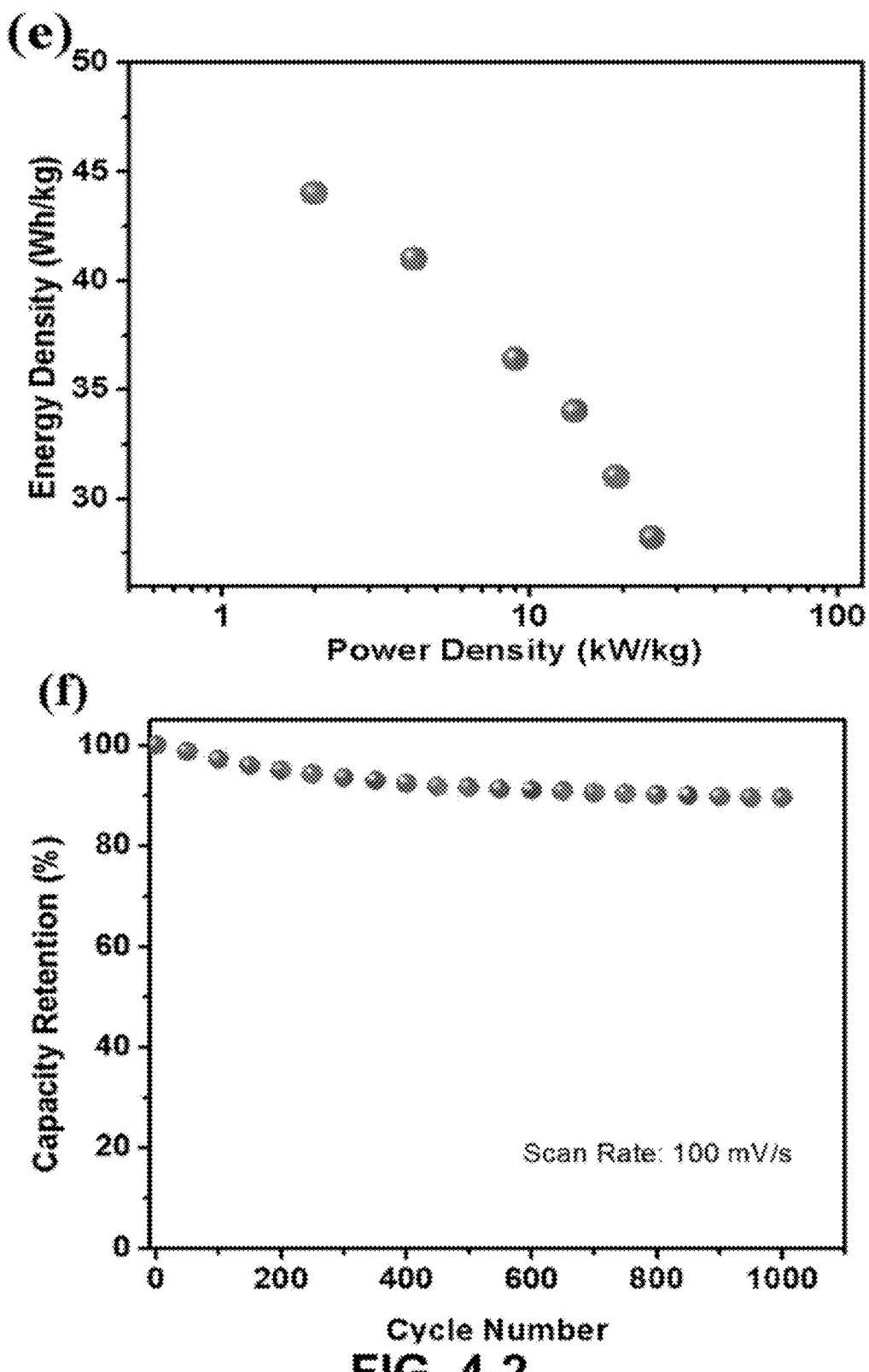
Figures 3, 4:
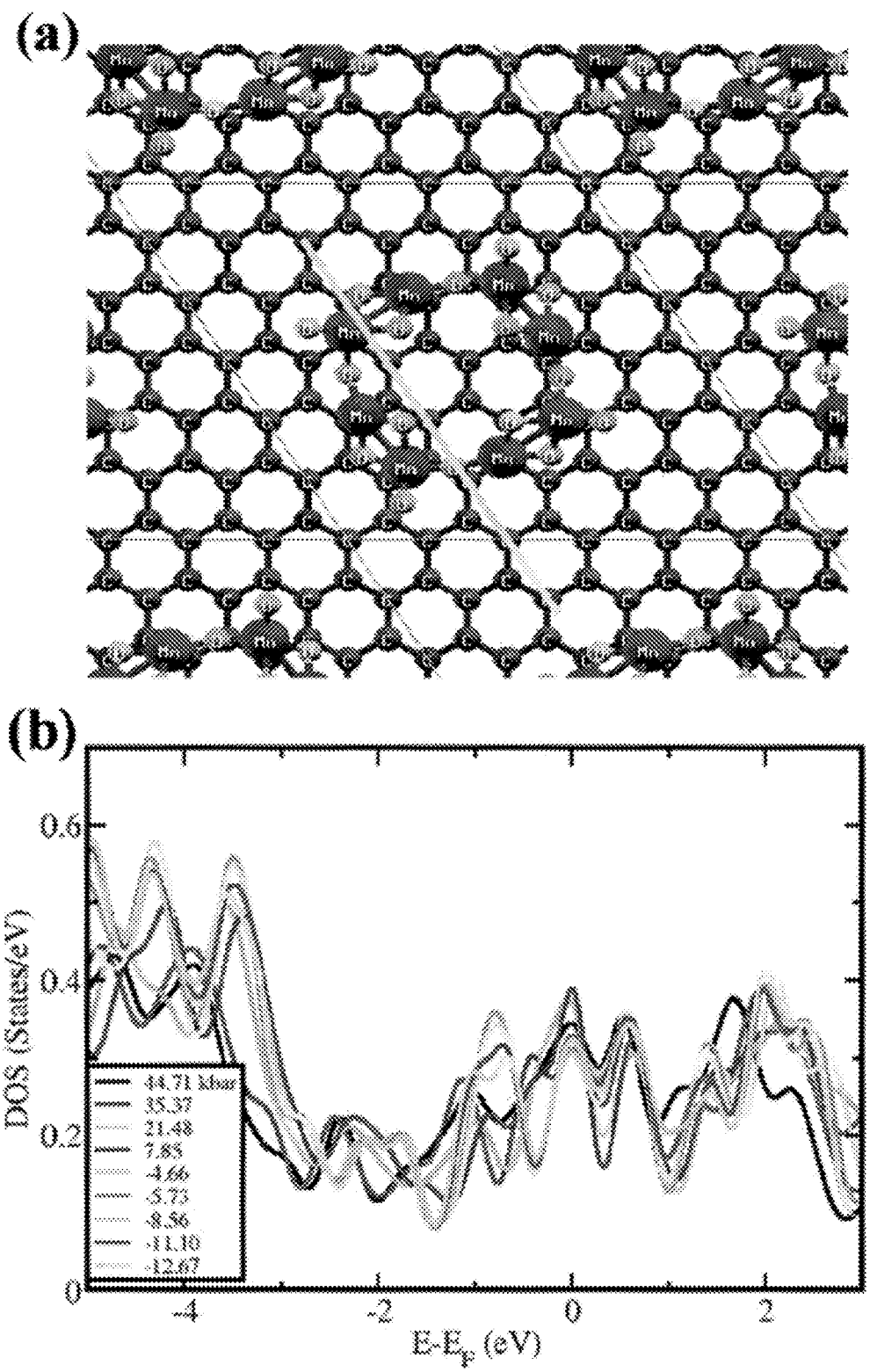
Figures 3, 4:
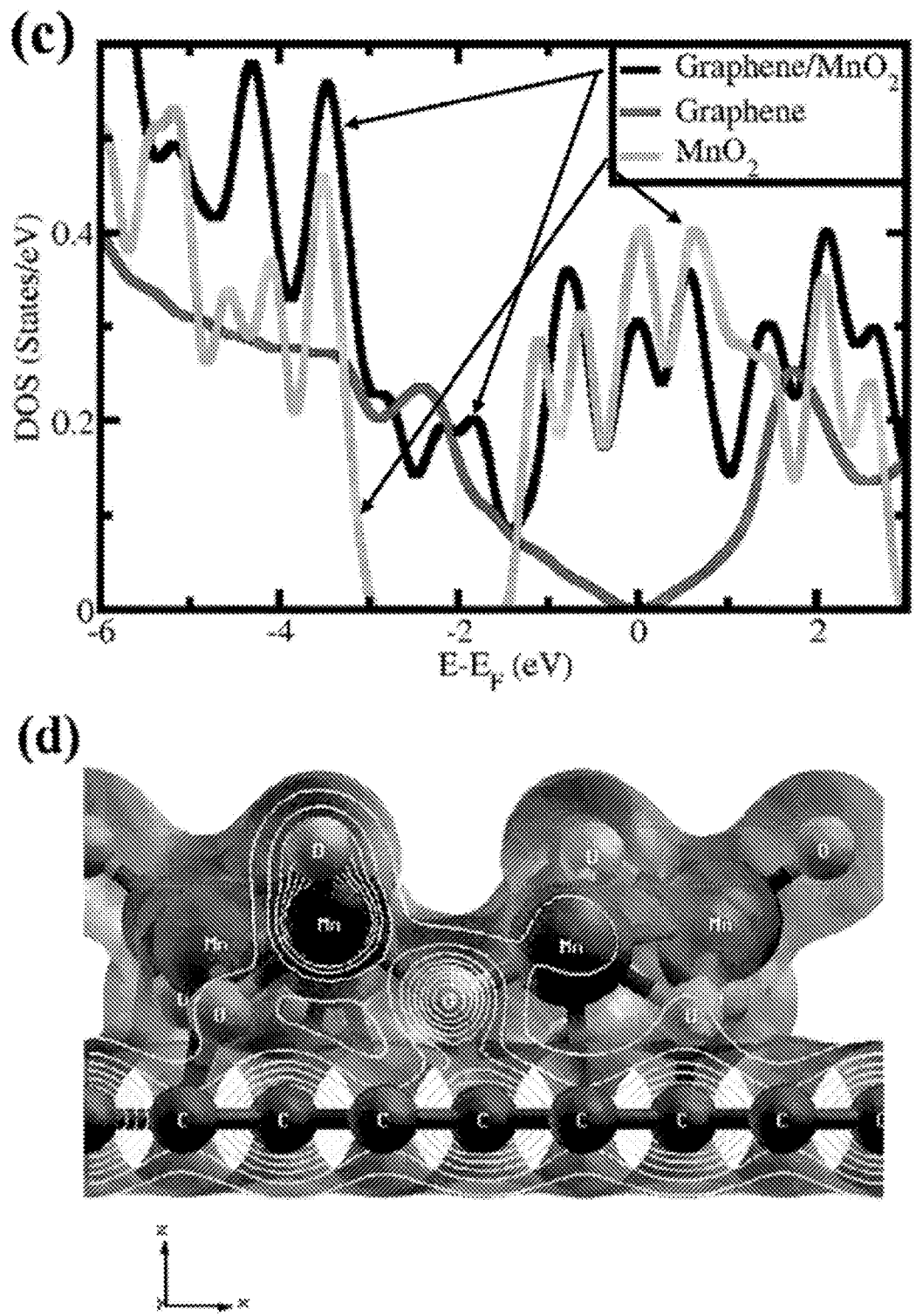
Figures 2, 5:
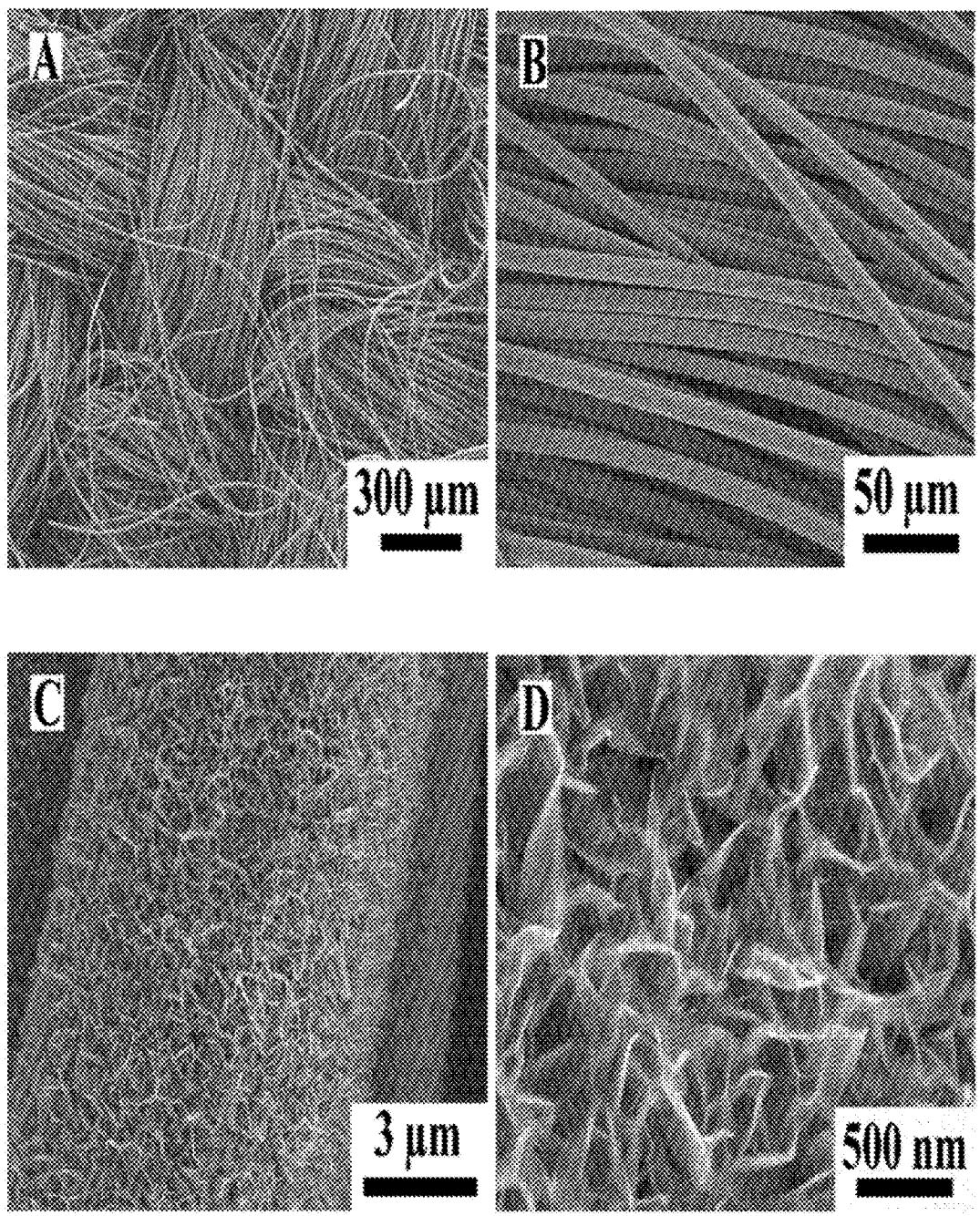
Figures 3, 5:
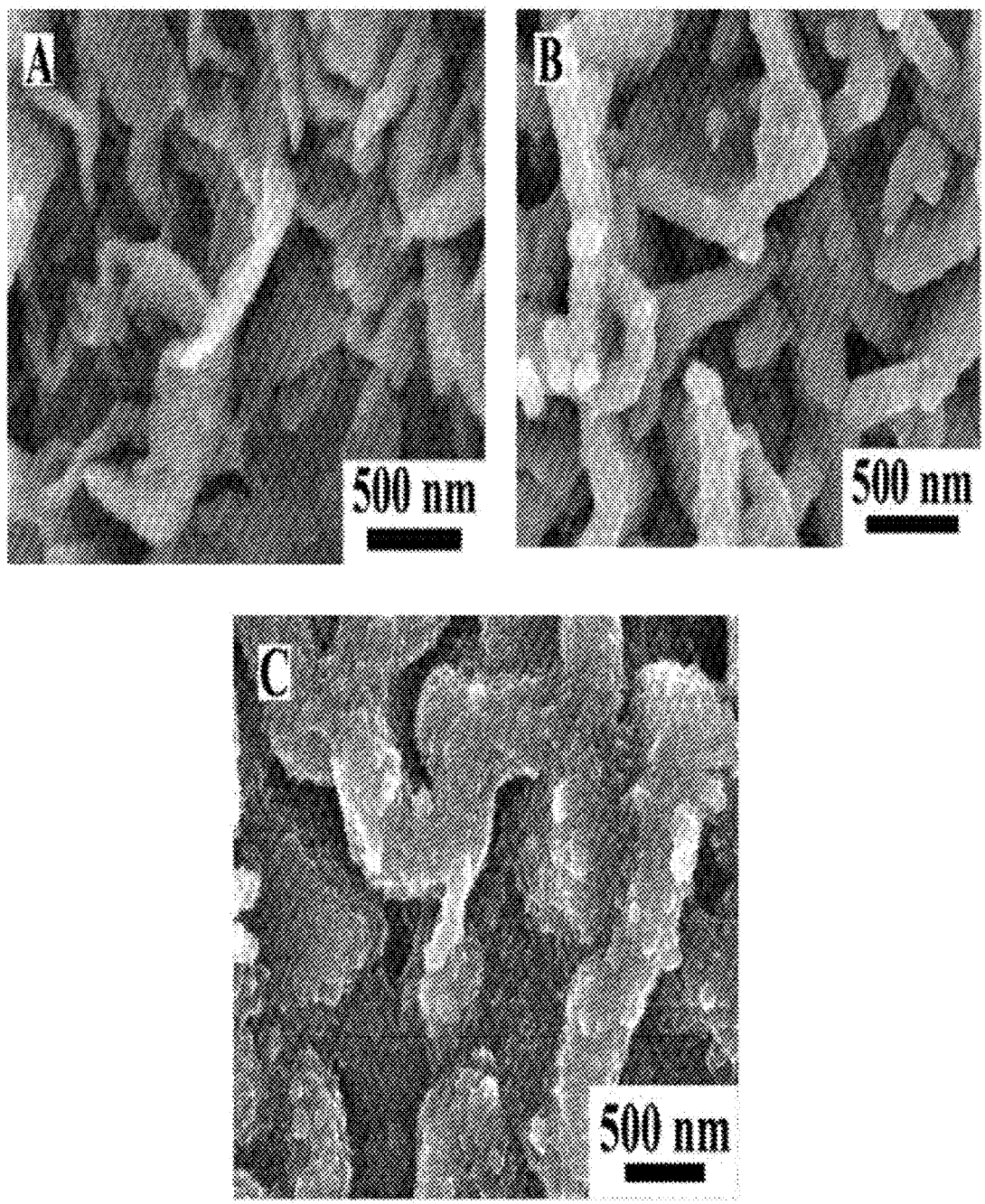
Figures 4, 5:
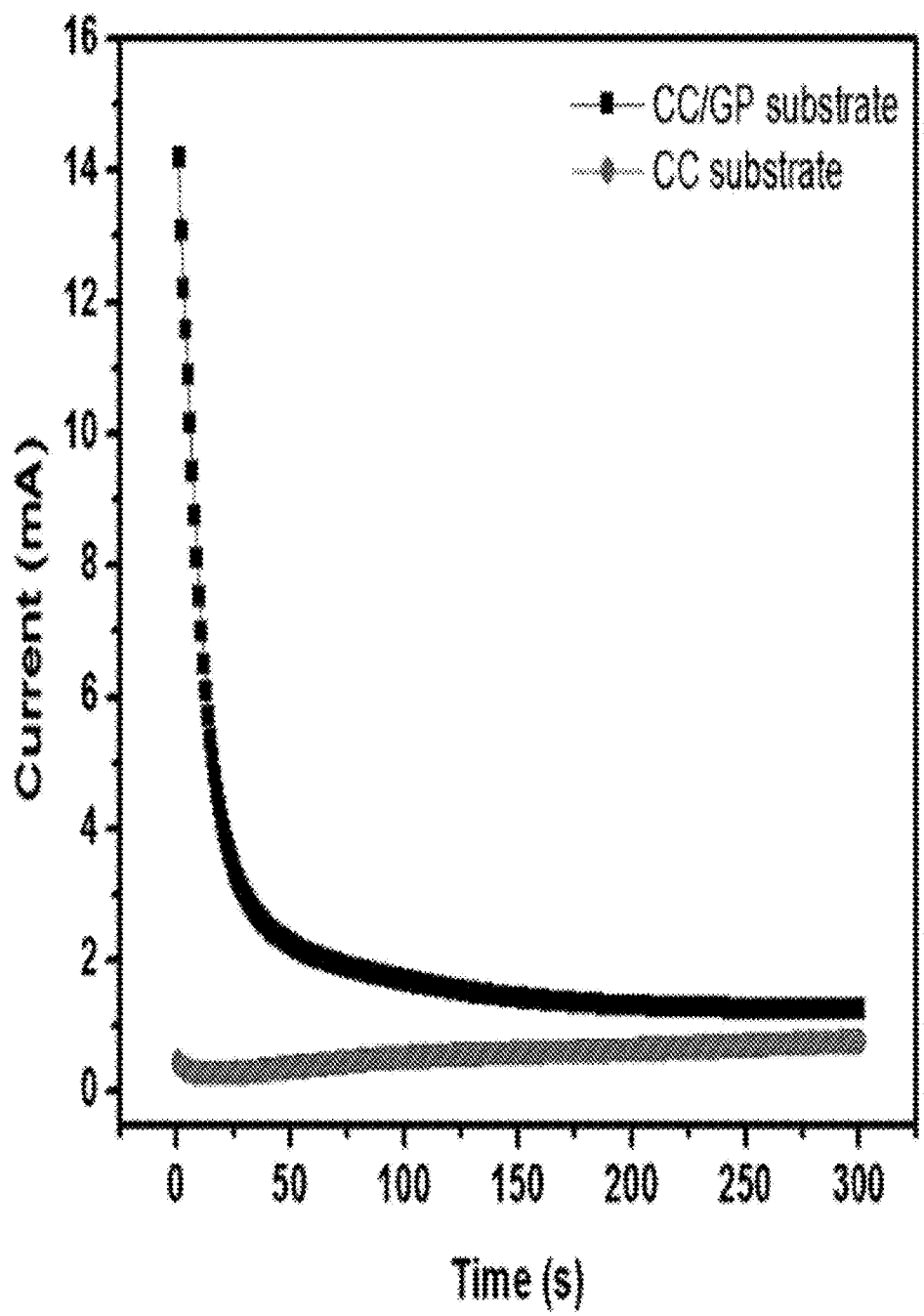
Figures 5, 5A:
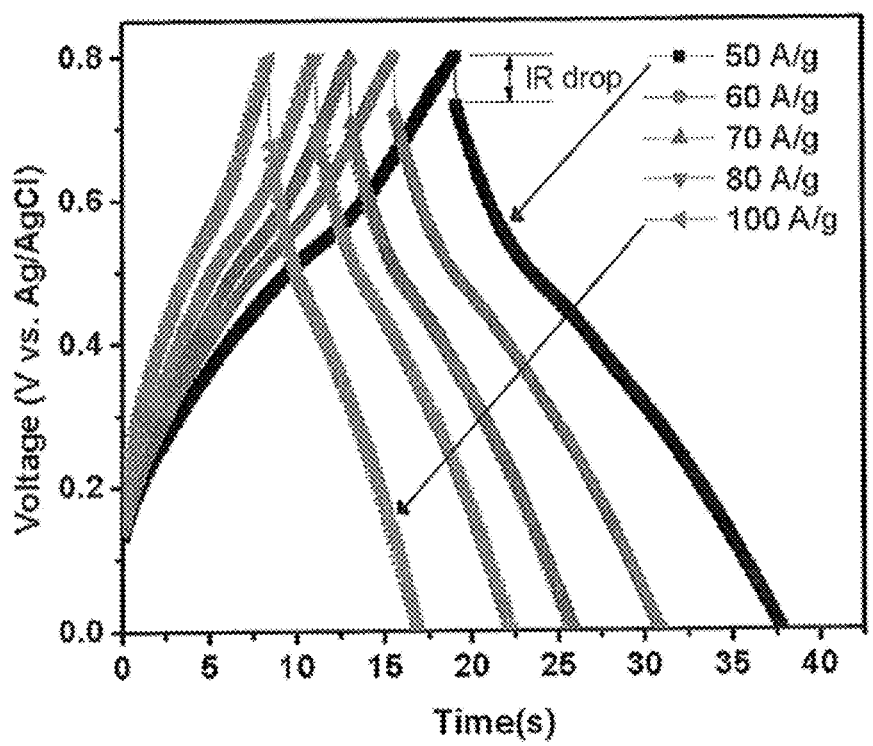
Figures 5, 5B:
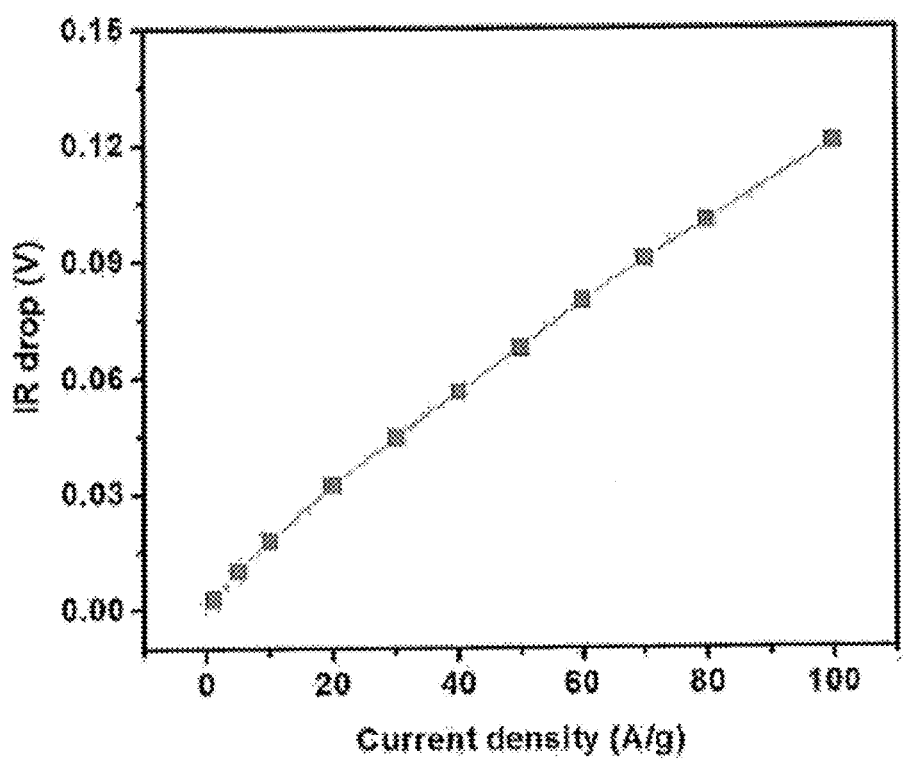
Figures 5, 6:
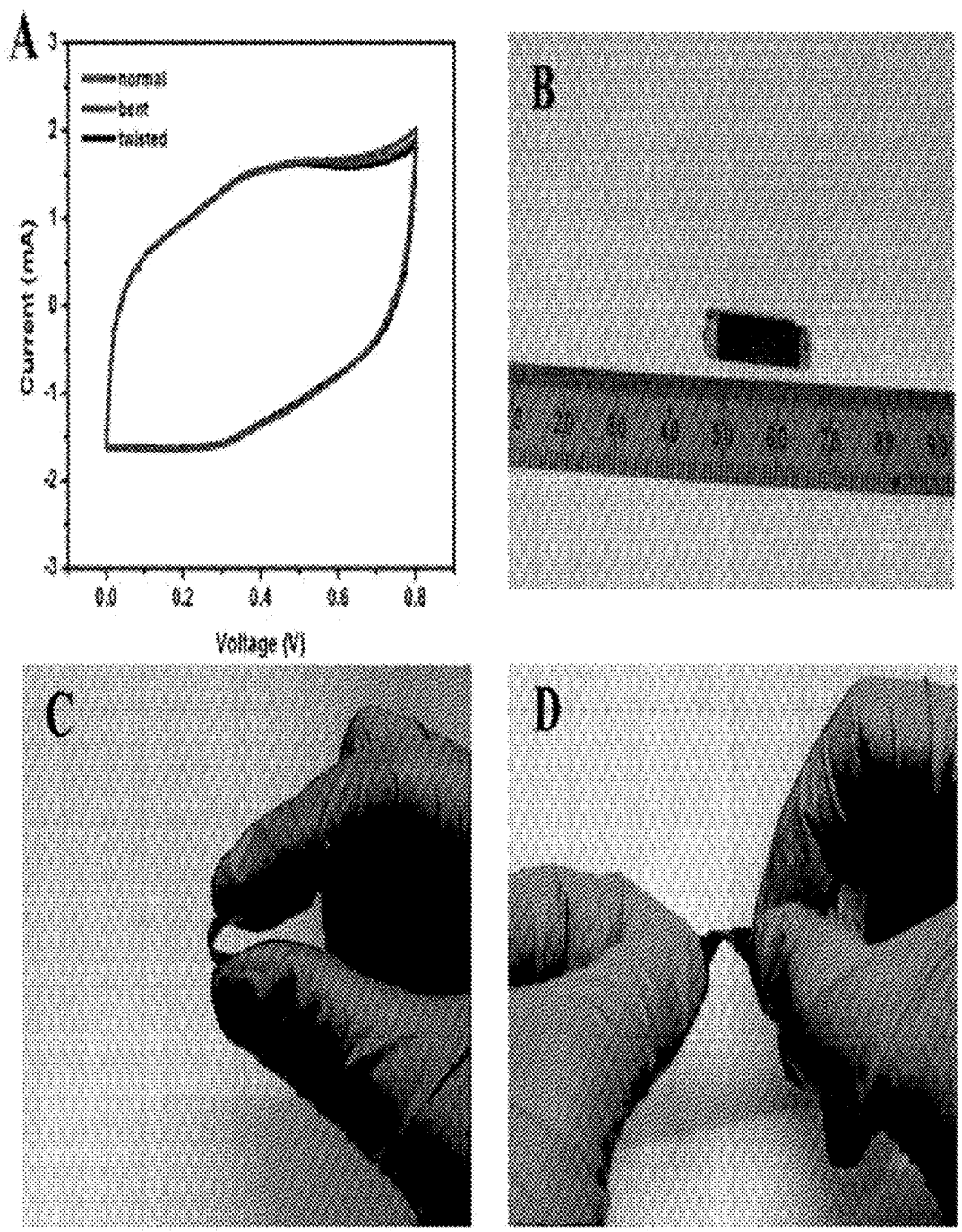
Figure 7:
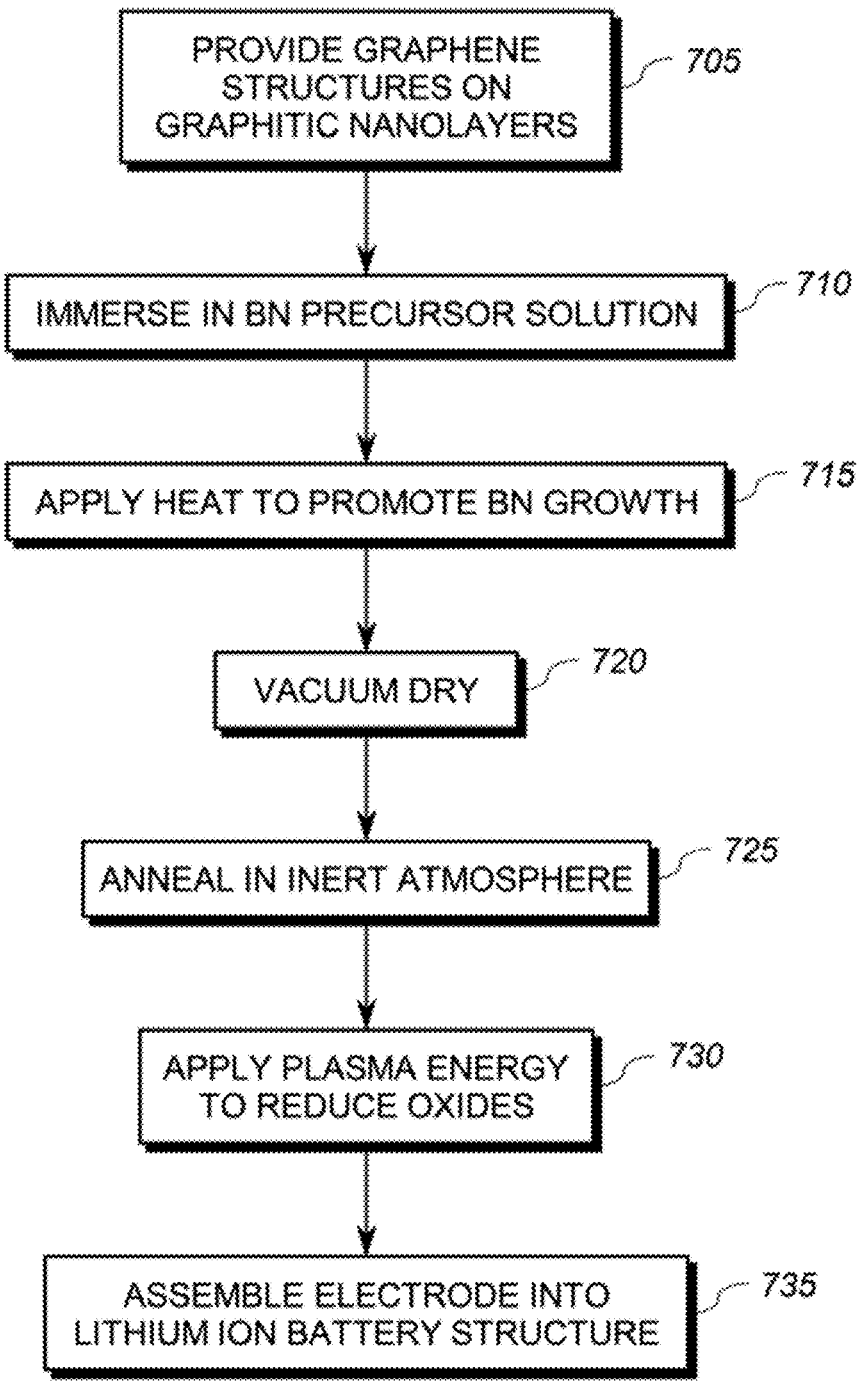
Figure 8:
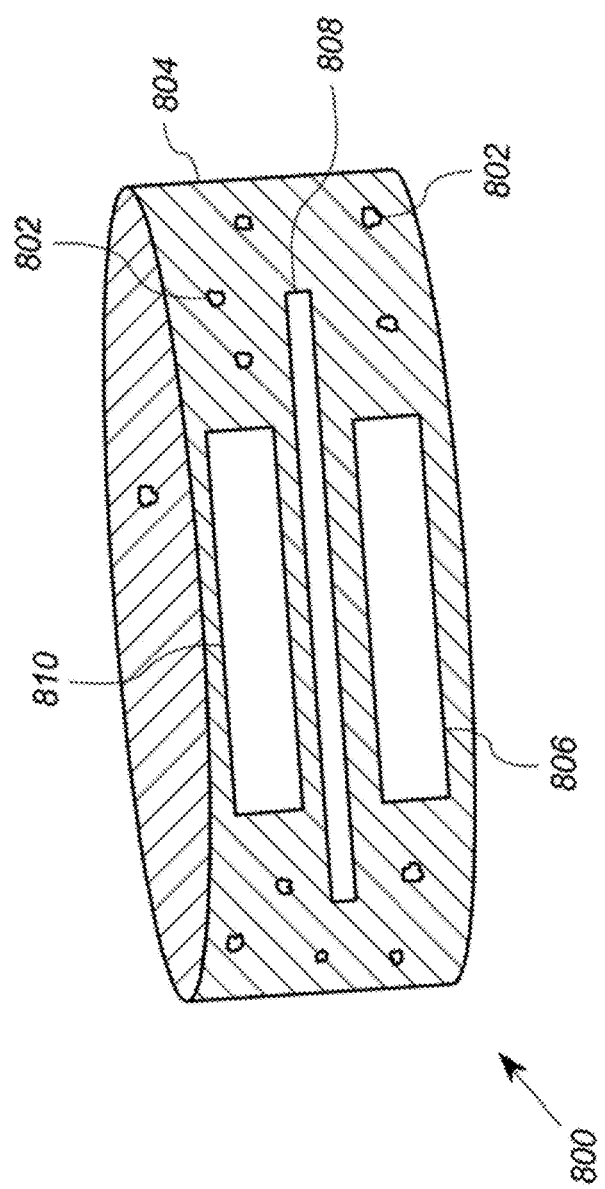
Figure 9:
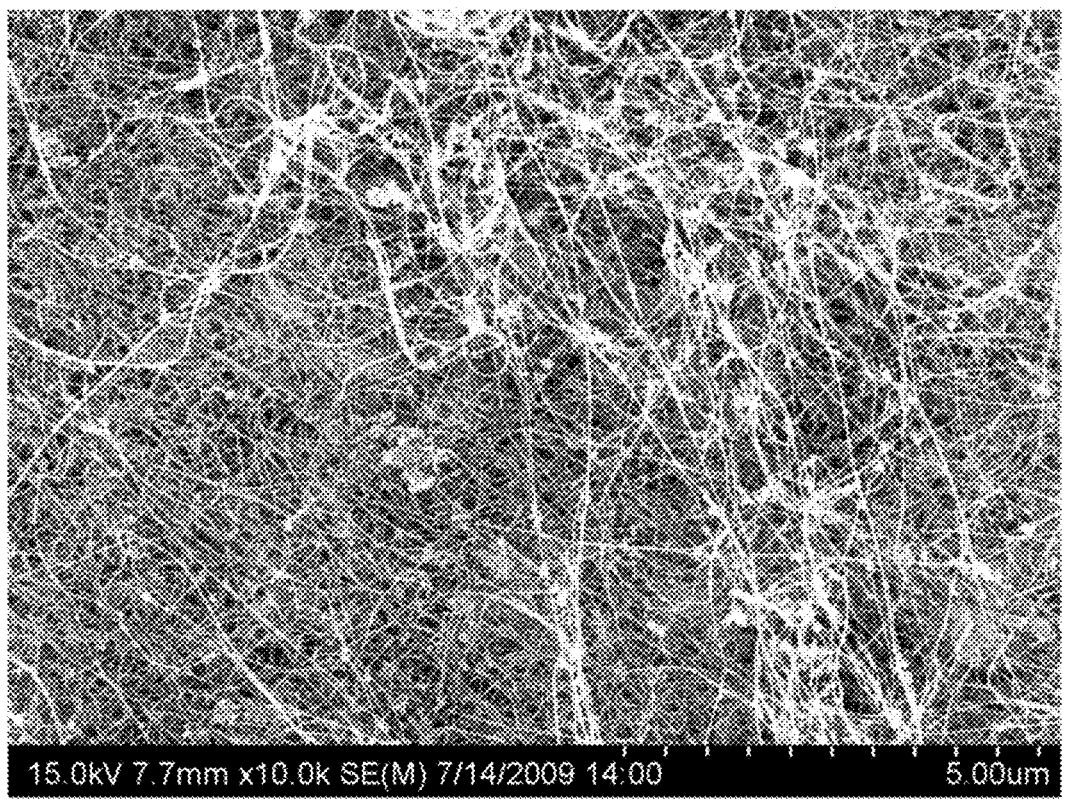
Figure 10:
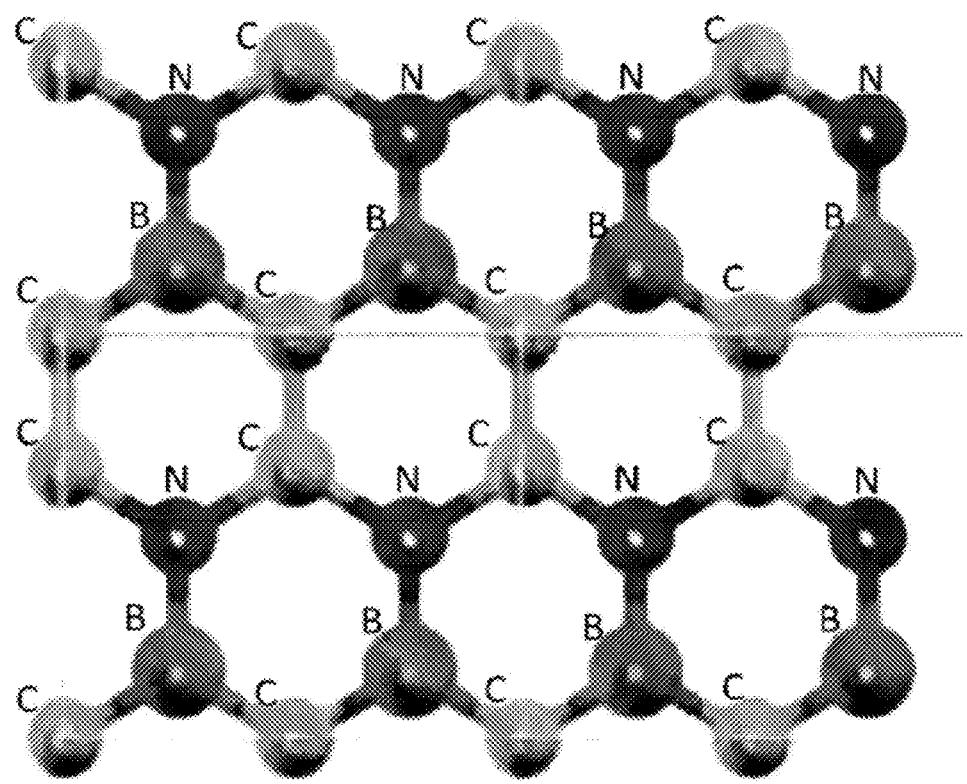
Figure 11:
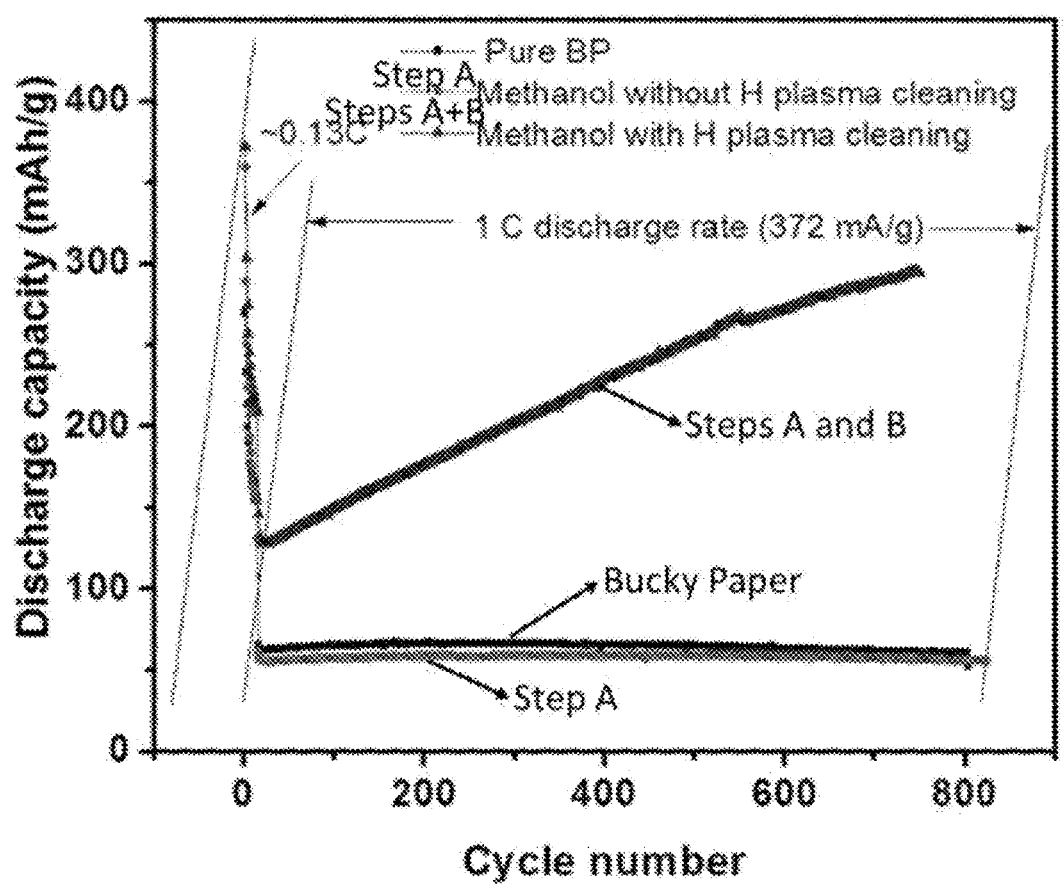

Another aspect for supercapacitor applications is cycling capability or cycling life. The cycling life tests over 2000 cycles for the CC/GPs/PANI hybrid electrode at a current density of 10 $mA/cm^2$ were carried out using constant current galvanostatic charge/discharge cycling techniques in the potential windows ranging from 0 to 0.8 V. FIG. 3-4D shows the specific capacitance retention of the CC/GPs/PANI hybrid electrode as a function of charge/discharge cycling numbers. The composite electrode showed ~7% loss in the capacitance after 2000 charge-discharge cycles, indicating long-term stability. Coulombic efficiency of the hybrid electrode is ~99.8%, indicating high efficiency of the rapid electron-transfer for charge storage and delivery.

The novel hybrid 3D nanostructure electrode shows excellent electrochemical properties in a three-electrode testing system, according to one embodiment. Furthermore, in the application level, the flexible composites also show potential as electrodes for advanced flexible all-solid-state supercapacitors with a two-terminal configuration. In another embodiment, paper-like CC/GPs/PANI supercapacitors are fabricated with improved supercapacitor performance. FIG. 3-5A shows the schematic illustration of all-solid state highly flexible CC/GPs/PANI supercapacitors based on PVA-$H_2SO_4$ polymer gel electrolyte. Macroscopically, as-fabricated devices possess superior mechanical properties and show no cracks or any performance degradation under highly flexible conditions, even in highly bent (180° angle bending) and twisted conditions.

Galvanostatic charge/discharge performances were carried out on an individual flexible device in FIG. 3-5B, which shows that charge/discharge curves of a CC/GPs/PANI paper-like supercapacitor at different constant current densities ranging from 1 Ag to 50 Ag. The charge/discharge curves maintain almost symmetric at all current densities. At a current density of 1 A/g, the calculated mass specific capacitance is ~1200 F/g and an area-normalized specific capacitance of ~1.5 $F/cm^2$ based on a single electrode. The internal resistance calculated based on the IR drop (0.0158 V) is 29Ω at 1 A/g, which is higher than that in aqueous electrolyte in three-electrode system due to the intrinsic lower ion conductivity of polymer electrolyte and the inhomogeneity of large area sample preparation during device fabrication process, which will be further optimized in the future.

Comparison of the specific energy and power density (per $cm^3$ of stack) of typical electrolytic capacitors, supercapacitors and batteries in a Ragone plot is shown in FIG. 3-5C. It compares the performance of our all-solid-state flexible device with the current various other energy storage devices. The CC/CPs/PANI based supercapacitor exhibit energy densities of up to 3.38 $mWh/cm^3$, a value that reaches the upper range of the lithium thin-film battery and almost ~10 times as high as that of the commercial 3.5V/25-mF supercapacitor. Additionally, the CC/CPs/PANI based supercapacitor is able to deliver a power density of 3 $W/cm^3$, which is two-orders of magnitude higher than that of the Lithium thin-film battery. The cycling life tests over 1000 cycles for the CC/GPs/PANI hybrid electrode at a current density of 5 $mA/cm^2$ were carried out using constant current galvanostatic charge/discharge cycling techniques in the potential windows from 0 to 0.8 V, as shown in FIG. 3-5D. ~10% loss in capacitance after 1000 cycles and coulombic efficiencies of the hybrid electrode of ~99.5% were measured for the device, indicating a relatively good stability and high efficiency of the rapid electron-transfer for charge storage and delivery.

Three supercapacitor units were prepared (each size ~0.5 cm×~2.0 cm) in series to light a green light-emitting-diode (LED, the lowest working potential is 1.5 V). The as-prepared supercapacitor group shows no performance degradation when in highly flexible conditions, as shown in FIG. 3-5E. CV curves of the supercapacitor group (scanning from 0 V to 2.5 V) in both normal and bend conditions almost overlaps, indicating the highly flexibility of the device. FIG. 3-5F demonstrated that three highly flexible devices in series, wrapped around a glass rod (inset), were used to light a green LED well. After being charged at 2.5 V for 15 min, the highly flexible device could light the LED very well for more than 30 min.

The ultrathin highly flexible and all-solid state supercapacitor device based on CC/GPs/PANI here has already demonstrated the improved flexibility and electrochemical performances to the current commercial supercapacitor devices. Many parameters such as the thickness of the polymer gel, force applied to compress two electrodes together, concentration of acid in polymer gel and good electrical contact between two individual devices, et al., can be optimized in order to fabricate highly flexible devices with better electrochemical properties.

One embodiment pertains to a novel 3D nanostructure based on CC/GPs/PANI for highly flexible supercapacitor electrode. Systematic studies were carried out to optimized the amount of PANI mass in order to utilize PANI to the maximum extent while also maintain a high area-normalized capacitance of the electrode in a three-electrode testing system. It is found that the existence of GPs significantly improves the comprehensive electrochemical properties of the hybrid electrode, due to the large specific surface area and unique sharp edge structures. The CC/GPs/PANI hybrid electrode shows outstanding electrochemical performances, such as high specific mass capacitance as well as high area-normalized and volumetric capacitance, good cycling life and high energy and power densities. All-solid-state supercapacitor, with two slightly separated CC/GPs/PANI nanocomposite electrodes and PVA-$H_2SO_4$ bifunctional polymer gel as solid-state electrolyte and separator were fabricated and tested. The flexible device shows excellent electrochemical performances in specific capacitance, energy and power density and cycling life. Features of one embodiment of the present invention were demonstrated to light a green LED out under highly flexible (testing) conditions to use of this lightweight, highly flexible and all-solid state polymer based supercapacitors.

Yet another embodiment of the present invention pertains to the use of flexible, conductive preferably carbon-based substrate. Commercial carbon cloth (CC, Fuel Cell Earth LLC), made of microfibers, were used directly as substrates without further processing for graphitic petal (GP) synthesis by microwave plasma enhanced chemical vapor deposition (MPCVD). The schematic diagram of the chamber for the growth process is shown in FIG. 2-1. The plasma source consists of a 2.45 GHz frequency microwave power supply with variable power. Carbon cloth substrates, elevated 15 mm above a 55-mm-diameter Mo puck by ceramic spacers, were subjected to MPCVD conditions of $H_2$ (50 sccm) and $CH_4$ (10 sccm) as the primary feed gases at 30 Torr total pressure. The GP growth time was 25 min. The plasma power is 700 W during the growth process. This plasma is sufficient to heat the samples from room temperature up to ~1100° C., as measured by a dual-wavelength pyrometer (Williamson PRO 92).

First, preparation of the $H_2SO_4$-polyvinyl alcohol (PVA) gel polymer electrolyte was prepared as follows: 6 g $H_2SO_4$ was mixed with 60 ml deionized water and then 6 g PVA powder was added. The whole mixture was heated up steadily from room temperature to ~90° C. under vigorous stirring until the solution became clear. Then the dilute polymer electrolyte solution was cooled down to room temperature.

Two pieces of the obtained CC/CPs/PANI nanocomposite sheets (each geometrical size ~0.5 cm×2.0 cm, with the edge of one side glued with silver paste for a well electrical contact) was immersed in the dilute polymer electrolyte solution (the part glued with silver paste was kept out) for 30 min and picked out. The dilute solution soaked the inside network of the electrode well and formed a coating layer around the surface of the electrode. Then the electrodes with the electrolyte solution coating on were left in the fume hood at room temperature for 4 h to vaporize the excess water. After the $H_2SO_4$-PVA electrolyte became solidified, the two electrodes were tightly pressed together into one integrated unit, by sandwiching a thin layer of viscous polymer electrolyte between them as an adhesive.

A Hitachi S-4800 field emission scanning electron microscope (FESEM) was used to image the surface morphology of the samples. A FEI Titan 80-300 operated at 300 kV was utilized for a high-resolution transmission electron microscopy (HRTEM) to characterize structure of the as-grown GPs. Raman characterization was performed with an Xplora spectrometer (Horiba Jobin Yvon Inc.) with a fixed laser excitation wavelength of 532 nm, power of 2.5 mW, spot size of 600 nm, and magnification of 100×.

Cyclic voltammetry (CV) measurements of the CC/GPs/PANI hybrid structure were carried out on a BASi Epsilon electrochemical system (Bioanalytical Systems Inc., Indiana, USA) to evaluate the specific capacitance at different scan rates from 2 mV/s to 100 mV/s. Galvanostatic charge/discharge measurements (Gamry Echem Testing System, Gamry Instruments, Inc., USA) were used to evaluate the specific capacitance (Cs), internal resistance (IR), energy density (Es), power density (Ps), coulombic efficiency (η) and cycling life of the devices. Different current densities (~1 Ag to 100 Ag) were applied and a current density of 10 mA/cm² was used for the cycling life tests for three-electrode configuration cell. The standard three-electrode cell consisted of Ag/AgCl as the reference electrode, Pt mesh as the counter electrode and the synthesized composite sample as the working electrode, respectively. A 1 M $H_2SO_4$ solution served as the electrolyte at room temperature. The potential was between 0 to 0.8 V (0 to 2.4 V for the tests of three in-series supercapacitor group).

Figures 1, 2:
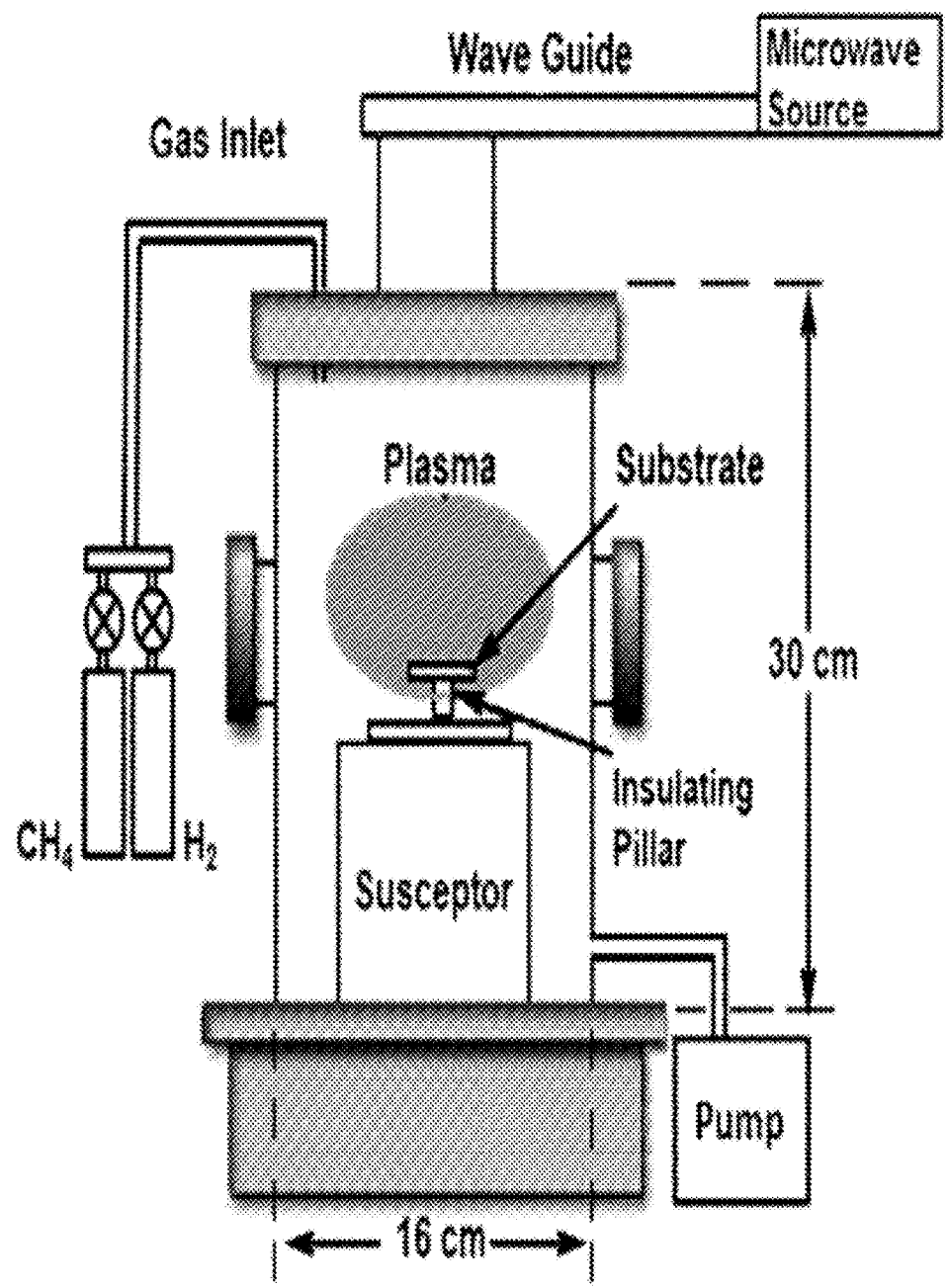
Figures 2, 2A:
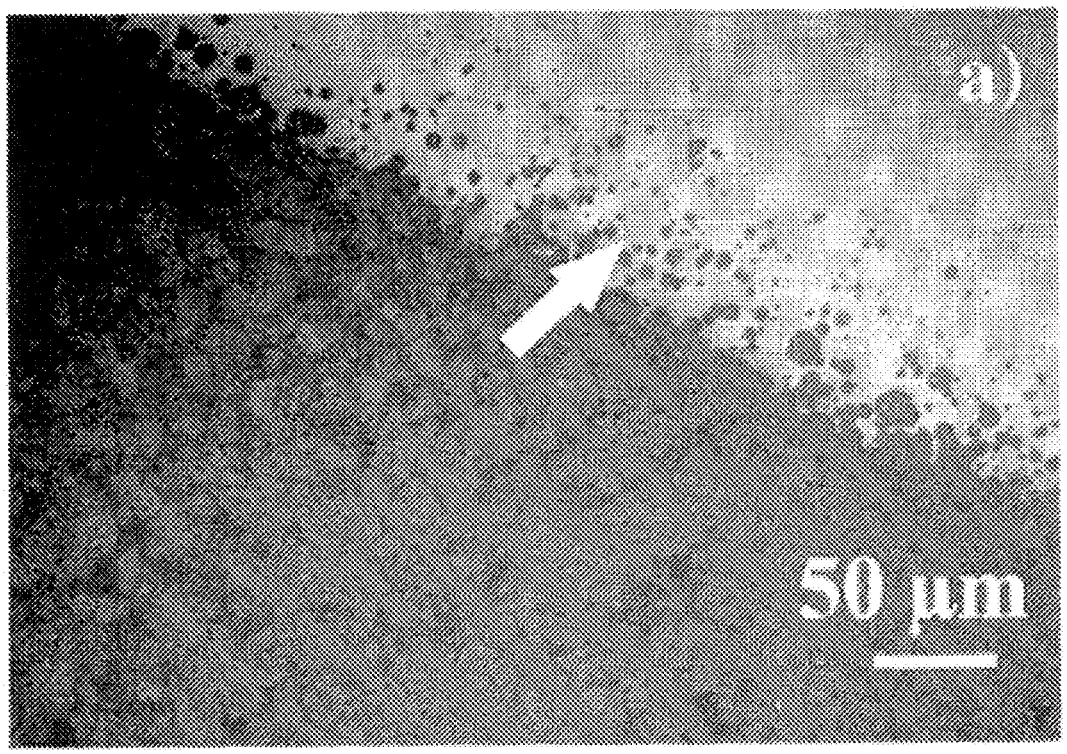
Figures 2, 2B:
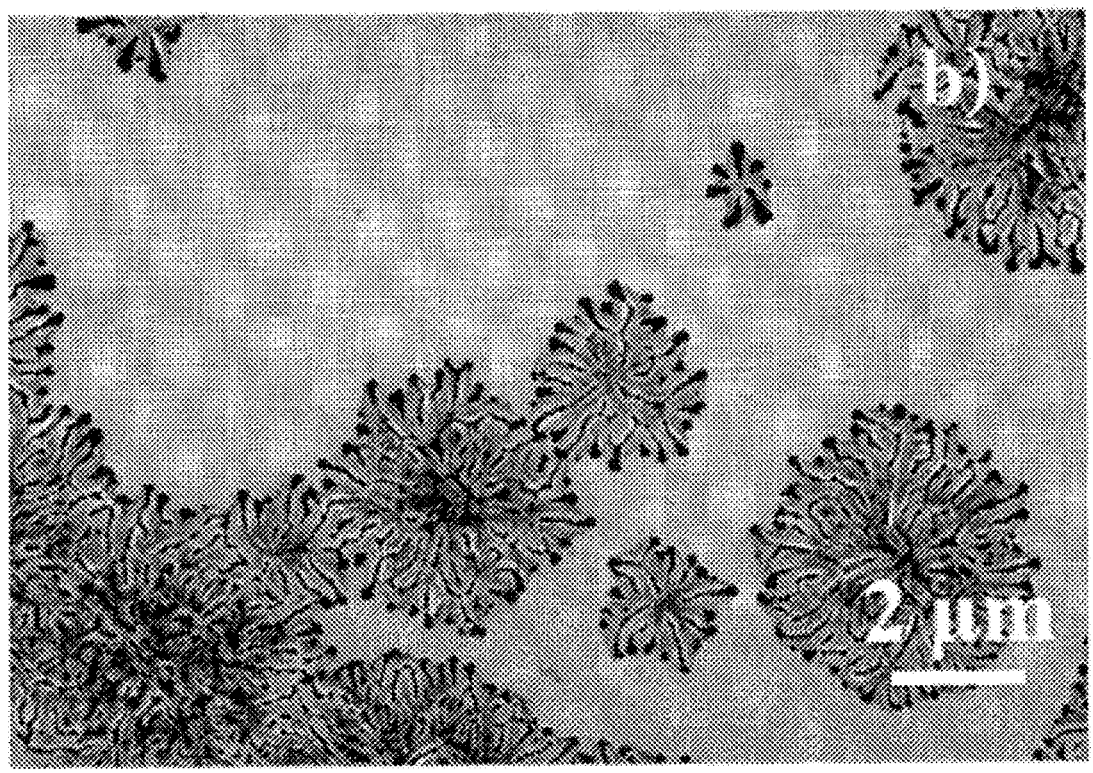
Figures 2, 3, 3A:
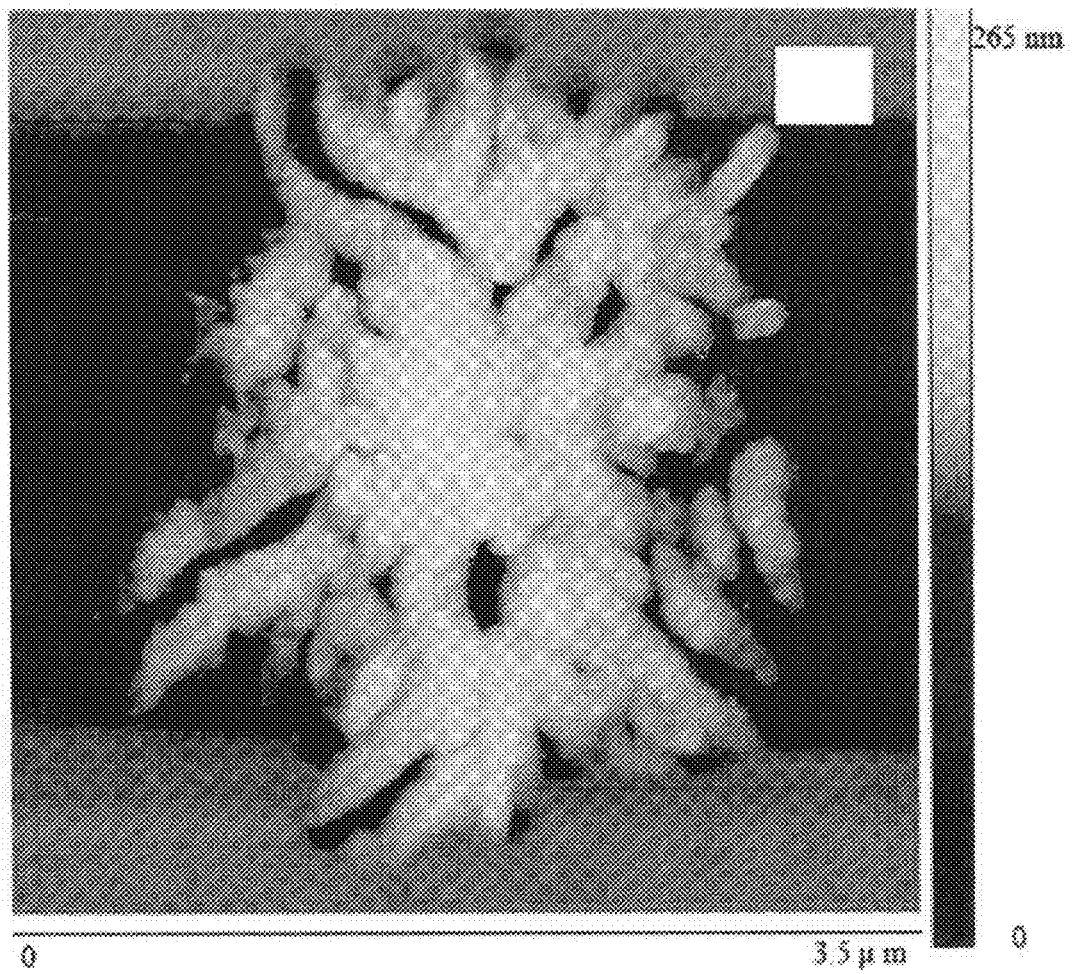
Figures 2, 3, 3B:
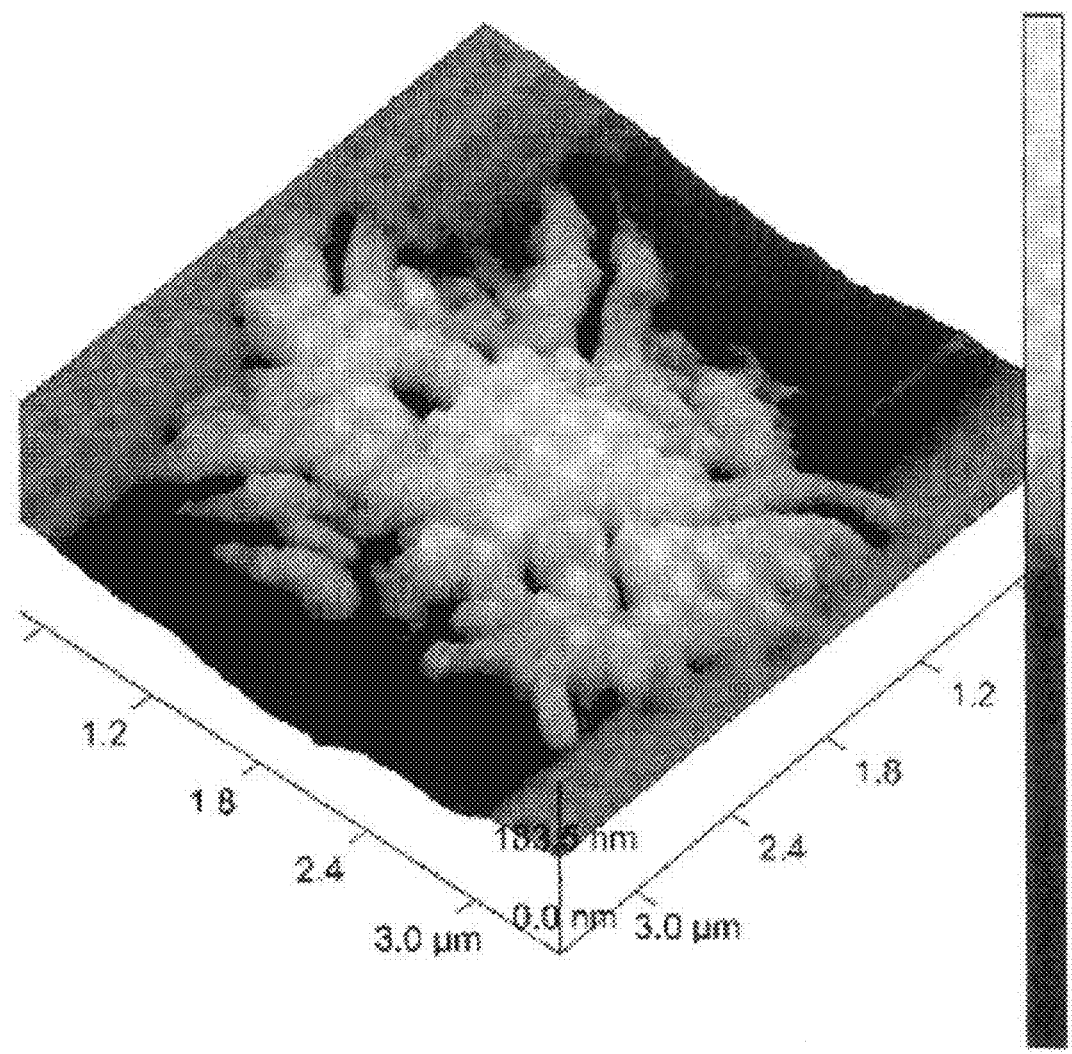
Figures 2, 3, 4, 5, 6, 7, 7A:
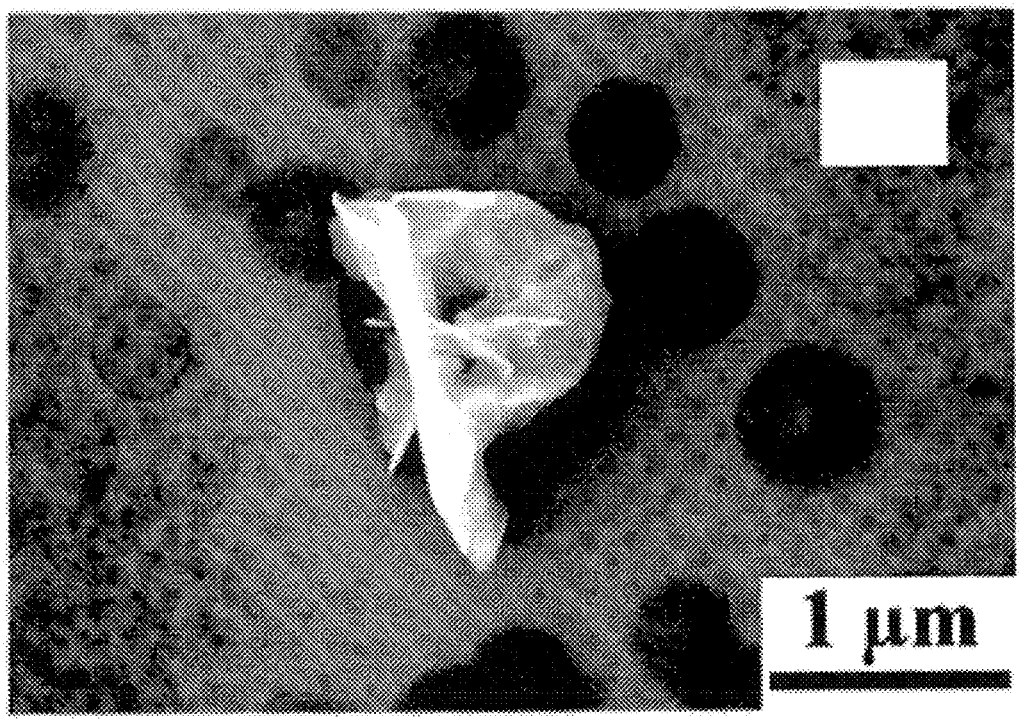
Figures 2, 3, 4, 5, 6, 7, 7B:
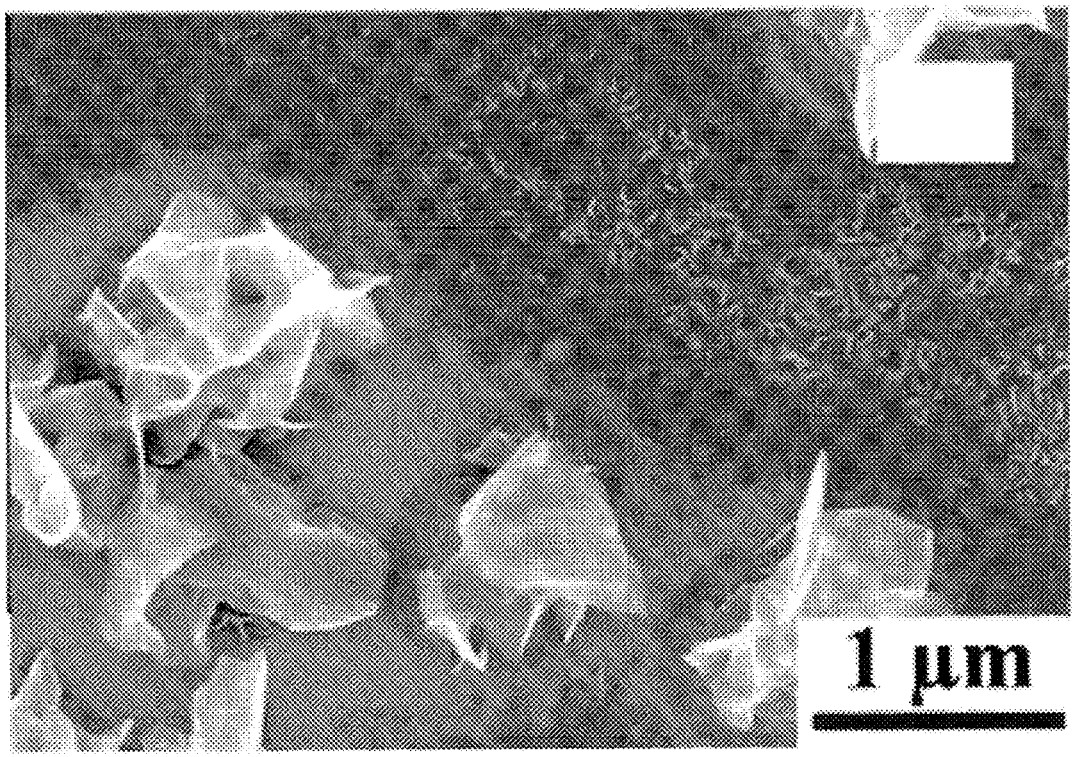
Figures 2, 3, 4, 5, 6, 7, 7C:
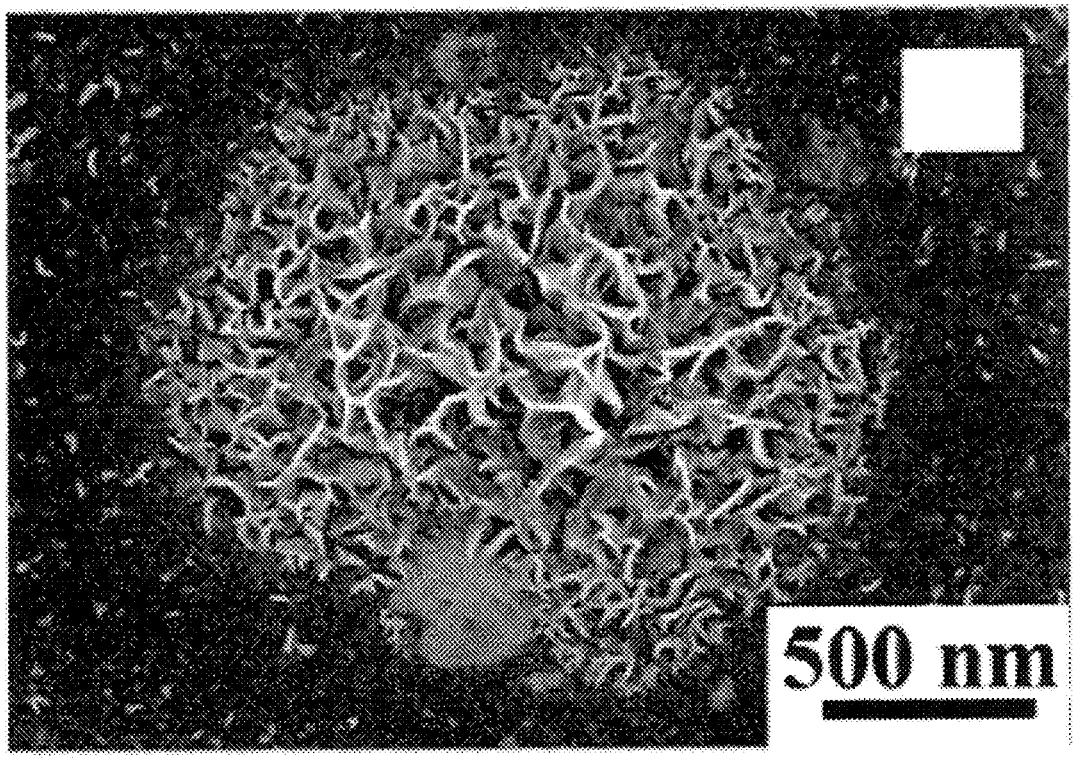
Figures 2, 3, 4, 5, 6, 7, 7D:
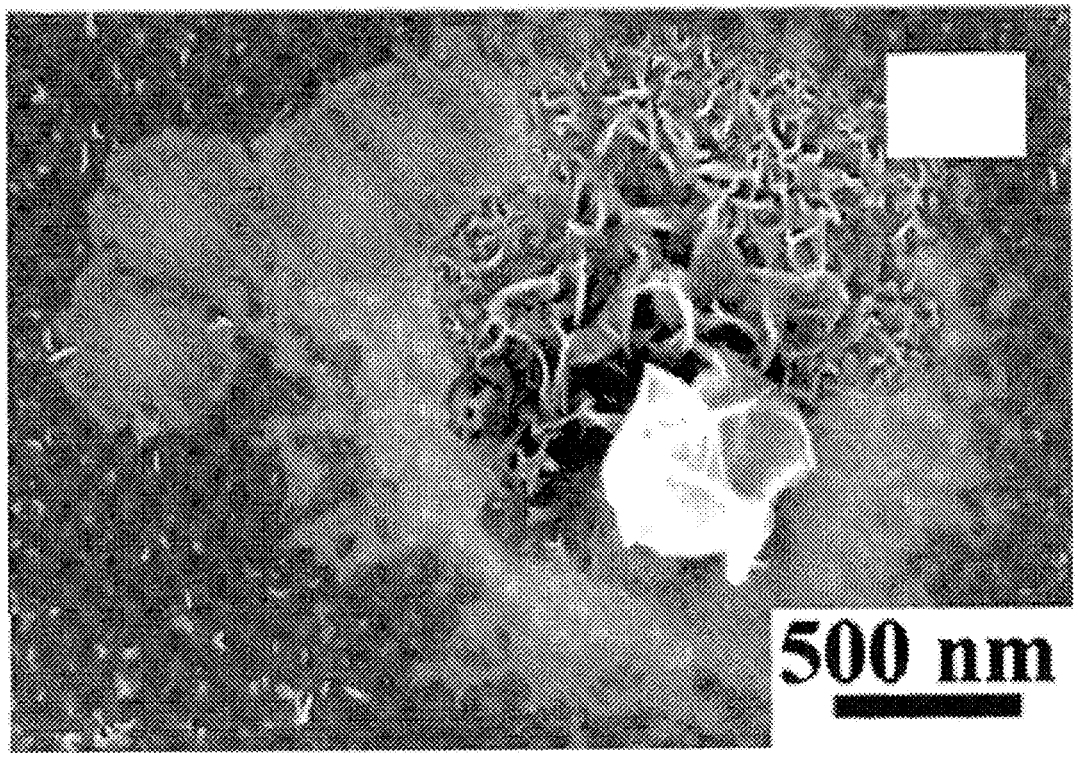

FIG. 5-2 displays a uniform and large area of GP coverage on CC substrates by MPCVD method. This device is useful as an electrode.

MPCVD-grown GPs are graphitic and therefore highly hydrophobic. In order to conformally coat GP surfaces with a thin layer of PANI film, prior to electropolymerization process, the as-prepared samples were treated with concentrated acid $H_2SO_4/HNO_3$ (3/1 v/v) at room temperature for 5 h to functionalize their surfaces so that they would be hydrophilic. The sample was thoroughly washed in deionized water until pH value is ~7.

The three-electrode system for PANI electropolymerization was constructed with a Pt mesh as a counter electrode, Ag/AgCl as a reference electrode and CC/PANI directly as a working electrode. The electrolyte was 0.5 M $H_2SO_4$ and 0.05 M aniline. PANI was in situ electropolymerized on CC/PANI at a constant potential of 0.8 V versus Ag/AgCl for different periods of time ranging from 30 s, 2 min, 5 min, 8 min, 10 min, 15 min to 20 min. FIG. 5-3 shows the SEM morphologies of PANI coated on GPs for 5 min and 15 min for the electropolymerization process. The mass of PANI can be controlled by the electropolymerization time. After the polymerization process, the as-prepared composite film was washed in deionized water and then dried at 80° C. over 2 hours.

FIG. 5-4 displays how current changes as a function of electropolymerization time at 0.8 V vs. Ag/AgCl for both CC and CC/GP substrates. More aniline monomers will react with the CC/GPs substrate with higher specific area, leading to higher current and more change transfer than that of only CC.

The internal resistance can be determined from the initial voltage drop of the discharge curves. FIG. 5-5 shows voltage drop ($V_{IR}$) vs. discharge current densities. The voltage drop increases linearly with the increment of current densities. At a high current density of about 100 A/g, the $V_{IR}$ is approximately 0.12 V, corresponding to a low internal resistance of 2.5Ω.

FIG. 5-6 shows the CV curves for a single flexible device from 0V to 0.8 V at different testing conditions (e.g., normal, bent and twisted). The CV curves almost overlaps, demonstrating the high flexibility of the device. The digital photos of those testing conditions are given in FIG. 5-5.

Specific capacitances derived from cyclic voltammetry (CV) tests can be calculated from the equation [2] [3]:

$$C = \frac{1}{2sM(V_h - V_l)} \int_{V_l \to V_h \to V_l} I(V) dV \quad (1)$$

where C is the specific capacitance in F/g, s is the scan rate in V/s, M is the mass of electrodes in g, $V_h$ and $V_l$ are high and low potential limits of the CV tests in V, I is the instantaneous current on CV curves, and V is the applied voltage in V.

Specific capacitances derived from galvanostatic charge/discharge tests can be calculated from the equation [4]:

$$C = \frac{I_d}{M_v} \quad (2)$$

where $I_d$ is the discharge current in A, and v is the slope of the discharge curve after IR drop.

The internal resistance R (in Ω) was determined from the voltage drop at the beginning of a discharge curve by [5, 6]:

$$R = \Delta V_{IR}/2I_d \quad (3)$$

where $\Delta V_{IR}$ is the voltage dropped across the internal resistance in V.

Specific energy (E) and specific power (P) derived from galvanostatic charge/discharge tests can be calculated from the following equations [5-7]:

$$E = \frac{CV^2}{2M} \quad (4)$$

$$P = \frac{E}{\Delta t} \quad (5)$$

$$P_{max} = \frac{V^2}{4RM} \quad (6)$$

where V is the applied voltage in volts and $\Delta t$ is the discharge time in seconds. $P_{max}$ is the maximum power density.

The coulombic efficiency ($\eta$) of a battery is the ratio of the number of charges that was input into the battery during charging compared to the number that can be extracted from the battery during discharging. The losses that reduce coulombic efficiency are primarily due to the loss in charge due to other redox reactions in the battery. It is calculated from the following equation [5]:

$$\eta = \frac{Q_{discharge}}{Q_{charge}} = \frac{it_{discharge}}{it_{charge}} = \frac{t_{discharge}}{t_{charge}} \quad (7)$$

TABLE 1

| | Flexibility of the substrate | Electrode and treatment | Specific capacitance | ED (Wh/Kg) | PD (kW/Kg) | Electrolyte | Stability |
|---|---|---|---|---|---|---|---|
| 1 3 | Flexible | PANI on CC/GP substrate | ~2000 F/g (PANI) 2.5 F/cm²; 237 F/cm³ at 1 A/g; | 109.9 | 47.7; 265.1 (max.) | 1M H$_2$SO$_4$ and PVA-H$_2$SO$_4$gel | ~7% loss after 2000 cycles |

X1. One embodiment of the present invention pertains to an apparatus comprising a substrate having a surface, a plurality of carbon mounds located on the surface, and a plurality of graphitic nanowalls, each nanowall growing from a corresponding one of mounds.

X2. Yet another embodiment of the present invention pertains to a method for depositing carbon on a surface, comprising providing a substrate having an outer surface, roughening the outer surface, and depositing carbon on the roughened outer surface, and growing a graphitic petal from the carbon on the roughened surface.

X3. Yet another embodiment of the present invention pertains to a method for depositing carbon on a surface, comprising providing a substrate having a first layer of a first material on top of a second layer of a second material, the first layer having an outer surface, diffusing a third material through the first layer, exposing the substrate during diffusing to an electrical field and depositing a fourth material containing carbon on the roughened outer surface.

X4. Yet another embodiment of the present invention pertains to a biosensor comprising an electrode comprising a wafer, multilayered petal nanosheets supported by the wafer, and platinum nanoparticles supported by the nanosheets, and an enzyme electrodeposited on the electrode.

X5. Yet another embodiment of the present invention pertains to a method of producing a biosensor, the method comprising providing an electrode comprising a substrate, petal nanosheets supported by the substrate, and electrodepositing platinum nanoparticles on the nanosheets, and electrodepositing an enzyme on the electrode.

X6. Yet another embodiment of the present invention pertains to an apparatus comprising a carbon nanotube substrate, a graphitic petal structure supported by the substrate, and a metal oxide supported by the graphitic petal structure, wherein the metal oxide is from a neutral precursor solution X7. Yet another embodiment of the present invention pertains to a method of graphitic petal synthesis, the method comprising subjecting carbon cloth substrate to microwave plasma enhanced chemical vapor deposition.

X8. Yet another embodiment of the present invention pertains to a method of coating of a graphitic petal surface, the method comprising providing a metal mesh counter electrode, a reference electrode and a working electrode, providing an electrolyte including an acid and aniline, and electropolymerizing the aniline to graphitic petal surface.

X9. Yet another embodiment of the present invention pertains to a three dimensional nanostructure comprising a carbon cloth substrate, graphitic petal structure supported by the substrate, and a film covering the graphitic petal structure.

Any of the preceding statements X1 through X9 wherein the mounds are substantially conically shaped.

Any of the preceding statements X1 through X9 wherein the surface is substantially coated with carbon, of the preceding statements X1 through X9 wherein nanowalls grown substantially vertically from mounds.

Any of the preceding statements X1 through X9 wherein the surface is coated with a layer of a carbide material.

Any of the preceding statements X1 through X9 wherein the material is silicone carbide.

Any of the preceding statements X1 through X9 wherein the surface is roughened prior to growth of nanowalls.

Any of the preceding statements X1 through X9 wherein the surface is roughened mechanically.

Any of the preceding statements X1 through X9 wherein the surface is roughened by plasma etching.

Any of the preceding statements X1 through X9 wherein the surface is roughened after gaseous diffusion through the surface.

Any of the preceding statements X1 through X9 wherein mounds are grown from the surface.

Any of the preceding statements X1 through X9 wherein mounds have a base diameter of less than about one micrometer.

Any of the preceding statements X1 through X9 wherein mounds have a base diameter greater than about one hundred nanometers.

Any of the preceding statements X1 through X9 wherein roughening is by mechanically etching the outer surface.

Any of the preceding statements X1 through X9 wherein the substrate includes a layer of an oxide.

Any of the preceding statements X1 through X9 wherein roughening includes diffusing hydrogen through the oxide.

Any of the preceding statements X1 through X9 which further comprises creating nanocones on the outer surface during depositing.

Any of the preceding statements X1 through X9 wherein growing is from a nanocone.

Any of the preceding statements X1 through X9 wherein nanocones have a base diameter of less than about one micrometer.

Any of the preceding statements X1 through X9 wherein nanocones have a base diameter greater than about one hundred nanometers.

Any of the preceding statements X1 through X9 wherein growing is by exposing the outer surface to a plasma containing a carbonaceous material.

Any of the preceding statements X1 through X9 wherein the carbonaceous material is a hydrocarbon.

Any of the preceding statements X1 through X9 wherein growing is without using a metal catalyst.

Any of the preceding statements X1 through X9 wherein roughening includes creating a plurality of upwardly extending peaks.

Any of the preceding statements X1 through X9 wherein growing is from a peak.

Any of the preceding statements X1 through X9 which further comprises creating a carbide layer on the outer surface.

Any of the preceding statements X1 through X9 wherein creating is before growing.

Any of the preceding statements X1 through X9 wherein the carbide is a catalyst for growing.

Any of the preceding statements X1 through X9 wherein the roughened surface includes a plurality of conically-shaped structures.

Any of the preceding statements X1 through X9 wherein after depositing the outer surface includes a plurality of carbon-covered upwardly extending shapes.

Any of the preceding statements X1 through X9 wherein the shapes are substantially conical.

Any of the preceding statements X1 through X9 wherein the base of the conical shapes are greater than about one hundred nanometers in diameter.

Any of the preceding statements X1 through X9 wherein the first layer has a thickness, and exposing includes reducing the thickness.

Any of the preceding statements X1 through X9 wherein the first layer has a first thickness before diffusing, and a second, lesser thickness before depositing.

Any of the preceding statements X1 through X9 which further comprises growing a graphitic structure from the deposited carbon.

Any of the preceding statements X1 through X9 wherein the graphitic structure is a petal.

Any of the preceding statements X1 through X9 wherein the first material is an oxide of the second material.

Any of the preceding statements X1 through X9 wherein the first material includes a silica.

Any of the preceding statements X1 through X9 wherein the second material includes silicon.

Any of the preceding statements X1 through X9 wherein the substrate is electrically isolated from ground during exposing.

Any of the preceding statements X1 through X9 wherein the electrical field comprises radio waves.

Any of the preceding statements X1 through X9 wherein the radio waves have a frequency greater than about one gigahertz.

Any of the preceding statements X1 through X9 wherein the radiated power of the field is greater than about 300 watts.

Any of the preceding statements X1 through X9 wherein the radiated power of the field is greater than about 500 watts.

Any of the preceding statements X1 through X9 wherein the electrical field heats the substrate to greater than about one thousand degrees Centigrade.

Any of the preceding statements X1 through X9 which further comprises heating the substrate to greater than about one thousand degrees Centigrade.

Any of the preceding statements X1 through X9 which further comprises heating the substrate during exposing.

Any of the preceding statements X1 through X9 wherein the third gaseous material is inorganic.

Any of the preceding statements X1 through X9 wherein the third gaseous material is hydrogen.

Any of the preceding statements X1 through X9 wherein the nanosheets are grown on the wafer through chemical vapor deposition.

Any of the preceding statements X1 through X9 wherein the nanoparticles are located along the edges of the nanosheets.

Any of the preceding statements X1 through X9 wherein the nanoparticles are grown along the edges of the nanosheets.

Any of the preceding statements X1 through X9 wherein the nanoparticles are grown by an electrodeposition process.

Any of the preceding statements X1 through X9 wherein the electrodeposition process includes current pulses of approximately 500 ms.

Any of the preceding statements X1 through X9 wherein the electrodeposition process includes current within the range of approximately 312 µA to approximately 5.0 mA.

Any of the preceding statements X1 through X9 wherein the electrodeposition process includes current selected from the group consisting of approximately 312 µA, approximately 625 IAA, approximately 1.25 mA, approximately 2.5 mA, and approximately 5.0 mA.

Any of the preceding statements X1 through X9 wherein the electrodeposition process includes currently of approximately 2.5 mA.

Any of the preceding statements X1 through X9 wherein the enzyme is glucose oxidase.

Any of the preceding statements X1 through X9 wherein the enzyme is encapsulated within the poly(3,4-ethylenedioxythiophene).

Any of the preceding statements X1 through X9 wherein the electrode is subjected to an oxygen plasma etch.

Any of the preceding statements X1 through X9 wherein electrodepositing nanoparticles includes growing nanoparticles along edges and planes of the nanosheets.

Any of the preceding statements X1 through X9 wherein the enzyme is glucose oxidase.

Any of the preceding statements X1 through X9 wherein the carbon nanotube substrate is buckypaper.

Any of the preceding statements X1 through X9 wherein a layer of manganese dioxide is coated on the graphitic petal structure, wherein the layer is within the range of approximately five to approximately ten nanometers in thickness.

Any of the preceding statements X1 through X9 wherein the microwave plasma enhanced chemical vapor deposition conditions include primary feed gases at 30 torr total pressure, a 2.45 GHz frequency microwave power supply, and 700 W plasma power.

Any of the preceding statements X1 through X9 wherein the primary feed gases include $H_2$ and $CH_4$.

Any of the preceding statements X1 through X9 wherein the $H_2$ flow rate is 50 standard cubic centimeters per minute.

Any of the preceding statements X1 through X9 wherein the CH flow rate is 10 standard cubic centimeters per minute.

Any of the preceding statements X1 through X9 wherein the microwave plasma enhanced chemical vapour deposition conditions include a 2.45 GHz frequency microwave power supply.

Any of the preceding statements X1 through X9 wherein the microwave plasma enhanced chemical vapor deposition conditions include a 700 W plasma power rating.

Any of the preceding statements X1 through X9 wherein subjecting carbon cloth substrates to microwave plasma enhanced chemical vapor deposition occurs for approximately 25 minutes.

Any of the preceding statements X1 through X9 wherein the carbon cloth substrate is heated from room temperature to approximately 1100° C.

Any of the preceding statements X1 through X9 wherein the carbon cloth substrate is made of microfibers.

Any of the preceding statements X1 through X9 wherein the substrate is elevated approximately 15 mm above the molybdenum puck.

Any of the preceding statements X1 through X9 wherein the molybdenum puck is approximately 55 mm in diameter.

Any of the preceding statements X1 through X9 wherein the substrate is elevated by at least one ceramic spacer.

Any of the preceding statements X1 through X9 further comprising the step of coating polyaniline (PANI) onto graphitic petals grown on carbon cloth.

Any of the preceding statements X1 through X9 further comprising the step of treating the surface of the graphitic petals with a three to one by volume mixture of sulfuric acid and nitric acid for approximately five hours.

Any of the preceding statements X1 through X9 further comprising the step of washing off the acid with deionized water until pH is approximately 7.

Any of the preceding statements X1 through X9 wherein the sulfuric acid and aniline are at approximately equal molarity.

Any of the preceding statements X1 through X9 wherein the concentration of each of sulfuric acid is approximately 0.5 M.

Any of the preceding statements X1 through X9 wherein electropolymerizing occurs at a constant potential of approximately 0.8 V relative to the reference electrode.

Any of the preceding statements X1 through X9 wherein the period of time for electropolymerizing is within the range of approximately 30 seconds to approximately twenty minutes.

Any of the preceding statements X1 through X9 further comprising the steps of washing the resultant composite film with deionized water and drying the composite film for approximately two hours at approximately eighty degrees Celsius.

Any of the preceding statements X1 through X9 wherein the graphitic petal structure is directly grown on substrate by microwave plasma enhanced chemical vapor deposition.

Any of the preceding statements X1 through X9 wherein the substrate is flexible.

Any of the preceding statements X1 through X9 wherein the polyaniline film is coated on the structure by electropolymerization.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

Another embodiment of the invention includes the decoration of graphitized carbon materials (graphene petal nanosheet structures or graphitic nanopetals (GNPs)) with Boron (B) and Nitrogen (N) atoms. The decoration is most useful when the B and N atoms are integrated directly into the layered C sheets, rather than when the B and N atoms are weakly physisorbed onto or between the C layers. The resulting B—C—N is a hexagonal solid material that can provide the benefits of intrinsically layered solids such as graphite and graphene with an additional advantage of higher thermal stability and wider band gap typical for hexagonal BN and BN nanosheets. Many prior studies have considered the growth of hybrid phases of B—C—N and numerous synthetic procedures to produce B—C—N materials include r.f. plasma-enhanced pulsed laser deposition, magnetron sputtering, ion beam sputtered deposition, arc discharge, and chemical vapor deposition.

These studies have shown that B—C—N materials are not single crystalline but rather nanocrystalline. As an example, chemical substitution reactions have been reported to replace C atoms in carbon nanotubes by B and N atoms to produce $(BN)_xC_y$ nanotubes. This technique demonstrates a cost effective way to produce B—C—N materials with nanoscale dimensions for which the stability and electronic properties can be theoretically studied using density functional theory. Such studies predict the properties will depend primarily on chemical composition rather than the nanoscale geometric structure. However, B—C—N sheets have been shown to prefer conformations consisting of distributed BN and graphene domains, as opposed to spatially uniform stoichiometry, and the overall properties can depend on the details of the domain structure and distribution. The importance of atomic-scale defects in graphitized carbon to promote the growth of distributed BN domains should not be underestimated. Defect-free forms of graphitized carbon—like highly oriented pyrolitic graphite (HOPG)—are likely to produce few BN domains, while GNPs, with their high propensity for atomic scale defects, are likely to favor the growth of the BN domains. The growth of BN domains are thought to be favored at step edges, grain boundaries, or other similar defect-like structures that promote enhanced chemical activity by taking advantage of weakly bonded C atoms.

A practical way to synthesize electrodes based on carbon nanomaterials (carbon nanotubes, carbon foams, graphitic nanopetals, etc.) which can then be further modified with boron (B) and nitrogen (N) is to take advantage of a facile microwave heating cycle. In one example, microwave-assisted chemical substitution reactions have been promoted to replace carbon atoms with boron and nitrogen to form an oxygen-resistant layer of B—C—N on the surface of pitch derived graphitic carbon foam. Typically, a 400 W microwave treatment for 5-30 minutes is used to accelerate foam surface modification by 12-15 times in comparison to thermal treatments, due to activation of reagents through phase change and high thermal gradients during microwave irradiation. It should be clear the microwave treatment requires a close coupling of the microwave plasma with the substrate material of interest. Such a coupling can be achieved, for example, by supporting the substrate above a platform, allowing it to be more fully enveloped by the hydrocarbon-rich plasma. Such a growth treatment is typically followed by high-temperature annealing in an inert atmosphere to complete the nanocarbon (in this case, carbon foam) surface conversion to B—C—N and to reduce excess oxygen content. The resultant material chemistry, morphology, and structure can then be characterized using standard materials characterization techniques (XPS, Raman, AFM, STM, etc.) and the performance of this material in battery and supercapacitor applications can then be ascertained.

FIG. 7 shows in further detail an exemplary method for forming the electrodes and for generating a lithium ion cell that uses the formed electrodes. In a first step 705, graphene nanopetals are formed on a substrate in any of the methods discussed further above. In this example, the nanopetals are grown on bucky paper using a microwave plasma chemical vapor deposition technique. In particular, in a chamber approximate 16 cm in diameter by 30 cm tall, a Mo puck is placed on a susceptor, a 7-30 mm log ceramic insulating pillar is placed on the Mo puck, and the substrate is placed on top of the insulating pillar. The microwave plasma CVD process then employs a $CH_4:H_2$ or $C_2H_2:H_2$ feedstock, a flow rate of 10 to 50 sccm, and a microwave frequency of approximately 2.45 GHz. The pressure in the chamber is 30 Torr, the plasma power is 400-700 W, and the growth time is 5-60 minutes. The bucky paper may suitably be nm diameter carbon nanotubes formed into paper that is 200 μm thick, available from Nanocomp Technologies. In some cases, the nanotubes of the bucky paper are sufficient for the subsequent process and nanopetals (or other additional structures) do not need to be formed.

Moreover, it will be appreciated that in the alternative to graphene nanopetals, other graphitic (carbon) nanosheet or nanowall-based structures may be used, such as nanotubes, nanohorns, carbon cloth, etc. It is preferable that the graphitic nanowall structure have defects or defect like structures, to facilitate BN growth.

In one preferred embodiment of step 705, however, multi-walled nanotube (MCNT) arrays were grown on carbon cloth from tri-layer catalysts (Ti/Al/Fe) by plasma enhanced CVD. The carbon nanotube arrays were grown in the shape of hollow channels on the surface of the carbon fibers as shown in FIG. 6-4.8. Graphitic or graphene petals were grown on the carbon nanotube arrays subsequently in the same chamber by plasma enhanced CVD to form willow-branch like nanostructures, as shown in FIG. 6-4.9. The hollow channel shape remained after graphitic petal growth. The structure of FIG. 6-4.9 has shown excellent results for electrochemical energy storage use in batteries and supercapacitors. The advantages of this embodiment is that the carbon nanotube/graphitic petal nanostructure has a hollow channel, with carbon fibers etched away by plasma and has a high specific area (area per mass, and per apparent area). In addition, the sharp edges of the graphene petals may have unique properties in enhancing ion diffusion and charge transfer. Finally, the nanostructure is flexible and can form into desired shapes for electrochemical storage.

It will be appreciated that the substrate may suitably be, in the alternative to bucky paper, silicon, silicon oxide, quartz, carbon foam, vertical carbon nanotube arrays (20-1000 μm thick, carbon cloth (e.g. 9 μm diameter carbon fibers woven into cloth), metal foils of copper, nickel, stainless steel, bucky paper, graphite foil (graphite flakes pressed into foil 20 μm to 200 μm thick from Alfa Aesar), or metal foam (e.g. 95% open porosity, 1.5 mm thick from MTI Corp.)

In any event, after the work piece having graphitic nanowalls and/or graphene nanostructures is formed in step 705, the work piece is immersed in a BN precursor solution in step 710. The BN precursor solution comprises urea (CO(NH$_2$)$_2$) and boric acid (B(OH)$_3$) dissolved in either water or methanol. In this embodiment, the immersed workpiece and BN precursor solution are sealed in a quartz vial having a size from 2 to 30 mL.

In step 715, a microwave synthesizer heats the immersed work piece. In this embodiment, the microwave synthesizer heats the quartz vial to approximately 100° C. to 200° C. for 5-60 minutes at a pressure of 10-40 bar. Microwave irradiation is particularly effective because the electric fields from the microwaves facilitate the process. The microwave synthesizer generates microwaves in this embodiment at a frequency of approximately 2.45 GHz. In step 715, significant BN growth occurs, wherein boron and nitrogen atoms are at least partly integrated into the graphitic layers. Boron oxide and byproducts may also be present. It should be appreciated that other compounds known to a person having ordinary skill in the art other than urea and boric acid and other solvents other than water and methanol can be used to provide boron and nitrogen as a source for incorporation into any carbon nanomaterial.

After microwave heating in step 715, the work piece is vacuum dried in step 720. To this end, the work piece is removed from the precursor solution and vacuum dried. In this embodiment, the work piece is placed onto a quartz boat and dried in a desiccator under rough vacuum for 5 to 24 hours. After step 720, the work piece is placed is annealed. In this embodiment, the work piece is annealed by placing the quartz boat with the work piece through a tube furnace, with an $N_2$ gas atmosphere, heated to temperatures of 500° C. 1100° C. The annealing step is thought to remove any unreacted chemicals and to form $C_xBN$.

Thereafter, in step 725, the work piece is processed with plasma energy to reduce any residual boron oxide from the surface of the electrodes. To this end, an $H_2$ plasma reduction may be used. In this embodiment, the work piece is placed in a chamber on a Mo puck at 10-30 Torr. The chamber is backfilled with $H_2$ gas and then the plasma is ignited to energies of about 300 to 500 W. The plasma energy reduction step should last about 5-60 minutes. In addition to removing surface oxides that can impede charge storage, step 725 also terminates the dangling bonds of the surface to inhibit other contamination, activates the domain and grain boundaries of the substrate to make them more chemically active. These features contribute to a reverse battery fade discussed further below in connection with FIG. 11.

Figures 2, 3, 4, 5, 6, 7, 8:
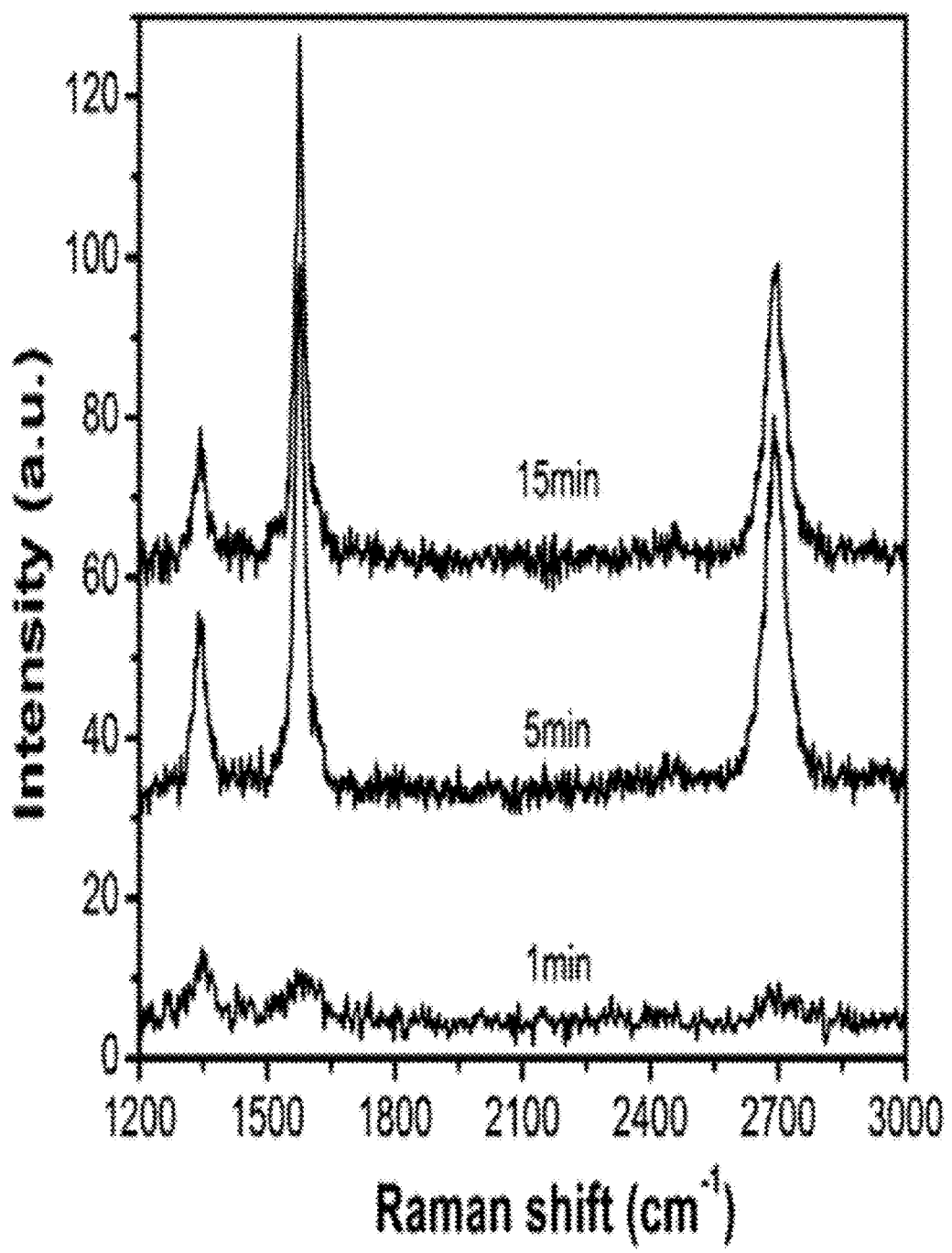

Thereafter, in step 735, the work piece is implemented within a lithium ion battery as the electrodes. To this end, the work piece can be shaped (e.g. punched) to a proper size and shape for use in a lithium ion cell. The work piece may then be assembled onto the other elements of the lithium ion cell in a known manner. FIG. 8 shows a non-limiting example of a lithium ion cell that incorporates the work piece formed by operations of steps 705-730. The lithium ion cell 800 comprises lithium ions 802 within a stainless steel case 804, a lithium foil anode 806, a separator 808 and a cathode 810.

The cathode 810 in this embodiment is the electrode formed by the work piece generated in accordance with steps 705-730. Other variants using the work piece may be employed. Other than the cathode, the elements of the lithium ion cell may suitably be conventional elements.

One of the aspects of this invention is the discovery that enhanced charge storage can result from electrodes formed from $C_xBN$ material. Experiment has shown that a significant enhancement in charge storage capacity can be achieved when C—B—N electrodes are arranged in a charge storage device.

Figures 2, 3, 4, 5, 6, 7, 8, 9:
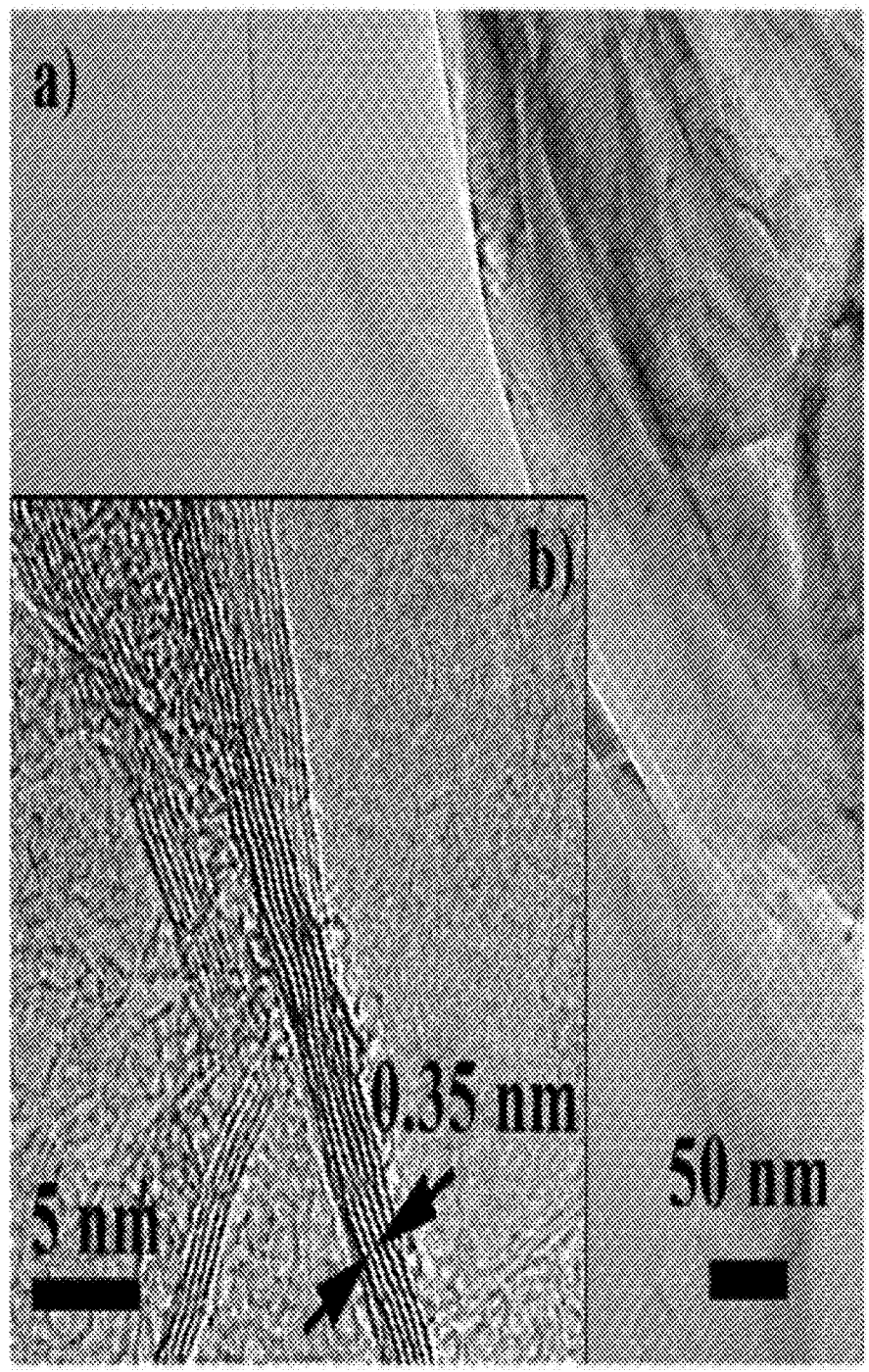
Figures 2, 3, 4, 5, 6, 7, 8, 9, 10, 10A:
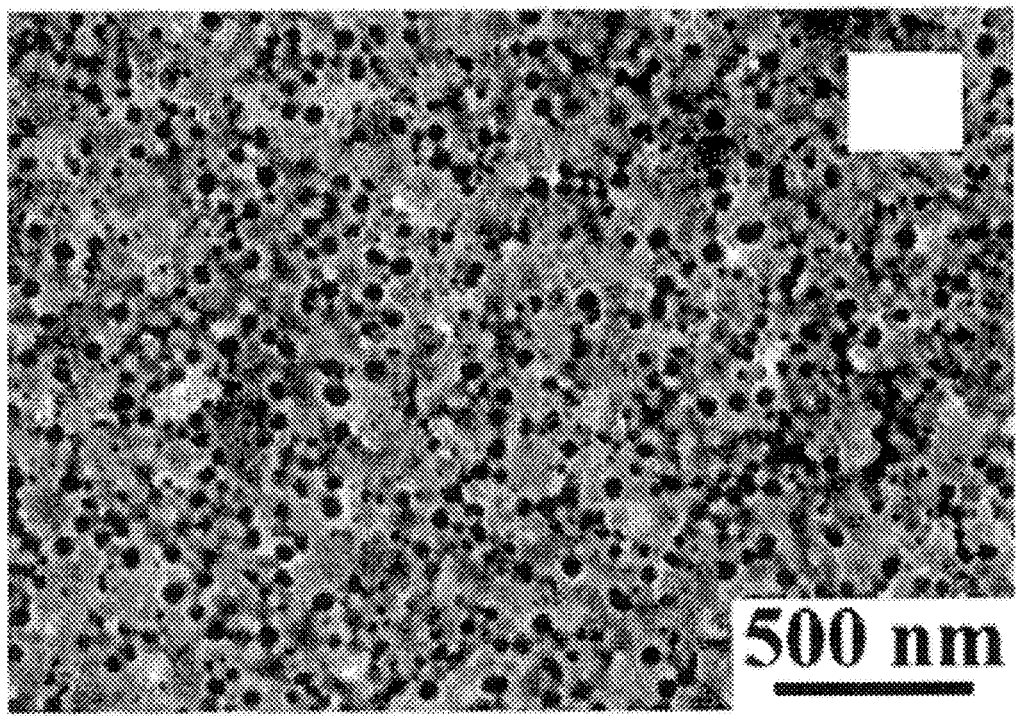
Figures 2, 3, 4, 5, 6, 7, 8, 9, 10, 10B:
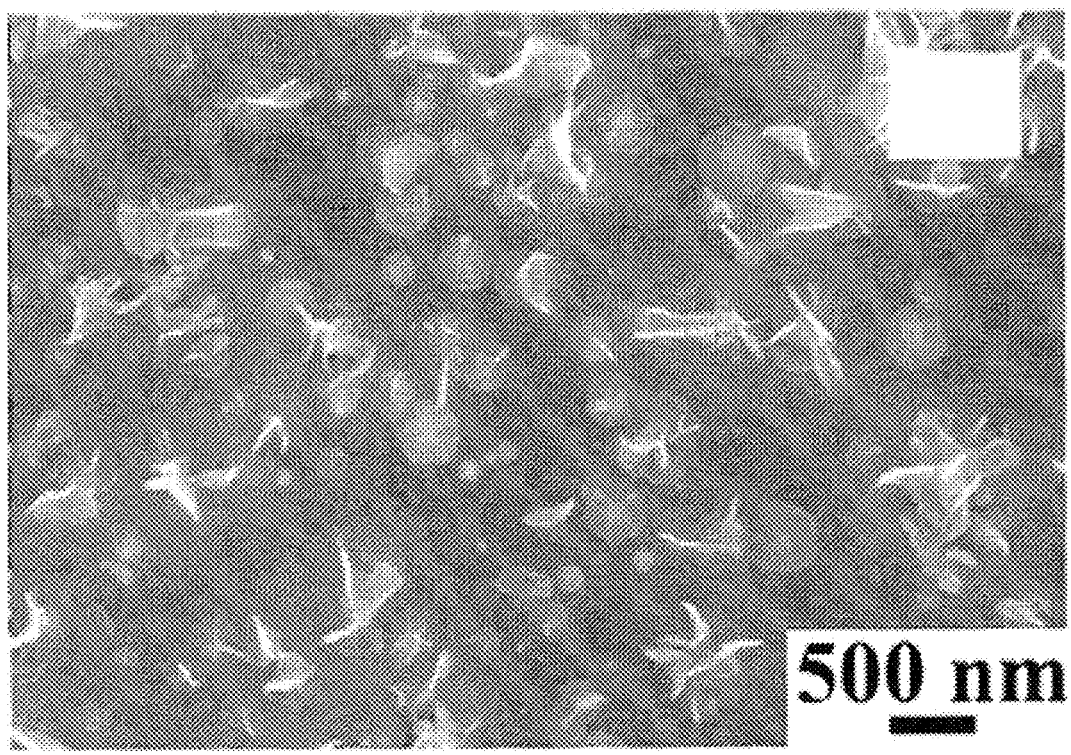
Figures 2, 3, 4, 5, 6, 7, 8, 9, 10, 10C:
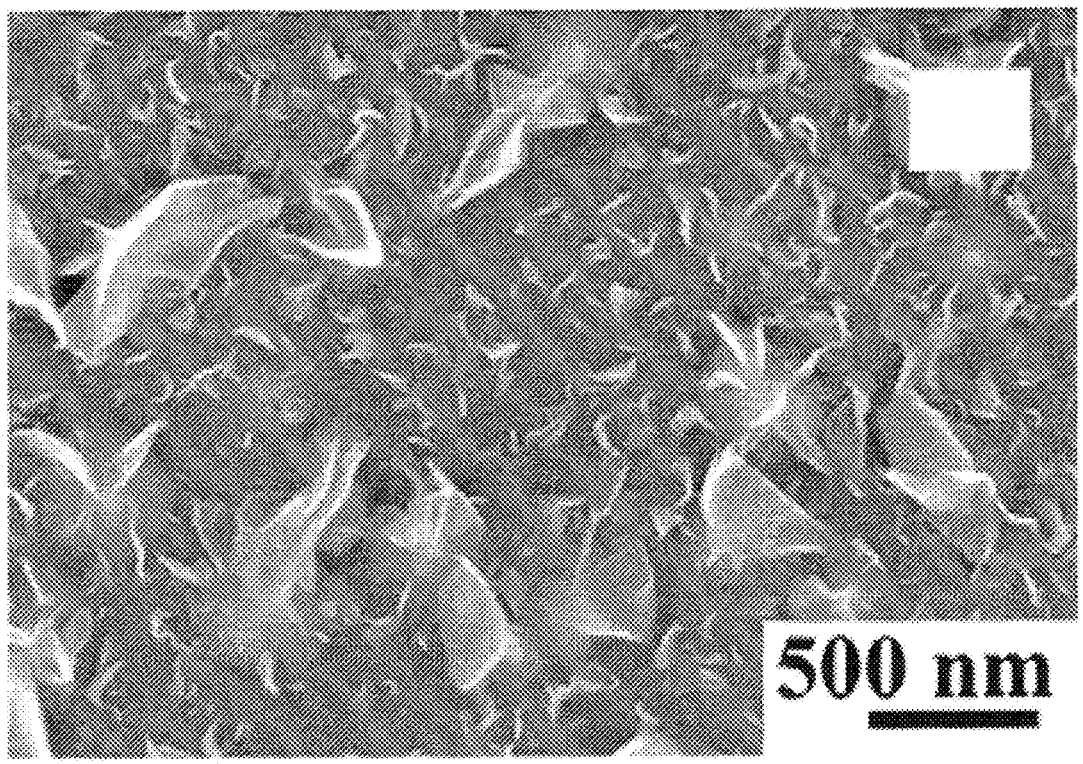
Figures 2, 3, 4, 5, 6, 7, 8, 9, 10, 10D:
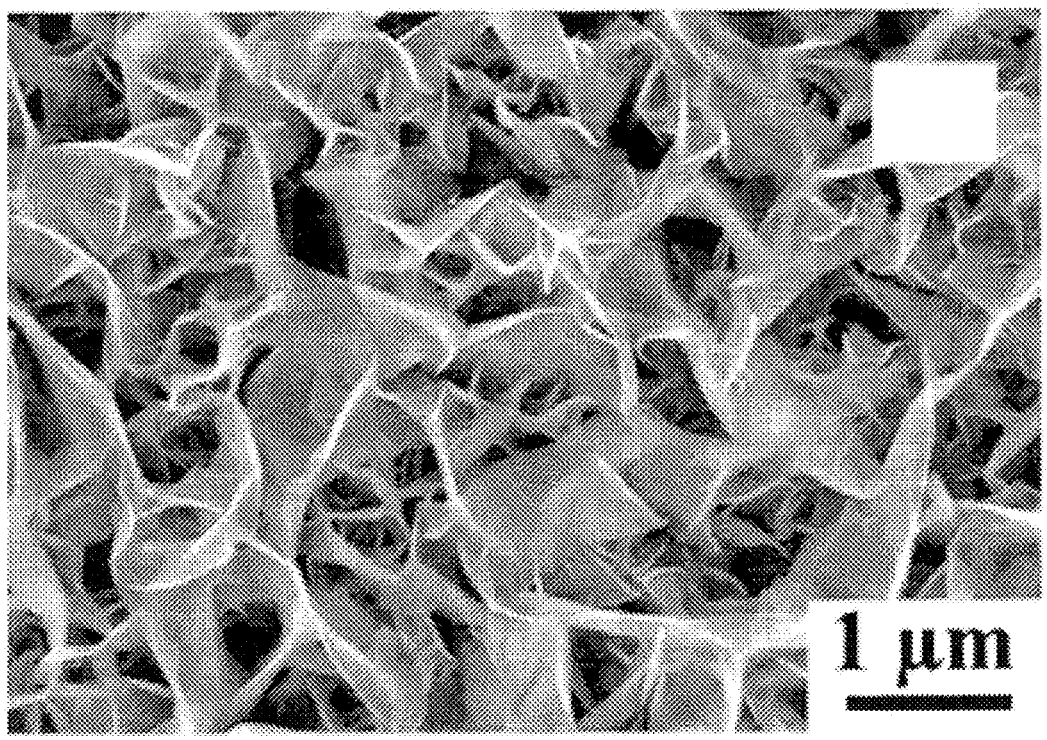

Referring to FIG. 9 below, a magnified image of a B—C—N modified, carbon nanotube-based electrode 900 is provided. The electrode 900 was formed using the process of FIG. 7. In particular, the electrode 900 is based on a graphitized carbon nanomaterial (carbon nanotubes, graphitized nanopetals, carbon cloth, etc.) which has been modified with boron (B) and nitrogen (N) through a facile microwave heating cycle at 20 bar pressure and at elevated temperatures near 180° C. During the microwave heating, the electrodes were immersed in a precursor solution including urea ($CO(NH_2)_2$) and boric acid ($B(OH)_3$) dissolved in water, methanol or other commonly known solvents. After microwave heating and vacuum drying for a period of time (e.g., 12 hours), the electrodes are again heated to 900° C. in an inert gaseous atmosphere, e.g., nitrogen, for a period of time, e.g., nine hours, to remove unreacted chemicals and further the formation of $C_xBN$. The x in $C_xBN$ represents 1, 2, or 4. An exemplary chemical structure for $C_2BN$ is depicted in FIG. 10, below. The above steps (e.g. steps 705-725 of FIG. 7) are identified as collectively "Step A." Thereafter, hydrogen plasma was then used to remove any residual boron oxide from the surface of the carbon nanomaterial electrodes. The latter step (step 730 of FIG. 7) is identified as "Step B."

Figures 2, 3, 4, 5, 6, 7, 8, 9, 10, 11, 11A:
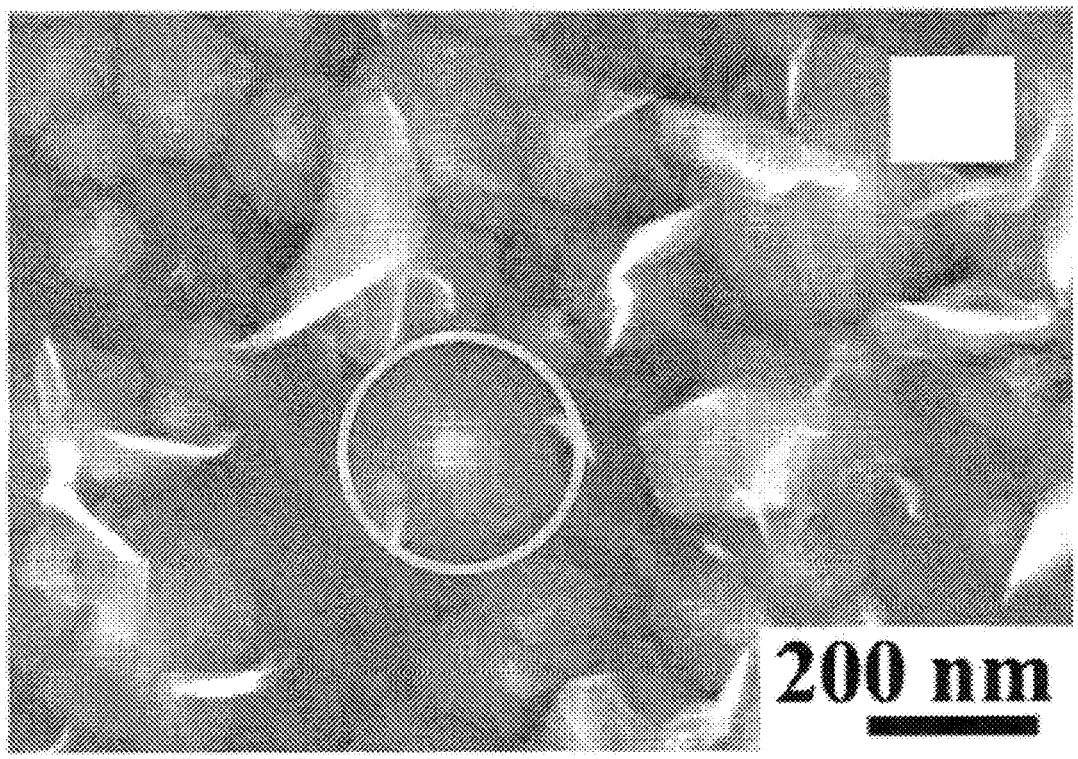
Figures 2, 3, 4, 5, 6, 7, 8, 9, 10, 11, 11B:
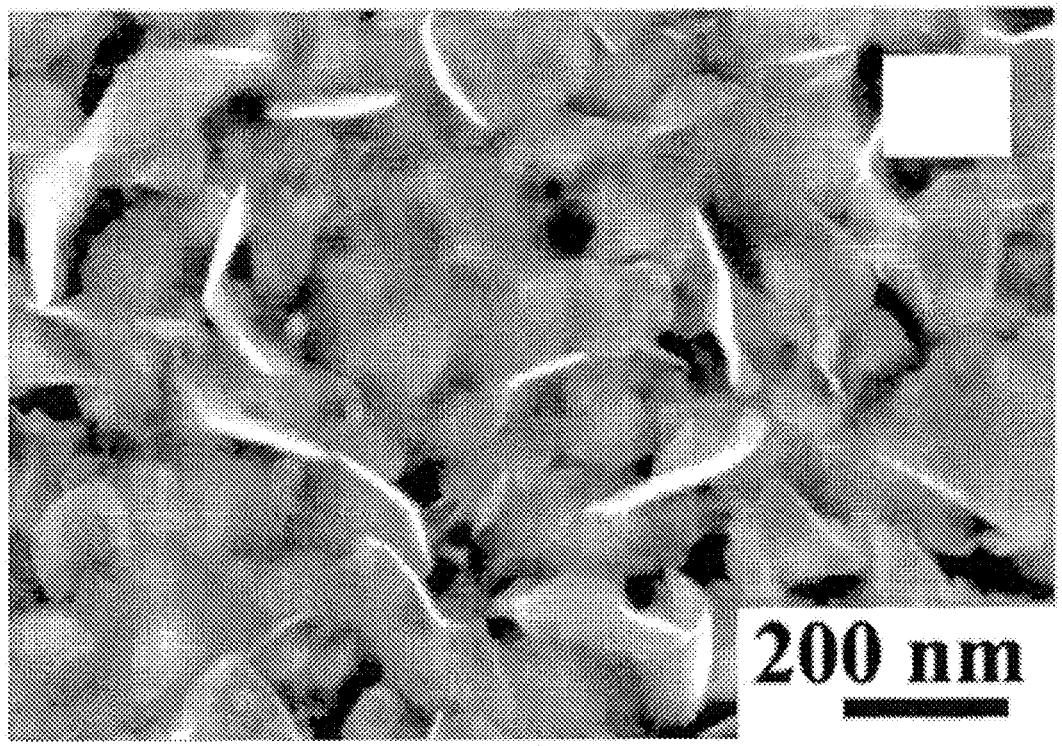
Figures 2, 3, 4, 5, 6, 7, 8, 9, 10, 11, 12, 12A:
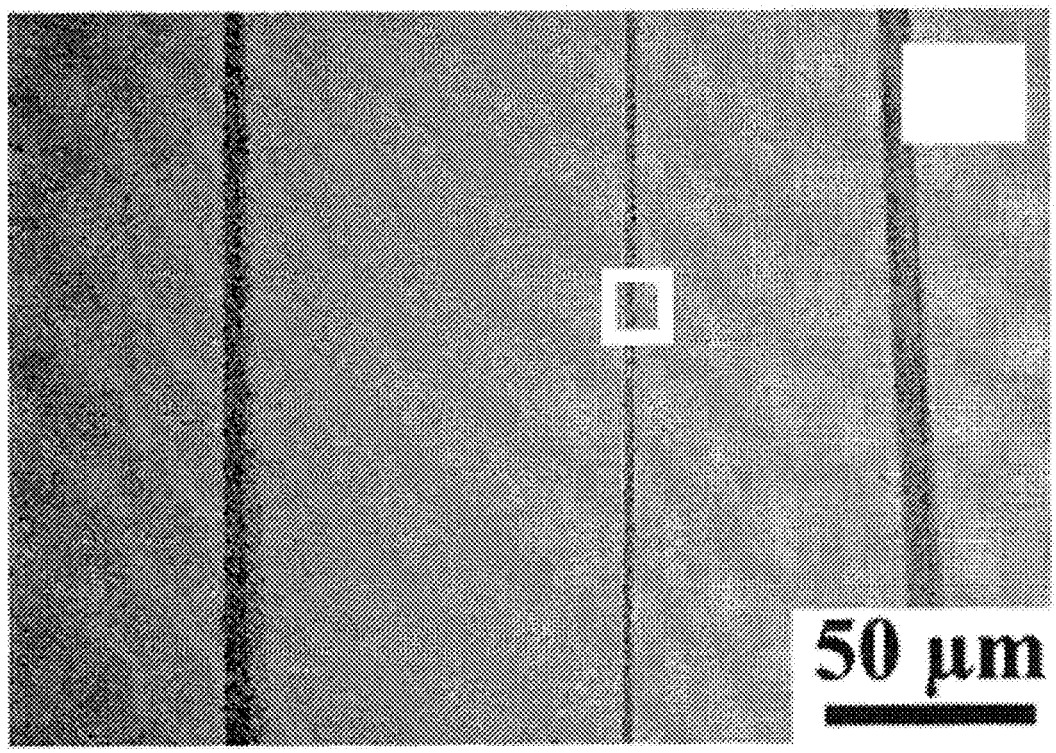
Figures 2, 3, 4, 5, 6, 7, 8, 9, 10, 11, 12, 12B:
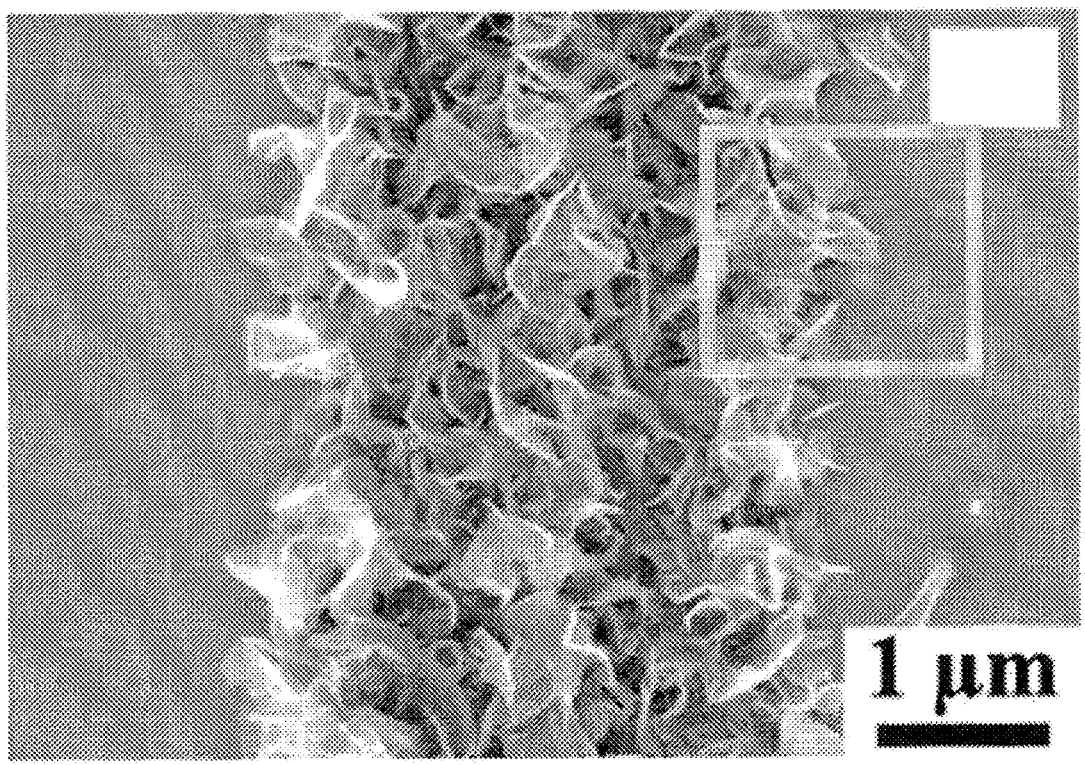
Figures 2, 3, 4, 5, 6, 7, 8, 9, 10, 11, 12, 12C:
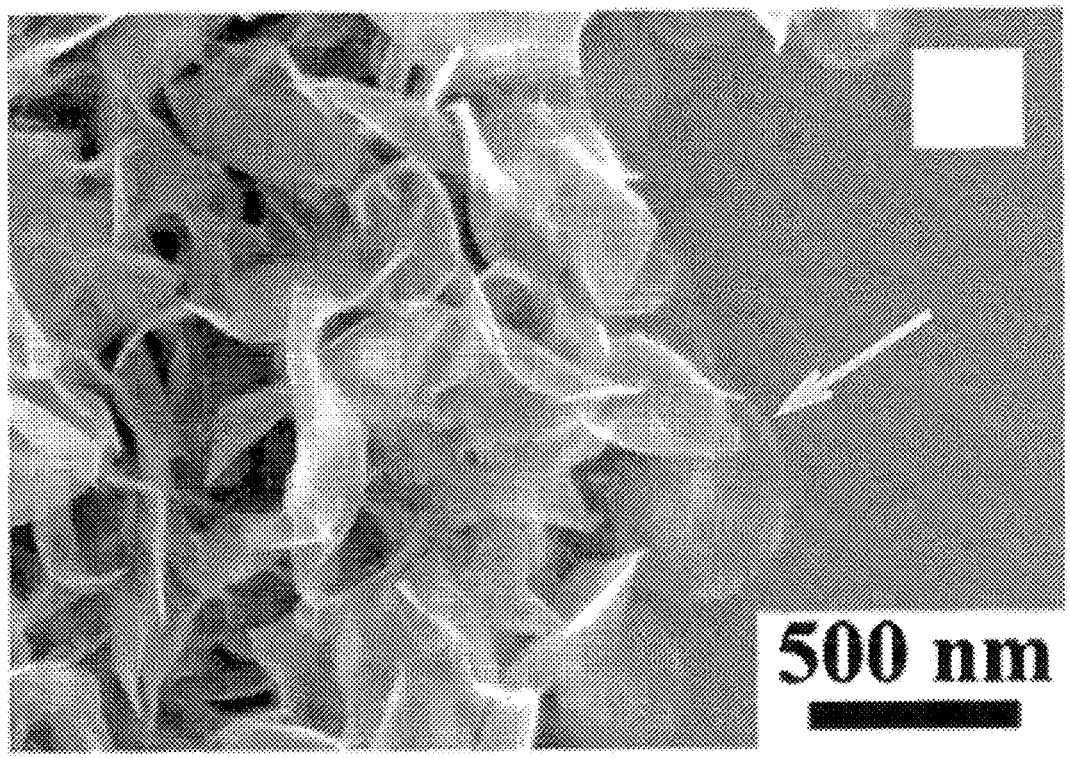
Figures 2, 3, 4, 5, 6, 7, 8, 9, 10, 11, 12, 12D:
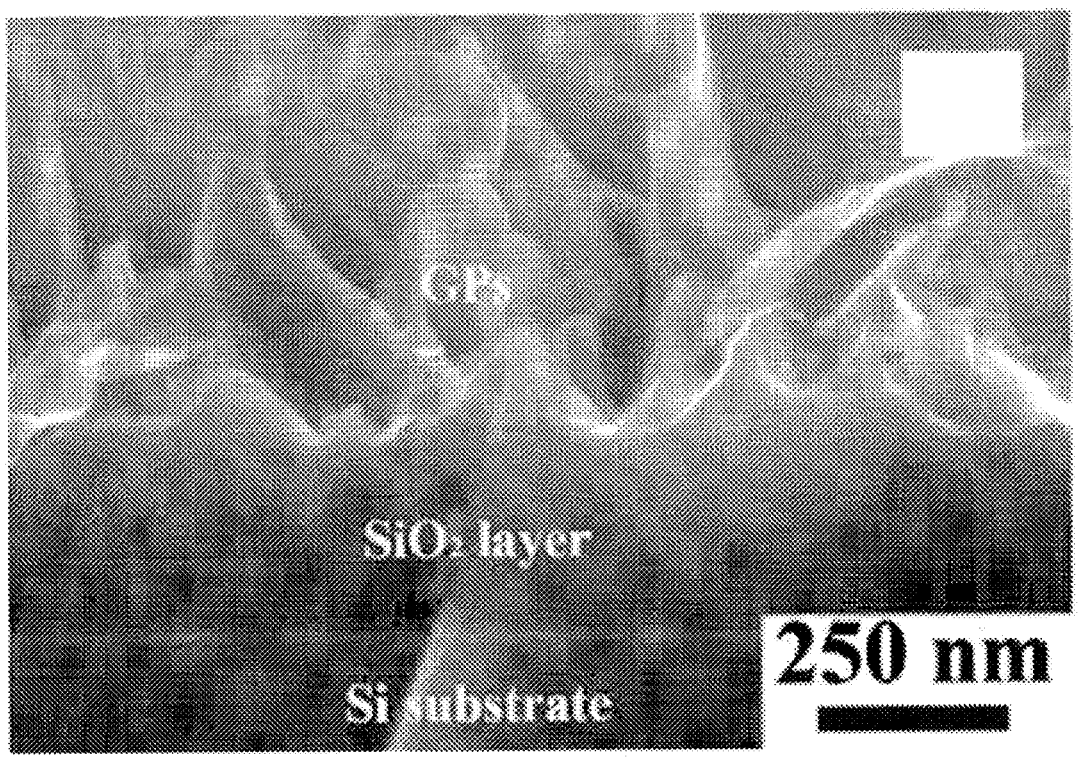

Various carbon nanomaterial electrodes were prepared following the procedures outlined above for testing and evaluation for battery applications. Various electrodes were formed from carbon-based materials i) without any of Steps A or B; ii) with only Step A; and iii) with both Steps A and B. These electrodes were tested for charge storage capacity through standard charge and discharge cycling experiments. Electrodes with carbon nanotubes modified with B and N exhibited substantially the same storage capacity (lithium capacity) as compared to pure carbon nanotube electrodes. However, electrodes processed with hydrogen plasma, exhibited significantly larger increases in capacity that increased with the number of charge-discharge cycles. The results are depicted in FIG. 11, which shows discharge capacity measured in mAh/g vs. cycle number for 1) bucky paper electrodes (i.e., electrodes made from carbon nanotubes formed into a paper-like material), 2) for bucky paper processed with Step A, and 3) for bucky paper with Steps A and B. It will be appreciated that the bucky paper in this example was not further processed to include nanopetals. It will be appreciated that the bucky paper nevertheless includes layered graphitic nanowalls or layered structures that make up the carbon nanotubes of the bucky paper, in which the boron and nitrogen atoms are integrated. It will be further appreciated that significant further improvement of operation should occur when nanopetals are grown on the bucky paper (or another substrate).

As shown in FIG. 11, the B and N modification appears to produce a highly unexpected and substantial cycle-to-cycle improvement in device charge/discharge storage capacity as the electrode cycles through hundreds of charge-discharge iterations. Further, this process can be applied to other carbon based electrodes, like graphine nanopetals, which themselves are recognized for their high performance, to add substantial further improvements.

The invention claimed is:

1. A biosensor comprising,
an electrode comprising:
a silica based wafer,
multilayered petal nanosheets supported by the wafer,
platinum nanoparticles supported by the nanosheets, and
an enzyme and a conductive polymer electrodeposited on the electrode.

2. The bio sensor of claim 1 wherein the nanosheets are grown on the wafer through chemical vapor deposition.

3. The biosensor of claim 1 wherein the nanoparticles are grown along the edges of the nano sheets.

4. The bio sensor of claim 1 wherein the nanoparticles are grown by an electrodeposition process.

5. The bio sensor of claim 4 wherein the electrodeposition process includes current pulses of approximately 500 ms.

6. The bio sensor of claim 1 wherein the enzyme comprises glucose oxidase.

7. The bio sensor of claim 6 wherein the enzyme is encapsulated within poly(3,4-ethylenedioxythiophene).

8. The bio sensor of claim 1 wherein the multilayered petal nano sheets include graphene petal nano sheets.

* * * * *